United States Patent

Uekawa et al.

[19]

[11] Patent Number: 6,103,750
[45] Date of Patent: Aug. 15, 2000

[54] FLUORINATED DIHYDROBENZOFURANYL AND DIHYDROISOBENZOFURANYL COMPOUNDS USEFUL AS INSECTICIDAL AND ACARICIDAL AGENTS

[75] Inventors: Toru Uekawa, Toyonaka; Hiroki Tomioka, Ikeda, both of Japan

[73] Assignee: Sumitomo Chemical Company, Limited, Osaka, Japan

[21] Appl. No.: 09/179,442

[22] Filed: Oct. 27, 1998

[30] Foreign Application Priority Data

Oct. 31, 1997 [JP] Japan ................................. 9-337632

[51] Int. Cl.$^7$ ..................... C07D 307/78; C07D 407/04; A01N 43/08; A01N 43/56
[52] U.S. Cl. ........................ 514/406; 514/407; 548/364.4
[58] Field of Search ..................... 548/364.4; 514/406, 514/407

[56] References Cited

U.S. PATENT DOCUMENTS

| | | | |
|---|---|---|---|
| 4,730,062 | 3/1988 | Seelye et al. | 549/462 |
| 4,767,779 | 8/1988 | Duggan | 514/403 |
| 5,580,843 | 12/1996 | Stetter et al. | 514/341 |
| 5,629,335 | 5/1997 | Manning et al. | 514/407 |
| 5,817,688 | 10/1998 | Huang et al. | 514/407 |
| 5,869,517 | 2/1999 | Muller et al. | 514/407 |
| 5,883,112 | 3/1999 | Pilato et al. | 514/404 |
| 5,885,607 | 3/1999 | Jeannin | 424/411 |

FOREIGN PATENT DOCUMENTS

| | | |
|---|---|---|
| 0285893-A2 | 10/1988 | European Pat. Off. . |
| 0310558-A2 | 4/1989 | European Pat. Off. . |
| 0372982-A2 | 6/1990 | European Pat. Off. . |
| 0396427-A1 | 11/1990 | European Pat. Off. . |
| 0517476-A2 | 12/1992 | European Pat. Off. . |
| 0780381-A1 | 6/1997 | European Pat. Off. . |
| 3903799-A1 | 8/1990 | Germany . |
| 2240063A | 9/1990 | Japan . |
| 525142A | 2/1993 | Japan . |

OTHER PUBLICATIONS

English Translation Abstract of Japanese Publication 5–025142, 1991.

Jensen–Korte et al., Chem. Abstract 114:6499, 1991.

*Primary Examiner*—Mukund J. Shah
*Assistant Examiner*—Deepak R. Rao
*Attorney, Agent, or Firm*—Birch, Stewart, Kolasch & Birch, LLP

[57] ABSTRACT

A heterocyclic compound represented by the formula (I)

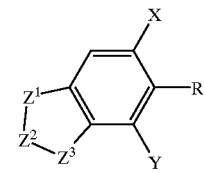

wherein X and Y, which may be same or different, represent a hydrogen atom, a halogen atom, a nitro group or a cyano group, the formula $-Z^1-Z^2-Z^3-$ is a group represented by $-CF_2-CF_2-O-$, $-CF_2-O-CF_2-$ or $-O-CF_2-O-$ and R is represented by the formula:

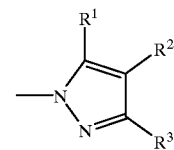

(II)

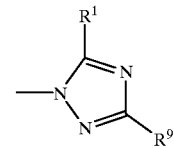

(III)

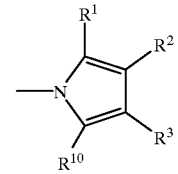

(IV)

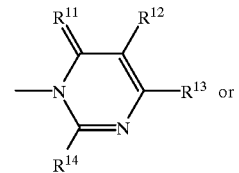

(V)

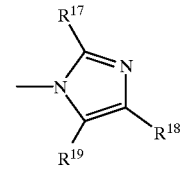

(VI)

and an insecticidal and acaricidal agent comprising same as an active ingredient.

7 Claims, No Drawings

FLUORINATED DIHYDROBENZOFURANYL AND DIHYDROISOBENZOFURANYL COMPOUNDS USEFUL AS INSECTICIDAL AND ACARICIDAL AGENTS

BACKGROUND OF THE INVENTION

The present invention relates to heterocyclic compounds and their uses.

A variety of insecticidal and acaricidal agents are known, but the development of insecticidal and acaricidal agents having a higher efficacy is required.

The present inventors have extensively studied for compounds having an excellent pesticidal effect and consequently found that the heterocyclic compounds represented by the following formula (I) have excellent insecticidal and acaricidal activities.

SUMMARY OF THE INVENTION

The present invention provides the heterocyclic compounds represented by the formula (I):

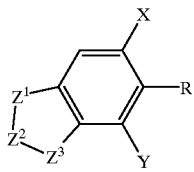

[wherein X and Y, which are the same or different, represent respectively a hydrogen atom, a halogen atom, a nitro group or a cyano group; —$Z^1$—$Z^2$—$Z^3$— is a formula represented by the group —$CF_2$—$CF_2$—O—, —$CF_2$—O—$CF_2$— or —O—$CF_2$—O—; and R is a group represented by the formula (II):

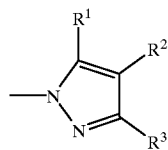

{wherein $R^1$ is a hydrogen atom, a $C_1$–$C_6$ alkyl group, a $C_1$–$C_6$ haloalkyl group, a halogen atom, a formyl group, a $C_2$–$C_8$ acyl group, a cyano group, a nitro group, a group represented by the formula $NR^4R^5$ (wherein $R^4$ and $R^5$ may be the same or different and represent respectively a hydrogen atom, a $C_1$–$C_6$ alkyl group, a $C_3$–$C_6$ cycloalkyl group, a ($C_1$–$C_6$ alkoxy) $C_1$–$C_6$ alkyl group, a ($C_1$–$C_6$ alkylthio) $C_1$–$C_6$ alkyl group, a ($C_1$–$C_6$ alkoxy) carbonyl group, a $C_2$–$C_8$ acyl group or a saturated heterocyclic group), a nitrogen-containing saturated heterocyclic group which is bonded at the nitrogen position and may be substituted, a 1-pyrrolyl group which may be substituted, a group represented by the formula N=$CR^6R^7$ (wherein $R^6$ is a hydrogen atom, a $C_1$–$C_6$ alkyl group or a phenyl group which may be substituted, and $R^7$ is a hydrogen atom, a $C_1$–$C_6$ alkyl group, a $C_1$–$C_6$ alkoxy group or a di($C_1$–$C_6$ alkyl) amino group), or a group represented by the formula $S(O)_nR^8$ (wherein $R^8$ is a $C_1$–$C_6$ alkyl group, a $C_1$–$C_6$ haloalkyl group or a $C_3$–$C_6$ cycloalkyl group, and n is a number of 0, 1 or 2); $R^2$ is a halogen atom, a cyano group, a ($C_1$–$C_6$ alkoxy) carbonyl group, a $C_2$–$C_8$ acyl group, a $C_2$–$C_8$ acyl group substituted with at least one halogen atom, a $C_1$–$C_6$ alkyl group, a $C_1$–$C_6$ haloalkyl group, a formyl group, a $C_3$–$C_6$ cycloalkyl group which may be substituted with at least one halogen atom, a sulfamoyl group which may be substituted with one or two $C_1$–$C_6$ alkyl groups, a carbamoyl group which may be substituted with one or two $C_1$–$C_6$ alkyl groups, or a group represented by the formula $S(O)_nR^8$ (wherein $R^8$ and n are as defined above); and $R^3$ is a hydrogen atom, a $C_1$–$C_6$ alkyl group, a thiocarbamoyl group, a $C_1$–$C_6$ haloalkyl group, a $C_3$–$C_6$ cycloalkyl group, a cyano group, a nitro group or a group represented by the formula $S(O)_nR^8$ (wherein $R^8$ and n are as defined above)}, a group represented by the formula (III):

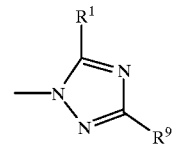

{wherein $R^1$ is as defined above; and $R^9$ is a $C_1$–$C_6$ alkyl group, a $C_1$–$C_6$ haloalkyl group, a $C_3$–$C_6$ cycloalkyl group which may be substituted with at least one halogen atom, a $C_1$–$C_6$ haloalkoxy group or a group represented by the formula $S(O)_nR^8$ (wherein $R^8$ and n are as defined above)}, a group represented by the formula (IV):

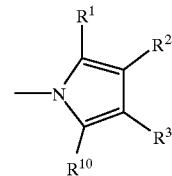

{wherein $R^1$, $R^2$ and $R^3$ are as defined above, and $R^{10}$ is a hydrogen atom, a $C_1$–$C_6$ alkyl group, a $C_1$–$C_6$ haloalkyl group or a halogen atom}, a group represented by the formula (V):

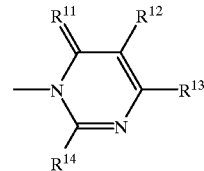

{wherein $R^{11}$ is an oxygen atom or a sulfur atom, $R^{12}$ is a hydrogen atom, a halogen atom, a $C_1$–$C_6$ alkyl group, a $C_1$–$C_6$ haloalkyl group, a cyano group, a $C_1$–$C_6$ alkoxy group, a $C_1$–$C_6$ haloalkoxy group, a formyl group, a nitro group or a group represented by the formula $S(O)_nR^8$ (wherein $R^8$ and n are as defined above), $R^{13}$ is a halogen atom, a nitro group, a $C_1$–$C_6$ haloalkyl group, a $C_1$–$C_6$ haloalkoxy group, a group represented by the formula $S(O)_n R^8$ (wherein $R^8$ and n are as defined above) or a group represented by the formula $NR^{15}R^{16}$ (wherein $R^{15}$ and $R^{16}$ may be the same or different and represent a hydrogen atom, a $C_1$–$C_6$ alkyl group or a $C_3$–$C_6$ cycloalkyl group), and $R^{14}$ is a hydrogen atom, a halogen atom or a group represented by the formula $NR^{15}R^{16}$ (wherein $R^{15}$ and $R^{16}$ are as defined above)}, or a group represented by the formula (VI):

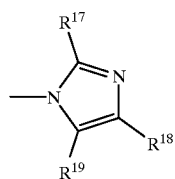

{wherein $R^{17}$ and $R^{19}$ may be the same or different and have the same definition as $R^1$ or represent a hydroxy group, and $R^{18}$ has the same definition as $R^2$} [these compounds being hereinafter referred to as the compounds of the present invention], and the insecticidal and acaricidal compositions containing these compounds as active ingredient.

DESCRIPTION OF THE INVENTION

The present invention is described in detail below.

Examples of the substituents in the optionally substituted phenyl group represented by $R^6$ include a hydroxy group, $C_1$–$C_6$ alkoxy group, $C_1$–$C_6$ alkyl group, nitro group, halogen atom, phenyl group, phenoxy group, $C_1$–$C_6$ alkylthio group, amino group, carboxyl group, cyano group, ($C_1$–$C_6$ alkoxy) carbonyl group, and $C_2$–$C_6$ acyloxy group.

The substituents defined in the compounds of the present invention include the following: $C_1$–$C_6$ alkoxy groups such as methoxy, ethoxy, isopropoxy, n-butoxy, sec-butoxy and tert-butoxy; $C_1$–$C_6$ alkyl groups such as methyl, ethyl, isopropyl, n-butyl, sec-butyl and tert-butyl; $C_1$–$C_6$ haloalkyl groups such as trifluoromethyl, pentafluoroethyl, difluoromethyl, chlorodifluorometyl, 1,1,2,2-tetrafluoroethyl, and 2,2,2-trifluoroethyl; halogen atoms such as chlorine atom, fluorine atom and bromine atom; $C_2$–$C_8$ acyl groups such as acetyl, propanoyl, butanoyl, 3-methylbutanoyl, 2-methylpropanoyl and pentanoyl; $C_3$–$C_6$ cycloalkyl groups such as cyclopropyl, cyclopentyl and cyclohexyl; ($C_1$–$C_6$ alkoxy) $C_1$–$C_6$ alkyl groups such as methoxymethyl, ethoxymethyl, propoxymethyl, isopropoxymethyl, butoxymethyl, isobutoxymethyl, 2-methoxyethyl, 1-methoxy-2,2-dimethylpropyl and 1-ethoxy-1,2,2-trimethylpropyl; ($C_1$–$C_6$ alkylthio) $C_1$–$C_6$ alkyl groups such as methylthiomethyl, ethylthiomethyl, isopropylthiomethyl, 2-methylthioethyl and 1-ethylthio-1,2,2-trimethylpropyl; ($C_1$–$C_6$ alkoxy) carbonyl groups such as methoxycarbonyl and ethoxycarbonyl; di($C_1$–$C_6$ alkyl) amino groups such as dimethylamino and diethylamino; and saturated heterocyclic groups such as tetrahydro-2H-pyran-2-yl.

Examples of the optionally substituted nitrogen-containing saturated heterocyclic groups bonded at the nitrogen position in the compounds of the present invention include 1-aziridinyl group, 1-azetidinyl group, 1-pyrrolidinyl group, morpholino group, thiomorpholino group, 2-isothiazolidinyl group, 3-oxazolidinyl group, and 3-thiazolidinyl group. The nitrogen-containing saturated heterocyclic groups may be substituted with, for example, $C_1$–$C_6$ alkyl group, halogen atom, $C_1$–$C_6$ alkoxyl group, hydroxyl group, mercapto group, ($C_1$–$C_6$ alkoxy) carbonyl group, oxo group, $C_2$–$C_8$ acyloxy group (such as acetoxy, pivaloyloxy and benzoyloxy) and the like.

Examples of the halogen-substituted $C_2$–$C_8$ acyl groups include a trifluoroacetyl group and difluoroacetyl group.

Examples of the sulfamoyl groups which may be substituted with one or two $C_1$–$C_6$ alkyl groups include a dimethylsulfamoyl group and ethylsulfamoyl group.

Examples of the carbamoyl group which may be substituted with one or two $C_1$–$C_6$ alkyl groups include a dimethylcarbamoyl group and ethylcarbamoyl group.

Examples of the $C_1$–$C_6$ haloalkoxy group include a trifluoromethoxy group, pentafluoroethoxy group and difluoromethoxy group.

In the compounds of the present invention, the preferred substituents for providing high insecticidal and acaricidal activities include the following:

$R^1$: a hydrogen atom, $C_1$–$C_6$ alkyl group, $C_1$–$C_6$ haloalkyl group, halogen atom, $C_2$–$C_8$ acyl group, the group represented by the formula $NR^4R^5$ (wherein $R^4$ and $R^5$ may be the same or different and represent respectively a hydrogen atom, a $C_1$–$C_6$ alkyl group, a $C_3$–$C_6$ cycloalkyl group, a ($C_1$–$C_6$ alkoxy) $C_1$–$C_6$ alkyl group, a ($C_1$–$C_6$ alkylthio) $C_1$–$C_6$ alkyl group, a ($C_1$–$C_6$ alkoxy) carbonyl group or a $C_2$–$C_8$ acyl group) or the groups represented by the formula $N=CR^6R^7$ (wherein $R^6$ is a hydrogen atom, a $C_1$–$C_6$ alkyl group or an optionally substituted phenyl group, and $R^7$ is a hydrogen atom, a $C_1$–$C_6$ alkyl group or a $C_1$–$C_6$ alkoxyl group).

$R^2$: a halogen atom, halogen-substituted $C_2$–$C_8$ acyl group, $C_1$–$C_6$ haloalkyl group, optionally halogen-substituted $C_3$–$C_6$ cycloalkyl group, and the group represented by the formula $S(O)_nR^8$ (wherein $R^8$ is a $C_1$–$C_6$ alkyl group or a $C_1$–$C_6$ haloalkyl group and n is as defined above).

$R^3$: a hydrogen atom, $C_1$–$C_6$ alkyl group, thiocarbamoyl group, $C_1$–$C_6$ haloalkyl group, cyano group, and the group represented by the formula $S(O)_nR^8$ (wherein $R^8$ is a $C_1$–$C_6$ alkyl group or a $C_1$–$C_6$ haloalkyl group, and n is as defined above).

$R^9$: a $C_1$–$C_6$ alkyl group, $C_1$–$C_6$ haloalkyl group and the group represented by the formula $S(O)_nR^8$ (wherein $R^8$ is a $C_1$–$C_6$ alkyl group or a $C_1$–$C_6$ haloalkyl group, and n is as defined above).

$R^{10}$: a hydrogen atom, $C_1$–$C_6$ haloalkyl group and halogen atom.

$R^{11}$: an oxygen atom.

$R^{12}$: a hydrogen atom, halogen atom and $C_1$–$C_6$ haloalkyl group.

$R^{13}$: a $C_1$–$C_6$ haloalkyl group and the group represented by the formula $S(O)_nR^8$ (wherein $R^8$ is a $C_1$–$C_6$ haloalkyl group or a $C_1$–$C_6$ haloalkyl group, and n is as defined above).

$R^{14}$: a hydrogen atom.

$R^{17}$: a hydrogen atom, $C_1$–$C_6$ alkyl group, $C_1$–$C_6$ haloalkyl group and halogen atom.

$R^{18}$: a $C_1$–$C_6$ alkyl group, $C_1$–$C_6$ haloalkyl group and the group represented by the formula $S(O)_nR^8$ (wherein $R^8$ is a $C_1$–$C_6$ alkyl group or a $C_1$–$C_6$ haloalkyl group, and n is as defined above).

$R^{19}$: a hydrogen atom, $C_1$–$C_6$ alkyl groups and $C_1$–$C_6$ haloalkyl groups.

The production processes of the compounds of the present invention will be described in detail below.

Production Process 1

The compounds of the present invention can be produced by reacting a compound represented by the formula (VII):

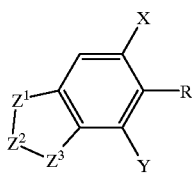

[wherein X, Y, $Z^1$, $Z^2$ and $Z^3$ are as defined above, and Z represents an leaving group (e.g. fluorine atom, chlorine atom, bromine atom, iodine atom, trifluoromethylsulfonyloxy group or methanesulfonyloxy group] with a compound represented by the formula (VIII):

[wherein R is as defined above] usually in a solvent in the presence of a base and, if necessary, a catalyst.

The reaction temperature used in the process of the present invention ranges usually from room temperature to the boiling point of the solvent used. The reaction time is usually between 10 minutes and 24 hours. As for the amounts of the reactants used in the reaction, the compound of the formula (VIII) is used in an amount of usually 1 to 5 moles, and the base in an amount of usually one mole to a large excess of the said base, per one mole of the compound of the formula (VII).

The solvents that may be used in the reaction include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane, chlorobenzene and dichlorobenzene; ethers such as diethyl ether, diisopropyl ether, dioxane, tetrahydrofuran and diethylene glycol dimethyl ether; ketones such as acetone, methyl ethyl ketone, methyl isobutyl ketone, isophoron and cyclohexanone; esters such as ethyl formate, ethyl acetate, butyl acetate and diethyl carbonate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and acetamide; sulfur compounds such as dimethyl sulfoxide and sulfolan; water, and mixtures thereof.

The bases that may be used in the reaction include inorganic bases such as sodium hydride, potassium hydride, sodium hydroxide, potassium hydroxide, sodium carbonate and potassium carbonate; and alkali metal alkoxides such as sodium methoxide and sodium ethoxide.

The catalysts that may be optionally used in the reaction include, for example, crown ether, potassium fluoride and copper.

After sufficient completion of the reaction, the reaction solution may be subjected to usual work-up such as organic solvent extraction, concentration, etc., to isolate the compound of the present invention. The isolated compound, if necessary, may be further purified by suitable means such as chromatography and recrystallization.

The compounds of the formula (VII) may be produced, for instance, by diazotizing the amino compounds obtained according to the methods described in U.S. Pat. Nos. 5,310,747 and 4,730,062, and subjecting them to a conventional reaction such as Schiemann reaction and Sandmeyer reaction. These compounds may also be obtained according to the methods described in JP-A-8-81456 and JP-A-8-81457.
Production Process II (Production of the Compounds of the Formula (I) Wherein R is a Group of the Formula (II), Hereinafter Referred to as the Compounds of the Present Invention (PR))

Method 1

[Production of the compounds of the present invention (PR) of the formula (I) wherein $R^1$ is an $NH_2$ group, a $C_1$–$C_6$ alkyl group or a $C_1$–$C_6$ haloalkyl group, R is a halogen atom, a cyano group, a ($C_1$–$C_6$ alkoxy) carbonyl group, a $C_2$–$C_8$ acyl group, a halogen-substituted $C_2$–$C_8$ acyl group, a $C_1$–$C_6$ alkyl group, a $C_1$–$C_6$ haloalkyl group, an optionally halogen-substituted $C_3$–$C_6$ cycloalkyl group, a sulfamoyl group which may be substituted with one or two $C_1$–$C_6$ alkyl groups, a carbamoyl group which may be substituted with one or two $C_1$–$C_6$ alkyl groups, or a group represented by the formula $S(O)_n R^8$ (wherein $R^8$ is a $C_1$–$C_6$ alkyl group, a $C_1$–$C_6$ haloalkyl group or a $C_3$–$C_6$ cycloalkyl group, and n is as defined above), and $R^3$ is a hydrogen atom, a $C_1$–$C_6$ alkyl group, a thiocarbamoyl group, a $C_1$–$C_6$ haloalkyl group, a $C_3$–$C_6$ cycloalkyl group, a cyano group, a nitro group or a group represented by the formula $S(O)_n R^8$ (wherein $R^8$ and n are as defined above)]

The above compounds can be produced by reacting a hydrazine compound represented by the formula (IX):

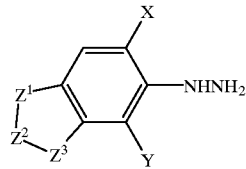

[wherein X, Y, $Z^1$, $Z^2$ and $Z^3$ are as defined above] with a compound represented by the formula (X):

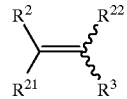

[wherein $R^2$ is a halogen atom, a cyano group, a ($C_1$–$C_6$ alkoxy) carbonyl group, a $C_2$–$C_8$ acyl group, a halogen-substituted $C_2$–$C_8$ acyl group, a $C_1$–$C_6$ alkyl group, a $C_1$–$C_6$ haloalkyl group, an optionally halogen-substituted $C_3$–$C_6$ cycloalkyl group, a sulfamoyl group which may be substituted with one or two $C_1$–$C_6$ alkyl groups, a carbamoyl group which may be substituted with one or two $C_1$–$C_6$ alkyl groups, or a group represented by the formula $S(O)_n R^8$ (wherein $R^8$ and n are as defined above), $R^3$ is as defined above, $R^{21}$ is a cyano group or a group represented by the formula $C(=O)R^{23}$ (wherein $R^{23}$ is a $C_1$–$C_6$ alkyl group or a $C_1$–$C_6$ haloalkyl group), and $R^{22}$ is a $C_1$–$C_6$ alkoxy group or a halogen atom] usually in a solvent and in the presence of a base.

The reaction temperature ranges usually from room temperature to the boiling point of the solvent used, and the reaction time is usually from 10 minutes to 24 hours.

As for the amounts of the reactants used in the reaction, the compound of the formula (X) is used in an amount of usually 1 to 5 moles, and the base in an amount of usually one mole to a large excess of the said base, per one mole of the compound of the formula (IX).

The solvents that may be used in the reaction include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane, chlorobenzene and dichlorobenzene; ethers such as diethyl ether, diisopropyl ether, dioxane, tetrahydrofuran and diethylene glycol dimethyl ether; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and acetamide; sulfur compounds such as dimethyl sulfoxide and sulfolan; water, and mixtures of materials.

The bases that may be used in the reaction include inorganic bases such as sodium hydride, potassium hydride, sodium hydroxide, potassium hydroxide, sodium carbonate and potassium carbonate, alkali metal alkoxides such as sodium methoxide and sodium ethoxide, and organic bases such as triethylamine, pyridine, 4-dimethylaminopyridine and N,N-dimethylaniline.

After sufficient completion of the reaction, the reaction solution is subjected to work-up such as organic solvent extraction and concentration to isolate the compound of the present invention. The isolated compound, if necessary, may be further purified by suitable means such as chromatography and recrystallization.

Method 2

[Production of the Compounds of the Formula (XIII)

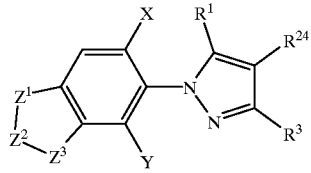

[wherein $R^1$, $R^3$, X, Y, $Z^1$, $Z^2$ and $Z^3$ are as defined above $R^{24}$ is a $C_2$–$C_8$ acyl group, a halogen-substituted $C_2$–$C_8$ acyl group, a halogen atom or a group represented by the formula $S(O)_nR^8$ (wherein $R^8$ and n are as defined above),] by reacting a pyrazole compound of the formula (XI):

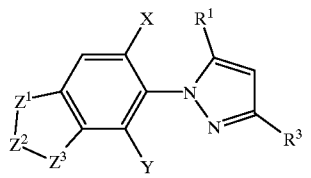

[wherein $R^1$, $R^3$, X, Y, $Z^1$, $Z^2$ and $Z^3$ are as defined above]with a compound of the formula (XII):

W—$R^{24}$

[wherein $R^{24}$ is as defined above and W is a halogen atom or a group represented by the formula O—$R^{24}$ (wherein $R^{24}$ is as defined above)].

The reaction is carried out usually in a solvent, if necessary in the presence of an acid or a base, at a temperature ranging usually from room temperature to the boiling point of the solvent being used and for a period usually from between 10 minutes to 24 hours. As for the amounts of the reactants, the compound of the formula (XII) is used in an amount of usually 1 to 5 moles per one mole of the compound of the formula (XI). In the case of using an acid or a base, the amount of said acid or base should not be less than the catalytic amount, and usually is 0.01 to 1 mole per one mole of the compound (XI).

The solvents that may be used in the reaction include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane, chlorobenzene and dichlorobenzene; ethers such as diethyl ether, dilsopropyl ether, dioxane, tetrahydrofuran and diethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and acetamide; sulfur compounds such as dimethyl sulfoxide and sulfolane, and mixtures thereof.

The acids that may be optionally used in the reaction include Lewis acids such as aluminum chloride and ferric chloride. The bases that may be optionally used in the reaction include organic bases such as triethylamine, pyridine, 4-dimethylaminopyridine and N,N-dimethylaniline.

After sufficient completion of the reaction, the reaction solution may be subjected to work-up such as organic solvent extraction and concentration to isolate the compound of the present invention. The isolated compound, if necessary, may be further purified by suitable means such as chromatography and recrystallization.

To produce the compounds of the formula (XIII) wherein $R^{24}$ is $SOR^8$ ($R^8$ being a $C_1$–$C_6$ haloalkyl group) according to the above process, there may be partly produced the compounds of the formula (XIII) wherein $R^{24}$ is $SR^8$ ($R^8$ being a $C_1$–$C_6$ haloalkyl group) depending on the reaction conditions.

The pyrazole compounds of the formula (XI) may be produced according to the process described above under the Method 1.

Among the pyrazole compounds of the formula (XI), the compounds of the said formula wherein $R^1$ is a group of the formula $NR^4R^5$ (wherein $R^4$ and $R^5$ are as defined above), other than those in which both of $R^4$ and $R^5$ are a hydrogen atom, and the compounds of the said formula wherein $R^1$ is a group of the formula $N=CR^6R^7$ (wherein $R^6$ and $R^7$ are as defined above) or a halogen atom, can be produced from the compounds of the formula (XI) wherein $R^1$ is an $NH_2$ group according to the methods described below as Methods 3–9.

Among the pyrazole compounds of the formula (XI), those of the said formula wherein $R^1$ is an $NH_2$ group and $R^3$ is a cyano group, can be produced by reacting a diazonium salt obtained by diazotizing an amino compound of the formula (XIV):

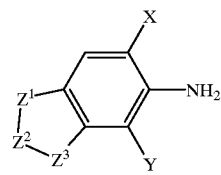

[wherein X, Y, $Z^1$, $Z^2$ and $Z^3$ are as defined above] with a dicyanopropionic ester represented by the formula (XV):

NCCH$_2$CH(CN)COOR$^{20}$

[wherein $R^{20}$ is a $C_1$–$C_6$ alkyl group, a $C_3$–$C_6$ alkenyl group or a $C_3$–$C_6$ alkynyl group]. (See JP-A-63-316771.)

Method 3-1
[Production of the compounds of the present invention (PR) of the formula (I) wherein $R^1$ is a group of the formula $NHR^{25}$ (wherein $R^{25}$ is a $C_1$–$C_6$ alkyl group, a $C_3$–$C_6$ cycloalkyl group, a ($C_1$–$C_6$ alkoxy) $C_1$–$C_6$ alkyl group, a ($C_1$–$C_6$ alkylthio) $C_1$–$C_6$ alkyl group, a ($C_1$–$C_6$ alkoxy) carbonyl group or a $C_2$–$C_8$ acyl group)]

The above compounds can be produced by reacting a compound of the present invention (PR) wherein $R^1$ is an $NH_2$ group with a halide represented by the formula (XVI):

$$R^{25}\text{—}R^{27}$$

[wherein $R^{25}$ is as defined above, and $R^{27}$ is a halogen atom] usually in a solvent in the presence of a base.

The reaction is carried out at a temperature usually in the range from –5° C. to 150° C. for a period of usually one to 24 hours. As for the amounts of the reactants used in the reaction, the halide of the formula (XVI) is used in an amount of usually 1 to 1.1 moles and a base in an amount of usually 1 to 2 moles per one mole of the compound of the formula (II) wherein $R^1$ is an $NH_2$ group.

The solvents that may be used in the reaction include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; esters such as ethyl acetate and butyl acetate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane, and mixtures of these materials.

The bases that may be used in the reaction include organic bases such as pyridine, triethylamine, N,N-diethylaniline, sodium methoxide and sodium ethoxide, and inorganic bases such as sodium hydroxide, potassium hydroxide, sodium carbonate, potassium carbonate, sodium hydrogencarbonate, calcium carbonate and sodium hydride.

The reaction solution after sufficient completion of the reaction may be subjected to work-up such as organic solvent extraction and concentration to isolate the compound of the present invention. The isolated compound, if necessary, may be further purified by suitable means such as chromatography and recrystallization.

Method 3-2
[Production of the compounds of the present invention (PR) of the formula (I) wherein $R^1$ is an $NR^{25}R^{26}$ group (wherein $R^{25}$ is as defined above and $R^{26}$ is a $C_1$–$C_6$ alkyl group, a $C_3$–$C_6$ cycloalkyl group, a ($C_1$–$C_6$ alkoxy) $C_1$–$C_6$ alkyl group, a ($C_1$–$C_6$ alkylthio) $C_1$–$C_6$ alkyl group, a ($C_1$–$C_6$ alkoxy) carbonyl group or a $C_2$–$C_8$ acyl group)]

The above compounds can be produced by reacting a compound of the present invention (PR) wherein $R^1$ is an $NHR^{25}$ group with a halide represented by the formula (XVII):

$$R^{26}\text{—}R^{27}$$

[wherein $R^{26}$ and $R^{27}$ are as defined above] usually in a solvent in the presence of a base.

The reaction is carried out at a temperature usually in the range from about –5° C. to 150° C. for a period usually from one to 24 hours. In the reaction, the halide of the formula (XVII) is used in an amount of usually 1 to 2 moles, and the base in an amount of usually 1 to 4 moles, per one mole of the compound of the formula (II) wherein $R^1$ is an $NHR^{25}$ group.

The solvents that may be used in the reaction include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; esters such as ethyl acetate and butyl acetate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane, and mixtures thereof.

The bases that may be used in the reaction include organic bases such as pyridine, triethylamine, N,N-diethylaniline, sodium methoxide and sodium ethoxide, and inorganic bases such as sodium hydroxide, potassium hydroxide, sodium carbonate, potassium carbonate, sodium hydrogencarbonate, potassium carbonate and sodium hydride.

After the reaction has been sufficiently completed, the reaction solution may be subjected to work-up such as organic solvent extraction, concentration, etc., to isolate the objective compound of the present invention. The isolated compound, if necessary, may be further purified by suitable means such as chromatography, recrystallization, etc.

Method 4
[Production of the compounds of the present invention (PR) of the formula (I) wherein $R^1$ is a halogen atom]

The above compounds can be produced by reacting a compound of the present invention (PR) of the formula (I) wherein $R^1$ is an $NH_2$ group with a nitrous acid ester represented by the formula (XVIII):

$$R^{28}\text{—}ONO$$

[wherein $R^{28}$ is a $C_1$–$C_6$ alkyl group (e.g. tert-butyl group or isoamyl group)] in the presence of a haloform (e.g. chloroform, bromoform or iodoform).

The reaction is carried out in a solvent or without a solvent, at a temperature usually in the range from about –5° C. to 150° C., and for a period of usually about one to 24 hours. As for the amounts of the reactants offered to the reaction, the nitrous acid ester of the formula (XVIII) is used in an amount of usually 1 to 4 moles, and the haloform is used in an amount of usually 1 to 50 moles per one mole of the compound of the formula (I) wherein $R^1$ is an $NH_2$ group.

Examples of solvents that may be used for the reaction are aliphatic hydrocarbons such as hexane, heptane, ligroin and petroleum ether; aromatic hydrocarbons such as benzene, toluene and xylene; ethers such as diethyl ether, diisopropyl ether, dioxane, tetrahydrofuran and ethylene glycol dimethyl ether; esters such as ethyl acetate and butyl acetate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane, and mixtures thereof.

After sufficient completion of the reaction, the reaction solution may be subjected to work-up such as concentration to isolate the compound of the present invention. The thus obtained compound may be further purified as desired by suitable means such as chromatography and recrystallization.

Method 5

[Production of the compounds of the present invention (PR) of the formula (I) wherein $R^1$ is an $NR^{29}R^{30}$ (wherein $R^{29}$ and $R^{30}$ represent the same as $R^4$ and $R^5$ except for the hydrogen atom, respectively]

The above compounds can be produced by reacting a compound of the present invention (PR) wherein $R^1$ is a halogen atom (fluorine atom, chlorine atom, bromine atom or iodine atom) with an amino compound represented by the formula (XIX):

$$HN(R^{29})R^{30}$$

[wherein $R^{29}$ and $R^{30}$ are as defined above] in a solvent or without a solvent in the presence of a base.

The reaction is carried out at a temperature usually in the range from about −5° C. to 150° C. for a period of usually one to 24 hours, and may be carried out in a pressure vessel if necessary. In the reaction, the amino compound of the formula (XIX) is used in an amount of usually 1 to 2 moles, and the base in an amount of usually 1 to 4 moles per one mole of the compound of the formula (I) wherein $R^1$ is a halogen atom. In the case the amino compound of the formula (XIX) is also a base and additionally serves the purpose of the base used herein, it may be used in large excess.

Examples of solvents that may be used for the reaction are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; ketones such as acetone, methyl ethyl ketone and methyl isobutyl ketone; esters such as ethyl acetate and butyl acetate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as formamide, N,N-dimethylformamide and N,N-dimethylacetamide; sulfur compounds such as dimethyl sulfoxide and sulfolane, and mixtures thereof.

The bases that may be used in the reaction include, beside the amino compounds of the formula (XIX), the organic bases such as pyridine, triethylamine and N,N-diethylaniline, inorganic bases such as sodium hydroxide, potassium hydroxide, sodium carbonate, potassium carbonate, sodium hydrogen carbonate, calcium carbonate and sodium hydride, and metal alkoxides such as sodium methoxide and sodium ethoxide.

After the reaction has been sufficiently completed, the reaction solution is subjected to work-up such as concentration to isolate the compound of the present invention. The isolated compound may be further purified by suitable means such as chromatography and recrystallization.

Method 6

[Production of the imidate compounds of the present invention (PR) of the formula (I) wherein $R^1$ is an $N=CR^{31}(OR^{32})$ group (wherein $R^{31}$ is a hydrogen atom or a $C_1$–$C_6$ alkyl group and $R^{32}$ is a $C_1$–$C_6$ alkyl group)]

The above compounds can be produced by reacting a compound of the present invention (PR) of the formula (I) wherein $R^1$ is an $NH_2$ group with an ortho-ester compound represented by the formula (XX):

$$R^{31}C(OR^{32})_3$$

[wherein $R^{31}$ and $R^{32}$ are as defined above] in a solvent or without a solvent in the presence of an acid catalyst.

The reaction is carried out at a temperature usually in the range from about −5° C. to 150° C. for a period of usually one to 24 hours. As for the amounts of the reactants used in the reaction, the ortho-ester compound of the formula (XX) is used in an amount of usually 1 to 7 moles and the acid catalyst is used in an amount of usually 0.01 to 1 mole per one mole of the compound of the present invention (PR) of the formula (I) wherein $R^1$ is an $NH_2$ group.

Examples of solvents that may be used for the reaction are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; esters such as ethyl acetate and butyl acetate; nitro compounds such as nitroethane and nitrobenzene; nitriles such as acetonitrile and isobutyronitrile; acid amides such as formamide, N,N-dimethylformamide and N,N-dimethylacetamide; sulfur compounds such as dimethyl sulfoxide and sulfolane, and mixtures thereof.

The acid catalysts that may be used in the reaction include Lewis acids, for example, inorganic acids such as hydrochloric acid and sulfuric acid, organic acids such as acetic acid and p-toluenesulfonic acid, and boron trifluoride.

After sufficient completion of the reaction, the reaction solution may be subjected to work-up such as concentration to isolate the compound of the present invention. If necessary, the obtained compound may be further purified by suitable means such as chromatography and recrystallization.

Method 7

[Production of the compounds of the present invention (PR) of the formula (I) wherein $R^1$ is an $NHR^{33}$ group (wherein $R^{33}$ is a $C_1$–$C_6$ alkyl group)]

The above compounds can be produced by reacting an imidate compound of the formula (I) wherein $R^1$ is $N=CR^{34}(OR^{32})$ (wherein $R^{34}$ is a hydrogen atom or a $C_1$–$C_5$ alkyl group, and $R^{32}$ is as defined above) with a metal hydride, or by hydrogenating the said imidate compound in the presence of a hydrogenation catalyst.

The reaction is conducted in a solvent, if necessary in the presence of an acid catalyst in the case of using a metal hydride, at a temperature usually in the range from −5° C. to 150° C. for a period of usually one to 24 hours. As for the amounts of the reactants used in the reaction, the metal hydride is usually 0.5 to 10 moles per one mole of the imidate compound.

The solvents used in the reaction include aliphatic hydrocarbons such as hexane, heptane, ligroin and petroleum ether; aromatic hydrocarbons such as benzene, toluene and xylene; halogenated hydrocarbons such as dichloroethane, chlorobenzene and dichlorobenzene; alcohols such as methanol, ethanol and isopropyl alcohol; ethers such as diethyl ether, diisopropyl ether, dioxane, tetrahydrofuran and ethylene glycol dimethyl ether; esters such as ethyl acetate and butyl acetate; and mixtures thereof.

The acids that may be optionally used in the reaction include Lewis acids, for example, inorganic acids such as hydrochloric acid and sulfuric acid, organic acids such as acetic acid and p-toluenesulfonic acid, and boron trifluoride.

Examples of the metal hydrides are sodium borohydride, lithium borohydride and the like.

As the catalyst used for hydrogenation, platinum oxide, Pd/C and the like may be used.

The reaction solution may be subjected to work-up such as organic solvent extraction and concentration to isolate the compound of the present invention, and the obtained compound may be further purified by suitable means such as chromatography and recrystallization if necessary.

Method 8

[Production of the compounds of the present invention (PR) of the formula (I) wherein (i) $R^1$ is an $NR^4R^5$ group, $R^4$ is a hydrogen atom and $R^5$ is a 2-tetrahydropyranyl group, (ii) $R^1$ is a 1-pyrrolyl group, or (iii) $R^1$ is an $N=CR^6R^{35}$ group (wherein $R^6$ is as defined above, and $R^{35}$ is a hydrogen atom, a $C_1$–$C_6$ alkyl group or a di($C_1$–$C_6$ alkyl) amino group)]

The above compounds can be produced by reacting a compound of the present invention (PR) of the formula (I) wherein $R^1$ is an $NH_2$ group with (i) dihydropyran, (ii) 2,6-dimethoxytetrahydrofuran, (iii-1) a carbonyl compound of the formula (XXI):

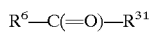

$R^6\text{---}C(=O)\text{---}R^{31}$

[wherein $R^6$ and $R^{31}$ are as defined above] or (iii-2) an acetal represented by the formula (XXII):

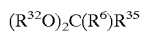

$(R^{32}O)_2C(R^6)R^{35}$

[wherein $R^6$, $R^{32}$ and $R^{35}$ are as defined above] in a solvent or without a solvent usually in the presence of an acid.

The reaction is carried out at a temperature usually in the range from about −5° C. to 150° C. for a period of usually one to 24 hours. As for the amounts of the reactants used in the reaction, dihydropyran, 2,6-dimethoxytetrahydrofuran, a carbonyl compound of the formula (XXI) and acetals of the formula (XXII) are used in an amount of usually 1 to 20 moles and the acid is used in an amount of usually 0.01 to 1 mole per one mole of the compound of the present invention (PR) of the formula (I) wherein $R^1$ is an amino group.

Examples of solvents that may be used for the reaction are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; esters such as ethyl acetate and butyl acetate; nitro compounds such as nitroethane and nitrobenzene; and mixtures thereof.

The acids that may be used in the reaction include Lewis acids, for example, inorganic acids such as hydrochloric acid and sulfuric acid, organic acids such as acetic acid and p-toluenesulfonic acid, and boron tetrafluoride.

After sufficient completion of the reaction, the reaction solution is subjected to work-up such as concentration to isolate the compound of the present invention. The obtained compound may be further purified as desired by suitable means such as chromatography and recrystallization if necessary.

Method 9

[Production of the compound of the present invention (PR) of the formula (I) wherein $R^1$ is $NHR^{36}$ (wherein $R^{36}$ is a ($C_1$–$C_6$ alkoxy) $C_1$–$C_6$ alkyl group or a ($C_1$–$C_6$ alkylthio) $C_1$–$C_6$ alkyl group)]

The above compounds can be produced by reacting a compound of the present invention (PR) of the formula (I) wherein $R^1$ is a group of the formula $N=CR^{37}R^{38}$ (wherein $R^{37}$ and $R^{38}$ may be the same or different and represent respectively a hydrogen atom or a $C_1$–$C_5$ alkyl group, and wherein the total of the carbon numbers of $R^{37}$ and $R^{38}$ is not more than 5) (the compounds can be produced, for example, according to the process described in Method 8) with an alcohol or a mercaptan represented by the formula (XXIII):

$R^{28}AH$

[wherein A is an oxygen atom or a sulfur atom, and $R^{28}$ is as defined above] in a solvent or without a solvent in the presence of an acid catalyst.

The reaction is carried out at a temperature usually in the range from about −5° C. to 150° C. for a period of usually one to 24 hours. As for the amounts of the reactants offered to the reaction, the alcohol or mercaptan of the formula (XXIII) is usually 1 to 10 moles and the acid catalyst is usually 0.01 to 1 mole per one mole of the compound of the formula (I) wherein $R^1$ is an $N=CR^{37}R^{38}$ group.

Examples of solvents that may be used for the reaction are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; esters such as ethyl acetate and butyl acetate; nitro compounds such as nitroethane and nitrobenzene; sulfur compounds such as dimethyl sulfoxide and sulfolane; and mixtures thereof.

The acid catalysts used in the reaction may be Lewis acids, for example, inorganic acids such as hydrochloric acid and sulfuric acid, organic acids such as acetic acid and p-toluenesulfonic acid, and boron trifluoride.

The reaction solution may be subjected to work-up such as concentration to isolate the compound of the present invention. The obtained compound may be further purified by suitable means such as chromatography and recrystallization if necessary.

Method 10

[Production of the compounds of the present invention (PR) of the formula (I) wherein $R^2$ is $SR^{39}$ (wherein $R^{39}$ is a $C_1$–$C_6$ haloalkyl group)]

The above compounds can be produced by reacting a disulfide compound represented by the formula (XXIV):

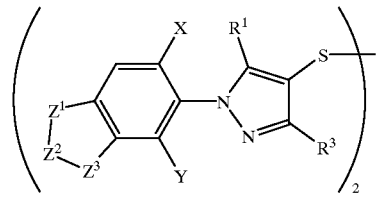

[wherein $R^1$, $R^3$, X, Y, $Z^1$, $Z^2$ and $Z^3$ are as defined above] with a halide represented by the formula (XXV):

$R^{39}\text{---}R^{40}$

[wherein $R^{39}$ is as defined above, and $R^{40}$ is a chlorine atom, a bromine atom or an iodine atom] in a solvent or without a solvent and in the presence of a reducing agent.

The reaction is carried out at a temperature usually in the range from about −20° C. to 150° C. for a period of usually one to 24 hours. As for the amounts of the reactants, the halide of the formula (XXV) is used in an amount of usually 2 moles to a large excess and the reducing agent is usually 2 to 6 moles based on the disulfide compound of the formula (XXIV).

Examples of solvents that may be used for the reaction are aliphatic hydrocarbons such as hexane, heptane, ligroin and petroleum ether; aromatic hydrocarbons such as benzene, toluene and xylene; halogenated hydrocarbons such as dichloroethane, chlorobenzene and dichlorobenzene; ethers such as diethyl ether, duisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl acetate and butyl acetate; nitriles such as acetonitrile and isobutyronitrile; nitro compounds such as nitroethane and nitrobenzene; acid amides such as formamide, N,N-dimethylformamide and N,N-dimethylacetamide; sulfur compounds such as dimethyl sulfoxide and sulfolane; and mixtures thereof.

The possible reducing agents used in the reaction include hydroxymethanesulfinates formed with various cations (e.g. alkali metal hydroxymethanesulfinates such as sodium hydroxymethanesulfinate) and alkali metal dithionites (e. g. sodium dithionite).

After the reaction has been sufficiently completed, the reaction solution may be subjected to work-up such as concentration to isolate the compound of the present invention. The obtained compound, if necessary, may be further purified by suitable means such as chromatography and recrystallization.

In the compounds of the present invention, those of the formula (I) wherein R is a group of the formula (III) may be produced according to the methods described in EP-780381-A, JP-A-1-230562, JP-A-2-91061, etc., those of the formula (I) wherein R is a group of the formula (IV) may be produced by the methods described in JP-A-2-243670, etc., and those of the formula (I) wherein R is a group of the formula (VI) may be produced by the methods described in JP-A-3-27361, etc.

The compounds of the present invention are exemplified in the following Tables 1-205, but not limited to those shown therein.

1) Heterocyclic Compounds of the Formula (I) Wherein R is a Group of the Formula (II)

TABLE 1

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | H | $SCF_3$ | H |
| Cl | H | $CF_2$ | O | $CF_2$ | $NH_2$ | $SCF_3$ | H |
| Cl | H | $CF_2$ | O | $CF_2$ | N=CHPh | $SCF_3$ | H |
| Cl | H | $CF_2$ | O | $CF_2$ | $CH_3$ | $SCF_3$ | H |
| Cl | H | $CF_2$ | O | $CF_2$ | $CF_3$ | $SCF_3$ | H |
| Cl | H | $CF_2$ | O | $CF_2$ | Cl | $SCF_3$ | H |
| Cl | H | $CF_2$ | O | $CF_2$ | F | $SCF_3$ | H |
| Cl | H | $CF_2$ | O | $CF_2$ | $COCH_3$ | $SCF_3$ | H |
| Cl | H | $CF_2$ | O | $CF_2$ | H | $SOCF_3$ | H |
| Cl | H | $CF_2$ | O | $CF_2$ | $NH_2$ | $SOCF_3$ | H |
| Cl | H | $CF_2$ | O | $CF_2$ | N=CHPh | $SOCF_3$ | H |
| Cl | H | $CF_2$ | O | $CF_2$ | $CH_3$ | $SOCF_3$ | H |
| Cl | H | $CF_2$ | O | $CF_2$ | $CF_3$ | $SOCF_3$ | H |
| Cl | H | $CF_2$ | O | $CF_2$ | Cl | $SOCF_3$ | H |
| Cl | H | $CF_2$ | O | $CF_2$ | F | $SOCF_3$ | H |
| Cl | H | $CF_2$ | O | $CF_2$ | $COCH_3$ | $SOCF_3$ | H |
| Cl | H | $CF_2$ | O | $CF_2$ | H | $SO_2CF_3$ | H |
| Cl | H | $CF_2$ | O | $CF_2$ | $NH_2$ | $SO_2CF_3$ | H |
| Cl | H | $CF_2$ | O | $CF_2$ | N=CHPh | $SO_2CF_3$ | H |
| Cl | H | $CF_2$ | O | $CF_2$ | CH | $SO_2CF_3$ | H |
| Cl | H | $CF_2$ | O | $CF_2$ | $CF_3$ | $SO_2CF_3$ | H |
| Cl | H | $CF_2$ | O | $CF_2$ | Cl | $SO_2CF_3$ | H |
| Cl | H | $CF_2$ | O | $CF_2$ | F | $SO_2CF_3$ | H |
| Cl | H | $CF_2$ | O | $CF_2$ | $COCH_3$ | $SO_2CF_3$ | H |
| Cl | H | $CF_2$ | O | $CF_2$ | H | $SCF_2CH_3$ | H |

TABLE 2

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $NH_2$ | $SCF_2CH_3$ | H |
| Cl | H | $CF_2$ | O | $CF_2$ | N=CHPh | $SCF_2CH_3$ | H |
| Cl | H | $CF_2$ | O | $CF_2$ | $CH_3$ | $SCF_2CH_3$ | H |
| Cl | H | $CF_2$ | O | $CF_2$ | $CF_3$ | $SCF_2CH_3$ | H |
| Cl | H | $CF_2$ | O | $CF_2$ | Cl | $SCF_2CH_3$ | H |
| Cl | H | $CF_2$ | O | $CF_2$ | F | $SCF_2CH_3$ | H |
| Cl | H | $CF_2$ | O | $CF_2$ | $COCH_3$ | $SCF_2CH_3$ | H |
| Cl | H | $CF_2$ | O | $CF_2$ | H | $SOCF_2CH_3$ | H |
| Cl | H | $CF_2$ | O | $CF_2$ | $NH_2$ | $SOCF_2CH_3$ | H |
| Cl | H | $CF_2$ | O | $CF_2$ | N=CHPh | $SOCF_2CH_3$ | H |
| Cl | H | $CF_2$ | O | $CF_2$ | $CH_3$ | $SOCF_2CH_3$ | H |
| Cl | H | $CF_2$ | O | $CF_2$ | CF3 | $SOCF_2CH_3$ | H |
| Cl | H | $CF_2$ | O | $CF_2$ | Cl | $SOCF_2CH_3$ | H |
| Cl | H | $CF_2$ | O | $CF_2$ | F | $SOCF_2CH_3$ | H |
| Cl | H | $CF_2$ | O | $CF_2$ | $COCH_3$ | $SOCF_2CH_3$ | H |
| Cl | H | $CF_2$ | O | $CF_2$ | H | $SO_2CS_2CH_3$ | H |
| Cl | H | $CF_2$ | O | $CF_2$ | $NH_2$ | $SO_2CF_2CH_3$ | H |
| Cl | H | $CF_2$ | O | $CF_2$ | N=CHPh | $SO_2CF_2CH_3$ | H |
| Cl | H | $CF_2$ | O | $CF_2$ | $CH_3$ | $SO_2CF_2CH_3$ | H |
| Cl | H | $CF_2$ | O | $CF_2$ | $CF_3$ | $SO_2CF_2CH_3$ | H |
| Cl | H | $CF_2$ | O | $CF_2$ | Cl | $SO_2CF_2CH_3$ | H |
| Cl | H | $CF_2$ | O | $CF_2$ | F | $SO_2CF_2CH_3$ | H |
| Cl | H | $CF_2$ | O | $CF_2$ | $COCH_3$ | $SO_2CF_2CH_3$ | H |
| Cl | H | $CF_2$ | O | $CF_2$ | $NH_2$ | $COCF_3$ | H |
| Cl | H | $CF_2$ | O | $CF_2$ | N=CHPh | $COCF_3$ | H |
| Cl | H | $CF_2$ | O | $CF_2$ | $CH_3$ | $COCF_3$ | H |

TABLE 3

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $CF_3$ | $COCF_3$ | H |
| Cl | H | $CF_2$ | O | $CF_2$ | Cl | $COCF_3$ | H |
| Cl | H | $CF_2$ | O | $CF_2$ | F | $COCF_3$ | H |
| Cl | H | $CF_2$ | O | $CF_2$ | $COCH_3$ | $COCF_3$ | H |
| Cl | H | $CF_2$ | O | $CF_2$ | H | $COCF_3$ | H |
| Cl | H | $CF_2$ | O | $CF_2$ | $NH_2$ | $COCF_3$ | H |
| Cl | H | $CF_2$ | O | $CF_2$ | N=CHPh | $COCF_3$ | H |
| Cl | H | $CF_2$ | O | $CF_2$ | $CH_3$ | $COCF_3$ | H |
| Cl | H | $CF_2$ | O | $CF_2$ | $CF_3$ | $COCF_3$ | H |
| Cl | H | $CF_2$ | O | $CF_2$ | Cl | $COCF_3$ | H |
| Cl | H | $CF_2$ | O | $CF_2$ | F | $COCF_3$ | H |
| Cl | H | $CF_2$ | O | $CF_2$ | $COCH_3$ | $COCF_3$ | H |
| Cl | H | $CF_2$ | O | $CF_2$ | $NH_2$ | $C_2F_5$ | H |
| Cl | H | $CF_2$ | O | $CF_2$ | N=CHPh | $C_2F_5$ | H |
| Cl | H | $CF_2$ | O | $CF_2$ | $CH_3$ | $C_2F_5$ | H |
| Cl | H | $CF_2$ | O | $CF_2$ | $CF_3$ | $C_2F_5$ | H |
| Cl | H | $CF_2$ | O | $CF_2$ | Cl | $C_2F_5$ | H |
| Cl | H | $CF_2$ | O | $CF_2$ | F | $C_2F_5$ | H |
| Cl | H | $CF_2$ | O | $CF_2$ | $COCH_3$ | $C_2F_5$ | H |
| Cl | H | $CF_2$ | O | $CF_2$ | H | $C_2F_5$ | H |
| Cl | H | $CF_2$ | O | $CF_2$ | $NH_2$ | $C_2F_5$ | H |
| Cl | H | $CF_2$ | O | $CF_2$ | N=CHPh | $C_2F_5$ | H |
| Cl | H | $CF_2$ | O | $CF_2$ | $CH_3$ | $C_2F_5$ | H |
| Cl | H | $CF_2$ | O | $CF_2$ | $CF_3$ | $C_2F_5$ | H |
| Cl | H | $CF_2$ | O | $CF_2$ | Cl | $C_2F_5$ | H |
| Cl | H | $CF_2$ | O | $CF_2$ | F | $C_2F_5$ | H |

TABLE 4

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $COCH_3$ | $C_2F_5$ | H |
| Cl | H | $CF_2$ | O | $CF_2$ | $NH_2$ | $SFCl_2$ | H |
| Cl | H | $CF_2$ | O | $CF_2$ | N=CHPh | $SFCl_2$ | H |
| Cl | H | $CF_2$ | O | $CF_2$ | $CH_3$ | $SFCl_2$ | H |
| Cl | H | $CF_2$ | O | $CF_2$ | $CF_3$ | $SFCl_2$ | H |
| Cl | H | $CF_2$ | O | $CF_2$ | Cl | $SFCl_2$ | H |
| Cl | H | $CF_2$ | O | $CF_2$ | F | $SFCl_2$ | H |
| Cl | H | $CF_2$ | O | $CF_2$ | $COCH_3$ | $SFCl_2$ | H |
| Cl | H | $CF_2$ | O | $CF_2$ | H | $SFCl_2$ | H |
| Cl | H | $CF_2$ | O | $CF_2$ | $NH_2$ | $SFCl_2$ | H |

TABLE 4-continued

| X | Y | Z¹ | Z² | Z³ | R¹ | R² | R³ |
|---|---|---|---|---|---|---|---|
| Cl | H | $CF_2$ | O | $CF_2$ | N=CHPh | $SFCl_2$ | H |
| Cl | H | $CF_2$ | O | $CF_2$ | $CH_3$ | $SFCl_2$ | H |
| Cl | H | $CF_2$ | O | $CF_2$ | $CF_3$ | $SFCl_2$ | H |
| Cl | H | $CF_2$ | O | $CF_2$ | Cl | $SFCl_2$ | H |
| Cl | H | $CF_2$ | O | $CF_2$ | F | $SFCl_2$ | H |
| Cl | H | $CF_2$ | O | $CF_2$ | $COCH_3$ | $SFCl_2$ | H |
| Cl | H | $CF_2$ | O | $CF_2$ | H | $SCF_3$ | $CF_3$ |
| Cl | H | $CF_2$ | O | $CF_2$ | $NH_2$ | $SCF_3$ | $CF_3$ |
| Cl | H | $CF_2$ | O | $CF_2$ | N=CHPh | $SCF_3$ | $CF_3$ |
| Cl | H | $CF_2$ | O | $CF_2$ | $CH_3$ | $SCF_3$ | $CF_3$ |
| Cl | H | $CF_2$ | O | $CF_2$ | $CF_3$ | $SCF_3$ | $CF_3$ |
| Cl | H | $CF_2$ | O | $CF_2$ | Cl | $SCF_3$ | $CF_3$ |
| Cl | H | $CF_2$ | O | $CF_2$ | F | $SCF_3$ | $CF_3$ |
| Cl | H | $CF_2$ | O | $CF_2$ | $COCH_3$ | $SCF_3$ | $CF_3$ |
| Cl | H | $CF_2$ | O | $CF_2$ | H | $SOCF_3$ | $CF_3$ |
| Cl | H | $CF_2$ | O | $CF_2$ | $NH_2$ | $SOCF_3$ | $CF_3$ |

TABLE 5

| X | Y | Z¹ | Z² | Z³ | R¹ | R² | R³ |
|---|---|---|---|---|---|---|---|
| Cl | H | $CF_2$ | O | $CF_2$ | N=CHPh | $SOCF_3$ | $CF_3$ |
| Cl | H | $CF_2$ | O | $CF_2$ | $CH_3$ | $SOCF_3$ | $CF_3$ |
| Cl | H | $CF_2$ | O | $CF_2$ | $CF_3$ | $SOCF_3$ | $CF_3$ |
| Cl | H | $CF_2$ | O | $CF_2$ | Cl | $SOCF_3$ | $CF_3$ |
| Cl | H | $CF_2$ | O | $CF_2$ | F | $SOCF_3$ | $CF_3$ |
| Cl | H | $CF_2$ | O | $CF_2$ | $COCH_3$ | $SOCF_3$ | $CF_3$ |
| Cl | H | $CF_2$ | O | $CF_2$ | H | $SO_2CF_3$ | $CF_3$ |
| Cl | H | $CF_2$ | O | $CF_2$ | $NH_2$ | $SO_2CF_3$ | $CF_3$ |
| Cl | H | $CF_2$ | O | $CF_2$ | N=CHPh | $SO_2CF_3$ | $CF_3$ |
| Cl | H | $CF_2$ | O | $CF_2$ | $CH_3$ | $SO_2CF_3$ | $CF_3$ |
| Cl | H | $CF_2$ | O | $CF_2$ | $CF_3$ | $SO_2CF_3$ | $CF_3$ |
| Cl | H | $CF_2$ | O | $CF_2$ | Cl | $SO_2CF_3$ | $CF_3$ |
| Cl | H | $CF_2$ | O | $CF_2$ | F | $SO_2CF_3$ | $CF_3$ |
| Cl | H | $CF_2$ | O | $CF_2$ | $COCH_3$ | $SO_2CF_3$ | $CF_3$ |
| Cl | H | $CF_2$ | O | $CF_2$ | H | $SCF_2CH_3$ | $CF_3$ |
| Cl | H | $CF_2$ | O | $CF_2$ | $NH_2$ | $SCF_2CH_3$ | $CF_3$ |
| Cl | H | $CF_2$ | O | $CF_2$ | N=CHPh | $SCF_2CH_3$ | $CF_3$ |
| Cl | H | $CF_2$ | O | $CF_2$ | $CH_3$ | $SCF_2CH_3$ | $CF_3$ |
| Cl | H | $CF_2$ | O | $CF_2$ | $CF_3$ | $SCF_2CH_3$ | $CF_3$ |
| Cl | H | $CF_2$ | O | $CF_2$ | Cl | $SCF_2CH_3$ | $CF_3$ |
| Cl | H | $CF_2$ | O | $CF_2$ | F | $SCF_2CH_3$ | $CF_3$ |
| Cl | H | $CF_2$ | O | $CF_2$ | $COCH_3$ | $SCF_2CH_3$ | $CF_3$ |
| Cl | H | $CF_2$ | O | $CF_2$ | H | $SOCF_2CH_3$ | $CF_3$ |
| Cl | H | $CF_2$ | O | $CF_2$ | $NH_2$ | $SOCF_2CH_3$ | $CF_3$ |
| Cl | H | $CF_2$ | O | $CF_2$ | N=CHPh | $SOCF_2CH_3$ | $CF_3$ |
| Cl | H | $CF_2$ | O | $CF_2$ | $CH_3$ | $SOCF_2CH_3$ | $CF_3$ |

TABLE 6

| X | Y | Z¹ | Z² | Z³ | R¹ | R² | R³ |
|---|---|---|---|---|---|---|---|
| Cl | H | $CF_2$ | O | $CF_2$ | $CF_3$ | $SOCF_2CH_3$ | $CF_3$ |
| Cl | H | $CF_2$ | O | $CF_2$ | Cl | $SOCF_2CH_3$ | $CF_3$ |
| Cl | H | $CF_2$ | O | $CF_2$ | F | $SOCF_2CH_3$ | $CF_3$ |
| Cl | H | $CF_2$ | O | $CF_2$ | $COCH_3$ | $SOCF_2CH_3$ | $CF_3$ |
| Cl | H | $CF_2$ | O | $CF_2$ | H | $SO_2CF_2CH_3$ | $CF_3$ |
| Cl | H | $CF_2$ | O | $CF_2$ | $NH_2$ | $SO_2CF_2CH_3$ | $CF_3$ |
| Cl | H | $CF_2$ | O | $CF_2$ | N=CHPh | $SO_2CF_2CH_3$ | $CF_3$ |
| Cl | H | $CF_2$ | O | $CF_2$ | $CH_3$ | $SO_2CF_2CH_3$ | $CF_3$ |
| Cl | H | $CF_2$ | O | $CF_2$ | $CF_3$ | $SO_2CF_2CH_3$ | $CF_3$ |
| Cl | H | $CF_2$ | O | $CF_2$ | Cl | $SO_2CF_2CH_3$ | $CF_3$ |
| Cl | H | $CF_2$ | O | $CF_2$ | F | $SO_2CF_2CH_3$ | $CF_3$ |
| Cl | H | $CF_2$ | O | $CF_2$ | $COCH_3$ | $SO_2CF_2CH_3$ | $CF_3$ |
| Cl | H | $CF_2$ | O | $CF_2$ | $NH_2$ | $COCF_3$ | $CF_3$ |
| Cl | H | $CF_2$ | O | $CF_2$ | N=CHPh | $COCF_3$ | $CF_3$ |
| Cl | H | $CF_2$ | O | $CF_2$ | $CH_3$ | $COCF_3$ | $CF_3$ |
| Cl | H | $CF_2$ | O | $CF_2$ | $CF_3$ | $COCF_3$ | $CF_3$ |
| Cl | H | $CF_2$ | O | $CF_2$ | Cl | $COCF_3$ | $CF_3$ |
| Cl | H | $CF_2$ | O | $CF_2$ | F | $COCF_3$ | $CF_3$ |
| Cl | H | $CF_2$ | O | $CF_2$ | $COCH_3$ | $COCF_3$ | $CF_3$ |
| Cl | H | $CF_2$ | O | $CF_2$ | H | $COCF_3$ | $CF_3$ |

TABLE 6-continued

| X | Y | Z¹ | Z² | Z³ | R¹ | R² | R³ |
|---|---|---|---|---|---|---|---|
| Cl | H | $CF_2$ | O | $CF_2$ | $NH_2$ | $COCF_3$ | $CF_3$ |
| Cl | H | $CF_2$ | O | $CF_2$ | N=CHPh | $COCF_3$ | $CF_3$ |
| Cl | H | $CF_2$ | O | $CF_2$ | $CH_3$ | $COCF_3$ | $CF_3$ |
| Cl | H | $CF_2$ | O | $CF_2$ | $CF_3$ | $COCF_3$ | $CF_3$ |
| Cl | H | $CF_2$ | O | $CF_2$ | Cl | $COCF_3$ | $CF_3$ |
| Cl | H | $CF_2$ | O | $CF_2$ | F | $COCF_3$ | $CF_3$ |

TABLE 7

| X | Y | Z¹ | Z² | Z³ | R¹ | R² | R³ |
|---|---|---|---|---|---|---|---|
| Cl | H | $CF_2$ | O | $CF_2$ | $COCH_3$ | $COCF_3$ | $CF_3$ |
| Cl | H | $CF_2$ | O | $CF_2$ | $NH_2$ | $C_2F_5$ | $CF_3$ |
| Cl | H | $CF_2$ | O | $CF_2$ | N=CHPh | $C_2F_5$ | $CF_3$ |
| Cl | H | $CF_2$ | O | $CF_2$ | $CH_3$ | $C_2F_5$ | $CF_3$ |
| Cl | H | $CF_2$ | O | $CF_2$ | $CF_3$ | $C_2F_5$ | $CF_3$ |
| Cl | H | $CF_2$ | O | $CF_2$ | Cl | $C_2F_5$ | $CF_3$ |
| Cl | H | $CF_2$ | O | $CF_2$ | F | $C_2F_5$ | $CF_3$ |
| Cl | H | $CF_2$ | O | $CF_2$ | $COCH_3$ | $C_2F_5$ | $CF_3$ |
| Cl | H | $CF_2$ | O | $CF_2$ | H | $C_2F_5$ | $CF_3$ |
| Cl | H | $CF_2$ | O | $CF_2$ | $NH_2$ | $C_2F_5$ | $CF_3$ |
| Cl | H | $CF_2$ | O | $CF_2$ | N=CHPh | $C_2F_5$ | $CF_3$ |
| Cl | H | $CF_2$ | O | $CF_2$ | $CH_3$ | $C_2F_5$ | $CF_3$ |
| Cl | H | $CF_2$ | O | $CF_2$ | $CF_3$ | $C_2F_5$ | $CF_3$ |
| Cl | H | $CF_2$ | O | $CF_2$ | Cl | $C_2F_5$ | $CF_3$ |
| Cl | H | $CF_2$ | O | $CF_2$ | F | $C_2F_5$ | $CF_3$ |
| Cl | H | $CF_2$ | O | $CF_2$ | $NH_2$ | $SFCl_2$ | $CF_3$ |
| Cl | H | $CF_2$ | O | $CF_2$ | N=CHPh | $SFCl_2$ | $CF_3$ |
| Cl | H | $CF_2$ | O | $CF_2$ | $CH_3$ | $SFCl_2$ | $CF_3$ |
| Cl | H | $CF_2$ | O | $CF_2$ | $CF_3$ | $SFCl_2$ | $CF_3$ |
| Cl | H | $CF_2$ | O | $CF_2$ | Cl | $SFCl_2$ | $CF_3$ |
| Cl | H | $CF_2$ | O | $CF_2$ | F | $SFCl_2$ | $CF_3$ |
| Cl | H | $CF_2$ | O | $CF_2$ | $COCH_3$ | $SFCl_2$ | $CF_3$ |
| Cl | H | $CF_2$ | O | $CF_2$ | H | $SFCl_2$ | $CF_3$ |
| Cl | H | $CF_2$ | O | $CF_2$ | $NH_2$ | $SFCl_2$ | $CF_3$ |
| Cl | H | $CF_2$ | O | $CF_2$ | N=CHPh | $SFCl_2$ | $CF_3$ |

TABLE 8

| X | Y | Z¹ | Z² | Z³ | R¹ | R² | R³ |
|---|---|---|---|---|---|---|---|
| Cl | H | $CF_2$ | O | $CF_2$ | $CH_3$ | $SFCl_2$ | $CF_3$ |
| Cl | H | $CF_2$ | O | $CF_2$ | $CF_3$ | $SFCl_2$ | $CF_3$ |
| Cl | H | $CF_2$ | O | $CF_2$ | Cl | $SFCl_2$ | $CF_3$ |
| Cl | H | $CF_2$ | O | $CF_2$ | F | $SFCl_2$ | $CF_3$ |
| Cl | H | $CF_2$ | O | $CF_2$ | $COCH_3$ | $SFCl_2$ | $CF_3$ |
| Cl | H | $CF_2$ | O | $CF_2$ | H | $SCF_3$ | $C_2F_5$ |
| Cl | H | $CF_2$ | O | $CF_2$ | $NH_2$ | $SCF_3$ | $C_2F_5$ |
| Cl | H | $CF_2$ | O | $CF_2$ | N=CHPh | $SCF_3$ | $C_2F_5$ |
| Cl | H | $CF_2$ | O | $CF_2$ | $CH_3$ | $SCF_3$ | $C_2F_5$ |
| Cl | H | $CF_2$ | O | $CF_2$ | $CF_3$ | $SCF_3$ | $C_2F_5$ |
| Cl | H | $CF_2$ | O | $CF_2$ | Cl | $SCF_3$ | $C_2F_5$ |
| Cl | H | $CF_2$ | O | $CF_2$ | F | $SCF_3$ | $C_2F_5$ |
| Cl | H | $CF_2$ | O | $CF_2$ | $COCH_3$ | $SCF_3$ | $C_2F_5$ |
| Cl | H | $CF_2$ | O | $CF_2$ | H | $SOCF_3$ | $C_2F_5$ |
| Cl | H | $CF_2$ | O | $CF_2$ | $NH_2$ | $SOCF_3$ | $C_2F_5$ |
| Cl | H | $CF_2$ | O | $CF_2$ | N=CHPh | $SOCF_3$ | $C_2F_5$ |
| Cl | H | $CF_2$ | O | $CF_2$ | $CH_3$ | $SOCF_3$ | $C_2F_5$ |
| Cl | H | $CF_2$ | O | $CF_2$ | $CF_3$ | $SOCF_3$ | $C_2F_5$ |
| Cl | H | $CF_2$ | O | $CF_2$ | Cl | $SOCF_3$ | $C_2F_5$ |
| Cl | H | $CF_2$ | O | $CF_2$ | F | $SOCF_3$ | $C_2F_5$ |
| Cl | H | $CF_2$ | O | $CF_2$ | $COCH_3$ | $SOCF_3$ | $C_2F_5$ |
| Cl | H | $CF_2$ | O | $CF_2$ | H | $SO_2CF_3$ | $C_2F_5$ |
| Cl | H | $CF_2$ | O | $CF_2$ | $NH_2$ | $SO_2CF_3$ | $C_2F_5$ |
| Cl | H | $CF_2$ | O | $CF_2$ | N=CHPh | $SO_2CF_3$ | $C_2F_5$ |
| Cl | H | $CF_2$ | O | $CF_2$ | $CH_3$ | $SO_2CF_3$ | $C_2F_5$ |
| Cl | H | $CF_2$ | O | $CF_2$ | $CF_3$ | $SO_2CF_3$ | $C_2F_5$ |

TABLE 9

| X | Y | Z¹ | Z² | Z³ | R¹ | R² | R³ |
|---|---|---|---|---|---|---|---|
| Cl | H | $CF_2$ | O | $CF_2$ | Cl | $SO_2CF_3$ | $C_2F_5$ |
| Cl | H | $CF_2$ | O | $CF_2$ | F | $SO_2CF_3$ | $C_2F_5$ |
| Cl | H | $CF_2$ | O | $CF_2$ | $COCH_3$ | $SO_2CF_3$ | $C_2F_5$ |
| Cl | H | $CF_2$ | O | $CF_2$ | H | $SCF_2CH_3$ | $C_2F_5$ |
| Cl | H | $CF_2$ | O | $CF_2$ | $NH_2$ | $SCF_2CH_3$ | $C_2F_5$ |
| Cl | H | $CF_2$ | O | $CF_2$ | N=CHPh | $SCF_2CH_3$ | $C_2F_5$ |
| Cl | H | $CF_2$ | O | $CF_2$ | $CH_3$ | $SCF_2CH_3$ | $C_2F_5$ |
| Cl | H | $CF_2$ | O | $CF_2$ | $CF_3$ | $SCF_2CH_3$ | $C_2F_5$ |
| Cl | H | $CF_2$ | O | $CF_2$ | Cl | $SCF_2CH_3$ | $C_2F_5$ |
| Cl | H | $CF_2$ | O | $CF_2$ | F | $SCF_2CH_3$ | $C_2F_5$ |
| Cl | H | $CF_2$ | O | $CF_2$ | $COCH_3$ | $SCF_2CH_3$ | $C_2F_5$ |
| Cl | H | $CF_2$ | O | $CF_2$ | H | $SOCF_2CH_3$ | $C_2F_5$ |
| Cl | H | $CF_2$ | O | $CF_2$ | $NH_2$ | $SOCF_2CH_3$ | $C_2F_5$ |
| Cl | H | $CF_2$ | O | $CF_2$ | N=CHPh | $SOCF_2CH_3$ | $C_2F_5$ |
| Cl | H | $CF_2$ | O | $CF_2$ | $CH_3$ | $SOCF_2CH_3$ | $C_2F_5$ |
| Cl | H | $CF_2$ | O | $CF_2$ | $CF_3$ | $SOCF_2CH_3$ | $C_2F_5$ |
| Cl | H | $CF_2$ | O | $CF_2$ | Cl | $SOCF_2CH_3$ | $C_2F_5$ |
| Cl | H | $CF_2$ | O | $CF_2$ | F | $SOCF_2CH_3$ | $C_2F_5$ |
| Cl | H | $CF_2$ | O | $CF_2$ | $COCH_3$ | $SOCF_2CH_3$ | $C_2F_5$ |
| Cl | H | $CF_2$ | O | $CF_2$ | H | $SO_2CF_2CH_3$ | $C_2F_5$ |
| Cl | H | $CF_2$ | O | $CF_2$ | $NH_2$ | $SO_2CF_2CH_3$ | $C_2F_5$ |
| Cl | H | $CF_2$ | O | $CF_2$ | N=CHPh | $SO_2CF_2CH_3$ | $C_2F_5$ |
| Cl | H | $CF_2$ | O | $CF_2$ | $CH_3$ | $SO_2CF_2CH_3$ | $C_2F_5$ |
| Cl | H | $CF_2$ | O | $CF_2$ | $CF_3$ | $SO_2CF_2CH_3$ | $C_2F_5$ |
| Cl | H | $CF_2$ | O | $CF_2$ | Cl | $SO_2CF_2CH_3$ | $C_2F_5$ |
| Cl | H | $CF_2$ | O | $CF_2$ | F | $SO_2CF_2CH_3$ | $C_2F_5$ |

TABLE 10

| X | Y | Z¹ | Z² | Z³ | R¹ | R² | R³ |
|---|---|---|---|---|---|---|---|
| Cl | H | $CF_2$ | O | $CF_2$ | $COCH_3$ | $SO_2CF_2CH_3$ | $C_2F_5$ |
| Cl | H | $CF_2$ | O | $CF_2$ | $NH_2$ | $COCF_3$ | $C_2F_5$ |
| Cl | H | $CF_2$ | O | $CF_2$ | N=CHPh | $COCF_3$ | $C_2F_5$ |
| Cl | H | $CF_2$ | O | $CF_2$ | $CH_3$ | $COCF_3$ | $C_2F_5$ |
| Cl | H | $CF_2$ | O | $CF_2$ | $CF_3$ | $COCF_3$ | $C_2F_5$ |
| Cl | H | $CF_2$ | O | $CF_2$ | Cl | $COCF_3$ | $C_2F_5$ |
| Cl | H | $CF_2$ | O | $CF_2$ | F | $COCF_3$ | $C_2F_5$ |
| Cl | H | $CF_2$ | O | $CF_2$ | $COCH_3$ | $COCF_3$ | $C_2F_5$ |
| Cl | H | $CF_2$ | O | $CF_2$ | H | $COCF_3$ | $C_2F_5$ |
| Cl | H | $CF_2$ | O | $CF_2$ | $NH_2$ | $COCF_3$ | $C_2F_5$ |
| Cl | H | $CF_2$ | O | $CF_2$ | N=CHPh | $COCF_3$ | $C_2F_5$ |
| Cl | H | $CF_2$ | O | $CF_2$ | $CH_3$ | $COCF_3$ | $C_2F_5$ |
| Cl | H | $CF_2$ | O | $CF_2$ | $CF_3$ | $COCF_3$ | $C_2F_5$ |
| Cl | H | $CF_2$ | O | $CF_2$ | Cl | $COCF_3$ | $C_2F_5$ |
| Cl | H | $CF_2$ | O | $CF_2$ | F | $COCF_3$ | $C_2F_5$ |
| Cl | H | $CF_2$ | O | $CF_2$ | $COCH3$ | $COCF_3$ | $C_2F_5$ |
| Cl | H | $CF_2$ | O | $CF_2$ | $NH_2$ | $C_2F_5$ | $C_2F_5$ |
| Cl | H | $CF_2$ | O | $CF_2$ | N=CHPh | $C_2F_5$ | $C_2F_5$ |
| Cl | H | $CF_2$ | O | $CF_2$ | $CH_3$ | $C_2F_5$ | $C_2F_5$ |
| Cl | H | $CF_2$ | O | $CF_2$ | $CF_3$ | $C_2F_5$ | $C_2F_5$ |
| Cl | H | $CF_2$ | O | $CF_2$ | Cl | $C_2F_5$ | $C_2F_5$ |
| Cl | H | $CF_2$ | O | $CF_2$ | F | $C_2F_5$ | $C_2F_5$ |
| Cl | H | $CF_2$ | O | $CF_2$ | $COCH3$ | $C_2F_5$ | $C_2F_5$ |
| Cl | H | $CF_2$ | O | $CF_2$ | H | $C_2F_5$ | $C_2F_5$ |
| Cl | H | $CF_2$ | O | $CF_2$ | $NH_2$ | $C_2F_5$ | $C_2F_5$ |
| Cl | H | $CF_2$ | O | $CF_2$ | N=CHPh | $C_2F_5$ | $C_2F_5$ |

TABLE 11

| X | Y | Z¹ | Z² | Z³ | R¹ | R² | R³ |
|---|---|---|---|---|---|---|---|
| Cl | H | $CF_2$ | O | $CF_2$ | $CH_3$ | $C_2F_5$ | $C_2F_5$ |
| Cl | H | $CF_2$ | O | $CF_2$ | $CF_3$ | $C_2F_5$ | $C_2F_5$ |
| Cl | H | $CF_2$ | O | $CF_2$ | Cl | $C_2F_5$ | $C_2F_5$ |
| Cl | H | $CF_2$ | O | $CF_2$ | F | $C_2F_5$ | $C_2F_5$ |
| Cl | H | $CF_2$ | O | $CF_2$ | $COCH_3$ | $C_2F_5$ | $C_2F_5$ |
| Cl | H | $CF_2$ | O | $CF_2$ | $NH_2$ | $SFCl_2$ | $C_2F_5$ |
| Cl | H | $CF_2$ | O | $CF_2$ | N=CHPh | $SFCl_2$ | $C_2F_5$ |
| Cl | H | $CF_2$ | O | $CF_2$ | $CH_3$ | $SFCl_2$ | $C_2F_5$ |
| Cl | H | $CF_2$ | O | $CF_2$ | $CF_3$ | $SFCl_2$ | $C_2F_5$ |
| Cl | H | $CF_2$ | O | $CF_2$ | Cl | $SFCl_2$ | $C_2F_5$ |

TABLE 11-continued

| X | Y | Z¹ | Z² | Z³ | R¹ | R² | R³ |
|---|---|---|---|---|---|---|---|
| Cl | H | $CF_2$ | O | $CF_2$ | F | $SFCl_2$ | $C_2F_5$ |
| Cl | H | $CF_2$ | O | $CF_2$ | $COCH_3$ | $SFCl_2$ | $C_2F_5$ |
| Cl | H | $CF_2$ | O | $CF_2$ | H | $SFCl_2$ | $C_2F_5$ |
| Cl | H | $CF_2$ | O | $CF_2$ | $NH_2$ | $SFCl_2$ | $C_2F_5$ |
| Cl | H | $CF_2$ | O | $CF_2$ | N=CHPh | $SFCl_2$ | $C_2F_5$ |
| Cl | H | $CF_2$ | O | $CF_2$ | $CH_3$ | $SFCl_2$ | $C_2F_5$ |
| Cl | H | $CF_2$ | O | $CF_2$ | $CF_3$ | $SFCl_2$ | $C_2F_5$ |
| Cl | H | $CF_2$ | O | $CF_2$ | Cl | $SFCl_2$ | $C_2F_5$ |
| Cl | H | $CF_2$ | O | $CF_2$ | F | $SFCl_2$ | $C_2F_5$ |
| Cl | H | $CF_2$ | O | $CF_2$ | $COCH_3$ | $SFCl_2$ | $C_2F_5$ |
| Cl | H | $CF_2$ | O | $CF_2$ | H | $SCF_3$ | $C(=S)NH_2$ |
| Cl | H | $CF_2$ | O | $CF_2$ | $NH_2$ | $SCF_3$ | $CSNH_2$ |
| Cl | H | $CF_2$ | O | $CF_2$ | N=CHPh | $SCF_3$ | $CSNH_2$ |
| Cl | H | $CF_2$ | O | $CF_2$ | $CH_3$ | $SCF_3$ | $CSNH_2$ |
| Cl | H | $CF_2$ | O | $CF_2$ | $CF_3$ | $SCF_3$ | $CSNH_2$ |
| Cl | H | $cf_2$ | O | $CF_2$ | Cl | $SCF_3$ | $CSNH_2$ |

TABLE 12

| X | Y | Z¹ | Z² | Z³ | R¹ | R² | R³ |
|---|---|---|---|---|---|---|---|
| Cl | H | $CF_2$ | O | $CF_2$ | F | $SCF_3$ | $CSNH_2$ |
| Cl | H | $CF_2$ | O | $CF_2$ | $COCH_3$ | $SCF_3$ | $CSNH_2$ |
| Cl | H | $CF_2$ | O | $CF_2$ | H | $SOCF_3$ | $CSNH_2$ |
| Cl | H | $CF_2$ | O | $CF_2$ | $NH_2$ | $SOCF_3$ | $CSNH_2$ |
| Cl | H | $CF_2$ | O | $CF_2$ | N=CHPh | $SOCF_3$ | $CSNH_2$ |
| Cl | H | $CF_2$ | O | $CF_2$ | $CH_3$ | $SOCF_3$ | $CSNH_2$ |
| Cl | H | $CF_2$ | O | $CF_2$ | $CF_3$ | $SOCF_3$ | $CSNH_2$ |
| Cl | H | $CF_2$ | O | $CF_2$ | Cl | $SOCF_3$ | $CSNH_2$ |
| Cl | H | $CF_2$ | O | $CF_2$ | F | $SOCF_3$ | $CSNH_2$ |
| Cl | H | $CF_2$ | O | $CF_2$ | $COCH_3$ | $SOCF_3$ | $CSNH_2$ |
| Cl | H | $CF_2$ | O | $CF_2$ | H | $SO_2CF_3$ | $CSNH_2$ |
| Cl | H | $CF_2$ | O | $CF_2$ | $NH_2$ | $SO_2CF_3$ | $CSNH_2$ |
| Cl | H | $CF_2$ | O | $CF_2$ | N=CHPh | $SO_2CF_3$ | $CSNH_2$ |
| Cl | H | $CF_2$ | O | $CF_2$ | $CH_3$ | $SO_2CF_3$ | $CSNH_2$ |
| Cl | H | $CF_2$ | O | $CF_2$ | $CF_3$ | $SO_2CF_3$ | $CSNH_2$ |
| Cl | H | $CF_2$ | O | $CF_2$ | Cl | $SO_2CF_3$ | $CSNH_2$ |
| Cl | H | $CF_2$ | O | $CF_2$ | F | $SO_2CF_3$ | $CSNH_2$ |
| Cl | H | $CF_2$ | O | $CF_2$ | $COCH_3$ | $SO_2CF_3$ | $CSNH_2$ |
| Cl | H | $CF_2$ | O | $CF_2$ | H | $SCF_2CH_3$ | $CSNH_2$ |
| Cl | H | $CF_2$ | O | $CF_2$ | $NH_2$ | $SCF_2CH_3$ | $CSNH_2$ |
| Cl | H | $CF_2$ | O | $CF_2$ | N=CHPh | $SCF_2CH_3$ | $CSNH_2$ |
| Cl | H | $CF_2$ | O | $CF_2$ | $CH_3$ | $SCF_2CH_3$ | $CSNH_2$ |
| Cl | H | $CF_2$ | O | $CF_2$ | $CF_3$ | $SCF_2CH_3$ | $CSNH_2$ |
| Cl | H | $CF_2$ | O | $CF_2$ | Cl | $SCF_2CH_3$ | $CSNH_2$ |
| Cl | H | $CF_2$ | O | $CF_2$ | F | $SCF_2CH_3$ | $CSNH_2$ |
| Cl | H | $CF_2$ | O | $CF_2$ | $COCH_3$ | $SCF_2CH_3$ | $CSNH_2$ |

TABLE 13

| X | Y | Z¹ | Z² | Z³ | R¹ | R² | R³ |
|---|---|---|---|---|---|---|---|
| Cl | H | $CF_2$ | O | $CF_2$ | H | $SOCF_2CH_3$ | $CSNH_2$ |
| Cl | H | $CF_2$ | O | $CF_2$ | $NH_2$ | $SOCF_2CH_3$ | $CSNH_2$ |
| Cl | H | $CF_2$ | O | $CF_2$ | N=CHPh | $SOCF_2CH_3$ | $CSNH_2$ |
| Cl | H | $CF_2$ | O | $CF_2$ | $CH_3$ | $SOCF_2CH_3$ | $CSNH_2$ |
| Cl | H | $CF_2$ | O | $CF_2$ | $CF_3$ | $SOCF_2CH_3$ | $CSNH_2$ |
| Cl | H | $CF_2$ | O | $CF_2$ | Cl | $SOCF_2CH_3$ | $CSNH_2$ |
| Cl | H | $CF_2$ | O | $CF_2$ | F | $SOCF_2CH_3$ | $CSNH_2$ |
| Cl | H | $CF_2$ | O | $CF_2$ | $COCH_3$ | $SOCF_2CH_3$ | $CSNH_2$ |
| Cl | H | $CF_2$ | O | $CF_2$ | H | $SO_2CF_2CH_3$ | $CSNH_2$ |
| Cl | H | $CF_2$ | O | $CF_2$ | $NH_2$ | $SO_2CF_2CH_3$ | $CSNH_2$ |
| Cl | H | $CF_2$ | O | $CF_2$ | N=CHPh | $SO_2CF_2CH_3$ | $CSNH_2$ |
| Cl | H | $CF_2$ | O | $CF_2$ | $CH_3$ | $SO_2CF_2CH_3$ | $CSNH_2$ |
| Cl | H | $cf_2$ | O | $CF_2$ | $CF_3$ | $SO_2CF_2CH_3$ | $CSNH_2$ |
| Cl | H | $CF_2$ | O | $CF_2$ | Cl | $SO_2CF_2CH_3$ | $CSNH_2$ |
| Cl | H | $CF_2$ | O | $CF_2$ | F | $SO_2CF_2CH_3$ | $CSNH_2$ |
| Cl | H | $CF_2$ | O | $CF_2$ | $COCH_3$ | $SO_2CF_2CH_3$ | $CSNH_2$ |
| Cl | H | $CF_2$ | O | $CF_2$ | $NH_2$ | $COCF_3$ | $CSNH_2$ |
| Cl | H | $CF_2$ | O | $CF_2$ | N=CHPh | $COCF_3$ | $CSNH_2$ |
| Cl | H | $CF_2$ | O | $CF_2$ | $CH_3$ | $COCF_3$ | $CSNH_2$ |

TABLE 13-continued

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $CF_3$ | $COCF_3$ | $CSNH_2$ |
| Cl | H | $CF_2$ | O | $CF_2$ | Cl | $COCF_3$ | $CSNH_2$ |
| Cl | H | $CF_2$ | O | $CF_2$ | F | $COCF_3$ | $CSNH_2$ |
| Cl | H | $CF_2$ | O | $CF_2$ | $COCH_3$ | $COCF_3$ | $CSNH_2$ |
| Cl | H | $CF_2$ | O | $CF_2$ | H | $COCF_3$ | $CSNH_2$ |
| Cl | H | $CF_2$ | O | $CF_2$ | $NH_2$ | $COCF_3$ | $CSNH_2$ |
| Cl | H | $CF_2$ | O | $CF_2$ | N=CHPh | $COCF_3$ | $CSNH_2$ |

TABLE 14

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $CH_3$ | $COCF_3$ | $CSNH_2$ |
| Cl | H | $CF_2$ | O | $CF_2$ | $CF_3$ | $COCF_3$ | $CSNH_2$ |
| Cl | H | $CF_2$ | O | $CF_2$ | Cl | $COCF_3$ | $CSNH_2$ |
| Cl | H | $CF_2$ | O | $CF_2$ | F | $COCF_3$ | $CSNH_2$ |
| Cl | H | $CF_2$ | O | $CF_2$ | $COCH_3$ | $COCF_3$ | $CSNH_2$ |
| Cl | H | $CF_2$ | O | $CF_2$ | $NH_2$ | $C_2F_5$ | $CSNH_2$ |
| Cl | H | $CF_2$ | O | $CF_2$ | N=CHPh | $C_2F_5$ | $CSNH_2$ |
| Cl | H | $CF_2$ | O | $CF_2$ | $CH_3$ | $C_2F_5$ | $CSNH_2$ |
| Cl | H | $CF_2$ | O | $CF_2$ | $CF_3$ | $C_2F_5$ | $CSNH_2$ |
| Cl | H | $CF_2$ | O | $CF_2$ | Cl | $C_2F_5$ | $CSNH_2$ |
| Cl | H | $CF_2$ | O | $CF_2$ | F | $C_2F_5$ | $CSNH_2$ |
| Cl | H | $CF_2$ | O | $CF_2$ | $COCH_3$ | $C_2F_5$ | $CSNH_2$ |
| Cl | H | $CF_2$ | O | $CF_2$ | H | $C_2F_5$ | $CSNH_2$ |
| Cl | H | $CF_2$ | O | $CF_2$ | $NH_2$ | $C_2F_5$ | $CSNH_2$ |
| Cl | H | $CF_2$ | O | $CF_2$ | N=CHPh | $C_2F_5$ | $CSNH_2$ |
| Cl | H | $CF_2$ | O | $CF_2$ | $CH_3$ | $C_2F_5$ | $CSNH_2$ |
| Cl | H | $CF_2$ | O | $CF_2$ | $CF_3$ | $C_2F_5$ | $CSNH_2$ |
| Cl | H | $CF_2$ | O | $CF_2$ | Cl | $C_2F_5$ | $CSNH_2$ |
| Cl | H | $CF_2$ | O | $CF_2$ | F | $C_2F_5$ | $CSNH_2$ |
| Cl | H | $CF_2$ | O | $CF_2$ | $COCH_3$ | $C_2F_5$ | $CSNH_2$ |
| Cl | H | $CF_2$ | O | $CF_2$ | $NH_2$ | $SFCl_2$ | $CSNH_2$ |
| Cl | H | $CF_2$ | O | $CF_2$ | N=CHPh | $SFCl_2$ | $CSNH_2$ |
| Cl | H | $CF_2$ | O | $CF_2$ | $CH_3$ | $SFCl_2$ | $CSNH_2$ |
| Cl | H | $CF_2$ | O | $CF_2$ | $CF_3$ | $SFCl_2$ | $CSNH_2$ |
| Cl | H | $CF_2$ | O | $CF_2$ | Cl | $SFCl_2$ | $CSNH_2$ |
| Cl | H | $CF_2$ | O | $CF_2$ | F | $SFCl_2$ | $CSNH_2$ |

TABLE 15

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $COCH_3$ | $SFCl_2$ | $CSNH_2$ |
| Cl | H | $CF_2$ | O | $CF_2$ | H | $SFCl_2$ | $CSNH_2$ |
| Cl | H | $CF_2$ | O | $CF_2$ | $NH_2$ | $SFCl_2$ | $CSNH_2$ |
| Cl | H | $CF_2$ | O | $CF_2$ | N=CHPh | $SFCl_2$ | $CSNH_2$ |
| Cl | H | $CF_2$ | O | $CF_2$ | $CH_3$ | $SFCl_2$ | $CSNH_2$ |
| Cl | H | $CF_2$ | O | $CF_2$ | $CF_3$ | $SFCl_2$ | $CSNH_2$ |
| Cl | H | $CF_2$ | O | $CF_2$ | Cl | $SFCl_2$ | $CSNH_2$ |
| Cl | H | $CF_2$ | O | $CF_2$ | F | $SFCl_2$ | $CSNH_2$ |
| Cl | H | $CF_2$ | O | $CF_2$ | $COCH_3$ | $SFCl_2$ | $CSNH_2$ |
| Cl | H | $CF_2$ | O | $CF_2$ | H | $SCF_3$ | CN |
| Cl | H | $CF_2$ | O | $CF_2$ | $NH_2$ | $SCF_3$ | CN |
| Cl | H | $CF_2$ | O | $CF_2$ | N=CHPh | $SCF_3$ | CN |
| Cl | H | $CF_2$ | O | $CF_2$ | $CH_3$ | $SCF_3$ | CN |
| Cl | H | $CF_2$ | O | $CF_2$ | $CF_3$ | $SCF_3$ | CN |
| Cl | H | $CF_2$ | O | $CF_2$ | Cl | $SCF_3$ | CN |
| Cl | H | $CF_2$ | O | $CF_2$ | F | $SCF_3$ | CN |
| Cl | H | $CF_2$ | O | $CF_2$ | $COCH_3$ | $SCF_3$ | CN |
| Cl | H | $CF_2$ | O | $CF_2$ | H | $SOCF_3$ | CN |
| Cl | H | $CF_2$ | O | $CF_2$ | $NH_2$ | $SOCF_3$ | CN |
| Cl | H | $CF_2$ | O | $CF_2$ | N=CHPh | $SOCF_3$ | CN |
| Cl | H | $CF_2$ | O | $CF_2$ | $CH_3$ | $SOCF_3$ | CN |
| Cl | H | $CF_2$ | O | $CF_2$ | $CF_3$ | $SOCF_3$ | CN |
| Cl | H | $CF_2$ | O | $CF_2$ | Cl | $SOCF_3$ | CN |
| Cl | H | $CF_2$ | O | $CF_2$ | F | $SOCF_3$ | CN |
| Cl | H | $CF_2$ | O | $CF_2$ | $COCH_3$ | $SOCF_3$ | CN |
| Cl | H | $CF_2$ | O | $CF_2$ | H | $SO_2CF_3$ | CN |

TABLE 16

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $NH_2$ | $SO_2CF_3$ | CN |
| Cl | H | $CF_2$ | O | $CF_2$ | N=CHPh | $SO_2CF_3$ | CN |
| Cl | H | $CF_2$ | O | $CF_2$ | $CH_3$ | $SO_2CF_3$ | CN |
| Cl | H | $CF_2$ | O | $CF_2$ | $CF_3$ | $SO_2CF_3$ | CN |
| Cl | H | $CF_2$ | O | $CF_2$ | Cl | $SO_2CF_3$ | CN |
| Cl | H | $CF_2$ | O | $CF_2$ | F | $SO_2CF_3$ | CN |
| Cl | H | $CF_2$ | O | $CF_2$ | $COCH_3$ | $SO_2CF_3$ | CN |
| Cl | H | $CF_2$ | O | $CF_2$ | H | $SCF_2CH_3$ | CN |
| Cl | H | $CF_2$ | O | $CF_2$ | $NH_2$ | $SCF_2CH_3$ | CN |
| Cl | H | $CF_2$ | O | $CF_2$ | N=CHPh | $SCF_2CH_3$ | CN |
| Cl | H | $CF_2$ | O | $CF_2$ | $CH_3$ | $SCF_2CH_3$ | CN |
| Cl | H | $CF_2$ | O | $CF_2$ | $CF_3$ | $SCF_2CH_3$ | CN |
| Cl | H | $CF_2$ | O | $CF_2$ | Cl | $SCF_2CH_3$ | CN |
| Cl | H | $CF_2$ | O | $CF_2$ | F | $SCF_2CH_3$ | CN |
| Cl | H | $CF_2$ | O | $CF_2$ | $COCH_3$ | $SCF_2CH_3$ | CN |
| Cl | H | $CF_2$ | O | $CF_2$ | H | $SOCF_2CH_3$ | CN |
| Cl | H | $CF_2$ | O | $CF_2$ | $NH_2$ | $SOCF_2CH_3$ | CN |
| Cl | H | $CF_2$ | O | $CF_2$ | N=CHPh | $SOCF_2CH_3$ | CN |
| Cl | H | $CF_2$ | O | $CF_2$ | $CH_3$ | $SOCF_2CH_3$ | CN |
| Cl | H | $CF_2$ | O | $CF_2$ | $CF_3$ | $SOCF_2CH_3$ | CN |
| Cl | H | $CF_2$ | O | $CF_2$ | Cl | $SOCF_2CH_3$ | CN |
| Cl | H | $CF_2$ | O | $CF_2$ | F | $SOCF_2CH_3$ | CN |
| Cl | H | $CF_2$ | O | $CF_2$ | $COCH_3$ | $SOCF_2CH_3$ | CN |
| Cl | H | $CF_2$ | O | $CF_2$ | H | $SO_2CF_2CH_3$ | CN |
| Cl | H | $CF_2$ | O | $CF_2$ | $NH_2$ | $SO_2CF_2CH_3$ | CN |
| Cl | H | $CF_2$ | O | $CF_2$ | N=CHPh | $SO_2CF_2CH_3$ | CN |

TABLE 17

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $CH_3$ | $SO_2CF_2CH_3$ | CN |
| Cl | H | $CF_2$ | O | $CF_2$ | CF3 | $SO_2CF_2CH_3$ | CN |
| Cl | H | $CF_2$ | O | $CF_2$ | Cl | $SO_2CF_2CH_3$ | CN |
| Cl | H | $CF_2$ | O | $CF_2$ | F | $SO_2CF_2CH_3$ | CN |
| Cl | H | $CF_2$ | O | $CF_2$ | $COCH_3$ | $SO_2CF_2CH_3$ | CN |
| Cl | H | $CF_2$ | O | $CF_2$ | $NH_2$ | $COCF_3$ | CN |
| Cl | H | $CF_2$ | O | $CF_2$ | N=CHPh | $COCF_3$ | CN |
| Cl | H | $CF_2$ | O | $CF_2$ | $CH_3$ | $COCF_3$ | CN |
| Cl | H | $CF_2$ | O | $CF_2$ | $CF_3$ | $COCF_3$ | CN |
| Cl | H | $CF_2$ | O | $CF_2$ | Cl | $COCF_3$ | CN |
| Cl | H | $CF_2$ | O | $CF_2$ | F | $COCF_3$ | CN |
| Cl | H | $CF_2$ | O | $CF_2$ | $COCH_3$ | $COCF_3$ | CN |
| Cl | H | $CF_2$ | O | $CF_2$ | H | $COCF_3$ | CN |
| Cl | H | $CF_2$ | O | $CF_2$ | $NH_2$ | $COCF_3$ | CN |
| Cl | H | $CF_2$ | O | $CF_2$ | N=CHPh | $COCF_3$ | CN |
| Cl | H | $CF_2$ | O | $CF_2$ | $CH_3$ | $COCF_3$ | CN |
| Cl | H | $CF_2$ | O | $CF_2$ | $CF_3$ | $COCF_3$ | CN |
| Cl | H | $CF_2$ | O | $CF_2$ | Cl | $COCF_3$ | CN |
| Cl | H | $CF_2$ | O | $CF_2$ | F | $COCF_3$ | CN |
| Cl | H | $CF_2$ | O | $CF_2$ | $COCH_3$ | $COCF_3$ | CN |
| Cl | H | $CF_2$ | O | $CF_2$ | $NH_2$ | $C_2F_5$ | CN |
| Cl | H | $CF_2$ | O | $CF_2$ | N=CHPh | $C_2F_5$ | CN |
| Cl | H | $CF_2$ | O | $CF_2$ | $CH_3$ | $C_2F_5$ | CN |
| Cl | H | $CF_2$ | O | $CF_2$ | $CF_3$ | $C_2F_5$ | CN |
| Cl | H | $CF_2$ | O | $CF_2$ | Cl | $C_2F_5$ | CN |
| Cl | H | $CF_2$ | O | $CF_2$ | F | $C_2F_5$ | CN |

TABLE 18

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | $COCH_3$ | $C_2F_5$ | CN |
| Cl | H | $CF_2$ | O | $CF_2$ | H | $C_2F_5$ | CN |
| Cl | H | $CF_2$ | O | $CF_2$ | $NH_2$ | $C_2F_5$ | CN |
| Cl | H | $CF_2$ | O | $CF_2$ | N=CHPh | $C_2F_5$ | CN |
| Cl | H | $CF_2$ | O | $CF_2$ | $CH_3$ | $C_2F_5$ | CN |
| Cl | H | $CF_2$ | O | $CF_2$ | $CF_3$ | $C_2F_5$ | CN |
| Cl | H | $CF_2$ | O | $CF_2$ | Cl | $C_2F_5$ | CN |
| Cl | H | $CF_2$ | O | $CF_2$ | F | $C_2F_5$ | CN |
| Cl | H | $CF_2$ | O | $CF_2$ | $COCH_3$ | $C_2F_5$ | CN |
| Cl | H | $CF_2$ | O | $CF_2$ | $NH_2$ | $SFCl_2$ | CN |

TABLE 18-continued

| X | Y | $Z^1$ | $Z^2$ | $Z^3$ | $R^1$ | $R^2$ | $R^3$ |
|---|---|---|---|---|---|---|---|
| Cl | H | $CF_2$ | O | $CF_2$ | N=CHPh | $SFCl_2$ | CN |
| Cl | H | $CF_2$ | O | $CF_2$ | $CH_3$ | $SFCl_2$ | CN |
| Cl | H | $CF_2$ | O | $CF_2$ | $CF_3$ | $SFCl_2$ | CN |
| Cl | H | $CF_2$ | O | $CF_2$ | Cl | $SFCl_2$ | CN |
| Cl | H | $CF_2$ | O | $CF_2$ | F | $SFCl_2$ | CN |
| Cl | H | $CF_2$ | O | $CF_2$ | $COCH_3$ | $SFCl_2$ | CN |
| Cl | H | $CF_2$ | O | $CF_2$ | H | $SFCl_2$ | CN |
| Cl | H | $CF_2$ | O | $CF_2$ | $NH_2$ | $SFCl_2$ | CN |
| Cl | H | $CF_2$ | O | $CF_2$ | N=CHPh | $SFCl_2$ | CN |
| Cl | H | $CF_2$ | O | $CF_2$ | $CH_3$ | $SFCl_2$ | CN |
| Cl | H | $CF_2$ | O | $CF_2$ | $CF_3$ | $SFCl_2$ | CN |
| Cl | H | $CF_2$ | O | $CF_2$ | Cl | $SFCl_2$ | CN |
| Cl | H | $CF_2$ | O | $CF_2$ | F | $SFCl_2$ | CN |
| Cl | H | $CF_2$ | O | $CF_2$ | $COCH_3$ | $SFCl_2$ | CN |
| F | H | $CF_2$ | O | $CF_2$ | H | $SCF_3$ | H |
| F | H | $CF_2$ | O | $CF_2$ | $NH_2$ | $SCF_3$ | H |

TABLE 19

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | N=CHPh | $SCF_3$ | H |
| F | H | $CF_2$ | O | $CF_2$ | $CH_3$ | $SCF_3$ | H |
| F | H | $CF_2$ | O | $CF_2$ | $CF_3$ | $SCF_3$ | H |
| F | H | $CF_2$ | O | $CF_2$ | Cl | $SCF_3$ | H |
| F | H | $CF_2$ | O | $CF_2$ | F | $SCF_3$ | H |
| F | H | $CF_2$ | O | $CF_2$ | $COCH_3$ | $SCF_3$ | H |
| F | H | $CF_2$ | O | $CF_2$ | H | $SOCF_3$ | H |
| F | H | $CF_2$ | O | $CF_2$ | $NH_2$ | $SOCF_3$ | H |
| F | H | $CF_2$ | O | $CF_2$ | N=CHPh | $SOCF_3$ | H |
| F | H | $CF_2$ | O | $CF_2$ | $CH_3$ | $SOCF_3$ | H |
| F | H | $CF_2$ | O | $CF_2$ | $CF_3$ | $SOCF_3$ | H |
| F | H | $CF_2$ | O | $CF_2$ | Cl | $SOCF_3$ | H |
| F | H | $CF_2$ | O | $CF_2$ | F | $SOCF_3$ | H |
| F | H | $CF_2$ | O | $CF_2$ | $COCH_3$ | $SOCF_3$ | H |
| F | H | $CF_2$ | O | $CF_2$ | H | $SO_2CF_3$ | H |
| F | H | $CF_2$ | O | $CF_2$ | $NH_2$ | $SO_2CF_3$ | H |
| F | H | $CF_2$ | O | $CF_2$ | N=CHPh | $SO_2CF_3$ | H |
| F | H | $CF_2$ | O | $CF_2$ | $CH_3$ | $SO_2CF_3$ | H |
| F | H | $CF_2$ | O | $CF_2$ | $CF_3$ | $SO_2CF_3$ | H |
| F | H | $CF_2$ | O | $CF_2$ | Cl | $SO_2CF_3$ | H |
| F | H | $CF_2$ | O | $CF_2$ | F | $SO_2CF_3$ | H |
| F | H | $CF_2$ | O | $CF_2$ | $COCH_3$ | $SO_2CF_3$ | H |
| F | H | $CF_2$ | O | $CF_2$ | H | $SCF_2CH_3$ | H |
| F | H | $CF_2$ | O | $CF_2$ | $NH_2$ | $SCF_2CH_3$ | H |
| F | H | $CF_2$ | O | $CF_2$ | N=CHPh | $SCF_2CH_3$ | H |
| F | H | $CF_2$ | O | $CF_2$ | $CH_3$ | $SCF_2CH_3$ | H |

TABLE 20

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | $CF_3$ | $SCF_2CH_3$ | H |
| F | H | $CF_2$ | O | $CF_2$ | Cl | $SCF_2CH_3$ | H |
| F | H | $CF_2$ | O | $CF_2$ | F | $SCF_2CH_3$ | H |
| F | H | $CF_2$ | O | $CF_2$ | $COCH_3$ | $SCF_2CH_3$ | H |
| F | H | $CF_2$ | O | $CF_2$ | H | $SOCF_2CH_3$ | H |
| F | H | $CF_2$ | O | $CF_2$ | $NH_2$ | $SOCF_2CH_3$ | H |
| F | H | $CF_2$ | O | $CF_2$ | N=CHPh | $SOCF_2CH_3$ | H |
| F | H | $CF_2$ | O | $CF_2$ | $CH_3$ | $SOCF_2CH_3$ | H |
| F | H | $CF_2$ | O | $CF_2$ | $CF_3$ | $SOCF_2CH_3$ | H |
| F | H | $CF_2$ | O | $CF_2$ | Cl | $SOCF_2CH_3$ | H |
| F | H | $CF_2$ | O | $CF_2$ | F | $SOCF_2CH_3$ | H |
| F | H | $CF_2$ | O | $CF_2$ | $COCH_3$ | $SOCF_2CH_3$ | H |
| F | H | $CF_2$ | O | $CF_2$ | H | $SO_2CF_2CH_3$ | H |
| F | H | $CF_2$ | O | $CF_2$ | $NH_2$ | $SO_2CF_2CH_3$ | H |
| F | H | $CF_2$ | O | $CF_2$ | N=CHPh | $SO_2CF_2CH_3$ | H |
| F | H | $CF_2$ | O | $CF_2$ | $CH_3$ | $SO_2CF_2CH_3$ | H |
| F | H | $CF_2$ | O | $CF_2$ | $CF_3$ | $SO_2CF_2CH_3$ | H |
| F | H | $CF_2$ | O | $CF_2$ | Cl | $SO_2CF_2CH_3$ | H |
| F | H | $CF_2$ | O | $CF_2$ | F | $SO_2CF_2CH_3$ | H |
| F | H | $CF_2$ | O | $CF_2$ | $COCH_3$ | $SO_2CF_2CH_3$ | H |

TABLE 20-continued

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | $NH_2$ | $COCF_3$ | H |
| F | H | $CF_2$ | O | $CF_2$ | N=CHPh | $COCF_3$ | H |
| F | H | $CF_2$ | O | $CF_2$ | $CH_3$ | $COCF_3$ | H |
| F | H | $CF_2$ | O | $CF_2$ | $CF_3$ | $COCF_3$ | H |
| F | H | $CF_2$ | O | $CF_2$ | Cl | $COCF_3$ | H |
| F | H | $CF_2$ | O | $CF_2$ | F | $COCF_3$ | H |

TABLE 21

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | $COCH_3$ | $COCF_3$ | H |
| F | H | $CF_2$ | O | $CF_2$ | H | $COCF_3$ | H |
| F | H | $CF_2$ | O | $CF_2$ | $NH_2$ | $COCF_3$ | H |
| F | H | $CF_2$ | O | $CF_2$ | N=CHPh | $COCF_3$ | H |
| F | H | $CF_2$ | O | $CF_2$ | $CH_3$ | $COCF_3$ | H |
| F | H | $CF_2$ | O | $CF_2$ | $CF_3$ | $COCF_3$ | H |
| F | H | $CF_2$ | O | $CF_2$ | Cl | $COCF_3$ | H |
| F | H | $CF_2$ | O | $CF_2$ | F | $COCF_3$ | H |
| F | H | $CF_2$ | O | $CF_2$ | $COCH_3$ | $COCF_3$ | H |
| F | H | $CF_2$ | O | $CF_2$ | $NH_2$ | $C_2F_5$ | H |
| F | H | $CF_2$ | O | $CF_2$ | N=CHPh | $C_2F_5$ | H |
| F | H | $CF_2$ | O | $CF_2$ | $CH_3$ | $C_2F_5$ | H |
| F | H | $CF_2$ | O | $CF_2$ | $CF_3$ | $C_2F_5$ | H |
| F | H | $CF_2$ | O | $CF_2$ | Cl | $C_2F_5$ | H |
| F | H | $CF_2$ | O | $CF_2$ | F | $C_2F_5$ | H |
| F | H | $CF_2$ | O | $CF_2$ | $COCH_3$ | $C_2F_5$ | H |
| F | H | $CF_2$ | O | $CF_2$ | H | $C_2F_5$ | H |
| F | H | $CF_2$ | O | $CF_2$ | $NH_2$ | $C_2F_5$ | H |
| F | H | $CF_2$ | O | $CF_2$ | N=CHPh | $C_2F_5$ | H |
| F | H | $CF_2$ | O | $CF_2$ | $CH_3$ | $C_2F_5$ | H |
| F | H | $CF_2$ | O | $CF_2$ | $CF_3$ | $C_2F_5$ | H |
| F | H | $CF_2$ | O | $CF_2$ | Cl | $C_2F_5$ | H |
| F | H | $CF_2$ | O | $CF_2$ | F | $C_2F_5$ | H |
| F | H | $CF_2$ | O | $CF_2$ | $COCH_3$ | $C_2F_5$ | H |
| F | H | $CF_2$ | O | $CF_2$ | $NH_2$ | $SFCl_2$ | H |
| F | H | $CF_2$ | O | $CF_2$ | N=CHPh | $SFCl_2$ | H |

TABLE 22

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | $CH_3$ | $SFCl_2$ | H |
| F | H | $CF_2$ | O | $CF_2$ | $CF_3$ | $SFCl_2$ | H |
| F | H | $CF_2$ | O | $CF_2$ | Cl | $SFCl_2$ | H |
| F | H | $CF_2$ | O | $CF_2$ | F | $SFCl_2$ | H |
| F | H | $CF_2$ | O | $CF_2$ | $COCH_3$ | $SFCl_2$ | H |
| F | H | $CF_2$ | O | $CF_2$ | H | $SFCl_2$ | H |
| F | H | $CF_2$ | O | $CF_2$ | $NH_2$ | $SFCl_2$ | H |
| F | H | $CF_2$ | O | $CF_2$ | N=CHPh | $SFCl_2$ | H |
| F | H | $CF_2$ | O | $CF_2$ | $CH_3$ | $SFCl_2$ | H |
| F | H | $CF_2$ | O | $CF_2$ | $CF_3$ | $SFCl_2$ | H |
| F | H | $CF_2$ | O | $CF_2$ | Cl | $SFCl_2$ | H |
| F | H | $CF_2$ | O | $CF_2$ | F | $SFCl_2$ | H |
| F | H | $CF_2$ | O | $CF_2$ | $COCH_3$ | $SFCl_2$ | H |
| F | H | $CF_2$ | O | $CF_2$ | H | $SCF_3$ | $CF_3$ |
| F | H | $CF_2$ | O | $CF_2$ | $NH_2$ | $SCF_3$ | $CF_3$ |
| F | H | $CF_2$ | O | $CF_2$ | N=CHPh | $SCF_3$ | $CF_3$ |
| F | H | $CF_2$ | O | $CF_2$ | $CH_3$ | $SCF_3$ | $CF_3$ |
| F | H | $CF_2$ | O | $CF_2$ | $CF_3$ | $SCF_3$ | $CF_3$ |
| F | H | $CF_2$ | O | $CF_2$ | Cl | $SCF_3$ | $CF_3$ |
| F | H | $CF_2$ | O | $CF_2$ | F | $SCF_3$ | $CF_3$ |
| F | H | $CF_2$ | O | $CF_2$ | $COCH_3$ | $SCF_3$ | $CF_3$ |
| F | H | $CF_2$ | O | $CF_2$ | H | $SOCF_3$ | $CF_3$ |
| F | H | $CF_2$ | O | $CF_2$ | $NH_2$ | $SOCF_3$ | $CF_3$ |
| F | H | $CF_2$ | O | $CF_2$ | N=CHPh | $SOCF_3$ | $CF_3$ |
| F | H | $CF_2$ | O | $CF_2$ | $CH_3$ | $SOCF_3$ | $CF_3$ |
| F | H | $CF_2$ | O | $CF_2$ | $CF_3$ | $SOCF_3$ | $CF_3$ |

TABLE 23

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | Cl | $SOCF_3$ | $CF_3$ |
| F | H | $CF_2$ | O | $CF_2$ | F | $SOCF_3$ | $CF_3$ |
| F | H | $CF_2$ | O | $CF_2$ | $COCH_3$ | $SOCF_3$ | $CF_3$ |
| F | H | $CF_2$ | O | $CF_2$ | H | $SO_2CF_3$ | $CF_3$ |
| F | H | $CF_2$ | O | $CF_2$ | $NH_2$ | $SO_2CF_3$ | $CF_3$ |
| F | H | $CF_2$ | O | $CF_2$ | N=CHPh | $SO_2CF_3$ | $CF_3$ |
| F | H | $CF_2$ | O | $CF_2$ | $CH_3$ | $SO_2CF_3$ | $CF_3$ |
| F | H | $CF_2$ | O | $CF_2$ | $CF_3$ | $SO_2CF_3$ | $CF_3$ |
| F | H | $CF_2$ | O | $CF_2$ | Cl | $SO_2CF_3$ | $CF_3$ |
| F | H | $CF_2$ | O | $CF_2$ | F | $SO_2CF_3$ | $CF_3$ |
| F | H | $CF_2$ | O | $CF_2$ | $COCH_3$ | $SO_2CF_3$ | $CF_3$ |
| F | H | $CF_2$ | O | $CF_2$ | H | $SCF_2CH_3$ | $CF_3$ |
| F | H | $CF_2$ | O | $CF_2$ | $NH_2$ | $SCF_2CH_3$ | $CF_3$ |
| F | H | $CF_2$ | O | $CF_2$ | N=CHPh | $SCF_2CH_3$ | $CF_3$ |
| F | H | $CF_2$ | O | $CF_2$ | $CH_3$ | $SCF_2CH_3$ | $CF_3$ |
| F | H | $CF_2$ | O | $CF_2$ | $CF_3$ | $SCF_2CH_3$ | $CF_3$ |
| F | H | $CF_2$ | O | $CF_2$ | Cl | $SCF_2CH_3$ | $CF_3$ |
| F | H | $CF_2$ | O | $CF_2$ | F | $SCF_2CH_3$ | $CF_3$ |
| F | H | $CF_2$ | O | $CF_2$ | $COCH_3$ | $SCF_2CH_3$ | $CF_3$ |
| F | H | $CF_2$ | O | $CF_2$ | H | $SOCF_2CH_3$ | $CF_3$ |
| F | H | $CF_2$ | O | $CF_2$ | $NH_2$ | $SOCF_2CH_3$ | $CF_3$ |
| F | H | $CF_2$ | O | $CF_2$ | N=CHPh | $SOCF_2CH_3$ | $CF_3$ |
| F | H | $CF_2$ | O | $CF_2$ | $CH_3$ | $SOCF_2CH_3$ | $CF_3$ |
| F | H | $CF_2$ | O | $CF_2$ | $CF_3$ | $SOCF_2CH_3$ | $CF_3$ |
| F | H | $CF_2$ | O | $CF_2$ | Cl | $SOCF_2CH_3$ | $CF_3$ |
| F | H | $CF_2$ | O | $CF_2$ | F | $SOCF_2CH_3$ | $CF_3$ |

TABLE 24

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | $COCH_3$ | $SOCF_2CH_3$ | $CF_3$ |
| F | H | $CF_2$ | O | $CF_2$ | H | $SO_2CF_2CH_3$ | $CF_3$ |
| F | H | $CF_2$ | O | $CF_2$ | $NH_2$ | $SO_2CF_2CH_3$ | $CF_3$ |
| F | H | $CF_2$ | O | $CF_2$ | N=CHPh | $SO_2CF_2CH_3$ | $CF_3$ |
| F | H | $CF_2$ | O | $CF_2$ | $CH_3$ | $SO_2CF_2CH_3$ | $CF_3$ |
| F | H | $CF_2$ | O | $CF_2$ | $CF_3$ | $SO_2CF_2CH_3$ | $CF_3$ |
| F | H | $CF_2$ | O | $CF_2$ | Cl | $SO_2CF_2CH_3$ | $CF_3$ |
| F | H | $CF_2$ | O | $CF_2$ | F | $SO_2CF_2CH_3$ | $CF_3$ |
| F | H | $CF_2$ | O | $CF_2$ | $COCH_3$ | $SO_2CF_2CH_3$ | $CF_3$ |
| F | H | $CF_2$ | O | $CF_2$ | $NH_2$ | $COCF_3$ | $CF_3$ |
| F | H | $CF_2$ | O | $CF_2$ | N=CHPh | $COCF_3$ | $CF_3$ |
| F | H | $CF_2$ | O | $CF_2$ | $CH_3$ | $COCF_3$ | $CF_3$ |
| F | H | $CF_2$ | O | $CF_2$ | $CF_3$ | $COCF_3$ | $CF_3$ |
| F | H | $CF_2$ | O | $CF_2$ | Cl | $COCF_3$ | $CF_3$ |
| F | H | $CF_2$ | O | $CF_2$ | F | $COCF_3$ | $CF_3$ |
| F | H | $CF_2$ | O | $CF_2$ | $COCH_3$ | $COCF_3$ | $CF_3$ |
| F | H | $CF_2$ | O | $CF_2$ | H | $COCF_3$ | $CF_3$ |
| F | H | $CF_2$ | O | $CF_2$ | $NH_2$ | $COCF_3$ | $CF_3$ |
| F | H | $CF_2$ | O | $CF_2$ | N=CHPh | $COCF_3$ | $CF_3$ |
| F | H | $CF_2$ | O | $CF_2$ | $CH_3$ | $COCF_3$ | $CF_3$ |
| F | H | $CF_2$ | O | $CF_2$ | $CF_3$ | $COCF_3$ | $CF_3$ |
| F | H | $CF_2$ | O | $CF_2$ | Cl | $COCF_3$ | $CF_3$ |
| F | H | $CF_2$ | O | $CF_2$ | F | $COCF_3$ | $CF_3$ |
| F | H | $CF_2$ | O | $CF_2$ | $COCH_3$ | $COCF_3$ | $CF_3$ |
| F | H | $CF_2$ | O | $CF_2$ | $NH_2$ | $C_2F_5$ | $CF_3$ |
| F | H | $CF_2$ | O | $CF_2$ | N=CHPh | $C_2F_5$ | $CF_3$ |

TABLE 25

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | $CH_3$ | $C_2F_5$ | $CF_3$ |
| F | H | $CF_2$ | O | $CF_2$ | $CF_3$ | $C_2F_5$ | $CF_3$ |
| F | H | $CF_2$ | O | $CF_2$ | Cl | $C_2F_5$ | $CF_3$ |
| F | H | $CF_2$ | O | $CF_2$ | F | $C_2F_5$ | $CF_3$ |
| F | H | $CF_2$ | O | $CF_2$ | $COCH_3$ | $C_2F_5$ | $CF_3$ |
| F | H | $CF_2$ | O | $CF_2$ | H | $C_2F_5$ | $CF_3$ |
| F | H | $CF_2$ | O | $CF_2$ | $NH_2$ | $C_2F_5$ | $CF_3$ |
| F | H | $CF_2$ | O | $CF_2$ | N=CHPh | $C_2F_5$ | $CF_3$ |
| F | H | $CF_2$ | O | $CF_2$ | $CH_3$ | $C_2F_5$ | $CF_3$ |
| F | H | $CF_2$ | O | $CF_2$ | $CF_3$ | $C_2F_5$ | $CF_3$ |

TABLE 25-continued

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | Cl | $C_2F_5$ | $CF_3$ |
| F | H | $CF_2$ | O | $CF_2$ | F | $C_2F_5$ | $CF_3$ |
| F | H | $CF_2$ | O | $CF_2$ | $COCH_3$ | $C_2F_5$ | $CF_3$ |
| F | H | $CF_2$ | O | $CF_2$ | $NH_2$ | $SFCl_2$ | $CF_3$ |
| F | H | $CF_2$ | O | $CF_2$ | N=CHPh | $SFCl_2$ | $CF_3$ |
| F | H | $CF_2$ | O | $CF_2$ | $CH_3$ | $SFCl_2$ | $CF_3$ |
| F | H | $CF_2$ | O | $CF_2$ | $CF_3$ | $SFCl_2$ | $CF_3$ |
| F | H | $CF_2$ | O | $CF_2$ | Cl | $SFCl_2$ | $CF_3$ |
| F | H | $CF_2$ | O | $CF_2$ | F | $SFCl_2$ | $CF_3$ |
| F | H | $CF_2$ | O | $CF_2$ | $COCH_3$ | $SFCl_2$ | $CF_3$ |
| F | H | $CF_2$ | O | $CF_2$ | H | $SFCl_2$ | $CF_3$ |
| F | H | $CF_2$ | O | $CF_2$ | $NH_2$ | $SFCl_2$ | $CF_3$ |
| F | H | $CF_2$ | O | $CF_2$ | N=CHPh | $SFCl_2$ | $CF_3$ |
| F | H | $CF_2$ | O | $CF_2$ | $CH_3$ | $SFCl_2$ | $CF_3$ |
| F | H | $CF_2$ | O | $CF_2$ | $CF_3$ | $SFCl_2$ | $CF_3$ |
| F | H | $CF_2$ | O | $CF_2$ | Cl | $SFCl_2$ | $CF_3$ |

TABLE 26

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | F | $SFCl_2$ | $CF_3$ |
| F | H | $CF_2$ | O | $CF_2$ | $COCH_3$ | $SFCl_2$ | $CF_3$ |
| F | H | $CF_2$ | O | $CF_2$ | H | $SCF_3$ | $C_2F_5$ |
| F | H | $CF_2$ | O | $CF_2$ | $NH_2$ | $SCF_3$ | $C_2F_5$ |
| F | H | $CF_2$ | O | $CF_2$ | N=CHPh | $SCF_3$ | $C_2F_5$ |
| F | H | $CF_2$ | O | $CF_2$ | $CH_3$ | $SCF_3$ | $C_2F_5$ |
| F | H | $CF_2$ | O | $CF_2$ | $CF_3$ | $SCF_3$ | $C_2F_5$ |
| F | H | $CF_2$ | O | $CF_2$ | Cl | $SCF_3$ | $C_2F_5$ |
| F | H | $CF_2$ | O | $CF_2$ | F | $SCF_3$ | $C_2F_5$ |
| F | H | $CF_2$ | O | $CF_2$ | $COCH_3$ | $SCF_3$ | $C_2F_5$ |
| F | H | $CF_2$ | O | $CF_2$ | H | $SOCF_3$ | $C_2F_5$ |
| F | H | $CF_2$ | O | $CF_2$ | $NH_2$ | $SOCF_3$ | $C_2F_5$ |
| F | H | $CF_2$ | O | $CF_2$ | N=CHPh | $SOCF_3$ | $C_2F_5$ |
| F | H | $CF_2$ | O | $CF_2$ | $CH_3$ | $SOCF_3$ | $C_2F_5$ |
| F | H | $CF_2$ | O | $CF_2$ | $CF_3$ | $SOCF_3$ | $C_2F_5$ |
| F | H | $CF_2$ | O | $CF_2$ | Cl | $SOCF_3$ | $C_2F_5$ |
| F | H | $CF_2$ | O | $CF_2$ | F | $SOCF_3$ | $C_2F_5$ |
| F | H | $CF_2$ | O | $CF_2$ | $COCH_3$ | $SOCF_3$ | $C_2F_5$ |
| F | H | $CF_2$ | O | $CF_2$ | H | $SO_2CF_3$ | $C_2F_5$ |
| F | H | $CF_2$ | O | $CF_2$ | $NH_2$ | $SO_2CF_3$ | $C_2F_5$ |
| F | H | $CF_2$ | O | $CF_2$ | N=CHPh | $SO_2CF_3$ | $C_2F_5$ |
| F | H | $CF_2$ | O | $CF_2$ | $CH_3$ | $SO_2CF_3$ | $C_2F_5$ |
| F | H | $CF_2$ | O | $CF_2$ | $CF_3$ | $SO_2CF_3$ | $C_2F_5$ |
| F | H | $CF_2$ | O | $CF_2$ | Cl | $SO_2CF_3$ | $C_2F_5$ |
| F | H | $CF_2$ | O | $CF_2$ | F | $SO_2CF_3$ | $C_2F_5$ |
| F | H | $CF_2$ | O | $CF_2$ | $COCH_3$ | $SO_2CF_3$ | $C_2F_5$ |

TABLE 27

| X | Y | $Z^1$ | $Z^2$ | $Z^3$ | $R^1$ | $R^2$ | $R^3$ |
|---|---|---|---|---|---|---|---|
| F | H | $CF_2$ | O | $CF_2$ | H | $SCF_2CH_3$ | $C_2F_5$ |
| F | H | $CF_2$ | O | $CF_2$ | $NH_2$ | $SCF_2CH_3$ | $C_2F_5$ |
| F | H | $CF_2$ | O | $CF_2$ | N=CHPh | $SCF_2CH_3$ | $C_2F_5$ |
| F | H | $CF_2$ | O | $CF_2$ | $CH_3$ | $SCF_2CH_3$ | $C_2F_5$ |
| F | H | $CF_2$ | O | $CF_2$ | $CF_3$ | $SCF_2CH_3$ | $C_2F_5$ |
| F | H | $CF_2$ | O | $CF_2$ | Cl | $SCF_2CH_3$ | $C_2F_5$ |
| F | H | $CF_2$ | O | $CF_2$ | F | $SCF_2CH_3$ | $C_2F_5$ |
| F | H | $CF_2$ | O | $CF_2$ | $COCH_3$ | $SCF_2CH_3$ | $C_2F_5$ |
| F | H | $CF_2$ | O | $CF_2$ | H | $SOCF_2CH_3$ | $C_2F_5$ |
| F | H | $CF_2$ | O | $CF_2$ | $NH_2$ | $SOCF_2CH_3$ | $C_2F_5$ |
| F | H | $CF_2$ | O | $CF_2$ | N=CHPh | $SOCF_2CH_3$ | $C_2F_5$ |
| F | H | $CF_2$ | O | $CF_2$ | $CH_3$ | $SOCF_2CH_3$ | $C_2F_5$ |
| F | H | $CF_2$ | O | $CF_2$ | $CF_3$ | $SOCF_2CH_3$ | $C_2F_5$ |
| F | H | $CF_2$ | O | $CF_2$ | Cl | $SOCF_2CH_3$ | $C_2F_5$ |
| F | H | $CF_2$ | O | $CF_2$ | F | $SOCF_2CH_3$ | $C_2F_5$ |
| F | H | $CF_2$ | O | $CF_2$ | $COCH_3$ | $SOCF_2CH_3$ | $C_2F_5$ |
| F | H | $CF_2$ | O | $CF_2$ | H | $SO_2CF_2CH_3$ | $C_2F_5$ |
| F | H | $CF_2$ | O | $CF_2$ | $NH_2$ | $SO_2CF_2CH_3$ | $C_2F_5$ |
| F | H | $CF_2$ | O | $CF_2$ | N=CHPh | $SO_2CF_2CH_3$ | $C_2F_5$ |
| F | H | $CF_2$ | O | $CF_2$ | $CH_3$ | $SO_2CF_2CH_3$ | $C_2F_5$ |

TABLE 27-continued

| X | Y | Z¹ | Z² | Z³ | R¹ | R² | R³ |
|---|---|---|---|---|---|---|---|
| F | H | $CF_2$ | O | $CF_2$ | $CF_3$ | $SO_2CF_2CH_3$ | $C_2F_5$ |
| F | H | $CF_2$ | O | $CF_2$ | Cl | $SO_2CF_2CH_3$ | $C_2F_5$ |
| F | H | $CF_2$ | O | $CF_2$ | F | $SO_2CF_2CH_3$ | $C_2F_5$ |
| F | H | $CF_2$ | O | $CF_2$ | $COCH_3$ | $SO_2CF_2CH_3$ | $C_2F_5$ |
| F | H | $CF_2$ | O | $CF_2$ | $NH_2$ | $COCF_3$ | $C_2F_5$ |
| F | H | $CF_2$ | O | $CF_2$ | N=CHPh | $COCF_3$ | $C_2F_5$ |

TABLE 28

| X | Y | Z¹ | Z² | Z³ | R¹ | R² | R³ |
|---|---|---|---|---|---|---|---|
| F | H | $CF_2$ | O | $CF_2$ | $CH_3$ | $COCF_3$ | $C_2F_5$ |
| F | H | $CF_2$ | O | $CF_2$ | $CF_3$ | $COCF_3$ | $C_2F_5$ |
| F | H | $CF_2$ | O | $CF_2$ | Cl | $COCF_3$ | $C_2F_5$ |
| F | H | $CF_2$ | O | $CF_2$ | F | $COCF_3$ | $C_2F_5$ |
| F | H | $CF_2$ | O | $CF_2$ | $COCH_3$ | $COCF_3$ | $C_2F_5$ |
| F | H | $CF_2$ | O | $CF_2$ | H | $COCF_3$ | $C_2F_5$ |
| F | H | $CF_2$ | O | $CF_2$ | $NH_2$ | $COCF_3$ | $C_2F_5$ |
| F | H | $CF_2$ | O | $CF_2$ | N=CHPh | $COCF_3$ | $C_2F_5$ |
| F | H | $CF_2$ | O | $CF_2$ | $CH_3$ | $COCF_3$ | $C_2F_5$ |
| F | H | $CF_2$ | O | $CF_2$ | $CF_3$ | $COCF_3$ | $C_2F_5$ |
| F | H | $CF_2$ | O | $CF_2$ | Cl | $COCF_3$ | $C_2F_5$ |
| F | H | $CF_2$ | O | $CF_2$ | F | $COCF_3$ | $C_2F_5$ |
| F | H | $CF_2$ | O | $CF_2$ | $COCH_3$ | $COCF_3$ | $C_2F_5$ |
| F | H | $CF_2$ | O | $CF_2$ | $NH_2$ | $C_2F_5$ | $C_2F_5$ |
| F | H | $CF_2$ | O | $CF_2$ | N=CHPh | $C_2F_5$ | $C_2F_5$ |
| F | H | $CF_2$ | O | $CF_2$ | $CH_3$ | $C_2F_5$ | $C_2F_5$ |
| F | H | $CF_2$ | O | $CF_2$ | $CF_3$ | $C_2F_5$ | $C_2F_5$ |
| F | H | $CF_2$ | O | $CF_2$ | Cl | $C_2F_5$ | $C_2F_5$ |
| F | H | $CF_2$ | O | $CF_2$ | F | $C_2F_5$ | $C_2F_5$ |
| F | H | $CF_2$ | O | $CF_2$ | $COCH_3$ | $C_2F_5$ | $C_2F_5$ |
| F | H | $CF_2$ | O | $CF_2$ | H | $C_2F_5$ | $C_2F_5$ |
| F | H | $CF_2$ | O | $CF_2$ | $NH_2$ | $C_2F_5$ | $C_2F_5$ |
| F | H | $CF_2$ | O | $CF_2$ | N=CHPh | $C_2F_5$ | $C_2F_5$ |
| F | H | $CF_2$ | O | $CF_2$ | $CH_3$ | $C_2F_5$ | $C_2F_5$ |
| F | H | $CF_2$ | O | $CF_2$ | $CF_3$ | $C_2F_5$ | $C_2F_5$ |
| F | H | $CF_2$ | O | $CF_2$ | Cl | $C_2F_5$ | $C_2F_5$ |

TABLE 29

| X | Y | Z¹ | Z² | Z³ | R¹ | R² | R³ |
|---|---|---|---|---|---|---|---|
| F | H | $CF_2$ | O | $CF_2$ | F | $C_2F_5$ | $C_2F_5$ |
| F | H | $CF_2$ | O | $CF_2$ | $COCH_3$ | $C_2F_5$ | $C_2F_5$ |
| F | H | $CF_2$ | O | $CF_2$ | $NH_2$ | $SFCl_2$ | $C_2F_5$ |
| F | H | $CF_2$ | O | $CF_2$ | N=CHPh | $SFCl_2$ | $C_2F_5$ |
| F | H | $CF_2$ | O | $CF_2$ | $CH_3$ | $SFCl_2$ | $C_2F_5$ |
| F | H | $CF_2$ | O | $CF_2$ | $CF_3$ | $SFCl_2$ | $C_2F_5$ |
| F | H | $CF_2$ | O | $CF_2$ | Cl | $SFCl_2$ | $C_2F_5$ |
| F | H | $CF_2$ | O | $CF_2$ | F | $SFCl_2$ | $C_2F_5$ |
| F | H | $CF_2$ | O | $CF_2$ | $COCH_3$ | $SFCl_2$ | $C_2F_5$ |
| F | H | $CF_2$ | O | $CF_2$ | H | $SFCl_2$ | $C_2F_5$ |
| F | H | $CF_2$ | O | $CF_2$ | $NH_2$ | $SFCl_2$ | $C_2F_5$ |
| F | H | $CF_2$ | O | $CF_2$ | N=CHPh | $SFCl_2$ | $C_2F_5$ |
| F | H | $CF_2$ | O | $CF_2$ | $CH_3$ | $SFCl_2$ | $C_2F_5$ |
| F | H | $CF_2$ | O | $CF_2$ | $CF_3$ | $SFCl_2$ | $C_2F_5$ |
| F | H | $CF_2$ | O | $CF_2$ | Cl | $SFCl_2$ | $C_2F_5$ |
| F | H | $CF_2$ | O | $CF_2$ | F | $SFCl_2$ | $C_2F_5$ |
| F | H | $CF_2$ | O | $CF_2$ | $COCH_3$ | $SFCl_2$ | $C_2F_5$ |
| F | H | $CF_2$ | O | $CF_2$ | H | $SCF_3$ | $CSNH_2$ |
| F | H | $CF_2$ | O | $CF_2$ | $NH_2$ | $SCF_3$ | $CSNH_2$ |
| F | H | $CF_2$ | O | $CF_2$ | N=CHPh | $SCF_3$ | $CSNH_2$ |
| F | H | $CF_2$ | O | $CF_2$ | $CH_3$ | $SCF_3$ | $CSNH_2$ |
| F | H | $CF_2$ | O | $CF_2$ | $CF_3$ | $SCF_3$ | $CSNH_2$ |
| F | H | $CF_2$ | O | $CF_2$ | Cl | $SCF_3$ | $CSNH_2$ |
| F | H | $CF_2$ | O | $CF_2$ | F | $SCF_3$ | $CSNH_2$ |
| F | H | $CF_2$ | O | $CF_2$ | $COCH_3$ | $SCF_3$ | $CSNH_2$ |
| F | H | $CF_2$ | O | $CF_2$ | H | $SOCF_3$ | $CSNH_2$ |

TABLE 30

| X | Y | Z¹ | Z² | Z³ | R¹ | R² | R³ |
|---|---|---|---|---|---|---|---|
| F | H | $CF_2$ | O | $CF_2$ | $NH_2$ | $SOCF_3$ | $CSNH_2$ |
| F | H | $CF_2$ | O | $CF_2$ | N=CHPh | $SOCF_3$ | $CSNH_2$ |
| F | H | $CF_2$ | O | $CF_2$ | $CH_3$ | $SOCF_3$ | $CSNH_2$ |
| F | H | $CF_2$ | O | $CF_2$ | $CF_3$ | $SOCF_3$ | $CSNH_2$ |
| F | H | $CF_2$ | O | $CF_2$ | Cl | $SOCF_3$ | $CSNH_2$ |
| F | H | $CF_2$ | O | $CF_2$ | F | $SOCF_3$ | $CSNH_2$ |
| F | H | $CF_2$ | O | $CF_2$ | $COCH_3$ | $SOCF_3$ | $CSNH_2$ |
| F | H | $CF_2$ | O | $CF_2$ | H | $SO_2CF_3$ | $CSNH_2$ |
| F | H | $CF_2$ | O | $CF_2$ | $NH_2$ | $SO_2CF_3$ | $CSNH_2$ |
| F | H | $CF_2$ | O | $CF_2$ | N=CHPh | $SO_2CF_3$ | $CSNH_2$ |
| F | H | $CF_2$ | O | $CF_2$ | $CH_3$ | $SO_2CF_3$ | $CSNH_2$ |
| F | H | $CF_2$ | O | $CF_2$ | $CF_3$ | $SO_2CF_3$ | $CSNH_2$ |
| F | H | $CF_2$ | O | $CF_2$ | Cl | $SO_2CF_3$ | $CSNH_2$ |
| F | H | $CF_2$ | O | $CF_2$ | F | $SO_2CF_3$ | $CSNH_2$ |
| F | H | $CF_2$ | O | $CF_2$ | $COCH_3$ | $SO_2CF_3$ | $CSNH_2$ |
| F | H | $CF_2$ | O | $CF_2$ | H | $SCF_2CH_3$ | $CSNH_2$ |
| F | H | $CF_2$ | O | $CF_2$ | $NH_2$ | $SCF_2CH_3$ | $CSNH_2$ |
| F | H | $CF_2$ | O | $CF_2$ | N=CHPh | $SCF_2CH_3$ | $CSNH_2$ |
| F | H | $CF_2$ | O | $CF_2$ | $CH_3$ | $SCF_2CH_3$ | $CSNH_2$ |
| F | H | $CF_2$ | O | $CF_2$ | $CF_3$ | $SCF_2CH_3$ | $CSNH_2$ |
| F | H | $CF_2$ | O | $CF_2$ | Cl | $SCF_2CH_3$ | $CSNH_2$ |
| F | H | $CF_2$ | O | $CF_2$ | F | $SCF_2CH_3$ | $CSNH_2$ |
| F | H | $CF_2$ | O | $CF_2$ | $COCH_3$ | $SCF_2CH_3$ | $CSNH_2$ |
| F | H | $CF_2$ | O | $CF_2$ | H | $SOCF_2CH_3$ | $CSNH_2$ |
| F | H | $CF_2$ | O | $CF_2$ | $NH_2$ | $SOCF_2CH_3$ | $CSNH_2$ |
| F | H | $CF_2$ | O | $CF_2$ | N=CHPh | $SOCF_2CH_3$ | $CSNH_2$ |

TABLE 31

| X | Y | Z¹ | Z² | Z³ | R¹ | R² | R³ |
|---|---|---|---|---|---|---|---|
| F | H | $CF_2$ | O | $CF_2$ | $CH_3$ | $SOCF_2CH_3$ | $CSNH_2$ |
| F | H | $CF_2$ | O | $CF_2$ | $CF_3$ | $SOCF_2CH_3$ | $CSNH_2$ |
| F | H | $CF_2$ | O | $CF_2$ | Cl | $SOCF_2CH_3$ | $CSNH_2$ |
| F | H | $CF_2$ | O | $CF_2$ | F | $SOCF_2CH_3$ | $CSNH_2$ |
| F | H | $CF_2$ | O | $CF_2$ | $COCH_3$ | $SOCF_2CH_3$ | $CSNH_2$ |
| F | H | $CF_2$ | O | $CF_2$ | H | $SO_2CF_2CH_3$ | $CSNH_2$ |
| F | H | $CF_2$ | O | $CF_2$ | $NH_2$ | $SO_2CF_2CH_3$ | $CSNH_2$ |
| F | H | $CF_2$ | O | $CF_2$ | N=CHPh | $SO_2CF_2CH_3$ | $CSNH_2$ |
| F | H | $CF_2$ | O | $CF_2$ | $CH_3$ | $SO_2CF_2CH_3$ | $CSNH_2$ |
| F | H | $CF_2$ | O | $CF_2$ | $CF_3$ | $SO_2CF_2CH_3$ | $CSNH_2$ |
| F | H | $CF_2$ | O | $CF_2$ | Cl | $SO_2CF_2CH_3$ | $CSNH_2$ |
| F | H | $CF_2$ | O | $CF_2$ | F | $SO_2CF_2CH_3$ | $CSNH_2$ |
| F | H | $CF_2$ | O | $CF_2$ | $COCH_3$ | $SO_2CF_2CH_3$ | $CSNH_2$ |
| F | H | $CF_2$ | O | $CF_2$ | $NH_2$ | $COCF_3$ | $CSNH_2$ |
| F | H | $CF_2$ | O | $CF_2$ | N=CHPh | $COCF_3$ | $CSNH_2$ |
| F | H | $CF_2$ | O | $CF_2$ | $CH_3$ | $COCF_3$ | $CSNH_2$ |
| F | H | $CF_2$ | O | $CF_2$ | $CF_3$ | $COCF_3$ | $CSNH_2$ |
| F | H | $CF_2$ | O | $CF_2$ | Cl | $COCF_3$ | $CSNH_2$ |
| F | H | $CF_2$ | O | $CF_2$ | F | $COCF_3$ | $CSNH_2$ |
| F | H | $CF_2$ | O | $CF_2$ | $COCH_3$ | $COCF_3$ | $CSNH_2$ |
| F | H | $CF_2$ | O | $CF_2$ | H | $COCF_3$ | $CSNH_2$ |
| F | H | $CF_2$ | O | $CF_2$ | $NH_2$ | $COCF_3$ | $CSNH_2$ |
| F | H | $CF_2$ | O | $CF_2$ | N=CHPh | $COCF_3$ | $CSNH_2$ |
| F | H | $CF_2$ | O | $CF_2$ | $CH_3$ | $COCF_3$ | $CSNH_2$ |
| F | H | $CF_2$ | O | $CF_2$ | $CF_3$ | $COCF_3$ | $CSNH_2$ |
| F | H | $CF_2$ | O | $CF_2$ | Cl | $COCF_3$ | $CSNH_2$ |

TABLE 32

| X | Y | Z¹ | Z² | Z³ | R¹ | R² | R³ |
|---|---|---|---|---|---|---|---|
| F | H | $CF_2$ | O | $CF_2$ | F | $COCF_3$ | $CSNH_2$ |
| F | H | $CF_2$ | O | $CF_2$ | $COCH_3$ | $COCF_3$ | $CSNH_2$ |
| F | H | $CF_2$ | O | $CF_2$ | $NH_2$ | $C_2F_5$ | $CSNH_2$ |
| F | H | $CF_2$ | O | $CF_2$ | N=CHPh | $C_2F_5$ | $CSNH_2$ |
| F | H | $CF_2$ | O | $CF_2$ | $CH_3$ | $C_2F_5$ | $CSNH_2$ |
| F | H | $CF_2$ | O | $CF_2$ | $CF_3$ | $C_2F_5$ | $CSNH_2$ |
| F | H | $CF_2$ | O | $CF_2$ | Cl | $C_2F_5$ | $CSNH_2$ |
| F | H | $CF_2$ | O | $CF_2$ | F | $C_2F_5$ | $CSNH_2$ |
| F | H | $CF_2$ | O | $CF_2$ | $COCH_3$ | $C_2F_5$ | $CSNH_2$ |
| F | H | $CF_2$ | O | $CF_2$ | H | $C_2F_5$ | $CSNH_2$ |

TABLE 32-continued

| X | Y | Z$^1$ | Z$^2$ | Z$^3$ | R$^1$ | R$^2$ | R$^3$ |
|---|---|---|---|---|---|---|---|
| F | H | CF$_2$ | O | CF$_2$ | NH$_2$ | C$_2$F$_5$ | CSNH$_2$ |
| F | H | CF$_2$ | O | CF$_2$ | N = CHPh | C$_2$F$_5$ | CSNH$_2$ |
| F | H | CF$_2$ | O | CF$_2$ | CH$_3$ | C$_2$F$_5$ | CSNH$_2$ |
| F | H | CF$_2$ | O | CF$_2$ | CF$_3$ | C$_2$F$_5$ | CSNH$_2$ |
| F | H | CF$_2$ | O | CF$_2$ | Cl | C$_2$F$_5$ | CSNH$_2$ |
| F | H | CF$_2$ | O | CF$_2$ | F | C$_2$F$_5$ | CSNH$_2$ |
| F | H | CF$_2$ | O | CF$_2$ | COCH$_3$ | C$_2$F$_5$ | CSNH$_2$ |
| F | H | CF$_2$ | O | CF$_2$ | NH$_2$ | SFCl$_2$ | CSNH$_2$ |
| F | H | CF$_2$ | O | CF$_2$ | N = CHPh | SFCl$_2$ | CSNH$_2$ |
| F | H | CF$_2$ | O | CF$_2$ | CH$_3$ | SFCl$_2$ | CSNH$_2$ |
| F | H | CF$_2$ | O | CF$_2$ | CF$_3$ | SFCl$_2$ | CSNH$_2$ |
| F | H | CF$_2$ | O | CF$_2$ | Cl | SFCl$_2$ | CSNH$_2$ |
| F | H | CF$_2$ | O | CF$_2$ | F | SFCl$_2$ | CSNH$_2$ |
| F | H | CF$_2$ | O | CF$_2$ | COCH$_3$ | SFCl$_2$ | CSNH$_2$ |
| F | H | CF$_2$ | O | CF$_2$ | H | SFCl$_2$ | CSNH$_2$ |
| F | H | CF$_2$ | O | CF$_2$ | NH$_2$ | SFCl$_2$ | CSNH$_2$ |

TABLE 33

| X | Y | Z$^1$ | Z$^2$ | Z$^3$ | R$^1$ | R$^2$ | R$^3$ |
|---|---|---|---|---|---|---|---|
| F | H | CF$_2$ | O | CF$_2$ | N = CHPh | SFCl$_2$ | CSNH$_2$ |
| F | H | CF$_2$ | O | CF$_2$ | CH$_3$ | SFCl$_2$ | CSNH$_2$ |
| F | H | CF$_2$ | O | CF$_2$ | CF$_3$ | SFCl$_2$ | CSNH$_2$ |
| F | H | CF$_2$ | O | CF$_2$ | Cl | SFCl$_2$ | CSNH$_2$ |
| F | H | CF$_2$ | O | CF$_2$ | F | SFCl$_2$ | CSNH$_2$ |
| F | H | CF$_2$ | O | CF$_2$ | COCH$_3$ | SFCl$_2$ | CSNH$_2$ |
| F | H | CF$_2$ | O | CF$_2$ | H | SCF$_3$ | CN |
| F | H | CF$_2$ | O | CF$_2$ | NH$_2$ | SCF$_3$ | CN |
| F | H | CF$_2$ | O | CF$_2$ | N = CHPh | SCF$_3$ | CN |
| F | H | CF$_2$ | O | CF$_2$ | CH$_3$ | SCF$_3$ | CN |
| F | H | CF$_2$ | O | CF$_2$ | CF$_3$ | SCF$_3$ | CN |
| F | H | CF$_2$ | O | CF$_2$ | Cl | SCF$_3$ | CN |
| F | H | CF$_2$ | O | CF$_2$ | F | SCF$_3$ | CN |
| F | H | CF$_2$ | O | CF$_2$ | COCH$_3$ | SCF$_3$ | CN |
| F | H | CF$_2$ | O | CF$_2$ | H | SOCF$_3$ | CN |
| F | H | CF$_2$ | O | CF$_2$ | NH$_2$ | SOCF$_3$ | CN |
| F | H | CF$_2$ | O | CF$_2$ | N = CHPh | SOCF$_3$ | CN |
| F | H | CF$_2$ | O | CF$_2$ | CH$_3$ | SOCF$_3$ | CN |
| F | H | CF$_2$ | O | CF$_2$ | CF$_3$ | SOCF$_3$ | CN |
| F | H | CF$_2$ | O | CF$_2$ | Cl | SOCF$_3$ | CN |
| F | H | CF$_2$ | O | CF$_2$ | F | SOCF$_3$ | CN |
| F | H | CF$_2$ | O | CF$_2$ | COCH$_3$ | SOCF$_3$ | CN |
| F | H | CF$_2$ | O | CF$_2$ | H | SO$_2$CF$_3$ | CN |
| F | H | CF$_2$ | O | CF$_2$ | NH$_2$ | SO$_2$CF$_3$ | CN |
| F | H | CF$_2$ | O | CF$_2$ | N = CHPh | SO$_2$CF$_3$ | CN |
| F | H | CF$_2$ | O | CF$_2$ | CH$_3$ | SO$_2$CF$_3$ | CN |

TABLE 34

| X | Y | Z$^1$ | Z$^2$ | Z$^3$ | R$^1$ | R$^2$ | R$^3$ |
|---|---|---|---|---|---|---|---|
| F | H | CF$_2$ | O | CF$_2$ | CF$_3$ | SO$_2$CF$_3$ | CN |
| F | H | CF$_2$ | O | CF$_2$ | Cl | SO$_2$CF$_3$ | CN |
| F | H | CF$_2$ | O | CF$_2$ | F | SO$_2$CF$_3$ | CN |
| F | H | CF$_2$ | O | CF$_2$ | COCH$_3$ | SO$_2$CF$_3$ | CN |
| F | H | CF$_2$ | O | CF$_2$ | H | SCF$_2$CH$_3$ | CN |
| F | H | CF$_2$ | O | CF$_2$ | NH$_2$ | SCF$_2$CH$_3$ | CN |
| F | H | CF$_2$ | O | CF$_2$ | N = CHPh | SCF$_2$CH$_3$ | CN |
| F | H | CF$_2$ | O | CF$_2$ | CH$_3$ | SCF$_2$CH$_3$ | CN |
| F | H | CF$_2$ | O | CF$_2$ | CF$_3$ | SCF$_2$CH$_3$ | CN |
| F | H | CF$_2$ | O | CF$_2$ | Cl | SCF$_2$CH$_3$ | CN |
| F | H | CF$_2$ | O | CF$_2$ | F | SCF$_2$CH$_3$ | CN |
| F | H | CF$_2$ | O | CF$_2$ | COCH$_3$ | SCF$_2$CH$_3$ | CN |
| F | H | CF$_2$ | O | CF$_2$ | H | SOCF$_2$CH$_3$ | CN |
| F | H | CF$_2$ | O | CF$_2$ | NH$_2$ | SOCF$_2$CH$_3$ | CN |
| F | H | CF$_2$ | O | CF$_2$ | N = CHPh | SOCF$_2$CH$_3$ | CN |
| F | H | CF$_2$ | O | CF$_2$ | CH$_3$ | SOCF$_2$CH$_3$ | CN |
| F | H | CF$_2$ | O | CF$_2$ | CF$_3$ | SOCF$_2$CH$_3$ | CN |
| F | H | CF$_2$ | O | CF$_2$ | Cl | SOCF$_2$CH$_3$ | CN |
| F | H | CF$_2$ | O | CF$_2$ | F | SOCF$_2$CH$_3$ | CN |
| F | H | CF$_2$ | O | CF$_2$ | COCH$_3$ | SOCF$_2$CH$_3$ | CN |

TABLE 34-continued

| X | Y | Z$^1$ | Z$^2$ | Z$^3$ | R$^1$ | R$^2$ | R$^3$ |
|---|---|---|---|---|---|---|---|
| F | H | CF$_2$ | O | CF$_2$ | H | SO$_2$CF$_2$CH$_3$ | CN |
| F | H | CF$_2$ | O | CF$_2$ | NH$_2$ | SO$_2$CF$_2$CH$_3$ | CN |
| F | H | CF$_2$ | O | CF$_2$ | N = CHPh | SO$_2$CF$_2$CH$_3$ | CN |
| F | H | CF$_2$ | O | CF$_2$ | CH$_3$ | SO$_2$CF$_2$CH$_3$ | CN |
| F | H | CF$_2$ | O | CF$_2$ | CF$_3$ | SO$_2$CF$_2$CH$_3$ | CN |
| F | H | CF$_2$ | O | CF$_2$ | Cl | SO$_2$CF$_2$CH$_3$ | CN |

TABLE 35

| X | Y | Z$^1$ | Z$^2$ | Z$^3$ | R$^1$ | R$^2$ | R$^3$ |
|---|---|---|---|---|---|---|---|
| F | H | CF$_2$ | O | CF$_2$ | F | SO$_2$CF$_2$CH$_3$ | CN |
| F | H | CF$_2$ | O | CF$_2$ | COCH$_3$ | SO$_2$CF$_2$CH$_3$ | CN |
| F | H | CF$_2$ | O | CF$_2$ | NH$_2$ | COCF$_3$ | CN |
| F | H | CF$_2$ | O | CF$_2$ | N = CHPh | COCF$_3$ | CN |
| F | H | CF$_2$ | O | CF$_2$ | CH$_3$ | COCF$_3$ | CN |
| F | H | CF$_2$ | O | CF$_2$ | CF$_3$ | COCF$_3$ | CN |
| F | H | CF$_2$ | O | CF$_2$ | Cl | COCF$_3$ | CN |
| F | H | CF$_2$ | O | CF$_2$ | F | COCF$_3$ | CN |
| F | H | CF$_2$ | O | CF$_2$ | COCH$_3$ | COCF$_3$ | CN |
| F | H | CF$_2$ | O | CF$_2$ | H | COCF$_3$ | CN |
| F | H | CF$_2$ | O | CF$_2$ | NH$_2$ | COCF$_3$ | CN |
| F | H | CF$_2$ | O | CF$_2$ | N = CHPh | COCF$_3$ | CN |
| F | H | CF$_2$ | O | CF$_2$ | CH$_3$ | COCF$_3$ | CN |
| F | H | CF$_2$ | O | CF$_2$ | CF$_3$ | COCF$_3$ | CN |
| F | H | CF$_2$ | O | CF$_2$ | Cl | COCF$_3$ | CN |
| F | H | CF$_2$ | O | CF$_2$ | F | COCF$_3$ | CN |
| F | H | CF$_2$ | O | CF$_2$ | COCH$_3$ | COCF$_3$ | CN |
| F | H | CF$_2$ | O | CF$_2$ | NH$_2$ | C$_2$F$_5$ | CN |
| F | H | CF$_2$ | O | CF$_2$ | N = CHPh | C$_2$F$_5$ | CN |
| F | H | CF$_2$ | O | CF$_2$ | CH$_3$ | C$_2$F$_5$ | CN |
| F | H | CF$_2$ | O | CF$_2$ | CF$_3$ | C$_2$F$_5$ | CN |
| F | H | CF$_2$ | O | CF$_2$ | Cl | C$_2$F$_5$ | CN |
| F | H | CF$_2$ | O | CF$_2$ | F | C$_2$F$_5$ | CN |
| F | H | CF$_2$ | O | CF$_2$ | COCH$_3$ | C$_2$F$_5$ | CN |
| F | H | CF$_2$ | O | CF$_2$ | H | C$_2$F$_5$ | CN |
| F | H | CF$_2$ | O | CF$_2$ | NH$_2$ | C$_2$F$_5$ | CN |

TABLE 36

| X | Y | Z$^1$ | Z$^2$ | Z$^3$ | R$^1$ | R$^2$ | R$^3$ |
|---|---|---|---|---|---|---|---|
| F | H | CF$_2$ | O | CF$_2$ | N = CHPh | C$_2$F$_5$ | CN |
| F | H | CF$_2$ | O | CF$_2$ | CH$_3$ | C$_2$F$_5$ | CN |
| F | H | CF$_2$ | O | CF$_2$ | CF$_3$ | C$_2$F$_5$ | CN |
| F | H | CF$_2$ | O | CF$_2$ | Cl | C$_2$F$_5$ | CN |
| F | H | CF$_2$ | O | CF$_2$ | F | C$_2$F$_5$ | CN |
| F | H | CF$_2$ | O | CF$_2$ | COCH$_3$ | C$_2$F$_5$ | CN |
| F | H | CF$_2$ | O | CF$_2$ | NH$_2$ | SFCl$_2$ | CN |
| F | H | CF$_2$ | O | CF$_2$ | N = CHPh | SFCl$_2$ | CN |
| F | H | CF$_2$ | O | CF$_2$ | CH$_3$ | SFCl$_2$ | CN |
| F | H | CF$_2$ | O | CF$_2$ | CF$_3$ | SFCl$_2$ | CN |
| F | H | CF$_2$ | O | CF$_2$ | Cl | SFCl$_2$ | CN |
| F | H | CF$_2$ | O | CF$_2$ | F | SFCl$_2$ | CN |
| F | H | CF$_2$ | O | CF$_2$ | COCH$_3$ | SFCl$_2$ | CN |
| F | H | CF$_2$ | O | CF$_2$ | H | SFCl$_2$ | CN |
| F | H | CF$_2$ | O | CF$_2$ | NH$_2$ | SFCl$_2$ | CN |
| F | H | CF$_2$ | O | CF$_2$ | N = CHPh | SFCl$_2$ | CN |
| F | H | CF$_2$ | O | CF$_2$ | CH$_3$ | SFCl$_2$ | CN |
| F | H | CF$_2$ | O | CF$_2$ | CF$_3$ | SFCl$_2$ | CN |
| F | H | CF$_2$ | O | CF$_2$ | Cl | SFCl$_2$ | CN |
| F | H | CF$_2$ | O | CF$_2$ | F | SFCl$_2$ | CN |
| F | H | CF$_2$ | O | CF$_2$ | COCH$_3$ | SFCl$_2$ | CN |
| Br | H | CF$_2$ | O | CF$_2$ | H | SCF$_3$ | H |
| Br | H | CF$_2$ | O | CF$_2$ | NH$_2$ | SCF$_3$ | H |
| Br | H | CF$_2$ | O | CF$_2$ | N = CHPh | SCF$_3$ | H |
| Br | H | CF$_2$ | O | CF$_2$ | CH$_3$ | SCF$_3$ | H |
| Br | H | CF$_2$ | O | CF$_2$ | CF$_3$ | SCF$_3$ | H |

TABLE 37

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | Cl | $SCF_3$ | H |
| Br | H | $CF_2$ | O | $CF_2$ | F | $SCF_3$ | H |
| Br | H | $CF_2$ | O | $CF_2$ | $COCH_3$ | $SCF_3$ | H |
| Br | H | $CF_2$ | O | $CF_2$ | H | $SOCF_3$ | H |
| Br | H | $CF_2$ | O | $CF_2$ | $NH_2$ | $SOCF_3$ | H |
| Br | H | $CF_2$ | O | $CF_2$ | N = CHPh | $SOCF_3$ | H |
| Br | H | $CF_2$ | O | $CF_2$ | $CH_3$ | $SOCF_3$ | H |
| Br | H | $CF_2$ | O | $CF_2$ | $CF_3$ | $SOCF_3$ | H |
| Br | H | $CF_2$ | O | $CF_2$ | Cl | $SOCF_3$ | H |
| Br | H | $CF_2$ | O | $CF_2$ | F | $SOCF_3$ | H |
| Br | H | $CF_2$ | O | $CF_2$ | $COCH_3$ | $SOCF_3$ | H |
| Br | H | $CF_2$ | O | $CF_2$ | H | $SO_2CF_3$ | H |
| Br | H | $CF_2$ | O | $CF_2$ | $NH_2$ | $SO_2CF_3$ | H |
| Br | H | $CF_2$ | O | $CF_2$ | N = CHPh | $SO_2CF_3$ | H |
| Br | H | $CF_2$ | O | $CF_2$ | $CH_3$ | $SO_2CF_3$ | H |
| Br | H | $CF_2$ | O | $CF_2$ | $CF_3$ | $SO_2CF_3$ | H |
| Br | H | $CF_2$ | O | $CF_2$ | Cl | $SO_2CF_3$ | H |
| Br | H | $CF_2$ | O | $CF_2$ | F | $SO_2CF_3$ | H |
| Br | H | $CF_2$ | O | $CF_2$ | $COCH_3$ | $SO_2CF_3$ | H |
| Br | H | $CF_2$ | O | $CF_2$ | H | $SCF_2CH_3$ | H |
| Br | H | $CF_2$ | O | $CF_2$ | $NH_2$ | $SCF_2CH_3$ | H |
| Br | H | $CF_2$ | O | $CF_2$ | N = CHPh | $SCF_2CH_3$ | H |
| Br | H | $CF_2$ | O | $CF_2$ | $CH_3$ | $SCF_2CH_3$ | H |
| Br | H | $CF_2$ | O | $CF_2$ | $CF_3$ | $SCF_2CH_3$ | H |
| Br | H | $CF_2$ | O | $CF_2$ | Cl | $SCF_2CH_3$ | H |
| Br | H | $CF_2$ | O | $CF_2$ | F | $SCF_2CH_3$ | H |

TABLE 38

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | $COCH_3$ | $SCF_2CH_3$ | H |
| Br | H | $CF_2$ | O | $CF_2$ | H | $SOCF_2CH_3$ | H |
| Br | H | $CF_2$ | O | $CF_2$ | $NH_2$ | $SOCF_2CH_3$ | H |
| Br | H | $CF_2$ | O | $CF_2$ | N = CHPh | $SOCF_2CH_3$ | H |
| Br | H | $CF_2$ | O | $CF_2$ | $CH_3$ | $SOCF_2CH_3$ | H |
| Br | H | $CF_2$ | O | $CF_2$ | $CF_3$ | $SOCF_2CH_3$ | H |
| Br | H | $CF_2$ | O | $CF_2$ | Cl | $SOCF_2CH_3$ | H |
| Br | H | $CF_2$ | O | $CF_2$ | F | $SOCF_2CH_3$ | H |
| Br | H | $CF_2$ | O | $CF_2$ | $COCH_3$ | $SOCF_2CH_3$ | H |
| Br | H | $CF_2$ | O | $CF_2$ | H | $SO_2CF_2CH_3$ | H |
| Br | H | $CF_2$ | O | $CF_2$ | $NH_2$ | $SO_2CF_2CH_3$ | H |
| Br | H | $CF_2$ | O | $CF_2$ | N = CHPh | $SO_2CF_2CH_3$ | H |
| Br | H | $CF_2$ | O | $CF_2$ | $CH_3$ | $SO_2CF_2CH_3$ | H |
| Br | H | $CF_2$ | O | $CF_2$ | $CF_3$ | $SO_2CF_2CH_3$ | H |
| Br | H | $CF_2$ | O | $CF_2$ | Cl | $SO_2CF_2CH_3$ | H |
| Br | H | $CF_2$ | O | $CF_2$ | F | $SO_2CF_2CH_3$ | H |
| Br | H | $CF_2$ | O | $CF_2$ | $COCH_3$ | $SO_2CF_2CH_3$ | H |
| Br | H | $CF_2$ | O | $CF_2$ | $NH_2$ | $COCF_3$ | H |
| Br | H | $CF_2$ | O | $CF_2$ | N = CHPh | $COCF_3$ | H |
| Br | H | $CF_2$ | O | $CF_2$ | $CH_3$ | $COCF_3$ | H |
| Br | H | $CF_2$ | O | $CF_2$ | $CF_3$ | $COCF_3$ | H |
| Br | H | $CF_2$ | O | $CF_2$ | Cl | $COCF_3$ | H |
| Br | H | $CF_2$ | O | $CF_2$ | F | $COCF_3$ | H |
| Br | H | $CF_2$ | O | $CF_2$ | $COCH_3$ | $COCF_3$ | H |
| Br | H | $CF_2$ | O | $CF_2$ | H | $COCF_3$ | H |
| Br | H | $CF_2$ | O | $CF_2$ | $NH_2$ | $COCF_3$ | H |

TABLE 39

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | N = CHPh | $COCF_3$ | H |
| Br | H | $CF_2$ | O | $CF_2$ | $CH_3$ | $COCF_3$ | H |
| Br | H | $CF_2$ | O | $CF_2$ | $CF_3$ | $COCF_3$ | H |
| Br | H | $CF_2$ | O | $CF_2$ | Cl | $COCF_3$ | H |
| Br | H | $CF_2$ | O | $CF_2$ | F | $COCF_3$ | H |
| Br | H | $CF_2$ | O | $CF_2$ | $COCH_3$ | $COCF_3$ | H |
| Br | H | $CF_2$ | O | $CF_2$ | $NH_2$ | $C_2F_5$ | H |
| Br | H | $CF_2$ | O | $CF_2$ | N = CHPh | $C_2F_5$ | H |
| Br | H | $CF_2$ | O | $CF_2$ | $CH_3$ | $C_2F_5$ | H |
| Br | H | $CF_2$ | O | $CF_2$ | $CF_3$ | $C_2F_5$ | H |
| Br | H | $CF_2$ | O | $CF_2$ | Cl | $C_2F_5$ | H |
| Br | H | $CF_2$ | O | $CF_2$ | F | $C_2F_5$ | H |
| Br | H | $CF_2$ | O | $CF_2$ | $COCH_3$ | $C_2F_5$ | H |
| Br | H | $CF_2$ | O | $CF_2$ | H | $C_2F_5$ | H |
| Br | H | $CF_2$ | O | $CF_2$ | $NH_2$ | $C_2F_5$ | H |
| Br | H | $CF_2$ | O | $CF_2$ | N = CHPh | $C_2F_5$ | H |
| Br | H | $CF_2$ | O | $CF_2$ | $CH_3$ | $C_2F_5$ | H |
| Br | H | $CF_2$ | O | $CF_2$ | $CF_3$ | $C_2F_5$ | H |
| Br | H | $CF_2$ | O | $CF_2$ | Cl | $C_2F_5$ | H |
| Br | H | $CF_2$ | O | $CF_2$ | F | $C_2F_5$ | H |
| Br | H | $CF_2$ | O | $CF_2$ | $COCH_3$ | $C_2F_5$ | H |
| Br | H | $CF_2$ | O | $CF_2$ | $NH_2$ | $SFCl_2$ | H |
| Br | H | $CF_2$ | O | $CF_2$ | N = CHPh | $SFCl_2$ | H |
| Br | H | $CF_2$ | O | $CF_2$ | $CH_3$ | $SFCl_2$ | H |
| Br | H | $CF_2$ | O | $CF_2$ | $CF_3$ | $SFCl_2$ | H |
| Br | H | $CF_2$ | O | $CF_2$ | Cl | $SFCl_2$ | H |

TABLE 40

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | F | $SFCl_2$ | H |
| Br | H | $CF_2$ | O | $CF_2$ | $COCH_3$ | $SFCl_2$ | H |
| Br | H | $CF_2$ | O | $CF_2$ | H | $SFCl_2$ | H |
| Br | H | $CF_2$ | O | $CF_2$ | $NH_2$ | $SFCl_2$ | H |
| Br | H | $CF_2$ | O | $CF_2$ | N = CHPh | $SFCl_2$ | H |
| Br | H | $CF_2$ | O | $CF_2$ | $CH_3$ | $SFCl_2$ | H |
| Br | H | $CF_2$ | O | $CF_2$ | $CF_3$ | $SFCl_2$ | H |
| Br | H | $CF_2$ | O | $CF_2$ | Cl | $SFCl_2$ | H |
| Br | H | $CF_2$ | O | $CF_2$ | F | $SFCl_2$ | H |
| Br | H | $CF_2$ | O | $CF_2$ | $COCH_3$ | $SFCl_2$ | H |
| Br | H | $CF_2$ | O | $CF_2$ | H | $SCF_3$ | $CF_3$ |
| Br | H | $CF_2$ | O | $CF_2$ | $NH_2$ | $SCF_3$ | $CF_3$ |
| Br | H | $CF_2$ | O | $CF_2$ | N = CHPh | $SCF_3$ | $CF_3$ |
| Br | H | $CF_2$ | O | $CF_2$ | $CH_3$ | $SCF_3$ | $CF_3$ |
| Br | H | $CF_2$ | O | $CF_2$ | $CF_3$ | $SCF_3$ | $CF_3$ |
| Br | H | $CF_2$ | O | $CF_2$ | Cl | $SCF_3$ | $CF_3$ |
| Br | H | $CF_2$ | O | $CF_2$ | F | $SCF_3$ | $CF_3$ |
| Br | H | $CF_2$ | O | $CF_2$ | $COCH_3$ | $SCF_3$ | $CF_3$ |
| Br | H | $CF_2$ | O | $CF_2$ | H | $SOCF_3$ | $CF_3$ |
| Br | H | $CF_2$ | O | $CF_2$ | $NH_2$ | $SOCF_3$ | $CF_3$ |
| Br | H | $CF_2$ | O | $CF_2$ | N = CHPh | $SOCF_3$ | $CF_3$ |
| Br | H | $CF_2$ | O | $CF_2$ | $CH_3$ | $SOCF_3$ | $CF_3$ |
| Br | H | $CF_2$ | O | $CF_2$ | $CF_3$ | $SOCF_3$ | $CF_3$ |
| Br | H | $CF_2$ | O | $CF_2$ | Cl | $SOCF_3$ | $CF_3$ |
| Br | H | $CF_2$ | O | $CF_2$ | F | $SOCF_3$ | $CF_3$ |
| Br | H | $CF_2$ | O | $CF_2$ | $COCH_3$ | $SOCF_3$ | $CF_3$ |

TABLE 41

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | H | $SO_2CF_3$ | $CF_3$ |
| Br | H | $CF_2$ | O | $CF_2$ | $NH_2$ | $SO_2CF_3$ | $CF_3$ |
| Br | H | $CF_2$ | O | $CF_2$ | N = CHPh | $SO_2CF_3$ | $CF_3$ |
| Br | H | $CF_2$ | O | $CF_2$ | $CH_3$ | $SO_2CF_3$ | $CF_3$ |
| Br | H | $CF_2$ | O | $CF_2$ | $CF_3$ | $SO_2CF_3$ | $CF_3$ |
| Br | H | $CF_2$ | O | $CF_2$ | Cl | $SO_2CF_3$ | $CF_3$ |
| Br | H | $CF_2$ | O | $CF_2$ | F | $SO_2CF_3$ | $CF_3$ |
| Br | H | $CF_2$ | O | $CF_2$ | $COCH_3$ | $SO_2CF_3$ | $CF_3$ |
| Br | H | $CF_2$ | O | $CF_2$ | H | $SCF_2CH_3$ | $CF_3$ |
| Br | H | $CF_2$ | O | $CF_2$ | $NH_2$ | $SCF_2CH_3$ | $CF_3$ |
| Br | H | $CF_2$ | O | $CF_2$ | N = CHPh | $SCF_2CH_3$ | $CF_3$ |
| Br | H | $CF_2$ | O | $CF_2$ | $CH_3$ | $SCF_2CH_3$ | $CF_3$ |
| Br | H | $CF_2$ | O | $CF_2$ | $CF_3$ | $SCF_2CH_3$ | $CF_3$ |
| Br | H | $CF_2$ | O | $CF_2$ | Cl | $SCF_2CH_3$ | $CF_3$ |
| Br | H | $CF_2$ | O | $CF_2$ | F | $SCF_2CH_3$ | $CF_3$ |
| Br | H | $CF_2$ | O | $CF_2$ | $COCH_3$ | $SCF_2CH_3$ | $CF_3$ |
| Br | H | $CF_2$ | O | $CF_2$ | H | $SOCF_2CH_3$ | $CF_3$ |
| Br | H | $CF_2$ | O | $CF_2$ | $NH_2$ | $SOCF_2CH_3$ | $CF_3$ |
| Br | H | $CF_2$ | O | $CF_2$ | N = CHPh | $SOCF_2CH_3$ | $CF_3$ |
| Br | H | $CF_2$ | O | $CF_2$ | $CH_3$ | $SOCF_2CH_3$ | $CF_3$ |

TABLE 41-continued

| X | Y | Z¹ | Z² | Z³ | R¹ | R² | R³ |
|---|---|---|---|---|---|---|---|
| Br | H | $CF_2$ | O | $CF_2$ | $CF_3$ | $SOCF_2CH_3$ | $CF_3$ |
| Br | H | $CF_2$ | O | $CF_2$ | Cl | $SOCF_2CH_3$ | $CF_3$ |
| Br | H | $CF_2$ | O | $CF_2$ | F | $SOCF_2CH_3$ | $CF_3$ |
| Br | H | $CF_2$ | O | $CF_2$ | $COCH_3$ | $SOCF_2CH_3$ | $CF_3$ |
| Br | H | $CF_2$ | O | $CF_2$ | H | $SO_2CF_2CH_3$ | $CF_3$ |
| Br | H | $CF_2$ | O | $CF_2$ | $NH_2$ | $SO_2CF_2CH_3$ | $CF_3$ |

TABLE 42

| X | Y | Z¹ | Z² | Z³ | R¹ | R² | R³ |
|---|---|---|---|---|---|---|---|
| Br | H | $CF_2$ | O | $CF_2$ | N=CHPh | $SO_2CF_2CH_3$ | $CF_3$ |
| Br | H | $CF_2$ | O | $CF_2$ | $CH_3$ | $SO_2CF_2CH_3$ | $CF_3$ |
| Br | H | $CF_2$ | O | $CF_2$ | $CF_3$ | $SO_2CF_2CH_3$ | $CF_3$ |
| Br | H | $CF_2$ | C | $CF_2$ | Cl | $SO_2CF_2CH_3$ | $CF_3$ |
| Br | H | $CF_2$ | O | $CF_2$ | F | $SO_2CF_2CH_3$ | $CF_3$ |
| Br | H | $CF_2$ | O | $CF_2$ | $COCH_3$ | $SO_2CF_2CH_3$ | $CF_3$ |
| Br | H | $CF_2$ | O | $CF_2$ | $NH_2$ | $COCF_3$ | $CF_3$ |
| Br | H | $CF_2$ | O | $CF_2$ | N = CHPh | $COCF_3$ | $CF_3$ |
| Br | H | $CF_2$ | O | $CF_2$ | $CH_3$ | $COCF_3$ | $CF_3$ |
| Br | H | $CF_2$ | O | $CF_2$ | $CF_3$ | $COCF_3$ | $CF_3$ |
| Br | H | $CF_2$ | O | $CF_2$ | Cl | $COCF_3$ | $CF_3$ |
| Br | H | $CF_2$ | O | $CF_2$ | F | $COCF_3$ | $CF_3$ |
| Br | H | $CF_2$ | O | $CF_2$ | $COCH_3$ | $COCF_3$ | $CF_3$ |
| Br | H | $CF_2$ | O | $CF_2$ | H | $COCF_3$ | $CF_3$ |
| Br | H | $CF_2$ | O | $CF_2$ | $NH_2$ | $COCF_3$ | $CF_3$ |
| Br | H | $CF_2$ | O | $CF_2$ | N = CHPh | $COCF_3$ | $CF_3$ |
| Br | H | $CF_2$ | O | $CF_2$ | $CH_3$ | $COCF_3$ | $CF_3$ |
| Br | H | $CF_2$ | O | $CF_2$ | $CF_3$ | $COCF_3$ | $CF_3$ |
| Br | H | $CF_2$ | O | $CF_2$ | Cl | $COCF_3$ | $CF_3$ |
| Br | H | $CF_2$ | O | $CF_2$ | F | $COCF_3$ | $CF_3$ |
| Br | H | $CF_2$ | O | $CF_2$ | $COCH_3$ | $COCF_3$ | $CF_3$ |
| Br | H | $CF_2$ | O | $CF_2$ | $NH_2$ | $C_2F_5$ | $CF_3$ |
| Br | H | $CF_2$ | O | $CF_2$ | N = CHPh | $C_2F_5$ | $CF_3$ |
| Br | H | $CF_2$ | O | $CF_2$ | $CH_3$ | $C_2F_5$ | $CF_3$ |
| Br | H | $CF_2$ | O | $CF_2$ | $CF_3$ | $C_2F_5$ | $CF_3$ |
| Br | H | $CF_2$ | O | $CF_2$ | Cl | $C_2F_5$ | $CF_3$ |

TABLE 43

| X | Y | Z¹ | Z² | Z³ | R¹ | R² | R³ |
|---|---|---|---|---|---|---|---|
| Br | H | $CF_2$ | O | $CF_2$ | F | $C_2F_5$ | $CF_3$ |
| Br | H | $CF_2$ | O | $CF_2$ | $COCH_3$ | $C_2F_5$ | $CF_3$ |
| Br | H | $CF_2$ | O | $CF_2$ | H | $C_2F_5$ | $CF_3$ |
| Br | H | $CF_2$ | O | $CF_2$ | $NH_2$ | $C_2F_5$ | $CF_3$ |
| Br | H | $CF_2$ | O | $CF_2$ | N = CHPh | $C_2F_5$ | $CF_3$ |
| Br | H | $CF_2$ | O | $CF_2$ | $CH_3$ | $C_2F_5$ | $CF_3$ |
| Br | H | $CF_2$ | O | $CF_2$ | $CF_3$ | $C_2F_5$ | $CF_3$ |
| Br | H | $CF_2$ | O | $CF_2$ | Cl | $C_2F_5$ | $CF_3$ |
| Br | H | $CF_2$ | O | $CF_2$ | F | $C_2F_5$ | $CF_3$ |
| Br | H | $CF_2$ | O | $CF_2$ | $COCH_3$ | $C_2F_5$ | $CF_3$ |
| Br | H | $CF_2$ | O | $CF_2$ | $NH_2$ | $SFCl_2$ | $CF_3$ |
| Br | H | $CF_2$ | O | $CF_2$ | N = CHPh | $SFCl_2$ | $CF_3$ |
| Br | H | $CF_2$ | O | $CF_2$ | $CH_3$ | $SFCl_2$ | $CF_3$ |
| Br | H | $CF_2$ | O | $CF_2$ | $CF_3$ | $SFCl_2$ | $CF_3$ |
| Br | H | $CF_2$ | O | $CF_2$ | Cl | $SFCl_2$ | $CF_3$ |
| Br | H | $CF_2$ | O | $CF_2$ | F | $SFCl_2$ | $CF_3$ |
| Br | H | $CF_2$ | O | $CF_2$ | $COCH_3$ | $SFCl_2$ | $CF_3$ |
| Br | H | $CF_2$ | O | $CF_2$ | H | $SFCl_2$ | $CF_3$ |
| Br | H | $CF_2$ | O | $CF_2$ | $NH_2$ | $SFCl_2$ | $CF_3$ |
| Br | H | $CF_2$ | O | $CF_2$ | N = CHPh | $SFCl_2$ | $CF_3$ |
| Br | H | $CF_2$ | O | $CF_2$ | $CH_3$ | $SFCl_2$ | $CF_3$ |
| Br | H | $CF_2$ | O | $CF_2$ | $CF_3$ | $SFCl_2$ | $CF_3$ |
| Br | H | $CF_2$ | O | $CF_2$ | Cl | $SFCl_2$ | $CF_3$ |
| Br | H | $CF_2$ | O | $CF_2$ | F | $SFCl_2$ | $CF_3$ |
| Br | H | $CF_2$ | O | $CF_2$ | $COCH_3$ | $SFCl_2$ | $CF_3$ |
| Br | H | $CF_2$ | O | $CF_2$ | H | $SCF_3$ | $C_2F_5$ |

TABLE 44

| X | Y | Z¹ | Z² | Z³ | R¹ | R² | R³ |
|---|---|---|---|---|---|---|---|
| Br | H | $CF_2$ | O | $CF_2$ | $NH_2$ | $SCF_3$ | $C_2F_5$ |
| Br | H | $CF_2$ | O | $CF_2$ | N = CHPh | $SCF_3$ | $C_2F_5$ |
| Br | H | $CF_2$ | O | $CF_2$ | $CH_3$ | $SCF_3$ | $C_2F_5$ |
| Br | H | $CF_2$ | O | $CF_2$ | $CF_3$ | $SCF_3$ | $C_2F_5$ |
| Br | H | $CF_2$ | O | $CF_2$ | Cl | $SCF_3$ | $C_2F_5$ |
| Br | H | $CF_2$ | O | $CF_2$ | F | $SCF_3$ | $C_2F_5$ |
| Br | H | $CF_2$ | O | $CF_2$ | $COCH_3$ | $SCF_3$ | $C_2F_5$ |
| Br | H | $CF_2$ | O | $CF_2$ | H | $SOCF_3$ | $C_2F_5$ |
| Br | H | $CF_2$ | O | $CF_2$ | $NH_2$ | $SOCF_3$ | $C_2F_5$ |
| Br | H | $CF_2$ | O | $CF_2$ | N = CHPh | $SOCF_3$ | $C_2F_5$ |
| Br | H | $CF_2$ | O | $CF_2$ | $CH_3$ | $SOCF_3$ | $C_2F_5$ |
| Br | H | $CF_2$ | O | $CF_2$ | $CF_3$ | $SOCF_3$ | $C_2F_5$ |
| Br | H | $CF_2$ | O | $CF_2$ | Cl | $SOCF_3$ | $C_2F_5$ |
| Br | H | $CF_2$ | O | $CF_2$ | F | $SOCF_3$ | $C_2F_5$ |
| Br | H | $CF_2$ | O | $CF_2$ | $COCH_3$ | $SOCF_3$ | $C_2F_5$ |
| Br | H | $CF_2$ | O | $CF_2$ | H | $SO_2CF_3$ | $C_2F_5$ |
| Br | H | $CF_2$ | O | $CF_2$ | $NH_2$ | $SO_2CF_3$ | $C_2F_5$ |
| Br | H | $CF_2$ | O | $CF_2$ | N = CHPh | $SO_2CF_3$ | $C_2F_5$ |
| Br | H | $CF_2$ | O | $CF_2$ | $CH_3$ | $SO_2CF_3$ | $C_2F_5$ |
| Br | H | $CF_2$ | O | $CF_2$ | $CF_3$ | $SO_2CF_3$ | $C_2F_5$ |
| Br | H | $CF_2$ | O | $CF_2$ | Cl | $SO_2CF_3$ | $C_2F_5$ |
| Br | H | $CF_2$ | O | $CF_2$ | F | $SO_2CF_3$ | $C_2F_5$ |
| Br | H | $CF_2$ | O | $CF_2$ | $COCH_3$ | $SO_2CF_3$ | $C_2F_5$ |
| Br | H | $CF_2$ | O | $CF_2$ | H | $SCF_2CH_3$ | $C_2F_5$ |
| Br | H | $CF_2$ | O | $CF_2$ | $NH_2$ | $SCF_2CH_3$ | $C_2F_5$ |
| Br | H | $CF_2$ | O | $CF_2$ | N = CHPh | $SCF_2CH_3$ | $C_2F_5$ |

TABLE 45

| X | Y | Z¹ | Z² | Z³ | R¹ | R² | R³ |
|---|---|---|---|---|---|---|---|
| Br | H | $CF_2$ | O | $CF_2$ | $CH_3$ | $SCF_2CH_3$ | $C_2F_5$ |
| Br | H | $CF_2$ | O | $CF_2$ | $CF_3$ | $SCF_2CH_3$ | $C_2F_5$ |
| Br | H | $CF_2$ | O | $CF_2$ | Cl | $SCF_2CH_3$ | $C_2F_5$ |
| Br | H | $CF_2$ | O | $CF_2$ | F | $SCF_2CH_3$ | $C_2F_5$ |
| Br | H | $CF_2$ | O | $CF_2$ | $COCH_3$ | $SCF_2CH_3$ | $C_2F_5$ |
| Br | H | $CF_2$ | O | $CF_2$ | H | $SOCF_2CH_3$ | $C_2F_5$ |
| Br | H | $CF_2$ | O | $CF_2$ | $NH_2$ | $SOCF_2CH_3$ | $C_2F_5$ |
| Br | H | $CF_2$ | O | $CF_2$ | N = CHPh | $SOCF_2CH_3$ | $C_2F_5$ |
| Br | H | $CF_2$ | O | $CF_2$ | $CH_3$ | $SOCF_2CH_3$ | $C_2F_5$ |
| Br | H | $CF_2$ | O | $CF_2$ | $CF_3$ | $SOCF_2CH_3$ | $C_2F_5$ |
| Br | H | $CF_2$ | O | $CF_2$ | Cl | $SOCF_2CH_3$ | $C_2F_5$ |
| Br | H | $CF_2$ | O | $CF_2$ | F | $SOCF_2CH_3$ | $C_2F_5$ |
| Br | H | $CF_2$ | O | $CF_2$ | $COCH_3$ | $SOCF_2CH_3$ | $C_2F_5$ |
| Br | H | $CF_2$ | O | $CF_2$ | H | $SO_2CF_2CH_3$ | $C_2F_5$ |
| Br | H | $CF_2$ | O | $CF_2$ | $NH_2$ | $SO_2CF_2CH_3$ | $C_2F_5$ |
| Br | H | $CF_2$ | O | $CF_2$ | N = CHPh | $SO_2CF_2CH_3$ | $C_2F_5$ |
| Br | H | $CF_2$ | O | $CF_2$ | $CH_3$ | $SO_2CF_2CH_3$ | $C_2F_5$ |
| Br | H | $CF_2$ | O | $CF_2$ | $CF_3$ | $SO_2CF_2CH_3$ | $C_2F_5$ |
| Br | H | $CF_2$ | O | $CF_2$ | Cl | $SO_2CF_2CH_3$ | $C_2F_5$ |
| Br | H | $CF_2$ | O | $CF_2$ | F | $SO_2CF_2CH_3$ | $C_2F_5$ |
| Br | H | $CF_2$ | O | $CF_2$ | $COCH_3$ | $SO_2CF_2CH_3$ | $C_2F_5$ |
| Br | H | $CF_2$ | O | $CF_2$ | $NH_2$ | $COCF_3$ | $C_2F_5$ |
| Br | H | $CF_2$ | O | $CF_2$ | N = CHPh | $COCF_3$ | $C_2F_5$ |
| Br | H | $CF_2$ | O | $CF_2$ | $CH_3$ | $COCF_3$ | $C_2F_5$ |
| Br | H | $CF_2$ | O | $CF_2$ | $CF_3$ | $COCF_3$ | $C_2F_5$ |
| Br | H | $CF_2$ | O | $CF_2$ | Cl | $COCF_3$ | $C_2F_5$ |

TABLE 46

| X | Y | Z¹ | Z² | Z³ | R¹ | R² | R³ |
|---|---|---|---|---|---|---|---|
| Br | H | $CF_2$ | O | $CF_2$ | F | $COCF_3$ | $C_2F_5$ |
| Br | H | $CF_2$ | O | $CF_2$ | $COCH_3$ | $COCF_3$ | $C_2F_5$ |
| Br | H | $CF_2$ | O | $CF_2$ | H | $COCF_3$ | $C_2F_5$ |
| Br | H | $CF_2$ | O | $CF_2$ | $NH_2$ | $COCF_3$ | $C_2F_5$ |
| Br | H | $CF_2$ | O | $CF_2$ | N = CHPh | $COCF_3$ | $C_2F_5$ |
| Br | H | $CF_2$ | O | $CF_2$ | $CH_3$ | $COCF_3$ | $C_2F_5$ |
| Br | H | $CF_2$ | O | $CF_2$ | $CF_3$ | $COCF_3$ | $C_2F_5$ |
| Br | H | $CF_2$ | O | $CF_2$ | Cl | $COCF_3$ | $C_2F_5$ |
| Br | H | $CF_2$ | O | $CF_2$ | F | $COCF_3$ | $C_2F_5$ |
| Br | H | $CF_2$ | O | $CF_2$ | $COCH_3$ | $COCF_3$ | $C_2F_5$ |

TABLE 46-continued

| X  | Y | Z¹  | Z² | Z³  | R¹      | R²      | R³      |
|----|---|-----|----|-----|---------|---------|---------|
| Br | H | CF₂ | O  | CF₂ | NH₂     | C₂F₅    | C₂F₅    |
| Br | H | CF₂ | O  | CF₂ | N = CHPh| C₂F₅    | C₂F₅    |
| Br | H | CF₂ | O  | CF₂ | CH₃     | C₂F₅    | C₂F₅    |
| Br | H | CF₂ | O  | CF₂ | CF₃     | C₂F₅    | C₂F₅    |
| Br | H | CF₂ | O  | CF₂ | Cl      | C₂F₅    | C₂F₅    |
| Br | H | CF₂ | O  | CF₂ | F       | C₂F₅    | C₂F₅    |
| Br | H | CF₂ | O  | CF₂ | COCH₃   | C₂F₅    | C₂F₅    |
| Br | H | CF₂ | O  | CF₂ | H       | C₂F₅    | C₂F₅    |
| Br | H | CF₂ | O  | CF₂ | NH₂     | C₂F₅    | C₂F₅    |
| Br | H | CF₂ | O  | CF₂ | N = CHPh| C₂F₅    | C₂F₅    |
| Br | H | CF₂ | O  | CF₂ | CH₃     | C₂F₅    | C₂F₅    |
| Br | H | CF₂ | O  | CF₂ | CF₃     | C₂F₅    | C₂F₅    |
| Br | H | CF₂ | O  | CF₂ | Cl      | C₂F₅    | C₂F₅    |
| Br | H | CF₂ | O  | CF₂ | F       | C₂F₅    | C₂F₅    |
| Br | H | CF₂ | O  | CF₂ | COCH₃   | C₂F₅    | C₂F₅    |
| Br | H | CF₂ | O  | CF₂ | NH₂     | SFCl₂   | C₂F₅    |

TABLE 47

| X  | Y | Z¹  | Z² | Z³  | R¹       | R²     | R³    |
|----|---|-----|----|-----|----------|--------|-------|
| Br | H | CF₂ | O  | CF₂ | N = CHPh | SFCl₂  | C₂F₅  |
| Br | H | CF₂ | O  | CF₂ | CH₃      | SFCl₂  | C₂F₅  |
| Br | H | CF₂ | O  | CF₂ | CF₃      | SFCl₂  | C₂F₅  |
| Br | H | CF₂ | O  | CF₂ | Cl       | SFCl₂  | C₂F₅  |
| Br | H | CF₂ | O  | CF₂ | F        | SFCl₂  | C₂F₅  |
| Br | H | CF₂ | O  | CF₂ | COCH₃    | SFCl₂  | C₂F₅  |
| Br | H | CF₂ | O  | CF₂ | H        | SFCl₂  | C₂F₅  |
| Br | H | CF₂ | O  | CF₂ | NH₂      | SFCl₂  | C₂F₅  |
| Br | H | CF₂ | O  | CF₂ | N = CHPh | SFCl₂  | C₂F₅  |
| Br | H | CF₂ | O  | CF₂ | CH₃      | SFCl₂  | C₂F₅  |
| Br | H | CF₂ | O  | CF₂ | CF₃      | SFCl₂  | C₂F₅  |
| Br | H | CF₂ | O  | CF₂ | Cl       | SFCl₂  | C₂F₅  |
| Br | H | CF₂ | O  | CF₂ | F        | SFCl₂  | C₂F₅  |
| Br | H | CF₂ | O  | CF₂ | COCH₃    | SFCl₂  | C₂F₅  |
| Br | H | CF₂ | O  | CF₂ | H        | SCF₃   | CSNH₂ |
| Br | H | CF₂ | O  | CF₂ | NH₂      | SCF₃   | CSNH₂ |
| Br | H | CF₂ | O  | CF₂ | N = CHPh | SCF₃   | CSNH₂ |
| Br | H | CF₂ | O  | CF₂ | CH₃      | SCF₃   | CSNH₂ |
| Br | H | CF₂ | O  | CF₂ | CF₃      | SCF₃   | CSNH₂ |
| Br | H | CF₂ | O  | CF₂ | Cl       | SCF₃   | CSNH₂ |
| Br | H | CF₂ | O  | CF₂ | F        | SCF₃   | CSNH₂ |
| Br | H | CF₂ | O  | CF₂ | COCH₃    | SCF₃   | CSNH₂ |
| Br | H | CF₂ | O  | CF₂ | H        | SOCF₃  | CSNH₂ |
| Br | H | CF₂ | O  | CF₂ | NH₂      | SOCF₃  | CSNH₂ |
| Br | H | CF₂ | O  | CF₂ | N = CHPh | SOCF₃  | CSNH₂ |
| Br | H | CF₂ | O  | CF₂ | CH₃      | SOCF₃  | CSNH₂ |

TABLE 48

| X  | Y | Z¹  | Z² | Z³  | R¹       | R²                   | R³    |
|----|---|-----|----|-----|----------|----------------------|-------|
| Br | H | CF₂ | O  | CF₂ | CF₃      | SOCF₃                | CSNH₂ |
| Br | H | CF₂ | O  | CF₂ | Cl       | SOCF₃                | CSNH₂ |
| Br | H | CF₂ | O  | CF₂ | F        | SOCF₃                | CSNH₂ |
| Br | H | CF₂ | O  | CF₂ | COCH₃    | SOCF₃                | CSNH₂ |
| Br | H | CF₂ | O  | CF₂ | H        | SO₂CF₃               | CSNH₂ |
| Br | H | CF₂ | O  | CF₂ | NH₂      | SO₂CF₃               | CSNH₂ |
| Br | H | CF₂ | O  | CF₂ | N = CHPh | SO₂CF₃               | CSNH₂ |
| Br | H | CF₂ | O  | CF₂ | CH₃      | SO₂CF₃               | CSNH₂ |
| Br | H | CF₂ | O  | CF₂ | CF₃      | SO₂CF₃               | CSNH₂ |
| Br | H | CF₂ | O  | CF₂ | Cl       | SO₂CF₃               | CSNH₂ |
| Br | H | CF₂ | O  | CF₂ | F        | SO₂CF₃               | CSNH₂ |
| Br | H | CF₂ | O  | CF₂ | COCH₃    | SO₂CF₃               | CSNH₂ |
| Br | H | CF₂ | O  | CF₂ | H        | SCF₂CH₃              | CSNH₂ |
| Br | H | CF₂ | O  | CF₂ | NH₂      | SCF₂CH₃              | CSNH₂ |
| Br | H | CF₂ | O  | CF₂ | N = CHPh | SCF₂CH₃              | CSNH₂ |
| Br | H | CF₂ | O  | CF₂ | CH₃      | SCF₂CH₃              | CSNH₂ |
| Br | H | CF₂ | O  | CF₂ | CF₃      | SCF₂CH₃              | CSNH₂ |
| Br | H | CF₂ | O  | CF₂ | Cl       | SCF₂CH₃              | CSNH₂ |
| Br | H | CF₂ | O  | CF₂ | F        | SCF₂CH₃              | CSNH₂ |
| Br | H | CF₂ | O  | CF₂ | COCH₃    | SCF₂CH₃              | CSNH₂ |

TABLE 48-continued

| X  | Y | Z¹  | Z² | Z³  | R¹       | R²        | R³    |
|----|---|-----|----|-----|----------|-----------|-------|
| Br | H | CF₂ | O  | CF₂ | H        | SOCF₂CH₃  | CSNH₂ |
| Br | H | CF₂ | O  | CF₂ | NH₂      | SOCF₂CH₃  | CSNH₂ |
| Br | H | CF₂ | O  | CF₂ | N = CHPh | SOCF₂CH₃  | CSNH₂ |
| Br | H | CF₂ | O  | CF₂ | CH₃      | SOCF₂CH₃  | CSNH₂ |
| Br | H | CF₂ | O  | CF₂ | CF₃      | SOCF₂CH₃  | CSNH₂ |
| Br | H | CF₂ | O  | CF₂ | Cl       | SOCF₂CH₃  | CSNH₂ |

TABLE 49

| X  | Y | Z¹  | Z² | Z³  | R¹       | R²        | R³    |
|----|---|-----|----|-----|----------|-----------|-------|
| Br | H | CF₂ | O  | CF₂ | F        | SOCF₂CH₃  | CSNH₂ |
| Br | H | CF₂ | O  | CF₂ | COCH₃    | SOCF₂CH₃  | CSNH₂ |
| Br | H | CF₂ | O  | CF₂ | H        | SO₂CF₂CH₃ | CSNH₂ |
| Br | H | CF₂ | O  | CF₂ | NH₂      | SO₂CF₂CH₃ | CSNH₂ |
| Br | H | CF₂ | O  | CF₂ | N = CHPh | SO₂CF₂CH₃ | CSNH₂ |
| Br | H | CF₂ | O  | CF₂ | CH₃      | SO₂CF₂CH₃ | CSNH₂ |
| Br | H | CF₂ | O  | CF₂ | CF₃      | SO₂CF₂CH₃ | CSNH₂ |
| Br | H | CF₂ | O  | CF₂ | Cl       | SO₂CF₂CH₃ | CSNH₂ |
| Br | H | CF₂ | O  | CF₂ | F        | SO₂CF₂CH₃ | CSNH₂ |
| Br | H | CF₂ | O  | CF₂ | COCH₃    | SO₂CF₂CH₃ | CSNH₂ |
| Br | H | CF₂ | O  | CF₂ | NH₂      | COCF₃     | CSNH₂ |
| Br | H | CF₂ | O  | CF₂ | N = CHPh | COCF₃     | CSNH₂ |
| Br | H | CF₂ | O  | CF₂ | CH₃      | COCF₃     | CSNH₂ |
| Br | H | CF₂ | O  | CF₂ | CF₃      | COCF₃     | CSNH₂ |
| Br | H | CF₂ | O  | CF₂ | Cl       | COCF₃     | CSNH₂ |
| Br | H | CF₂ | O  | CF₂ | F        | COCF₃     | CSNH₂ |
| Br | H | CF₂ | O  | CF₂ | COCH₃    | COCF₃     | CSNH₂ |
| Br | H | CF₂ | O  | CF₂ | H        | COCF₃     | CSNH₂ |
| Br | H | CF₂ | O  | CF₂ | NH₂      | COCF₃     | CSNH₂ |
| Br | H | CF₂ | O  | CF₂ | N = CHPh | COCF₃     | CSNH₂ |
| Br | H | CF₂ | O  | CF₂ | CH₃      | COCF₃     | CSNH₂ |
| Br | H | CF₂ | O  | CF₂ | CF₃      | COCF₃     | CSNH₂ |
| Br | H | CF₂ | O  | CF₂ | Cl       | COCF₃     | CSNH₂ |
| Br | H | CF₂ | O  | CF₂ | F        | COCF₃     | CSNH₂ |
| Br | H | CF₂ | O  | CF₂ | COCH₃    | COCF₃     | CSNH₂ |
| Br | H | CF₂ | O  | CF₂ | NH₂      | C₂F₅      | CSNH₂ |

TABLE 50

| X  | Y | Z¹  | Z² | Z³  | R¹       | R²     | R³    |
|----|---|-----|----|-----|----------|--------|-------|
| Br | H | CF₂ | O  | CF₂ | N = CHPh | C₂F₅   | CSNH₂ |
| Br | H | CF₂ | O  | CF₂ | CH₃      | C₂F₅   | CSNH₂ |
| Br | H | CF₂ | O  | CF₂ | CF₃      | C₂F₅   | CSNH₂ |
| Br | H | CF₂ | O  | CF₂ | Cl       | C₂F₅   | CSNH₂ |
| Br | H | CF₂ | O  | CF₂ | F        | C₂F₅   | CSNH₂ |
| Br | H | CF₂ | O  | CF₂ | COCH₃    | C₂F₅   | CSNH₂ |
| Br | H | CF₂ | O  | CF₂ | H        | C₂F₅   | CSNH₂ |
| Br | H | CF₂ | O  | CF₂ | NH₂      | C₂F₅   | CSNH₂ |
| Br | H | CF₂ | O  | CF₂ | N = CHPh | C₂F₅   | CSNH₂ |
| Br | H | CF₂ | O  | CF₂ | CH₃      | C₂F₅   | CSNH₂ |
| Br | H | CF₂ | O  | CF₂ | CF₃      | C₂F₅   | CSNH₂ |
| Br | H | CF₂ | O  | CF₂ | Cl       | C₂F₅   | CSNH₂ |
| Br | H | CF₂ | O  | CF₂ | F        | C₂F₅   | CSNH₂ |
| Br | H | CF₂ | O  | CF₂ | COCH₃    | C₂F₅   | CSNH₂ |
| Br | H | CF₂ | O  | CF₂ | NH₂      | SFCl₂  | CSNH₂ |
| Br | H | CF₂ | O  | CF₂ | N = CHPh | SFCl₂  | CSNH₂ |
| Br | H | CF₂ | O  | CF₂ | CH₃      | SFCl₂  | CSNH₂ |
| Br | H | CF₂ | O  | CF₂ | CF₃      | SFCl₂  | CSNH₂ |
| Br | H | CF₂ | O  | CF₂ | Cl       | SFCl₂  | CSNH₂ |
| Br | H | CF₂ | O  | CF₂ | F        | SFCl₂  | CSNH₂ |
| Br | H | CF₂ | O  | CF₂ | COCH₃    | SFCl₂  | CSNH₂ |
| Br | H | CF₂ | O  | CF₂ | H        | SFCl₂  | CSNH₂ |
| Br | H | CF₂ | O  | CF₂ | NH₂      | SFCl₂  | CSNH₂ |
| Br | H | CF₂ | O  | CF₂ | N = CHPh | SFCl₂  | CSNH₂ |
| Br | H | CF₂ | O  | CF₂ | CH₃      | SFCl₂  | CSNH₂ |
| Br | H | CF₂ | O  | CF₂ | CF₃      | SFCl₂  | CSNH₂ |

TABLE 51

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | Cl | $SFCl_2$ | $CSNH_2$ |
| Br | H | $CF_2$ | O | $CF_2$ | F | $SFCl_2$ | $CSNH_2$ |
| Br | H | $CF_2$ | O | $CF_2$ | $COCH_3$ | $SFCl_2$ | $CSNH_2$ |
| Br | H | $CF_2$ | O | $CF_2$ | H | $SCF_3$ | CN |
| Br | H | $CF_2$ | O | $CF_2$ | $NH_2$ | $SCF_3$ | CN |
| Br | H | $CF_2$ | O | $CF_2$ | N = CHPh | $SCF_3$ | CN |
| Br | H | $CF_2$ | O | $CF_2$ | $CH_3$ | $SCF_3$ | CN |
| Br | H | $CF_2$ | O | $CF_2$ | $CF_3$ | $SCF_3$ | CN |
| Br | H | $CF_2$ | O | $CF_2$ | Cl | $SCF_3$ | CN |
| Br | H | $CF_2$ | O | $CF_2$ | F | $SCF_3$ | CN |
| Br | H | $CF_2$ | O | $CF_2$ | $COCH_3$ | $SCF_3$ | CN |
| Br | H | $CF_2$ | O | $CF_2$ | H | $SOCF_3$ | CN |
| Br | H | $CF_2$ | O | $CF_2$ | $NH_2$ | $SOCF_3$ | CN |
| Br | H | $CF_2$ | O | $CF_2$ | N = CHPh | $SOCF_3$ | CN |
| Br | H | $CF_2$ | O | $CF_2$ | $CH_3$ | $SOCF_3$ | CN |
| Br | H | $CF_2$ | O | $CF_2$ | $CF_3$ | $SOCF_3$ | CN |
| Br | H | $CF_2$ | O | $CF_2$ | Cl | $SOCF_3$ | CN |
| Br | H | $CF_2$ | O | $CF_2$ | F | $SOCF_3$ | CN |
| Br | H | $CF_2$ | O | $CF_2$ | $COCH_3$ | $SOCF_3$ | CN |
| Br | H | $CF_2$ | O | $CF_2$ | H | $SO_2CF_3$ | CN |
| Br | H | $CF_2$ | O | $CF_2$ | $NH_2$ | $SO_2CF_3$ | CN |
| Br | H | $CF_2$ | O | $CF_2$ | N = CHPh | $SO_2CF_3$ | CN |
| Br | H | $CF_2$ | O | $CF_2$ | $CH_3$ | $SO_2CF_3$ | CN |
| Br | H | $CF_2$ | O | $CF_2$ | $CF_3$ | $SO_2CF_3$ | CN |
| Br | H | $CF_2$ | O | $CF_2$ | Cl | $SO_2CF_3$ | CN |
| Br | H | $CF_2$ | O | $CF_2$ | F | $SO_2CF_3$ | CN |

TABLE 52

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | $COCH_3$ | $SO_2CF_3$ | CN |
| Br | H | $CF_2$ | O | $CF_2$ | H | $SCF_2CH_3$ | CN |
| Br | H | $CF_2$ | O | $CF_2$ | $NH_2$ | $SCF_2CH_3$ | CN |
| Br | H | $CF_2$ | O | $CF_2$ | N = CHPh | $SCF_2CH_3$ | CN |
| Br | H | $CF_2$ | O | $CF_2$ | $CH_3$ | $SCF_2CH_3$ | CN |
| Br | H | $CF_2$ | O | $CF_2$ | $CF_3$ | $SCF_2CH_3$ | CN |
| Br | H | $CF_2$ | O | $CF_2$ | Cl | $SCF_2CH_3$ | CN |
| Br | H | $CF_2$ | O | $CF_2$ | F | $SCF_2CH_3$ | CN |
| Br | H | $CF_2$ | O | $CF_2$ | $COCH_3$ | $SCF_2CH_3$ | CN |
| Br | H | $CF_2$ | O | $CF_2$ | H | $SOCF_2CH_3$ | CN |
| Br | H | $CF_2$ | O | $CF_2$ | $NH_2$ | $SOCF_2CH_3$ | CN |
| Br | H | $CF_2$ | O | $CF_2$ | N = CHPh | $SOCF_2CH_3$ | CN |
| Br | H | $CF_2$ | O | $CF_2$ | $CH_3$ | $SOCF_2CH_3$ | CN |
| Br | H | $CF_2$ | O | $CF_2$ | $CF_3$ | $SOCF_2CH_3$ | CN |
| Br | H | $CF_2$ | O | $CF_2$ | Cl | $SOCF_2CH_3$ | CN |
| Br | H | $CF_2$ | O | $CF_2$ | F | $SOCF_2CH_3$ | CN |
| Br | H | $CF_2$ | O | $CF_2$ | $COCH_3$ | $SOCF_2CH_3$ | CN |
| Br | H | $CF_2$ | O | $CF_2$ | H | $SO_2CF_2CH_3$ | CN |
| Br | H | $CF_2$ | O | $CF_2$ | $NH_2$ | $SO_2CF_2CH_3$ | CN |
| Br | H | $CF_2$ | O | $CF_2$ | N = CHPh | $SO_2CF_2CH_3$ | CN |
| Br | H | $CF_2$ | O | $CF_2$ | $CH_3$ | $SO_2CF_2CH_3$ | CN |
| Br | H | $CF_2$ | O | $CF_2$ | $CF_3$ | $SO_2CF_2CH_3$ | CN |
| Br | H | $CF_2$ | O | $CF_2$ | Cl | $SO_2CF_2CH_3$ | CN |
| Br | H | $CF_2$ | O | $CF_2$ | F | $SO_2CF_2CH_3$ | CN |
| Br | H | $CF_2$ | O | $CF_2$ | $COCH_3$ | $SO_2CFphd 2CH_3$ | CN |
| Br | H | $CF_2$ | O | $CF_2$ | $NH_2$ | $COCF_3$ | CN |

TABLE 53

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | N = CHPh | $COCF_3$ | CN |
| Br | H | $CF_2$ | O | $CF_2$ | $CH_3$ | $COCF_3$ | CN |
| Br | H | $CF_2$ | O | $CF_2$ | $CF_3$ | $COCF_3$ | CN |
| Br | H | $CF_2$ | O | $CF_2$ | Cl | $COCF_3$ | CN |
| Br | H | $CF_2$ | O | $CF_2$ | F | $COCF_3$ | CN |
| Br | H | $CF_2$ | O | $CF_2$ | $COCH_3$ | $COCF_3$ | CN |
| Br | H | $CF_2$ | O | $CF_2$ | H | $COCF_3$ | CN |
| Br | H | $CF_2$ | O | $CF_2$ | $NH_2$ | $COCF_3$ | CN |
| Br | H | $CF_2$ | O | $CF_2$ | N = CHPh | $COCF_3$ | CN |
| Br | H | $CF_2$ | O | $CF_2$ | $CH_3$ | $COCF_3$ | CN |

TABLE 53-continued

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | $CF_3$ | $COCF_3$ | CN |
| Br | H | $CF_2$ | O | $CF_2$ | Cl | $COCF_3$ | CN |
| Br | H | $CF_2$ | O | $CF_2$ | F | $COCF_3$ | CN |
| Br | H | $CF_2$ | O | $CF_2$ | $COCH_3$ | $COCF_3$ | CN |
| Br | H | $CF_2$ | O | $CF_2$ | $NH_2$ | $C_2F_5$ | CN |
| Br | H | $CF_2$ | O | $CF_2$ | N = CHPh | $C_2F_5$ | CN |
| Br | H | $CF_2$ | O | $CF_2$ | $CH_3$ | $C_2F_5$ | CN |
| Br | H | $CF_2$ | O | $CF_2$ | $CF_3$ | $C_2F_5$ | CN |
| Br | H | $CF_2$ | O | $CF_2$ | Cl | $C_2F_5$ | CN |
| Br | H | $CF_2$ | O | $CF_2$ | F | $C_2F_5$ | CN |
| Br | H | $CF_2$ | O | $CF_2$ | $COCH_3$ | $C_2F_5$ | CN |
| Br | H | $CF_2$ | O | $CF_2$ | H | $C_2F_5$ | CN |
| Br | H | $CF_2$ | O | $CF_2$ | $NH_2$ | $C_2F_5$ | CN |
| Br | H | $CF_2$ | O | $CF_2$ | N = CHPh | $C_2F_5$ | CN |
| Br | H | $CF_2$ | O | $CF_2$ | $CH_3$ | $C_2F_5$ | CN |
| Br | H | $CF_2$ | O | $CF_2$ | $CF_3$ | $C_2F_5$ | CN |

TABLE 54

| X | Y | $Z^1$ | $Z^2$ | $Z^3$ | $R^1$ | $R^2$ | $R^3$ |
|---|---|---|---|---|---|---|---|
| Br | H | $CF_2$ | O | $CF_2$ | Cl | $C_2F_5$ | CN |
| Br | H | $CF_2$ | O | $CF_2$ | F | $C_2F_5$ | CN |
| Br | H | $CF_2$ | O | $CF_2$ | $COCH_3$ | $C_2F_5$ | CN |
| Br | H | $CF_2$ | O | $CF_2$ | $NH_2$ | $SFCl_2$ | CN |
| Br | H | $CF_2$ | O | $CF_2$ | N = CHPh | $SFCl_2$ | CN |
| Br | H | $CF_2$ | O | $CF_2$ | $CH_3$ | $SFCl_2$ | CN |
| Br | H | $CF_2$ | O | $CF_2$ | $CF_3$ | $SFCl_2$ | CN |
| Br | H | $CF_2$ | O | $CF_2$ | Cl | $SFCl_2$ | CN |
| Br | H | $CF_2$ | O | $CF_2$ | F | $SFCl_2$ | CN |
| Br | H | $CF_2$ | O | $CF_2$ | $COCH_3$ | $SFCl_2$ | CN |
| Br | H | $CF_2$ | O | $CF_2$ | H | $SFCl_2$ | CN |
| Br | H | $CF_2$ | O | $CF_2$ | $NH_2$ | $SFCl_2$ | CN |
| Br | H | $CF_2$ | O | $CF_2$ | N = CHPh | $SFCl_2$ | CN |
| Br | H | $CF_2$ | O | $CF_2$ | $CH_3$ | $SFCl_2$ | CN |
| Br | H | $CF_2$ | O | $CF_2$ | $CF_3$ | $SFCl_2$ | CN |
| Br | H | $CF_2$ | O | $CF_2$ | Cl | $SFCl_2$ | CN |
| Br | H | $CF_2$ | O | $CF_2$ | F | $SFCl_2$ | CN |
| Br | H | $CF_2$ | O | $CF_2$ | $COCH_3$ | $SFCl_2$ | CN |
| CN | H | $CF_2$ | O | $CF_2$ | H | $SCF_3$ | H |
| CN | H | $CF_2$ | O | $CF_2$ | $NH_2$ | $SCF_3$ | H |
| CN | H | $CF_2$ | O | $CF_2$ | N = CHPh | $SCF_3$ | H |
| CN | H | $CF_2$ | O | $CF_2$ | $CH_3$ | $SCF_3$ | H |
| CN | H | $CF_2$ | O | $CF_2$ | $CF_3$ | $SCF_3$ | H |
| CN | H | $CF_2$ | O | $CF_2$ | Cl | $SCF_3$ | H |
| CN | H | $CF_2$ | O | $CF_2$ | F | $SCF_3$ | H |
| CN | H | $CF_2$ | O | $CF_2$ | $COCH_3$ | $SCF_3$ | H |

TABLE 55

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | H | $SOCF_3$ | H |
| CN | H | $CF_2$ | O | $CF_2$ | $NH_2$ | $SOCF_3$ | H |
| CN | H | $CF_2$ | O | $CF_2$ | N = CHPh | $SOCF_3$ | H |
| CN | H | $CF_2$ | O | $CF_2$ | $CH_3$ | $SOCF_3$ | H |
| CN | H | $CF_2$ | O | $CF_2$ | $CF_3$ | $SOCF_3$ | H |
| CN | H | $CF_2$ | O | $CF_2$ | Cl | $SOCF_3$ | H |
| CN | H | $CF_2$ | O | $CF_2$ | F | $SOCF_3$ | H |
| CN | H | $CF_2$ | O | $CF_2$ | $COCH_3$ | $SOCF_3$ | H |
| CN | H | $CF_2$ | O | $CF_2$ | H | $SO_2CF_3$ | H |
| CN | H | $CF_2$ | O | $CF_2$ | $NH_2$ | $SO_2CF_3$ | H |
| CN | H | $CF_2$ | O | $CF_2$ | N = CHPh | $SO_2CF_3$ | H |
| CN | H | $CF_2$ | O | $CF_2$ | $CH_3$ | $SO_2CF_3$ | H |
| CN | H | $CF_2$ | O | $CF_2$ | $CF_3$ | $SO_2CF_3$ | H |
| CN | H | $CF_2$ | O | $CF_2$ | Cl | $SO_2CF_3$ | H |
| CN | H | $CF_2$ | O | $CF_2$ | F | $SO_2CF_3$ | H |
| CN | H | $CF_2$ | O | $CF_2$ | $COCH_3$ | $SO_2CF_3$ | H |
| CN | H | $CF_2$ | O | $CF_2$ | H | $SCF_2CH_3$ | H |
| CN | H | $CF_2$ | O | $CF_2$ | $NH_2$ | $SCF_2CH_3$ | H |
| CN | H | $CF_2$ | O | $CF_2$ | N = CHPh | $SCF_2CH_3$ | H |
| CN | H | $CF_2$ | O | $CF_2$ | $CH_3$ | $SCF_2CH_3$ | H |

TABLE 55-continued

| X | Y | Z¹ | Z² | Z³ | R¹ | R² | R³ |
|---|---|---|---|---|---|---|---|
| CN | H | CF$_2$ | O | CF$_2$ | CF$_3$ | SCF$_2$CH$_3$ | H |
| CN | H | CF$_2$ | O | CF$_2$ | Cl | SCF$_2$CH$_3$ | H |
| CN | H | CF$_2$ | O | CF$_2$ | F | SCF$_2$CH$_3$ | H |
| CN | H | CF$_2$ | O | CF$_2$ | COCH$_3$ | SCF$_2$CH$_3$ | H |
| CN | H | CF$_2$ | O | CF$_2$ | H | SOCF$_2$CH$_3$ | H |
| CN | H | CF$_2$ | O | CF$_2$ | NH$_2$ | SOCF$_2$CH$_3$ | H |

TABLE 56

| X | Y | Z¹ | Z² | Z³ | R¹ | R² | R³ |
|---|---|---|---|---|---|---|---|
| CN | H | CF$_2$ | O | CF$_2$ | N=CHPh | SOCF$_2$CH$_3$ | H |
| CN | H | CF$_2$ | O | CF$_2$ | CH$_3$ | SOCF$_2$CH$_3$ | H |
| CN | H | CF$_2$ | O | CF$_2$ | CF$_3$ | SOCF$_2$CH$_3$ | H |
| CN | H | CF$_2$ | O | CF$_2$ | Cl | SOCF$_2$CH$_3$ | H |
| CN | H | CF$_2$ | O | CF$_2$ | F | SOCF$_2$CH$_3$ | H |
| CN | H | CF$_2$ | O | CF$_2$ | COCH$_3$ | SOCF$_2$CH$_3$ | H |
| CN | H | CF$_2$ | O | CF$_2$ | H | SO$_2$CF$_2$CH$_3$ | H |
| CN | H | CF$_2$ | O | CF$_2$ | NH$_2$ | SO$_2$CF$_2$CH$_3$ | H |
| CN | H | CF$_2$ | O | CF$_2$ | N=CHPh | SO$_2$CF$_2$CH$_3$ | H |
| CN | H | CF$_2$ | O | CF$_2$ | CH$_3$ | SO$_2$CF$_2$CH$_3$ | H |
| CN | H | CF$_2$ | O | CF$_2$ | CF$_3$ | SO$_2$CF$_2$CH$_3$ | H |
| CN | H | CF$_2$ | O | CF$_2$ | Cl | SO$_2$CF$_2$CH$_3$ | H |
| CN | H | CF$_2$ | O | CF$_2$ | F | SO$_2$CF$_2$CH$_3$ | H |
| CN | H | CF$_2$ | O | CF$_2$ | COCH$_3$ | SO$_2$CF$_2$CH$_3$ | H |
| CN | H | CF$_2$ | O | CF$_2$ | NH$_2$ | COCF$_3$ | H |
| CN | H | CF$_2$ | O | CF$_2$ | N=CHPh | COCF$_3$ | H |
| CN | H | CF$_2$ | O | CF$_2$ | CH$_3$ | COCF$_3$ | H |
| CN | H | CF$_2$ | O | CF$_2$ | CF$_3$ | COCF$_3$ | H |
| CN | H | CF$_2$ | O | CF$_2$ | Cl | COCF$_3$ | H |
| CN | H | CF$_2$ | O | CF$_2$ | F | COCF$_3$ | H |
| CN | H | CF$_2$ | O | CF$_2$ | COCH$_3$ | COCF$_3$ | H |
| CN | H | CF$_2$ | O | CF$_2$ | H | COCF$_3$ | H |
| CN | H | CF$_2$ | O | CF$_2$ | NH$_2$ | COCF$_3$ | H |
| CN | H | CF$_2$ | O | CF$_2$ | N=CHPh | COCF$_3$ | H |
| CN | H | CF$_2$ | O | CF$_2$ | CH$_3$ | COCF$_3$ | H |
| CN | H | CF$_2$ | O | CF$_2$ | CF$_3$ | COCF$_3$ | H |

TABLE 57

| X | Y | Z¹ | Z² | Z³ | R¹ | R² | R³ |
|---|---|---|---|---|---|---|---|
| CN | H | CF$_2$ | O | CF$_2$ | Cl | COCF$_3$ | H |
| CN | H | CF$_2$ | O | CF$_2$ | F | COCF$_3$ | H |
| CN | H | CF$_2$ | O | CF$_2$ | COCH$_3$ | COCF$_3$ | H |
| CN | H | CF$_2$ | O | CF$_2$ | NH$_2$ | C$_2$F$_5$ | H |
| CN | H | CF$_2$ | O | CF$_2$ | N=CHPh | C$_2$F$_5$ | H |
| CN | H | CF$_2$ | O | CF$_2$ | CH$_3$ | C$_2$F$_5$ | H |
| CN | H | CF$_2$ | O | CF$_2$ | CF$_3$ | C$_2$F$_5$ | H |
| CN | H | CF$_2$ | O | CF$_2$ | Cl | C$_2$F$_5$ | H |
| CN | H | CF$_2$ | O | CF$_2$ | F | C$_2$F$_5$ | H |
| CN | H | CF$_2$ | O | CF$_2$ | COCH$_3$ | C$_2$F$_5$ | H |
| CN | H | CF$_2$ | O | CF$_2$ | H | C$_2$F$_5$ | H |
| CN | H | CF$_2$ | O | CF$_2$ | NH$_2$ | C$_2$F$_5$ | H |
| CN | H | CF$_2$ | O | CF$_2$ | N=CHPh | C$_2$F$_5$ | H |
| CN | H | CF$_2$ | O | CF$_2$ | CH$_3$ | C$_2$F$_5$ | H |
| CN | H | CF$_2$ | O | CF$_2$ | CF$_3$ | C$_2$F$_5$ | H |
| CN | H | CF$_2$ | O | CF$_2$ | Cl | C$_2$F$_5$ | H |
| CN | H | CF$_2$ | O | CF$_2$ | F | C$_2$F$_5$ | H |
| CN | H | CF$_2$ | O | CF$_2$ | COCH$_3$ | C$_2$F$_5$ | H |
| CN | H | CF$_2$ | O | CF$_2$ | NH$_2$ | SFCl$_2$ | H |
| CN | H | CF$_2$ | O | CF$_2$ | N=CHPh | SFCl$_2$ | H |
| CN | H | CF$_2$ | O | CF$_2$ | CH$_3$ | SFCl$_2$ | H |
| CN | H | CF$_2$ | O | CF$_2$ | CF$_3$ | SFCl$_2$ | H |
| CN | H | CF$_2$ | O | CF$_2$ | Cl | SFCl$_2$ | H |
| CN | H | CF$_2$ | O | CF$_2$ | F | SFCl$_2$ | H |
| CN | H | CF$_2$ | O | CF$_2$ | COCH$_3$ | SFCl$_2$ | H |
| CN | H | CF$_2$ | O | CF$_2$ | H | SFCl$_2$ | H |

TABLE 58

| X | Y | Z¹ | Z² | Z³ | R¹ | R² | R³ |
|---|---|---|---|---|---|---|---|
| CN | H | CF$_2$ | O | CF$_2$ | NH$_2$ | SFCl$_2$ | H |
| CN | H | CF$_2$ | O | CF$_2$ | N=CHPh | SFCl$_2$ | H |
| CN | H | CF$_2$ | O | CF$_2$ | CH$_3$ | SFCl$_2$ | H |
| CN | H | CF$_2$ | O | CF$_2$ | CF$_3$ | SFCl$_2$ | H |
| CN | H | CF$_2$ | O | CF$_2$ | Cl | SFCl$_2$ | H |
| CN | H | CF$_2$ | O | CF$_2$ | F | SFCl$_2$ | H |
| CN | H | CF$_2$ | O | CF$_2$ | COCH$_3$ | SFCl$_2$ | H |
| CN | H | CF$_2$ | O | CF$_2$ | H | SCF$_3$ | CF$_3$ |
| CN | H | CF$_2$ | O | CF$_2$ | NH$_2$ | SCF$_3$ | CF$_3$ |
| CN | H | CF$_2$ | O | CF$_2$ | N=CHPh | SCF$_3$ | CF$_3$ |
| CN | H | CF$_2$ | O | CF$_2$ | CH$_3$ | SCF$_3$ | CF$_3$ |
| CN | H | CF$_2$ | O | CF$_2$ | CF$_3$ | SCF$_3$ | CF$_3$ |
| CN | H | CF$_2$ | O | CF$_2$ | Cl | SCF$_3$ | CF$_3$ |
| CN | H | CF$_2$ | O | CF$_2$ | F | SCF$_3$ | CF$_3$ |
| CN | H | CF$_2$ | O | CF$_2$ | COCH$_3$ | SCF$_3$ | CF$_3$ |
| CN | H | CF$_2$ | O | CF$_2$ | H | SOCF$_3$ | CF$_3$ |
| CN | H | CF$_2$ | O | CF$_2$ | NH$_2$ | SOCF$_3$ | CF$_3$ |
| CN | H | CF$_2$ | O | CF$_2$ | N=CHPh | SOCF$_3$ | CF$_3$ |
| CN | H | CF$_2$ | O | CF$_2$ | CH$_3$ | SOCF$_3$ | CF$_3$ |
| CN | H | CF$_2$ | O | CF$_2$ | CF$_3$ | SOCF$_3$ | CF$_3$ |
| CN | H | CF$_2$ | O | CF$_2$ | Cl | SOCF$_3$ | CF$_3$ |
| CN | H | CF$_2$ | O | CF$_2$ | F | SOCF$_3$ | CF$_3$ |
| CN | H | CF$_2$ | O | CF$_2$ | COCH$_3$ | SOCF$_3$ | CF$_3$ |
| CN | H | CF$_2$ | O | CF$_2$ | H | SO$_2$CF$_3$ | CF$_3$ |
| CN | H | CF$_2$ | O | CF$_2$ | NH$_2$ | SO$_2$CF$_3$ | CF$_3$ |
| CN | H | CF$_2$ | O | CF$_2$ | N=CHPh | SO$_2$CF$_3$ | CF$_3$ |

TABLE 59

| X | Y | Z¹ | Z² | Z³ | R¹ | R² | R³ |
|---|---|---|---|---|---|---|---|
| CN | H | CF$_2$ | O | CF$_2$ | CH$_3$ | SO$_2$CF$_3$ | CF$_3$ |
| CN | H | CF$_2$ | O | CF$_2$ | CF$_3$ | SO$_2$CF$_3$ | CF$_3$ |
| CN | H | CF$_2$ | O | CF$_2$ | Cl | SO$_2$CF$_3$ | CF$_3$ |
| CN | H | CF$_2$ | O | CF$_2$ | F | SO$_2$CF$_3$ | CF$_3$ |
| CN | H | CF$_2$ | O | CF$_2$ | COCH$_3$ | SO$_2$CF$_3$ | CF$_3$ |
| CN | H | CF$_2$ | O | CF$_2$ | H | SCF$_2$CH$_3$ | CF$_3$ |
| CN | H | CF$_2$ | O | CF$_2$ | NH$_2$ | SCF$_2$CH$_3$ | CF$_3$ |
| CN | H | CF$_2$ | O | CF$_2$ | N=CHPh | SCF$_2$CH$_3$ | CF$_3$ |
| CN | H | CF$_2$ | O | CF$_2$ | CH$_3$ | SCF$_2$CH$_3$ | CF$_3$ |
| CN | H | CF$_2$ | O | CF$_2$ | CF$_3$ | SCF$_2$CH$_3$ | CF$_3$ |
| CN | H | CF$_2$ | O | CF$_2$ | Cl | SCF$_2$CH$_3$ | CF$_3$ |
| CN | H | CF$_2$ | O | CF$_2$ | F | SCF$_2$CH$_3$ | CF$_3$ |
| CN | H | CF$_2$ | O | CF$_2$ | COCH$_3$ | SCF$_2$CH$_3$ | CF$_3$ |
| CN | H | CF$_2$ | O | CF$_2$ | H | SOCF$_2$CH$_3$ | CF$_3$ |
| CN | H | CF$_2$ | O | CF$_2$ | NH$_2$ | SOCF$_2$CH$_3$ | CF$_3$ |
| CN | H | CF$_2$ | O | CF$_2$ | N=CHPh | SOCF$_2$CH$_3$ | CF$_3$ |
| CN | H | CF$_2$ | O | CF$_2$ | CH$_3$ | SOCF$_2$CH$_3$ | CF$_3$ |
| CN | H | CF$_2$ | O | CF$_2$ | CF$_3$ | SOCF$_2$CH$_3$ | CF$_3$ |
| CN | H | CF$_2$ | O | CF$_2$ | Cl | SOCF$_2$CH$_3$ | CF$_3$ |
| CN | H | CF$_2$ | O | CF$_2$ | F | SOCF$_2$CH$_3$ | CF$_3$ |
| CN | H | CF$_2$ | O | CF$_2$ | COCH$_3$ | SOCF$_2$CH$_3$ | CF$_3$ |
| CN | H | CF$_2$ | O | CF$_2$ | H | SO$_2$CF$_2$CH$_3$ | CF$_3$ |
| CN | H | CF$_2$ | O | CF$_2$ | NH$_2$ | SO$_2$CF$_2$CH$_3$ | CF$_3$ |
| CN | H | CF$_2$ | O | CF$_2$ | N=CHPh | SO$_2$CF$_2$CH$_3$ | CF$_3$ |
| CN | H | CF$_2$ | O | CF$_2$ | CH$_3$ | SO$_2$CF$_2$CH$_3$ | CF$_3$ |
| CN | H | CF$_2$ | O | CF$_2$ | CF$_3$ | SO$_2$CF$_2$CH$_3$ | CF$_3$ |

TABLE 60

| X | Y | Z¹ | Z² | Z³ | R¹ | R² | R³ |
|---|---|---|---|---|---|---|---|
| CN | H | CF$_2$ | O | CF$_2$ | Cl | SO$_2$CF$_2$CH$_3$ | CF$_3$ |
| CN | H | CF$_2$ | O | CF$_2$ | F | SO$_2$CF$_2$CH$_3$ | CF$_3$ |
| CN | H | CF$_2$ | O | CF$_2$ | COCH$_3$ | SO$_2$CF$_2$CH$_3$ | CF$_3$ |
| CN | H | CF$_2$ | O | CF$_2$ | NH$_2$ | COCF$_3$ | CF$_3$ |
| CN | H | CF$_2$ | O | CF$_2$ | N=CHPh | COCF$_3$ | CF$_3$ |
| CN | H | CF$_2$ | O | CF$_2$ | CH$_3$ | COCF$_3$ | CF$_3$ |
| CN | H | CF$_2$ | O | CF$_2$ | CF$_3$ | COCF$_3$ | CF$_3$ |
| CN | H | CF$_2$ | O | CF$_2$ | Cl | COCF$_3$ | CF$_3$ |
| CN | H | CF$_2$ | O | CF$_2$ | F | COCF$_3$ | CF$_3$ |
| CN | H | CF$_2$ | O | CF$_2$ | COCH$_3$ | COCF$_3$ | CF$_3$ |

TABLE 60-continued

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | H | $COCF_3$ | $CF_3$ |
| CN | H | $CF_2$ | O | $CF_2$ | $NH_2$ | $COCF_3$ | $CF_3$ |
| CN | H | $CF_2$ | O | $CF_2$ | N=CHPh | $COCF_3$ | $CF_3$ |
| CN | H | $CF_2$ | O | $CF_2$ | $CH_3$ | $COCF_3$ | $CF_3$ |
| CN | H | $CF_2$ | O | $CF_2$ | $CF_3$ | $COCF_3$ | $CF_3$ |
| CN | H | $CF_2$ | O | $CF_2$ | Cl | $COCF_3$ | $CF_3$ |
| CN | H | $CF_2$ | O | $CF_2$ | F | $COCF_3$ | $CF_3$ |
| CN | H | $CF_2$ | O | $CF_2$ | $COCH_3$ | $COCF_3$ | $CF_3$ |
| CN | H | $CF_2$ | O | $CF_2$ | $NH_2$ | $C_2F_5$ | $CF_3$ |
| CN | H | $CF_2$ | O | $CF_2$ | N=CHPh | $C_2F_5$ | $CF_3$ |
| CN | H | $CF_2$ | O | $CF_2$ | $CH_3$ | $C_2F_5$ | $CF_3$ |
| CN | H | $CF_2$ | O | $CF_2$ | $CF_3$ | $C_2F_5$ | $CF_3$ |
| CN | H | $CF_2$ | O | $CF_2$ | Cl | $C_2F_5$ | $CF_3$ |
| CN | H | $CF_2$ | O | $CF_2$ | F | $C_2F_5$ | $CF_3$ |
| CN | H | $CF_2$ | O | $CF_2$ | $COCH_3$ | $C_2F_5$ | $CF_3$ |
| CN | H | $CF_2$ | O | $CF_2$ | H | $C_2F_5$ | $CF_3$ |

TABLE 61

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | $NH_2$ | $C_2F_5$ | $CF_3$ |
| CN | H | $CF_2$ | O | $CF_2$ | N=CHPh | $C_2F_5$ | $CF_3$ |
| CN | H | $CF_2$ | O | $CF_2$ | $CH_3$ | $C_2F_5$ | $CF_3$ |
| CN | H | $CF_2$ | O | $CF_2$ | $CF_3$ | $C_2F_5$ | $CF_3$ |
| CN | H | $CF_2$ | O | $CF_2$ | Cl | $C_2F_5$ | $CF_3$ |
| CN | H | $CF_2$ | O | $CF_2$ | F | $C_2F_5$ | $CF_3$ |
| CN | H | $CF_2$ | O | $CF_2$ | $COCH_3$ | $C_2F_5$ | $CF_3$ |
| CN | H | $CF_2$ | O | $CF_2$ | $NH_2$ | $SFCl_2$ | $CF_3$ |
| CN | H | $CF_2$ | O | $CF_2$ | N=CHPh | $SFCl_2$ | $CF_3$ |
| CN | H | $CF_2$ | O | $CF_2$ | $CH_3$ | $SFCl_2$ | $CF_3$ |
| CN | H | $CF_2$ | O | $CF_2$ | $CF_3$ | $SFCl_2$ | $CF_3$ |
| CN | H | $CF_2$ | O | $CF_2$ | Cl | $SFCl_2$ | $CF_3$ |
| CN | H | $CF_2$ | O | $CF_2$ | F | $SFCl_2$ | $CF_3$ |
| CN | H | $CF_2$ | O | $CF_2$ | $COCH_3$ | $SFCl_2$ | $CF_3$ |
| CN | H | $CF_2$ | O | $CF_2$ | H | $SFCl_2$ | $CF_3$ |
| CN | H | $CF_2$ | O | $CF_2$ | $NH_2$ | $SFCl_2$ | $CF_3$ |
| CN | H | $CF_2$ | O | $CF_2$ | N=CHPh | $SFCl_2$ | $CF_3$ |
| CN | H | $CF_2$ | O | $CF_2$ | $CH_3$ | $SFCl_2$ | $CF_3$ |
| CN | H | $CF_2$ | O | $CF_2$ | $CF_3$ | $SFCl_2$ | $CF_3$ |
| CN | H | $CF_2$ | O | $CF_2$ | Cl | $SFCl_2$ | $CF_3$ |
| CN | H | $CF_2$ | O | $CF_2$ | F | $SFCl_2$ | $CF_3$ |
| CN | H | $CF_2$ | O | $CF_2$ | $COCH_3$ | $SFCl_2$ | $CF_3$ |
| CN | H | $CF_2$ | O | $CF_2$ | H | $SCF_3$ | $C_2F_5$ |
| CN | H | $CF_2$ | O | $CF_2$ | $NH_2$ | $SCF_3$ | $C_2F_5$ |
| CN | H | $CF_2$ | O | $CF_2$ | N=CHPh | $SCF_3$ | $C_2F_5$ |
| CN | H | $CF_2$ | O | $CF_2$ | $CH_3$ | $SCF_3$ | $C_2F_5$ |

TABLE 62

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | $CF_3$ | $SCF_3$ | $C_2F_5$ |
| CN | H | $CF_2$ | O | $CF_2$ | Cl | $SCF_3$ | $C_2F_5$ |
| CN | H | $CF_2$ | O | $CF_2$ | F | $SCF_3$ | $C_2F_5$ |
| CN | H | $CF_2$ | O | $CF_2$ | $COCH_3$ | $SCF_3$ | $C_2F_5$ |
| CN | H | $CF_2$ | O | $CF_2$ | H | $SOCF_3$ | $C_2F_5$ |
| CN | H | $CF_2$ | O | $CF_2$ | $NH_2$ | $SOCF_3$ | $C_2F_5$ |
| CN | H | $CF_2$ | O | $CF_2$ | N=CHPh | $SOCF_3$ | $C_2F_5$ |
| CN | H | $CF_2$ | O | $CF_2$ | $CH_3$ | $SOCF_3$ | $C_2F_5$ |
| CN | H | $CF_2$ | O | $CF_2$ | $CF_3$ | $SOCF_3$ | $C_2F_5$ |
| CN | H | $CF_2$ | O | $CF_2$ | Cl | $SOCF_3$ | $C_2F_5$ |
| CN | H | $CF_2$ | O | $CF_2$ | F | $SOCF_3$ | $C_2F_5$ |
| CN | H | $CF_2$ | O | $CF_2$ | $COCH_3$ | $SOCF_3$ | $C_2F_5$ |
| CN | H | $CF_2$ | O | $CF_2$ | H | $SO_2CF_3$ | $C_2F_5$ |
| CN | H | $CF_2$ | O | $CF_2$ | $NH_2$ | $SO_2CF_3$ | $C_2F_5$ |
| CN | H | $CF_2$ | O | $CF_2$ | N=CHPh | $SO_2CF_3$ | $C_2F_5$ |
| CN | H | $CF_2$ | O | $CF_2$ | $CH_3$ | $SO_2CF_3$ | $C_2F_5$ |
| CN | H | $CF_2$ | O | $CF_2$ | $CF_3$ | $SO_2CF_3$ | $C_2F_5$ |
| CN | H | $CF_2$ | O | $CF_2$ | Cl | $SO_2CF_3$ | $C_2F_5$ |
| CN | H | $CF_2$ | O | $CF_2$ | F | $SO_2CF_3$ | $C_2F_5$ |
| CN | H | $CF_2$ | O | $CF_2$ | $COCH_3$ | $SO_2CF_3$ | $C_2F_5$ |

TABLE 62-continued

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | H | $SCF_2CH_3$ | $C_2F_5$ |
| CN | H | $CF_2$ | O | $CF_2$ | $NH_2$ | $SCF_2CH_3$ | $C_2F_5$ |
| CN | H | $CF_2$ | O | $CF_2$ | N=CHPh | $SCF_2CH_3$ | $C_2F_5$ |
| CN | H | $CF_2$ | O | $CF_2$ | $CH_3$ | $SCF_2CH_3$ | $C_2F_5$ |
| CN | H | $CF_2$ | O | $CF_2$ | $CF_3$ | $SCF_2CH_3$ | $C_2F_5$ |
| CN | H | $CF_2$ | O | $CF_2$ | Cl | $SCF_2CH_3$ | $C_2F_5$ |

TABLE 63

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | F | $SCF_2CH_3$ | $C_2F_5$ |
| CN | H | $CF_2$ | O | $CF_2$ | $COCH_3$ | $SCF_2CH_3$ | $C_2F_5$ |
| CN | H | $CF_2$ | O | $CF_2$ | H | $SOCF_2CH_3$ | $C_2F_5$ |
| CN | H | $CF_2$ | O | $CF_2$ | $NH_2$ | $SOCF_2CH_3$ | $C_2F_5$ |
| CN | H | $CF_2$ | O | $CF_2$ | N=CHPh | $SOCF_2CH_3$ | $C_2F_5$ |
| CN | H | $CF_2$ | O | $CF_2$ | $CH_3$ | $SOCF_2CH_3$ | $C_2F_5$ |
| CN | H | $CF_2$ | O | $CF_2$ | $CF_3$ | $SOCF_2CH_3$ | $C_2F_5$ |
| CN | H | $CF_2$ | O | $CF_2$ | Cl | $SOCF_2CH_3$ | $C_2F_5$ |
| CN | H | $CF_2$ | O | $CF_2$ | F | $SOCF_2CH_3$ | $C_2F_5$ |
| CN | H | $CF_2$ | O | $CF_2$ | $COCH_3$ | $SOCF_2CH_3$ | $C_2F_5$ |
| CN | H | $CF_2$ | O | $CF_2$ | H | $SO_2CF_2CH_3$ | $C_2F_5$ |
| CN | H | $CF_2$ | O | $CF_2$ | $NH_2$ | $SO_2CF_2CH_3$ | $C_2F_5$ |
| CN | H | $CF_2$ | O | $CF_2$ | N=CHPh | $SO_2CF_2CH_3$ | $C_2F_5$ |
| CN | H | $CF_2$ | O | $CF_2$ | $CH_3$ | $SO_2CF_2CH_3$ | $C_2F_5$ |
| CN | H | $CF_2$ | O | $CF_2$ | $CF_3$ | $SO_2CF_2CH_3$ | $C_2F_5$ |
| CN | H | $CF_2$ | O | $CF_2$ | Cl | $SO_2CF_2CH_3$ | $C_2F_5$ |
| CN | H | $CF_2$ | O | $CF_2$ | F | $SO_2CF_2CH_3$ | $C_2F_5$ |
| CN | H | $CF_2$ | O | $CF_2$ | $COCH_3$ | $SO_2CF_2CH_3$ | $C_2F_5$ |
| CN | H | $CF_2$ | O | $CF_2$ | $NH_2$ | $COCF_3$ | $C_2F_5$ |
| CN | H | $CF_2$ | O | $CF_2$ | N=CHPh | $COCF_3$ | $C_2F_5$ |
| CN | H | $CF_2$ | O | $CF_2$ | $CH_3$ | $COCF_3$ | $C_2F_5$ |
| CN | H | $CF_2$ | O | $CF_2$ | $CF_3$ | $COCF_3$ | $C_2F_5$ |
| CN | H | $CF_2$ | O | $CF_2$ | Cl | $COCF_3$ | $C_2F_5$ |
| CN | H | $CF_2$ | O | $CF_2$ | F | $COCF_3$ | $C_2F_5$ |
| CN | H | $CF_2$ | O | $CF_2$ | $COCH_3$ | $COCF_3$ | $C_2F_5$ |
| CN | H | $CF_2$ | O | $CF_2$ | H | $COCF_3$ | $C_2F_5$ |

TABLE 64

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | $NH_2$ | $COCF_3$ | $C_2F_5$ |
| CN | H | $CF_2$ | O | $CF_2$ | N=CHPh | $COCF_3$ | $C_2F_5$ |
| CN | H | $CF_2$ | O | $CF_2$ | $CH_3$ | $COCF_3$ | $C_2F_5$ |
| CN | H | $CF_2$ | O | $CF_2$ | $CF_3$ | $COCF_3$ | $C_2F_5$ |
| CN | H | $CF_2$ | G | $CF_2$ | Cl | $COCF_3$ | $C_2F_5$ |
| CN | H | $CF_2$ | O | $CF_2$ | F | $COCF_3$ | $C_2F_5$ |
| CN | H | $CF_2$ | O | $CF_2$ | $COCH_3$ | $COCF_3$ | $C_2F_5$ |
| CN | H | $CF_2$ | O | $CF_2$ | $NH_2$ | $C_2F_5$ | $C_2F_5$ |
| CN | H | $CF_2$ | O | $CF_2$ | N=CHPh | $C_2F_5$ | $C_2F_5$ |
| CN | H | $CF_2$ | O | $CF_2$ | $CH_3$ | $C_2F_5$ | $C_2F_5$ |
| CN | H | $CF_2$ | O | $CF_2$ | $CF_3$ | $C_2F_5$ | $C_2F_5$ |
| CN | H | $CF_2$ | O | $CF_2$ | Cl | $C_2F_5$ | $C_2F_5$ |
| CN | H | $CF_2$ | O | $CF_2$ | F | $C_2F_5$ | $C_2F_5$ |
| CN | H | $CF_2$ | O | $CF_2$ | $COCH_3$ | $C_2F_5$ | $C_2F_5$ |
| CN | H | $CF_2$ | O | $CF_2$ | H | $C_2F_5$ | $C_2F_5$ |
| CN | H | $CF_2$ | O | $CF_2$ | $NH_2$ | $C_2F_5$ | $C_2F_5$ |
| CN | H | $CF_2$ | O | $CF_2$ | N=CHPh | $C_2F_5$ | $C_2F_5$ |
| CN | H | $CF_2$ | O | $CF_2$ | $CH_3$ | $C_2F_5$ | $C_2F_5$ |
| CN | H | $CF_2$ | O | $CF_2$ | $CF_3$ | $C_2F_5$ | $C_2F_5$ |
| CN | H | $CF_2$ | O | $CF_2$ | Cl | $C_2F_5$ | $C_2F_5$ |
| CN | H | $CF_2$ | O | $CF_2$ | F | $C_2F_5$ | $C_2F_5$ |
| CN | H | $CF_2$ | O | $CF_2$ | $COCH_3$ | $C_2F_5$ | $C_2F_5$ |
| CN | H | $CF_2$ | O | $CF_2$ | $NH_2$ | $SFCl_2$ | $C_2F_5$ |
| CN | H | $CF_2$ | O | $CF_2$ | N=CHPh | $SFCl_2$ | $C_2F_5$ |
| CN | H | $CF_2$ | O | $CF_2$ | $CH_3$ | $SFCl_2$ | $C_2F_5$ |
| CN | H | $CF_2$ | O | $CF_2$ | $CF_3$ | $SFCl_2$ | $C_2F_5$ |

TABLE 65

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | Cl | $SFCl_2$ | $C_2F_5$ |
| CN | H | $CF_2$ | O | $CF_2$ | F | $SFCl_2$ | $C_2F_5$ |
| CN | H | $CF_2$ | O | $CF_2$ | $COCH_3$ | $SFCl_2$ | $C_2F_5$ |
| CN | H | $CF_2$ | O | $CF_2$ | H | $SFCl_2$ | $C_2F_5$ |
| CN | H | $CF_2$ | O | $CF_2$ | $NH_2$ | $SFCl_2$ | $C_2F_5$ |
| CN | H | $CF_2$ | O | $CF_2$ | N = CHPh | $SFCl_2$ | $C_2F_5$ |
| CN | H | $CF_2$ | O | $CF_2$ | $CH_3$ | $SFCl_2$ | $C_2F_5$ |
| CN | H | $CF_2$ | O | $CF_2$ | $CF_3$ | $SFCl_2$ | $C_2F_5$ |
| CN | H | $CF_2$ | O | $CF_2$ | Cl | $SFCl_2$ | $C_2F_5$ |
| CN | H | $CF_2$ | O | $CF_2$ | F | $SFCl_2$ | $C_2F_5$ |
| CN | H | $CF_2$ | O | $CF_2$ | $COCH_3$ | $SFCl_2$ | $C_2F_5$ |
| CN | H | $CF_2$ | O | $CF_2$ | H | $SCF_3$ | $CSNH_2$ |
| CN | H | $CF_2$ | O | $CF_2$ | $NH_2$ | $SCF_3$ | $CSNH_2$ |
| CN | H | $CF_2$ | O | $CF_2$ | N = CHPh | $SCF_3$ | $CSNH_2$ |
| CN | H | $CF_2$ | O | $CF_2$ | $CH_3$ | $SCF_3$ | $CSNH_2$ |
| CN | H | $CF_2$ | O | $CF_2$ | $CF_3$ | $SCF_3$ | $CSNH_2$ |
| CN | H | $CF_2$ | O | $CF_2$ | Cl | $SCF_3$ | $CSNH_2$ |
| CN | H | $CF_2$ | O | $CF_2$ | F | $SCF_3$ | $CSNH_2$ |
| CN | H | $CF_2$ | O | $CF_2$ | $COCH_3$ | $SCF_3$ | $CSNH_2$ |
| CN | H | $CF_2$ | O | $CF_2$ | H | $SOCF_3$ | $CSNH_2$ |
| CN | H | $CF_2$ | O | $CF_2$ | $NH_2$ | $SOCF_3$ | $CSNH_2$ |
| CN | H | $CF_2$ | O | $CF_2$ | N = CHPh | $SOCF_3$ | $CSNH_2$ |
| CN | H | $CF_2$ | O | $CF_2$ | $CH_3$ | $SOCF_3$ | $CSNH_2$ |
| CN | H | $CF_2$ | O | $CF_2$ | $CF_3$ | $SOCF_3$ | $CSNH_2$ |
| CN | H | $CF_2$ | O | $CF_2$ | Cl | $SOCF_3$ | $CSNH_2$ |
| CN | H | $CF_2$ | O | $CF_2$ | F | $SOCF_3$ | $CSNH_2$ |

TABLE 66

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | $COCH_3$ | $SOCF_3$ | $CSNH_2$ |
| CN | H | $CF_2$ | O | $CF_2$ | H | $SO_2CF_3$ | $CSNH_2$ |
| CN | H | $CF_2$ | O | $CF_2$ | $NH_2$ | $SO_2CF_3$ | $CSNH_2$ |
| CN | H | $CF_2$ | O | $CF_2$ | N = CHPh | $SO_2CF_3$ | $CSNH_2$ |
| CN | H | $CF_2$ | O | $CF_2$ | $CH_3$ | $SO_2CF_3$ | $CSNH_2$ |
| CN | H | $CF_2$ | O | $CF_2$ | $CF_3$ | $SO_2CF_3$ | $CSNH_2$ |
| CN | H | $CF_2$ | O | $CF_2$ | Cl | $SO_2CF_3$ | $CSNH_2$ |
| CN | H | $CF_2$ | O | $CF_2$ | F | $SO_2CF_3$ | $CSNH_2$ |
| CN | H | $CF_2$ | O | $CF_2$ | $COCH_3$ | $SO_2CF_3$ | $CSNH_2$ |
| CN | H | $CF_2$ | O | $CF_2$ | H | $SCF_2CH.3$ | $CSNH_2$ |
| CN | H | $CF_2$ | O | $CF_2$ | $NH_2$ | $SCF_2CH_3$ | $CSNH_2$ |
| CN | H | $CF_2$ | O | $CF_2$ | N = CHPh | $SCF_2CH_3$ | $CSNH_2$ |
| CN | H | $CF_2$ | O | $CF_2$ | $CH_3$ | $SCF_2CH_3$ | $CSNH_2$ |
| CN | H | $CF_2$ | O | $CF_2$ | $CF_3$ | $SCF_2CH_3$ | $CSNH_2$ |
| CN | H | $CF_2$ | O | $CF_2$ | Cl | $SCF_2CH_3$ | $CSNH_2$ |
| CN | H | $CF_2$ | O | $CF_2$ | F | $SCF_2CH_3$ | $CSNH_2$ |
| CN | H | $CF_2$ | O | $CF_2$ | $COCH_3$ | $SCF_2CH_3$ | $CSNH_2$ |
| CN | H | $CF_2$ | O | $CF_2$ | H | $SOCF_2CH_3$ | $CSNH_2$ |
| CN | H | $CF_2$ | O | $CF_2$ | $NH_2$ | $SOCF_2CH_3$ | $CSNH_2$ |
| CN | H | $CF_2$ | O | $CF_2$ | N = CHPh | $SOCF_2CH_3$ | $CSNH_2$ |
| CN | H | $CF_2$ | O | $CF_2$ | $CH_3$ | $SOCF_2CH_3$ | $CSNH_2$ |
| CN | H | $CF_2$ | O | $CF_2$ | $CF_3$ | $SOCF_2CH_3$ | $CSNH_2$ |
| CN | H | $CF_2$ | O | $CF_2$ | Cl | $SOCF_2CH_3$ | $CSNH_2$ |
| CN | H | $CF_2$ | O | $CF_2$ | F | $SOCF_2CH_3$ | $CSNH_2$ |
| CN | H | $CF_2$ | O | $CF_2$ | $COCH_3$ | $SOCF_2CH_3$ | $CSNH_2$ |
| CN | H | $CF_2$ | O | $CF_2$ | H | $SO_2CF_2CH_3$ | $CSNH_2$ |

TABLE 67

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | $NH_2$ | $SO_2CF_2CH_3$ | $CSNH_2$ |
| CN | H | $CF_2$ | O | $CF_2$ | N#=CHPh | $SO_2CF_2CH_3$ | $CSNH_2$ |
| CN | H | $CF_2$ | O | $CF_2$ | $CH_3$ | $SO_2CF_2CH_3$ | $CSNH_2$ |
| CN | H | $CF_2$ | O | $CF_2$ | $CF_3$ | $SO_2CF_2CH_3$ | $CSNH_2$ |
| CN | H | $CF_2$ | O | $CF_2$ | Cl | $SO_2CF_2CH_3$ | $CSNH_2$ |
| CN | H | $CF_2$ | O | $CF_2$ | F | $SO_2CF_2CH_3$ | $CSNH_2$ |
| CN | H | $CF_2$ | O | $CF_2$ | $COCH_3$ | $SO_2CF_2CH_3$ | $CSNH_2$ |
| CN | H | $CF_2$ | O | $CF_2$ | $NH_2$ | $COCF_3$ | $CSNH_2$ |
| CN | H | $CF_2$ | O | $CF_2$ | N = CHPh | $COCF_3$ | $CSNH_2$ |
| CN | H | $CF_2$ | O | $CF_2$ | $CH_3$ | $COCF_3$ | $CSNH_2$ |
| CN | H | $CF_2$ | O | $CF_2$ | $CF_3$ | $COCF_3$ | $CSNH_2$ |
| CN | H | $CF_2$ | O | $CF_2$ | Cl | $COCF_3$ | $CSNH_2$ |
| CN | H | $CF_2$ | O | $CF_2$ | F | $COCF_3$ | $CSNH_2$ |
| CN | H | $CF_2$ | O | $CF_2$ | $COCH_3$ | $COCF_3$ | $CSNH_2$ |
| CN | H | $CF_2$ | O | $CF_2$ | H | $COCF_3$ | $CSNH_2$ |
| CN | H | $CF_2$ | O | $CF_2$ | $NH_2$ | $COCF_3$ | $CSNH_2$ |
| CN | H | $CF_2$ | O | $CF_2$ | N = CHPh | $COCF_3$ | $CSNH_2$ |
| CN | H | $CF_2$ | O | $CF_2$ | $CH_3$ | $COCF_3$ | $CSNH_2$ |
| CN | H | $CF_2$ | O | $CF_2$ | $CF_3$ | $COCF_3$ | $CSNH_2$ |
| CN | H | $CF_2$ | O | $CF_2$ | Cl | $COCF_3$ | $CSNH_2$ |
| CN | H | $CF_2$ | O | $CF_2$ | F | $COCF_3$ | $CSNH_2$ |
| CN | H | $CF_2$ | O | $CF_2$ | $COCH_3$ | $COCF_3$ | $CSNH_2$ |
| CN | H | $CF_2$ | O | $CF_2$ | $NH_2$ | $C_2F_5$ | $CSNH_2$ |
| CN | H | $CF_2$ | O | $CF_2$ | N = CHPh | $C_2F_5$ | $CSNH_2$ |
| CN | H | $CF_2$ | O | $CF_2$ | $CH_3$ | $C_2F_5$ | $CSNH_2$ |
| CN | H | $CF_2$ | O | $CF_2$ | $CF_3$ | $C_2F_5$ | $CSNH_2$ |

TABLE 68

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | Cl | $C_2F_5$ | $CSNH_2$ |
| CN | H | $CF_2$ | O | $CF_2$ | F | $C_2F_5$ | $CSNH_2$ |
| CN | H | $CF_2$ | O | $CF_2$ | $COCH_3$ | $C_2F_5$ | $CSNH_2$ |
| CN | H | $CF_2$ | O | $CF_2$ | H | $C_2F_5$ | $CSNH_2$ |
| CN | H | $CF_2$ | O | $CF_2$ | $NH_2$ | $C_2F_5$ | $CSNH_2$ |
| CN | H | $CF_2$ | O | $CF_2$ | N = CHPh | $C_2F_5$ | $CSNH_2$ |
| CN | H | $CF_2$ | O | $CF_2$ | $CH_3$ | $C_2F_5$ | $CSNH_2$ |
| CN | H | $CF_2$ | O | $CF_2$ | $CF_3$ | $C_2F_5$ | $CSNH_2$ |
| CN | H | $CF_2$ | O | $CF_2$ | Cl | $C_2F_5$ | $CSNH_2$ |
| CN | H | $CF_2$ | O | $CF_2$ | F | $C_2F_5$ | $CSNH_2$ |
| CN | H | $CF_2$ | O | $CF_2$ | $COCH_3$ | $C_2F_5$ | $CSNH_2$ |
| CN | H | $CF_2$ | O | $CF_2$ | $NH_2$ | $SFCl_2$ | $CSNH_2$ |
| CN | H | $CF_2$ | O | $CF_2$ | N = CHPh | $SFCl_2$ | $CSNH_2$ |
| CN | H | $CF_2$ | O | $CF_2$ | $CH_3$ | $SFCl_2$ | $CSNH_2$ |
| CN | H | $CF_2$ | O | $CF_2$ | $CF_3$ | $SFCl_2$ | $CSNH_2$ |
| CN | H | $CF_2$ | O | $CF_2$ | Cl | $SFCl_2$ | $CSNH_2$ |
| CN | H | $CF_2$ | O | $CF_2$ | F | $SFCl_2$ | $CSNH_2$ |
| CN | H | $CF_2$ | O | $CF_2$ | $COCH_3$ | $SFCl_2$ | $CSNH_2$ |
| CN | H | $CF_2$ | O | $CF_2$ | H | $SFCl_2$ | $CSNH_2$ |
| CN | H | $CF_2$ | O | $CF_2$ | $NH_2$ | $SFCl_2$ | $CSNH_2$ |
| CN | H | $CF_2$ | O | $CF_2$ | N = CHPh | $SFCl_2$ | $CSNH_2$ |
| CN | H | $CF_2$ | O | $CF_2$ | $CH_3$ | $SFCl_2$ | $CSNH_2$ |
| CN | H | $CF_2$ | O | $CF_2$ | $CF_3$ | $SFCl_2$ | $CSNH_2$ |
| CN | H | $CF_2$ | O | $CF_2$ | Cl | $SFCl_2$ | $CSNH_2$ |
| CN | H | $CF_2$ | O | $CF_2$ | F | $SFCl_2$ | $CSNH_2$ |
| CN | H | $CF_2$ | O | $CF_2$ | $COCH_3$ | $SFCl_2$ | $CSNH_2$ |

TABLE 69

| X | Y | $Z^1$ | $Z^2$ | $Z^3$ | $R^1$ | $R^2$ | $R^3$ |
|---|---|---|---|---|---|---|---|
| CN | H | $CF_2$ | O | $CF_2$ | H | $SCF_3$ | CN |
| CN | H | $CF_2$ | O | $CF_2$ | $NH_2$ | $SCF_3$ | CN |
| CN | H | $CF_2$ | O | $CF_2$ | N = CHPh | $SCF_3$ | CN |
| CN | H | $CF_2$ | O | $CF_2$ | $CH_3$ | $SCF_3$ | CN |
| CN | H | $CF_2$ | O | $CF_2$ | $CF_3$ | $SCF_3$ | CN |
| CN | H | $CF_2$ | O | $CF_2$ | Cl | $SCF_3$ | CN |
| CN | H | $CF_2$ | O | $CF_2$ | F | $SCF_3$ | CN |
| CN | H | $CF_2$ | O | $CF_2$ | $COCH_3$ | $SCF_3$ | CN |
| CN | H | $CF_2$ | O | $CF_2$ | H | $SOCF_3$ | CN |
| CN | H | $CF_2$ | O | $CF_2$ | $NH_2$ | $SOCF_3$ | CN |
| CN | H | $CF_2$ | O | $CF_2$ | N = CHPh | $SOCF_3$ | CN |
| CN | H | $CF_2$ | O | $CF_2$ | $CH_3$ | $SOCF_3$ | CN |
| CN | H | $CF_2$ | O | $CF_2$ | $CF_3$ | $SOCF_3$ | CN |
| CN | H | $CF_2$ | O | $CF_2$ | Cl | $SOCF_3$ | CN |
| CN | H | $CF_2$ | O | $CF_2$ | F | $SOCF_3$ | CN |
| CN | H | $CF_2$ | O | $CF_2$ | $COCH_3$ | $SOCF_3$ | CN |
| CN | H | $CF_2$ | O | $CF_2$ | H | $SO_2CF_3$ | CN |
| CN | H | $CF_2$ | O | $CF_2$ | $NH_2$ | $SO_2CF_3$ | CN |
| CN | H | $CF_2$ | O | $CF_2$ | N = CHPh | $SO_2CF_3$ | CN |
| CN | H | $CF_2$ | O | $CF_2$ | $CH_3$ | $SO_2CF_3$ | CN |

TABLE 69-continued

| X | Y | Z¹ | Z² | Z³ | R¹ | R² | R³ |
|---|---|----|----|----|----|----|----|
| CN | H | $CF_2$ | O | $CF_2$ | $CF_3$ | $SO_2CF_3$ | CN |
| CN | H | $CF_2$ | O | $CF_2$ | Cl | $SO_2CF_3$ | CN |
| CN | H | $CF_2$ | O | $CF_2$ | F | $SO_2CF_3$ | CN |
| CN | H | $CF_2$ | O | $CF_2$ | $COCH_3$ | $SO_2CF_3$ | CN |
| CN | H | $CF_2$ | O | $CF_2$ | H | $SCF_2CH_3$ | CN |
| CN | H | $CF_2$ | O | $CF_2$ | $NH_2$ | $SCF_2CH_3$ | CN |

TABLE 70

| X | Y | Z¹ | Z² | Z³ | R¹ | R² | R³ |
|---|---|----|----|----|----|----|----|
| CN | H | $CF_2$ | O | $CF_2$ | N=CHPh | $SCF_2CH_3$ | CN |
| CN | H | $CF_2$ | O | $CF_2$ | $CH_3$ | $SCF_2CH_3$ | CN |
| CN | H | $CF_2$ | O | $CF_2$ | $CF_3$ | $SCF_2CH_3$ | CN |
| CN | H | $CF_2$ | O | $CF_2$ | Cl | $SCF_2CH_3$ | CN |
| CN | H | $CF_2$ | O | $CF_2$ | F | $SCF_2CH_3$ | CN |
| CN | H | $CF_2$ | O | $CF_2$ | $COCH_3$ | $SCF_2CH_3$ | CN |
| CN | H | $CF_2$ | O | $CF_2$ | H | $SOCF_2CH_3$ | CN |
| CN | H | $CF_2$ | O | $CF_2$ | $NH_2$ | $SOCF_2CH_3$ | CN |
| CN | H | $CF_2$ | O | $CF_2$ | N=CHPh | $SOCF_2CH_3$ | CN |
| CN | H | $CF_2$ | O | $CF_2$ | $CH_3$ | $SOCF_2CH_3$ | CN |
| CN | H | $CF_2$ | O | $CF_2$ | $CF_3$ | $SOCF_2CH_3$ | CN |
| CN | H | $CF_2$ | O | $CF_2$ | Cl | $SOCF_2CH_3$ | CN |
| CN | H | $CF_2$ | O | $CF_2$ | F | $SOCF_2CH_3$ | CN |
| CN | H | $CF_2$ | O | $CF_2$ | $COCH_3$ | $SOCF_2CH_3$ | CN |
| CN | H | $CF_2$ | O | $CF_2$ | H | $SO_2CF_2CH_3$ | CN |
| CN | H | $CF_2$ | O | $CF_2$ | $NH_2$ | $SO_2CF_2CH_3$ | CN |
| CN | H | $CF_2$ | O | $CF_2$ | N=CHPh | $SO_2CF_2CH_3$ | CN |
| CN | H | $CF_2$ | O | $CF_2$ | $CH_3$ | $SO_2CF_2CH_3$ | CN |
| CN | H | $CF_2$ | O | $CF_2$ | $CF_3$ | $SO_2CF_2CH_3$ | CN |
| CN | H | $CF_2$ | O | $CF_2$ | Cl | $SO_2CF_2CH_3$ | CN |
| CN | H | $CF_2$ | O | $CF_2$ | F | $SO_2CF_2CH_3$ | CN |
| CN | H | $CF_2$ | O | $CF_2$ | $COCH_3$ | $SO_2CF_2CH_3$ | CN |
| CN | H | $CF_2$ | O | $CF_2$ | $NH_2$ | $COCF_3$ | CN |
| CN | H | $CF_2$ | O | $CF_2$ | N=CHPh | $COCF_3$ | CN |
| CN | H | $CF_2$ | O | $CF_2$ | $CH_3$ | $COCF_3$ | CN |
| CN | H | $CF_2$ | O | $CF_2$ | $CF_3$ | $COCF_3$ | CN |

TABLE 71

| X | Y | Z¹ | Z² | Z³ | R¹ | R² | R³ |
|---|---|----|----|----|----|----|----|
| CN | H | $CF_2$ | O | $CF_2$ | Cl | $COCF_3$ | CN |
| CN | H | $CF_2$ | O | $CF_2$ | F | $COCF_3$ | CN |
| CN | H | $CF_2$ | O | $CF_2$ | $COCH_3$ | $COCF_3$ | CN |
| CN | H | $CF_2$ | O | $CF_2$ | H | $COCF_3$ | CN |
| CN | H | $CF_2$ | O | $CF_2$ | $NH_2$ | $COCF_3$ | CN |
| CN | H | $CF_2$ | O | $CF_2$ | N=CHPh | $COCF_3$ | CN |
| CN | H | $CF_2$ | O | $CF_2$ | $CH_3$ | $COCF_3$ | CN |
| CN | H | $CF_2$ | O | $CF_2$ | $CF_3$ | $COCF_3$ | CN |
| CN | H | $CF_2$ | O | $CF_2$ | Cl | $COCF_3$ | CN |
| CN | H | $CF_2$ | O | $CF_2$ | F | $COCF_3$ | CN |
| CN | H | $CF_2$ | O | $CF_2$ | $COCH_3$ | $COCF_3$ | CN |
| CN | H | $CF_2$ | O | $CF_2$ | $NH_2$ | $C_2F_5$ | CN |
| CN | H | $CF_2$ | O | $CF_2$ | N=CHPh | $C_2F_5$ | CN |
| CN | H | $CF_2$ | O | $CF_2$ | $CH_3$ | $C_2F_5$ | CN |
| CN | H | $CF_2$ | O | $CF_2$ | $CF_3$ | $C_2F_5$ | CN |
| CN | H | $CF_2$ | O | $CF_2$ | Cl | $C_2F_5$ | CN |
| CN | H | $CF_2$ | O | $CF_2$ | F | $C_2F_5$ | CN |
| CN | H | $CF_2$ | O | $CF_2$ | $COCH_3$ | $C_2F_5$ | CN |
| CN | H | $CF_2$ | O | $CF_2$ | H | $C_2F_5$ | CN |
| CN | H | $CF_2$ | O | $CF_2$ | $NH_2$ | $C_2F_5$ | CN |
| CN | H | $CF_2$ | O | $CF_2$ | N=CHPh | $C_2F_5$ | CN |
| CN | H | $CF_2$ | O | $CF_2$ | $CH_3$ | $C_2F_5$ | CN |
| CN | H | $CF_2$ | O | $CF_2$ | $CF_3$ | $C_2F_5$ | CN |
| CN | H | $CF_2$ | O | $CF_2$ | Cl | $C_2F_5$ | CN |
| CN | H | $CF_2$ | O | $CF_2$ | F | $C_2F_5$ | CN |
| CN | H | $CF_2$ | O | $CF_2$ | $COCH_3$ | $C_2F_5$ | CN |

TABLE 72

| X | Y | Z¹ | Z² | Z³ | R¹ | R² | R³ |
|---|---|----|----|----|----|----|----|
| CN | H | $CF_2$ | O | $CF_2$ | $NH_2$ | $SFCl_2$ | CN |
| CN | H | $CF_2$ | O | $CF_2$ | N=CHPh | $SFCl_2$ | CN |
| CN | H | $CF_2$ | O | $CF_2$ | $CH_3$ | $SFCl_2$ | CN |
| CN | H | $CF_2$ | O | $CF_2$ | $CF_3$ | $SFCl_2$ | CN |
| CN | H | $CF_2$ | O | $CF_2$ | Cl | $SFCl_2$ | CN |
| CN | H | $CF_2$ | O | $CF_2$ | F | $SFCl_2$ | CN |
| CN | H | $CF_2$ | O | $CF_2$ | $COCH_3$ | $SFCl_2$ | CN |
| CN | H | $CF_2$ | O | $CF_2$ | H | $SFCl_2$ | CN |
| CN | H | $CF_2$ | O | $CF_2$ | $NH_2$ | $SFCl_2$ | CN |
| CN | H | $CF_2$ | O | $CF_2$ | N=CHPh | $SFCl_2$ | CN |
| CN | H | $CF_2$ | O | $CF_2$ | $CH_3$ | $SFCl_2$ | CN |
| CN | H | $CF_2$ | O | $CF_2$ | $CF_3$ | $SFCl_2$ | CN |
| CN | H | $CF_2$ | O | $CF_2$ | Cl | $SFCl_2$ | CN |
| CN | H | $CF_2$ | O | $CF_2$ | F | $SFCl_2$ | CN |
| CN | H | $CF_2$ | O | $CF_2$ | $COCH_3$ | $SFCl_2$ | CN |
| $NO_2$ | H | $CF_2$ | O | $CF_2$ | H | $SCF_3$ | H |
| $NO_2$ | H | $CF_2$ | O | $CF_2$ | $NH_2$ | $SCF_3$ | H |
| $NO_2$ | H | $CF_2$ | O | $CF_2$ | N=CHPh | $SCF_3$ | H |
| $NO_2$ | H | $CF_2$ | O | $CF_2$ | $CH_3$ | $SCF_3$ | H |
| $NO_2$ | H | $CF_2$ | O | $CF_2$ | $CF_3$ | $SCF_3$ | H |
| $NO_2$ | H | $CF_2$ | O | $CF_2$ | Cl | $SCF_3$ | H |
| $NO_2$ | H | $CF_2$ | O | $CF_2$ | F | $SCF_3$ | H |
| $NO_2$ | H | $CF_2$ | O | $CF_2$ | $COCH_3$ | $SCF_3$ | H |
| $NO_2$ | H | $CF_2$ | O | $CF_2$ | H | $SOCF_3$ | H |
| $NO_2$ | H | $CF_2$ | O | $CF_2$ | $NH_2$ | $SOCF_3$ | H |
| $NO_2$ | H | $CF_2$ | O | $CF_2$ | N=CHPh | $SOCF_3$ | H |

TABLE 73

| X | Y | Z¹ | Z² | Z³ | R¹ | R² | R³ |
|---|---|----|----|----|----|----|----|
| $NO_2$ | H | $CF_2$ | O | $CF_2$ | $CH_3$ | $SOCF_3$ | H |
| $NO_2$ | H | $CF_2$ | O | $CF_2$ | $CF_3$ | $SOCF_3$ | H |
| $NO_2$ | H | $CF_2$ | O | $CF_2$ | Cl | $SOCF_3$ | H |
| $NO_2$ | H | $CF_2$ | O | $CF_2$ | F | $SOCF_3$ | H |
| $NO_2$ | H | $CF_2$ | O | $CF_2$ | $COCH_3$ | $SOCF_3$ | H |
| $NO_2$ | H | $CF_2$ | O | $CF_2$ | H | $SO_2CF_3$ | H |
| $NO_2$ | H | $CF_2$ | O | $CF_2$ | $NH_2$ | $SO_2CF_3$ | H |
| $NO_2$ | H | $CF_2$ | O | $CF_2$ | N=CHPh | $SO_2CF_3$ | H |
| $NO_2$ | H | $CF_2$ | O | $CF_2$ | $CH_3$ | $SO_2CF_3$ | H |
| $NO_2$ | H | $CF_2$ | O | $CF_2$ | $CF_3$ | $SO_2CF_3$ | H |
| $NO_2$ | H | $CF_2$ | O | $CF_2$ | Cl | $SO_2CF_3$ | H |
| $NO_2$ | H | $CF_2$ | O | $CF_2$ | F | $SO_2CF_3$ | H |
| $NO_2$ | H | $CF_2$ | O | $CF_2$ | $COCH_3$ | $SO_2CF_3$ | H |
| $NO_2$ | H | $CF_2$ | O | $CF_2$ | H | $SCF_2CH_3$ | H |
| $NO_2$ | H | $CF_2$ | O | $CF_2$ | $NH_2$ | $SCF_2CH_3$ | H |
| $NO_2$ | H | $CF_2$ | O | $CF_2$ | N=CHPh | $SCF_2CH_3$ | H |
| $NO_2$ | H | $CF_2$ | O | $CF_2$ | $CH_3$ | $SCF_2CH_3$ | H |
| $NO_2$ | H | $CF_2$ | O | $CF_2$ | $CF_3$ | $SCF_2CH_3$ | H |
| $NO_2$ | H | $CF_2$ | O | $CF_2$ | Cl | $SCF_2CH_3$ | H |
| $NO_2$ | H | $CF_2$ | O | $CF_2$ | F | $SCF_2CH_3$ | H |
| $NO_2$ | H | $CF_2$ | O | $CF_2$ | $COCH_3$ | $SCF_2CH_3$ | H |
| $NO_2$ | H | $CF_2$ | O | $CF_2$ | H | $SOCF_2CH_3$ | H |
| $NO_2$ | H | $CF_2$ | O | $CF_2$ | $NH_2$ | $SOCF_2CH_3$ | H |
| $NO_2$ | H | $CF_2$ | O | $CF_2$ | N=CHPh | $SOCF_2CH_3$ | H |
| $NO_2$ | H | $CF_2$ | O | $CF_2$ | $CH_3$ | $SOCF_2CH_3$ | H |
| $NO_2$ | H | $CF_2$ | O | $CF_2$ | $CF_3$ | $SOCF_2CH_3$ | H |

TABLE 74

| X | Y | Z¹ | Z² | Z³ | R¹ | R² | R³ |
|---|---|----|----|----|----|----|----|
| $NO_2$ | H | $CF_2$ | O | $CF_2$ | Cl | $SOCF_2CH_3$ | H |
| $NO_2$ | H | $CF_2$ | O | $CF_2$ | F | $SOCF_2CH_3$ | H |
| $NO_2$ | H | $CF_2$ | O | $CF_2$ | $COCH_3$ | $SOCF_2CH_3$ | H |
| $NO_2$ | H | $CF_2$ | O | $CF_2$ | H | $SO_2CF_2CH_3$ | H |
| $NO_2$ | H | $CF_2$ | O | $CF_2$ | $NH_2$ | $SO_2CF_2CH_3$ | H |
| $NO_2$ | H | $CF_2$ | O | $CF_2$ | N=CHPh | $SO_2CF_2CH_3$ | H |
| $NO_2$ | H | $CF_2$ | O | $CF_2$ | $CH_3$ | $SO_2CF_2CH_3$ | H |
| $NO_2$ | H | $CF_2$ | O | $CF_2$ | $CF_3$ | $SO_2CF_2CH_3$ | H |
| $NO_2$ | H | $CF_2$ | O | $CF_2$ | Cl | $SO_2CF_2CH_3$ | H |
| $NO_2$ | H | $CF_2$ | O | $CF_2$ | F | $SO_2CF_2CH_3$ | H |

TABLE 74-continued

| X | Y | Z¹ | Z² | Z³ | R¹ | R² | R³ |
|---|---|----|----|----|----|----|----|
| $NO_2$ | H | $CF_2$ | O | $CF_2$ | $COCH_3$ | $SO_2CF_2CH_3$ | H |
| $NO_2$ | H | $CF_2$ | O | $CF_2$ | $NH_2$ | $COCF_3$ | H |
| $NO_2$ | H | $CF_2$ | O | $CF_2$ | N=CHPh | $COCF_3$ | H |
| $NO_2$ | H | $CF_2$ | O | $CF_2$ | $CH_3$ | $COCF_3$ | H |
| $NO_2$ | H | $CF_2$ | O | $CF_2$ | $CF_3$ | $COCF_3$ | H |
| $NO_2$ | H | $CF_2$ | O | $CF_2$ | Cl | $COCF_3$ | H |
| $NO_2$ | H | $CF_2$ | O | $CF_2$ | F | $COCF_3$ | H |
| $NO_2$ | H | $CF_2$ | O | $CF_2$ | $COCH_3$ | $COCF_3$ | H |
| $NO_2$ | H | $CF_2$ | O | $CF_2$ | H | $COCF_3$ | H |
| $NO_2$ | H | $CF_2$ | O | $CF_2$ | $NH_2$ | $COCF_3$ | H |
| $NO_2$ | H | $CF_2$ | O | $CF_2$ | N=CHPh | $COCF_3$ | H |
| $NO_2$ | H | $CF_2$ | O | $CF_2$ | $CH_3$ | $COCF_3$ | H |
| $NO_2$ | H | $CF_2$ | O | $CF_2$ | $CF_3$ | $COCF_3$ | H |
| $NO_2$ | H | $CF_2$ | O | $CF_2$ | Cl | $COCF_3$ | H |
| $NO_2$ | H | $CF_2$ | O | $CF_2$ | F | $COCF_3$ | H |
| $NO_2$ | H | $CF_2$ | O | $CF_2$ | $COCH_3$ | $COCF_3$ | H |

TABLE 75

| X | Y | Z¹ | Z² | Z³ | R¹ | R² | R³ |
|---|---|----|----|----|----|----|----|
| $NO_2$ | H | $CF_2$ | O | $CF_2$ | $NH_2$ | $C_2F_5$ | H |
| $NO_2$ | H | $CF_2$ | O | $CF_2$ | N=CHPh | $C_2F_5$ | H |
| $NO_2$ | H | $CF_2$ | O | $CF_2$ | $CH_3$ | $C_2F_5$ | H |
| $NO_2$ | H | $CF_2$ | O | $CF_2$ | $CF_3$ | $C_2F_5$ | H |
| $NO_2$ | H | $CF_2$ | O | $CF_2$ | Cl | $C_2F_5$ | H |
| $NO_2$ | H | $CF_2$ | O | $CF_2$ | F | $C_2F_5$ | H |
| $NO_2$ | H | $CF_2$ | O | $CF_2$ | $COCH_3$ | $C_2F_5$ | H |
| $NO_2$ | H | $CF_2$ | O | $CF_2$ | H | $C_2F_5$ | H |
| $NO_2$ | H | $CF_2$ | O | $CF_2$ | $NH_2$ | $C_2F_5$ | H |
| $NO_2$ | H | $CF_2$ | O | $CF_2$ | N=CHPh | $C_2F_5$ | H |
| $NO_2$ | H | $CF_2$ | O | $CF_2$ | $CH_3$ | $C_2F_5$ | H |
| $NO_2$ | H | $CF_2$ | O | $CF_2$ | $CF_3$ | $C_2F_5$ | H |
| $NO_2$ | H | $CF_2$ | O | $CF_2$ | Cl | $C_2F_5$ | H |
| $NO_2$ | H | $CF_2$ | O | $CF_2$ | F | $C_2F_5$ | H |
| $NO_2$ | H | $CF_2$ | O | $CF_2$ | $COCH_3$ | $C_2F_5$ | H |
| $NO_2$ | H | $CF_2$ | O | $CF_2$ | $NH_2$ | $SFCl_2$ | H |
| $NO_2$ | H | $CF_2$ | O | $CF_2$ | N=CHPh | $SFCl_2$ | H |
| $NO_2$ | H | $CF_2$ | O | $CF_2$ | $CH_3$ | $SFCl_2$ | H |
| $NO_2$ | H | $CF_2$ | O | $CF_2$ | $CF_3$ | $SFCl_2$ | H |
| $NO_2$ | H | $CF_2$ | O | $CF_2$ | Cl | $SFCl_2$ | H |
| $NO_2$ | H | $CF_2$ | O | $CF_2$ | F | $SFCl_2$ | H |
| $NO_2$ | H | $CF_2$ | O | $CF_2$ | $COCH_3$ | $SFCl_2$ | H |
| $NO_2$ | H | $CF_2$ | O | $CF_2$ | H | $SFCl_2$ | H |
| $NO_2$ | H | $CF_2$ | O | $CF_2$ | $NH_2$ | $SFCl_2$ | H |
| $NO_2$ | H | $CF_2$ | O | $CF_2$ | N=CHPh | $SFCl_2$ | H |
| $NO_2$ | H | $CF_2$ | O | $CF_2$ | $CH_3$ | $SFCl_2$ | H |

TABLE 76

| X | Y | Z¹ | Z² | Z³ | R¹ | R² | R³ |
|---|---|----|----|----|----|----|----|
| $NO_2$ | H | $CF_2$ | O | $CF_2$ | $CF_3$ | $SFCl_2$ | H |
| $NO_2$ | H | $CF_2$ | O | $CF_2$ | Cl | $SFCl_2$ | H |
| $NO_2$ | H | $CF_2$ | O | $CF_2$ | F | $SFCl_2$ | H |
| $NO_2$ | H | $CF_2$ | O | $CF_2$ | $COCH_3$ | $SFCl_2$ | H |
| $NO_2$ | H | $CF_2$ | O | $CF_2$ | H | $SCF_3$ | $CF_3$ |
| $NO_2$ | H | $CF_2$ | O | $CF_2$ | $NH_2$ | $SCF_3$ | $CF_3$ |
| $NO_2$ | H | $CF_2$ | O | $CF_2$ | N=CHPh | $SCF_3$ | $CF_3$ |
| $NO_2$ | H | $CF_2$ | O | $CF_2$ | $CH_3$ | $SCF_3$ | $CF_3$ |
| $NO_2$ | H | $CF_2$ | O | $CF_2$ | $CF_3$ | $SCF_3$ | $CF_3$ |
| $NO_2$ | H | $CF_2$ | O | $CF_2$ | Cl | $SCF_3$ | $CF_3$ |
| $NO_2$ | H | $CF_2$ | O | $CF_2$ | F | $SCF_3$ | $CF_3$ |
| $NO_2$ | H | $CF_2$ | O | $CF_2$ | $COCH_3$ | $SCF_3$ | $CF_3$ |
| $NO_2$ | H | $CF_2$ | O | $CF_2$ | H | $SOCF_3$ | $CF_3$ |
| $NO_2$ | H | $CF_2$ | O | $CF_2$ | $NH_2$ | $SOCF_3$ | $CF_3$ |
| $NO_2$ | H | $CF_2$ | O | $CF_2$ | N=CHPh | $SOCF_3$ | $CF_3$ |
| $NO_2$ | H | $CF_2$ | O | $CF_2$ | $CH_3$ | $SOCF_3$ | $CF_3$ |
| $NO_2$ | H | $CF_2$ | O | $CF_2$ | $CF_3$ | $SOCF_3$ | $CF_3$ |
| $NO_2$ | H | $CF_2$ | O | $CF_2$ | Cl | $SOCF_3$ | $CF_3$ |
| $NO_2$ | H | $CF_2$ | O | $CF_2$ | F | $SOCF_3$ | $CF_3$ |
| $NO_2$ | H | $CF_2$ | O | $CF_2$ | $COCH_3$ | $SOCF_3$ | $CF_3$ |

TABLE 76-continued

| X | Y | Z¹ | Z² | Z³ | R¹ | R² | R³ |
|---|---|----|----|----|----|----|----|
| $NO_2$ | H | $CF_2$ | O | $CF_2$ | H | $SO_2CF_3$ | $CF_3$ |
| $NO_2$ | H | $CF_2$ | O | $CF_2$ | $NH_2$ | $SO_2CF_3$ | $CF_3$ |
| $NO_2$ | H | $CF_2$ | O | $CF_2$ | N=CHPh | $SO_2CF_3$ | $CF_3$ |
| $NO_2$ | H | $CF_2$ | O | $CF_2$ | $CH_3$ | $SO_2CF_3$ | $CF_3$ |
| $NO_2$ | H | $CF_2$ | O | $CF_2$ | $CF_3$ | $SO_2CF_3$ | $CF_3$ |
| $NO_2$ | H | $CF_2$ | O | $CF_2$ | Cl | $SO_2CF_3$ | $CF_3$ |

TABLE 77

| X | Y | Z¹ | Z² | Z³ | R¹ | R² | R³ |
|---|---|----|----|----|----|----|----|
| $NO_2$ | H | $CF_2$ | O | $CF_2$ | F | $SO_2CF_3$ | $CF_3$ |
| $NO_2$ | H | $CF_2$ | O | $CF_2$ | $COCH_3$ | $SO_2CF_3$ | $CF_3$ |
| $NO_2$ | H | $CF_2$ | O | $CF_2$ | H | $SCF_2CH_3$ | $CF_3$ |
| $NO_2$ | H | $CF_2$ | O | $CF_2$ | $NH_2$ | $SCF_2CH_3$ | $CF_3$ |
| $NO_2$ | H | $CF_2$ | O | $CF_2$ | N=CHPh | $SCF_2CH_3$ | $CF_3$ |
| $NO_2$ | H | $CF_2$ | O | $CF_2$ | $CH_3$ | $SCF_2CH_3$ | $CF_3$ |
| $NO_2$ | H | $CF_2$ | O | $CF_2$ | $CF_3$ | $SCF_2CH_3$ | $CF_3$ |
| $NO_2$ | H | $CF_2$ | O | $CF_2$ | Cl | $SCF_2CH_3$ | $CF_3$ |
| $NO_2$ | H | $CF_2$ | O | $CF_2$ | F | $SCF_2CH_3$ | $CF_3$ |
| $NO_2$ | H | $CF_2$ | O | $CF_2$ | $COCH_3$ | $SCF_2CH_3$ | $CF_3$ |
| $NO_2$ | H | $CF_2$ | O | $CF_2$ | H | $SOCF_2CH_3$ | $CF_3$ |
| $NO_2$ | H | $CF_2$ | O | $CF_2$ | $NH_2$ | $SOCF_2CH_3$ | $CF_3$ |
| $NO_2$ | H | $CF_2$ | O | $CF_2$ | N=CHPh | $SOCF_2CH_3$ | $CF_3$ |
| $NO_2$ | H | $CF_2$ | O | $CF_2$ | $CH_3$ | $SOCF_2CH_3$ | $CF_3$ |
| $NO_2$ | H | $CF_2$ | O | $CF_2$ | $CF_3$ | $SOCF_2CH_3$ | $CF_3$ |
| $NO_2$ | H | $CF_2$ | O | $CF_2$ | Cl | $SOCF_2CH_3$ | $CF_3$ |
| $NO_2$ | H | $CF_2$ | O | $CF_2$ | F | $SOCF_2CH_3$ | $CF_3$ |
| $NO_2$ | H | $CF_2$ | O | $CF_2$ | $COCH_3$ | $SOCF_2CH_3$ | $CF_3$ |
| $NO_2$ | H | $CF_2$ | O | $CF_2$ | H | $SO_2CF_2CH_3$ | $CF_3$ |
| $NO_2$ | H | $CF_2$ | O | $CF_2$ | $NH_2$ | $SO_2CF_2CH_3$ | $CF_3$ |
| $NO_2$ | H | $CF_2$ | O | $CF_2$ | N=CHPh | $SO_2CF_2CH_3$ | $CF_3$ |
| $NO_2$ | H | $CF_2$ | O | $CF_2$ | $CH_3$ | $SO_2CF_2CH_3$ | $CF_3$ |
| $NO_2$ | H | $CF_2$ | O | $CF_2$ | $CF_3$ | $SO_2CF_2CH_3$ | $CF_3$ |
| $NO_2$ | H | $CF_2$ | O | $CF_2$ | Cl | $SO_2CF_2CH_3$ | $CF_3$ |
| $NO_2$ | H | $CF_2$ | O | $CF_2$ | F | $SO_2CF_2CH_3$ | $CF_3$ |
| $NO_2$ | H | $CF_2$ | O | $CF_2$ | $COCH_3$ | $SO_2CF_2CH_3$ | $CF_3$ |

TABLE 78

| X | Y | Z¹ | Z² | Z³ | R¹ | R² | R³ |
|---|---|----|----|----|----|----|----|
| $NO_2$ | H | $CF_2$ | O | $CF_2$ | $NH_2$ | $COCF_3$ | $CF_3$ |
| $NO_2$ | H | $CF_2$ | O | $CF_2$ | N=CHPh | $COCF_3$ | $CF_3$ |
| $NO_2$ | H | $CF_2$ | O | $CF_2$ | $CH_3$ | $COCF_3$ | $CF_3$ |
| $NO_2$ | H | $CF_2$ | O | $CF_2$ | $CF_3$ | $COCF_3$ | $CF_3$ |
| $NO_2$ | H | $CF_2$ | O | $CF_2$ | Cl | $COCF_3$ | $CF_3$ |
| $NO_2$ | H | $CF_2$ | O | $CF_2$ | F | $COCF_3$ | $CF_3$ |
| $NO_2$ | H | $CF_2$ | O | $CF_2$ | $COCH_3$ | $COCF_3$ | $CF_3$ |
| $NO_2$ | H | $CF_2$ | O | $CF_2$ | H | $COCF_3$ | $CF_3$ |
| $NO_2$ | H | $CF_2$ | O | $CF_2$ | $NH_2$ | $COCF_3$ | $CF_3$ |
| $NO_2$ | H | $CF_2$ | O | $CF_2$ | N=CHPh | $COCF_3$ | $CF_3$ |
| $NO_2$ | H | $CF_2$ | O | $CF_2$ | $CH_3$ | $COCF_3$ | $CF_3$ |
| $NO_2$ | H | $CF_2$ | O | $CF_2$ | $CF_3$ | $COCF_3$ | $CF_3$ |
| $NO_2$ | H | $CF_2$ | O | $CF_2$ | Cl | $COCF_3$ | $CF_3$ |
| $NO_2$ | H | $CF_2$ | O | $CF_2$ | F | $COCF_3$ | $CF_3$ |
| $NO_2$ | H | $CF_2$ | O | $CF_2$ | $COCH_3$ | $COCF_3$ | $CF_3$ |
| $NO_2$ | H | $CF_2$ | O | $CF_2$ | $NH_2$ | $C_2F_5$ | $CF_3$ |
| $NO_2$ | H | $CF_2$ | O | $CF_2$ | N=CHPh | $C_2F_5$ | $CF_3$ |
| $NO_2$ | H | $CF_2$ | O | $CF_2$ | $CH_3$ | $C_2F_5$ | $CF_3$ |
| $NO_2$ | H | $CF_2$ | O | $CF_2$ | $CF_3$ | $C_2F_5$ | $CF_3$ |
| $NO_2$ | H | $CF_2$ | O | $CF_2$ | Cl | $C_2F_5$ | $CF_3$ |
| $NO_2$ | H | $CF_2$ | O | $CF_2$ | F | $C_2F_5$ | $CF_3$ |
| $NO_2$ | H | $CF_2$ | O | $CF_2$ | $COCH_3$ | $C_2F_5$ | $CF_3$ |
| $NO_2$ | H | $CF_2$ | O | $CF_2$ | H | $C_2F_5$ | $CF_3$ |
| $NO_2$ | H | $CF_2$ | O | $CF_2$ | $NH_2$ | $C_2F_5$ | $CF_3$ |
| $NO_2$ | H | $CF_2$ | O | $CF_2$ | N=CHPh | $C_2F_5$ | $CF_3$ |
| $NO_2$ | H | $CF_2$ | O | $CF_2$ | $CH_3$ | $C_2F_5$ | $CF_3$ |

TABLE 79

| X | Y | $Z^1$ | $Z^2$ | $Z^3$ | $R^1$ | $R^2$ | $R^3$ |
|---|---|---|---|---|---|---|---|
| $NO_2$ | H | $CF_2$ | O | $CF_2$ | $CF_3$ | $C_2F_5$ | $CF_3$ |
| $NO_2$ | H | $CF_2$ | O | $CF_2$ | Cl | $C_2F_5$ | $CF_3$ |
| $NO_2$ | H | $CF_2$ | O | $CF_2$ | F | $C_2F_5$ | $CF_3$ |
| $NO_2$ | H | $CF_2$ | O | $CF_2$ | $COCH_3$ | $C_2F_5$ | $CF_3$ |
| $NO_2$ | H | $CF_2$ | O | $CF_2$ | $NH_2$ | $SFCl_2$ | $CF_3$ |
| $NO_2$ | H | $CF_2$ | O | $CF_2$ | N = CHPh | $SFCl_2$ | $CF_3$ |
| $NO_2$ | H | $CF_2$ | O | $CF_2$ | $CH_3$ | $SFCl_2$ | $CF_3$ |
| $NO_2$ | H | $CF_2$ | O | $CF_2$ | $CF_3$ | $SFCl_2$ | $CF_3$ |
| $NO_2$ | H | $CF_2$ | O | $CF_2$ | Cl | $SFCl_2$ | $CF_3$ |
| $NO_2$ | H | $CF_2$ | O | $CF_2$ | F | $SFCl_2$ | $CF_3$ |
| $NO_2$ | H | $CF_2$ | O | $CF_2$ | $COCH_3$ | $SFCl_2$ | $CF_3$ |
| $NO_2$ | H | $CF_2$ | O | $CF_2$ | H | $SFCl_2$ | $CF_3$ |
| $NO_2$ | H | $CF_2$ | O | $CF_2$ | $NH_2$ | $SFCl_2$ | $CF_3$ |
| $NO_2$ | H | $CF_2$ | O | $CF_2$ | N = CHPh | $SFCl_2$ | $CF_3$ |
| $NO_2$ | H | $CF_2$ | O | $CF_2$ | $CH_3$ | $SFCl_2$ | $CF_3$ |
| $NO_2$ | H | $CF_2$ | O | $CF_2$ | $CF_3$ | $SFCl_2$ | $CF_3$ |
| $NO_2$ | H | $CF_2$ | O | $CF_2$ | Cl | $SFCl_2$ | $CF_3$ |
| $NO_2$ | H | $CF_2$ | O | $CF_2$ | F | $SFCl_2$ | $CF_3$ |
| $NO_2$ | H | $CF_2$ | O | $CF_2$ | $COCH_3$ | $SFCl_2$ | $CF_3$ |
| $NO_2$ | H | $CF_2$ | O | $CF_2$ | H | $SCF_3$ | $C_2F_5$ |
| $NO_2$ | H | $CF_2$ | O | $CF_2$ | $NH_2$ | $SCF_3$ | $C_2F_5$ |
| $NO_2$ | H | $CF_2$ | O | $CF_2$ | N = CHPh | $SCF_3$ | $C_2F_5$ |
| $NO_2$ | H | $CF_2$ | O | $CF_2$ | $CH_3$ | $SCF_3$ | $C_2F_5$ |
| $NO_2$ | H | $CF_2$ | O | $CF_2$ | $CF_3$ | $SCF_3$ | $C_2F_5$ |
| $NO_2$ | H | $CF_2$ | O | $CF_2$ | Cl | $SCF_3$ | $C_2F_5$ |
| $NO_2$ | H | $CF_2$ | O | $CF_2$ | F | $SCF_3$ | $C_2F_5$ |

TABLE 80

| X | Y | $Z^1$ | $Z^2$ | $Z^3$ | $R^1$ | $R^2$ | $R^3$ |
|---|---|---|---|---|---|---|---|
| $NO_2$ | H | $CF_2$ | O | $CF_2$ | $COCH_3$ | $SCF_3$ | $C_2F_5$ |
| $NO_2$ | H | $CF_2$ | O | $CF_2$ | H | $SOCF_3$ | $C_2F_5$ |
| $NO_2$ | H | $CF_2$ | O | $CF_2$ | $NH_2$ | $SOCF_3$ | $C_2F_5$ |
| $NO_2$ | H | $CF_2$ | O | $CF_2$ | N = CHPh | $SOCF_3$ | $C_2F_5$ |
| $NO_2$ | H | $CF_2$ | O | $CF_2$ | $CH_3$ | $SOCF_3$ | $C_2F_5$ |
| $NO_2$ | H | $CF_2$ | O | $CF_2$ | $CF_3$ | $SOCF_3$ | $C_2F_5$ |
| $NO_2$ | H | $CF_2$ | O | $CF_2$ | Cl | $SOCF_3$ | $C_2F_5$ |
| $NO_2$ | H | $CF_2$ | O | $CF_2$ | F | $SOCF_3$ | $C_2F_5$ |
| $NO_2$ | H | $CF_2$ | O | $CF_2$ | $COCH_3$ | $SOCF_3$ | $C_2F_5$ |
| $NO_2$ | H | $CF_2$ | O | $CF_2$ | H | $SO_2CF_3$ | $C_2F_5$ |
| $NO_2$ | H | $CF_2$ | O | $CF_2$ | $NH_2$ | $SO_2CF_3$ | $C_2F_5$ |
| $NO_2$ | H | $CF_2$ | O | $CF_2$ | N = CHPh | $SO_2CF_3$ | $C_2F_5$ |
| $NO_2$ | H | $CF_2$ | O | $CF_2$ | $CH_3$ | $SO_2CF_3$ | $C_2F_5$ |
| $NO_2$ | H | $CF_2$ | O | $CF_2$ | $CF_3$ | $SO_2CF_3$ | $C_2F_5$ |
| $NO_2$ | H | $CF_2$ | O | $CF_2$ | Cl | $SO_2CF_3$ | $C_2F_5$ |
| $NO_2$ | H | $CF_2$ | O | $CF_2$ | F | $SO_2CF_3$ | $C_2F_5$ |
| $NO_2$ | H | $CF_2$ | O | $CF_2$ | $COCH_3$ | $SO_2CF_3$ | $C_2F_5$ |
| $NO_2$ | H | $CF_2$ | O | $CF_2$ | H | $SCF_2CH_3$ | $C_2F_5$ |
| $NO_2$ | H | $CF_2$ | O | $CF_2$ | $NH_2$ | $SCF_2CH_3$ | $C_2F_5$ |
| $NO_2$ | H | $CF_2$ | O | $CF_2$ | N = CHPh | $SCF_2CH_3$ | $C_2F_5$ |
| $NO_2$ | H | $CF_2$ | O | $CF_2$ | $CH_3$ | $SCF_2CH_3$ | $C_2F_5$ |
| $NO_2$ | H | $CF_2$ | O | $CF_2$ | $CF_3$ | $SCF_2CH_3$ | $C_2F_5$ |
| $NO_2$ | H | $CF_2$ | O | $CF_2$ | Cl | $SCF_2CH_3$ | $C_2F_5$ |
| $NO_2$ | H | $CF_2$ | O | $CF_2$ | F | $SCF_2CH_3$ | $C_2F_5$ |
| $NO_2$ | H | $CF_2$ | O | $CF_2$ | $COCH_3$ | $SCF_2CH_3$ | $C_2F_5$ |
| $NO_2$ | H | $CF_2$ | O | $CF_2$ | H | $SOCF_2CH_3$ | $C_2F_5$ |

TABLE 81

| X | Y | $Z^1$ | $Z^2$ | $Z^3$ | $R^1$ | $R^2$ | $R^3$ |
|---|---|---|---|---|---|---|---|
| $NO_2$ | H | $CF_2$ | O | $CF_2$ | $NH_2$ | $SOCF_2CH_3$ | $C_2F_5$ |
| $NO_2$ | H | $CF_2$ | O | $CF_2$ | N = CHPh | $SOCF_2CH_3$ | $C_2F_5$ |
| $NO_2$ | H | $CF_2$ | O | $CF_2$ | $CH_3$ | $SOCF_2CH_3$ | $C_2F_5$ |
| $NO_2$ | H | $CF_2$ | O | $CF_2$ | $CF_3$ | $SOCF_2CH_3$ | $C_2F_5$ |
| $NO_2$ | H | $CF_2$ | O | $CF_2$ | Cl | $SOCF_2CH_3$ | $C_2F_5$ |
| $NO_2$ | H | $CF_2$ | O | $CF_2$ | F | $SOCF_2CH_3$ | $C_2F_5$ |
| $NO_2$ | H | $CF_2$ | O | $CF_2$ | $COCH_3$ | $SOCF_2CH_3$ | $C_2F_5$ |
| $NO_2$ | H | $CF_2$ | O | $CF_2$ | H | $SO_2CF_2CH_3$ | $C_2F_5$ |
| $NO_2$ | H | $CF_2$ | O | $CF_2$ | $NH_2$ | $SO_2CF_2CH_3$ | $C_2F_5$ |
| $NO_2$ | H | $CF_2$ | O | $CF_2$ | N = CHPh | $SO_2CF_2CH_3$ | $C_2F_5$ |

TABLE 81-continued

| X | Y | $Z^1$ | $Z^2$ | $Z^3$ | $R^1$ | $R^2$ | $R^3$ |
|---|---|---|---|---|---|---|---|
| $NO_2$ | H | $CF_2$ | O | $CF_2$ | $CH_3$ | $SO_2CF_2CH_3$ | $C_2F_5$ |
| $NO_2$ | H | $CF_2$ | O | $CF_2$ | $CF_3$ | $SO_2CF_2CH_3$ | $C_2F_5$ |
| $NO_2$ | H | $CF_2$ | O | $CF_2$ | Cl | $SO_2CF_2CH_3$ | $C_2F_5$ |
| $NO_2$ | H | $CF_2$ | O | $CF_2$ | F | $SO_2CF_2CH_3$ | $C_2F_5$ |
| $NO_2$ | H | $CF_2$ | O | $CF_2$ | $COCH_3$ | $SO_2CF_2CH_3$ | $C_2F_5$ |
| $NO_2$ | H | $CF_2$ | O | $CF_2$ | $NH_2$ | $COCF_3$ | $C_2F_5$ |
| $NO_2$ | H | $CF_2$ | O | $CF_2$ | N = CHPh | $COCF_3$ | $C_2F_5$ |
| $NO_2$ | H | $CF_2$ | O | $CF_2$ | $CH_3$ | $COCF_3$ | $C_2F_5$ |
| $NO_2$ | H | $CF_2$ | O | $CF_2$ | $CF_3$ | $COCF_3$ | $C_2F_5$ |
| $NO_2$ | H | $CF_2$ | O | $CF_2$ | Cl | $COCF_3$ | $C_2F_5$ |
| $NO_2$ | H | $CF_2$ | O | $CF_2$ | F | $COCF_3$ | $C_2F_5$ |
| $NO_2$ | H | $CF_2$ | O | $CF_2$ | $COCH_3$ | $COCF_3$ | $C_2F_5$ |
| $NO_2$ | H | $CF_2$ | O | $CF_2$ | H | $COCF_3$ | $C_2F_5$ |
| $NO_2$ | H | $CF_2$ | O | $CF_2$ | $NH_2$ | $COCF_3$ | $C_2F_5$ |
| $NO_2$ | H | $CF_2$ | O | $CF_2$ | N = CHPh | $COCF_3$ | $C_2F_5$ |
| $NO_2$ | H | $CF_2$ | O | $CF_2$ | $CH_3$ | $COCF_3$ | $C_2F_5$ |

TABLE 82

| X | Y | $Z^1$ | $Z^2$ | $Z^3$ | $R^1$ | $R^2$ | $R^3$ |
|---|---|---|---|---|---|---|---|
| $NO_2$ | H | $CF_2$ | O | $CF_2$ | $CF_3$ | $COCF_3$ | $C_2F_5$ |
| $NO_2$ | H | $CF_2$ | O | $CF_2$ | Cl | $COCF_3$ | $C_2F_5$ |
| $NO_2$ | H | $CF_2$ | O | $CF_2$ | F | $COCF_3$ | $C_2F_5$ |
| $NO_2$ | H | $CF_2$ | O | $CF_2$ | $COCH_3$ | $COCF_3$ | $C_2F_5$ |
| $NO_2$ | H | $CF_2$ | O | $CF_2$ | $NH_2$ | $C_2F_5$ | $C_2F_5$ |
| $NO_2$ | H | $CF_2$ | O | $CF_2$ | N = CHPh | $C_2F_5$ | $C_2F_5$ |
| $NO_2$ | H | $CF_2$ | O | $CF_2$ | $CH_3$ | $C_2F_5$ | $C_2F_5$ |
| $NO_2$ | H | $CF_2$ | O | $CF_2$ | $CF_3$ | $C_2F_5$ | $C_2F_5$ |
| $NO_2$ | H | $CF_2$ | O | $CF_2$ | Cl | $C_2F_5$ | $C_2F_5$ |
| $NO_2$ | H | $CF_2$ | O | $CF_2$ | F | $C_2F_5$ | $C_2F_5$ |
| $NO_2$ | H | $CF_2$ | O | $CF_2$ | $COCH_3$ | $C_2F_5$ | $C_2F_5$ |
| $NO_2$ | H | $CF_2$ | O | $CF_2$ | H | $C_2F_5$ | $C_2F_5$ |
| $NO_2$ | H | $CF_2$ | O | $CF_2$ | $NH_2$ | $C_2F_5$ | $C_2F_5$ |
| $NO_2$ | H | $CF_2$ | O | $CF_2$ | N = CHPh | $C_2F_5$ | $C_2F_5$ |
| $NO_2$ | H | $CF_2$ | O | $CF_2$ | $CH_3$ | $C_2F_5$ | $C_2F_5$ |
| $NO_2$ | H | $CF_2$ | O | $CF_2$ | $CF_3$ | $C_2F_5$ | $C_2F_5$ |
| $NO_2$ | H | $CF_2$ | O | $CF_2$ | Cl | $C_2F_5$ | $C_2F_5$ |
| $NO_2$ | H | $CF_2$ | O | $CF_2$ | F | $C_2F_5$ | $C_2F_5$ |
| $NO_2$ | H | $CF_2$ | O | $CF_2$ | $COCH_3$ | $C_2F_5$ | $C_2F_5$ |
| $NO_2$ | H | $CF_2$ | O | $CF_2$ | $NH_2$ | $SFCl_2$ | $C_2F_5$ |
| $NO_2$ | H | $CF_2$ | O | $CF_2$ | N = CHPh | $SFCl_2$ | $C_2F_5$ |
| $NO_2$ | H | $CF_2$ | O | $CF_2$ | $CH_3$ | $SFCl_2$ | $C_2F_5$ |
| $NO_2$ | H | $CF_2$ | O | $CF_2$ | $CF_3$ | $SFCl_2$ | $C_2F_5$ |
| $NO_2$ | H | $CF_2$ | O | $CF_2$ | Cl | $SFCl_2$ | $C_2F_5$ |
| $NO_2$ | H | $CF_2$ | O | $CF_2$ | F | $SFCl_2$ | $C_2F_5$ |
| $NO_2$ | H | $CF_2$ | O | $CF_2$ | $COCH_3$ | $SFCl_2$ | $C_2F_5$ |

TABLE 83

| X | Y | $Z^1$ | $Z^2$ | $Z^3$ | $R^1$ | $R^2$ | $R^3$ |
|---|---|---|---|---|---|---|---|
| $NO_2$ | H | $CF_2$ | O | $CF_2$ | H | $SFCl_2$ | $C_2F_5$ |
| $NO_2$ | H | $CF_2$ | O | $CF_2$ | $NH_2$ | $SFCl_2$ | $C_2F_5$ |
| $NO_2$ | H | $CF_2$ | O | $CF_2$ | N = CHPh | $SFCl_2$ | $C_2F_5$ |
| $NO_2$ | H | $CF_2$ | O | $CF_2$ | $CH_3$ | $SFCl_2$ | $C_2F_5$ |
| $NO_2$ | H | $CF_2$ | O | $CF_2$ | $CF_3$ | $SFCl_2$ | $C_2F_5$ |
| $NO_2$ | H | $CF_2$ | O | $CF_2$ | Cl | $SFCl_2$ | $C_2F_5$ |
| $NO_2$ | H | $CF_2$ | O | $CF_2$ | F | $SFCl_2$ | $C_2F_5$ |
| $NO_2$ | H | $CF_2$ | O | $CF_2$ | $COCH_3$ | $SFCl_2$ | $C_2F_5$ |
| $NO_2$ | H | $CF_2$ | O | $CF_2$ | H | $SCF_3$ | $CSNH_2$ |
| $NO_2$ | H | $CF_2$ | O | $CF_2$ | $NH_2$ | $SCF_3$ | $CSNH_2$ |
| $NO_2$ | H | $CF_2$ | O | $CF_2$ | N = CHPh | $SCF_3$ | $CSNH_2$ |
| $NO_2$ | H | $CF_2$ | O | $CF_2$ | $CH_3$ | $SCF_3$ | $CSNH_2$ |
| $NO_2$ | H | $CF_2$ | O | $CF_2$ | $CF_3$ | $SCF_3$ | $CSNH_2$ |
| $NO_2$ | H | $CF_2$ | O | $CF_2$ | Cl | $SCF_3$ | $CSNH_2$ |
| $NO_2$ | H | $CF_2$ | O | $CF_2$ | F | $SCF_3$ | $CSNH_2$ |
| $NO_2$ | H | $CF_2$ | O | $CF_2$ | $COCH_3$ | $SCF_3$ | $CSNH_2$ |
| $NO_2$ | H | $CF_2$ | O | $CF_2$ | H | $SOCF_3$ | $CSNH_2$ |
| $NO_2$ | H | $CF_2$ | O | $CF_2$ | $NH_2$ | $SOCF_3$ | $CSNH_2$ |
| $NO_2$ | H | $CF_2$ | O | $CF_2$ | N = CHPh | $SOCF_3$ | $CSNH_2$ |
| $NO_2$ | H | $CF_2$ | O | $CF_2$ | $CH_3$ | $SOCF_3$ | $CSNH_2$ |

TABLE 83-continued

| X | Y | Z¹ | Z² | Z³ | R¹ | R² | R³ |
|---|---|---|---|---|---|---|---|
| NO₂ | H | CF₂ | O | CF₂ | CF₃ | SOCF₃ | CSNH₂ |
| NO₂ | H | CF₂ | O | CF₂ | Cl | SOCF₃ | CSNH₂ |
| NO₂ | H | CF₂ | O | CF₂ | F | SOCF₃ | CSNH₂ |
| NO₂ | H | CF₂ | O | CF₂ | COCH₃ | SOCF₃ | CSNH₂ |
| NO₂ | H | CF₂ | O | CF₂ | H | SO₂CF₃ | CSNH₂ |
| NO₂ | H | CF₂ | O | CF₂ | NH₂ | SO₂CF₃ | CSNH₂ |

TABLE 84

| X | Y | Z¹ | Z² | Z³ | R¹ | R² | R³ |
|---|---|---|---|---|---|---|---|
| NO₂ | H | CF₂ | O | CF₂ | N=CHPh | SO₂CF₃ | CSNH₂ |
| NO₂ | H | CF₂ | O | CF₂ | CH₃ | SO₂CF₃ | CSNH₂ |
| NO₂ | H | CF₂ | O | CF₂ | CF₃ | SO₂CF₃ | CSNH₂ |
| NO₂ | H | CF₂ | O | CF₂ | Cl | SO₂CF₃ | CSNH₂ |
| NO₂ | H | CF₂ | O | CF₂ | F | SO₂CF₃ | CSNH₂ |
| NO₂ | H | CF₂ | O | CF₂ | COCH₃ | SO₂CF₃ | CSNH₂ |
| NO₂ | H | CF₂ | O | CF₂ | H | SCF₂CH₃ | CSNH₂ |
| NO₂ | H | CF₂ | O | CF₂ | NH₂ | SCF₂CH₃ | CSNH₂ |
| NO₂ | H | CF₂ | O | CF₂ | N=CHPh | SCF₂CH₃ | CSNH₂ |
| NO₂ | H | CF₂ | O | CF₂ | CH₃ | SCF₂CH₃ | CSNH₂ |
| NO₂ | H | CF₂ | O | CF₂ | CF₃ | SCF₂CH₃ | CSNH₂ |
| NO₂ | H | CF₂ | O | CF₂ | Cl | SCF₂CH₃ | CSNH₂ |
| NO₂ | H | CF₂ | O | CF₂ | F | SCF₂CH₃ | CSNH₂ |
| NO₂ | H | CF₂ | O | CF₂ | COCH₃ | SCF₂CH₃ | CSNH₂ |
| NO₂ | H | CF₂ | O | CF₂ | H | SOCF₂CH₃ | CSNH₂ |
| NO₂ | H | CF₂ | O | CF₂ | NH₂ | SOCF₂CH₃ | CSNH₂ |
| NO₂ | H | CF₂ | O | CF₂ | N=CHPh | SOCF₂CH₃ | CSNH₂ |
| NO₂ | H | CF₂ | O | CF₂ | CH₃ | SOCF₂CH₃ | CSNH₂ |
| NO₂ | H | CF₂ | O | CF₂ | CF₃ | SOCF₂CH₃ | CSNH₂ |
| NO₂ | H | CF₂ | O | CF₂ | Cl | SOCF₂CH₃ | CSNH₂ |
| NO₂ | H | CF₂ | O | CF₂ | F | SOCF₂CH₃ | CSNH₂ |
| NO₂ | H | CF₂ | O | CF₂ | COCH₃ | SOCF₂CH₃ | CSNH₂ |
| NO₂ | H | CF₂ | O | CF₂ | H | SO₂CF₂CH₃ | CSNH₂ |
| NO₂ | H | CF₂ | O | CF₂ | NH₂ | SO₂CF₂CH₃ | CSNH₂ |
| NO₂ | H | CF₂ | O | CF₂ | N=CHPh | SO₂CF₂CH₃ | CSNH₂ |
| NO₂ | H | CF₂ | O | CF₂ | CH₃ | SO₂CF₂CH₃ | CSNH₂ |

TABLE 85

| X | Y | Z¹ | Z² | Z³ | R¹ | R² | R³ |
|---|---|---|---|---|---|---|---|
| NO₂ | H | CF₂ | O | CF₂ | CF₃ | SO₂CF₂CH₃ | CSNH₂ |
| NO₂ | H | CF₂ | O | CF₂ | Cl | SO₂CF₂CH₃ | CSNH₂ |
| NO₂ | H | CF₂ | O | CF₂ | F | SO₂CF₂CH₃ | CSNH₂ |
| NO₂ | H | CF₂ | O | CF₂ | COCH₃ | SO₂CF₂CH³ | CSNH₂ |
| NO₂ | H | CF₂ | O | CF₂ | NH₂ | COCF₃ | CSNH₂ |
| NO₂ | H | CF₂ | O | CF₂ | N=CHPh | COCF₃ | CSNH₂ |
| NO₂ | H | CF₂ | O | CF₂ | CH₃ | COCF₃ | CSNH₂ |
| NO₂ | H | CF₂ | O | CF₂ | CF₃ | COCF₃ | CSNH₂ |
| NO₂ | H | CF₂ | O | CF₂ | Cl | COCF₃ | CSNH₂ |
| NO₂ | H | CF₂ | O | CF₂ | F | COCF₃ | CSNH₂ |
| NO₂ | H | CF₂ | O | CF₂ | COCH₃ | COCF₃ | CSNH₂ |
| NO₂ | H | CF₂ | O | CF₂ | H | COCF₃ | CSNH₂ |
| NO₂ | H | CF₂ | O | CF₂ | NH₂ | COCF₃ | CSNH₂ |
| NO₂ | H | CF₂ | O | CF₂ | N=CHPh | COCF₃ | CSNH₂ |
| NO₂ | H | CF₂ | O | CF₂ | CH₃ | COCF₃ | CSNH₂ |
| NO₂ | H | CF₂ | O | CF₂ | CF₃ | COCF₃ | CSNH₂ |
| NO₂ | H | CF₂ | O | CF₂ | Cl | COCF₃ | CSNH₂ |
| NO₂ | H | CF₂ | O | CF₂ | F | COCF₃ | CSNH₂ |
| NO₂ | H | CF₂ | O | CF₂ | COCH₃ | COCF₃ | CSNH₂ |
| NO₂ | H | CF₂ | O | CF₂ | NH₂ | C₂F₅ | CSNH₂ |
| NO₂ | H | CF₂ | O | CF₂ | N=CHPh | C₂F₅ | CSNH₂ |
| NO₂ | H | CF₂ | O | CF₂ | CH₃ | C₂F₅ | CSNH₂ |
| NO₂ | H | CF₂ | O | CF₂ | CF₃ | C₂F₅ | CSNH₂ |
| NO₂ | H | CF₂ | O | CF₂ | Cl | C₂F₅ | CSNH₂ |
| NO₂ | H | CF₂ | O | CF₂ | F | C₂F₅ | CSNH₂ |
| NO₂ | H | CF₂ | O | CF₂ | COCH₃ | C₂F₅ | CSNH₂ |

TABLE 86

| X | Y | Z¹ | Z² | Z³ | R¹ | R² | R³ |
|---|---|---|---|---|---|---|---|
| NO₂ | H | CF₂ | O | CF₂ | H | C₂F₅ | CSNH₂ |
| NO₂ | H | CF₂ | O | CF₂ | NH₂ | C₂F₅ | CSNH₂ |
| NO₂ | H | CF₂ | O | CF₂ | N=CHPh | C₂F₅ | CSNH₂ |
| NO₂ | H | CF₂ | O | CF₂ | CH₃ | C₂F₅ | CSNH₂ |
| NO₂ | H | CF₂ | O | CF₂ | CF₃ | C₂F₅ | CSNH₂ |
| NO₂ | H | CF₂ | O | CF₂ | Cl | C₂F₅ | CSNH₂ |
| NO₂ | H | CF₂ | O | CF₂ | F | C₂F₅ | CSNH₂ |
| NO₂ | H | CF₂ | O | CF₂ | COCH₃ | C₂F₅ | CSNH₂ |
| NO₂ | H | CF₂ | O | CF₂ | NH₂ | SFCl₂ | CSNH₂ |
| NO₂ | H | CF₂ | O | CF₂ | N=CHPh | SFCl₂ | CSNH₂ |
| NO₂ | H | CF₂ | O | CF₂ | CH₃ | SFCl₂ | CSNH₂ |
| NO₂ | H | CF₂ | O | CF₂ | CF₃ | SFCl₂ | CSNH₂ |
| NO₂ | H | CF₂ | O | CF₂ | Cl | SFCl₂ | CSNH₂ |
| NO₂ | H | CF₂ | O | CF₂ | F | SFCl₂ | CSNH₂ |
| NO₂ | H | CF₂ | O | CF₂ | COCH₃ | SFCl₂ | CSNH₂ |
| NO₂ | H | CF₂ | O | CF₂ | H | SFCl₂ | CSNH₂ |
| NO₂ | H | CF₂ | O | CF₂ | NH₂ | SFCl₂ | CSNH₂ |
| NO₂ | H | CF₂ | O | CF₂ | N=CHPh | SFCl₂ | CSNH₂ |
| NO₂ | H | CF₂ | O | CF₂ | CH₃ | SFCl₂ | CSNH₂ |
| NO₂ | H | CF₂ | O | CF₂ | CF₃ | SFCl₂ | CSNH₂ |
| NO₂ | H | CF₂ | O | CF₂ | Cl | SFCl₂ | CSNH₂ |
| NO₂ | H | CF₂ | O | CF₂ | F | SFCl₂ | CSNH₂ |
| NO₂ | H | CF₂ | O | CF₂ | COCH₃ | SFCl₂ | CSNH₂ |
| NO₂ | H | CF₂ | O | CF₂ | H | SCF₃ | CN |
| NO₂ | H | CF₂ | O | CF₂ | NH₂ | SCF₃ | CN |
| NO₂ | H | CF₂ | O | CF₂ | N=CHPh | SCF₃ | CN |

TABLE 87

| X | Y | Z¹ | Z² | Z³ | R¹ | R² | R³ |
|---|---|---|---|---|---|---|---|
| NO₂ | H | CF₂ | O | CF₂ | CH₃ | SCF₃ | CN |
| NO₂ | H | CF₂ | O | CF₂ | CF₃ | SCF₃ | CN |
| NO₂ | H | CF₂ | O | CF₂ | Cl | SCF₃ | CN |
| NO₂ | H | CF₂ | O | CF₂ | F | SCF₃ | CN |
| NO₂ | H | CF₂ | O | CF₂ | COCH₃ | SCF₃ | CN |
| NO₂ | H | CF₂ | O | CF₂ | H | SOCF₃ | CN |
| NO₂ | H | CF₂ | O | CF₂ | NH₂ | SOCF₃ | CN |
| NO₂ | H | CF₂ | O | CF₂ | N=CHPh | SOCF₃ | CN |
| NO₂ | H | CF₂ | O | CF₂ | CH₃ | SOCF₃ | CN |
| NO₂ | H | CF₂ | O | CF₂ | CF₃ | SOCF₃ | CN |
| NO₂ | H | CF₂ | O | CF₂ | Cl | SOCF₃ | CN |
| NO₂ | H | CF₂ | O | CF₂ | F | SOCF₃ | CN |
| NO₂ | H | CF₂ | O | CF₂ | COCH₃ | SOCF₃ | CN |
| NO₂ | H | CF₂ | O | CF₂ | H | SO₂CF₃ | CN |
| NO₂ | H | CF₂ | O | CF₂ | NH₂ | SO₂CF₃ | CN |
| NO₂ | H | CF₂ | O | CF₂ | N=CHPh | SO₂CF₃ | CN |
| NO₂ | H | CF₂ | O | CF₂ | CH₃ | SO₂CF₃ | CN |
| NO₂ | H | CF₂ | O | CF₂ | CF₃ | SO₂CF₃ | CN |
| NO₂ | H | CF₂ | O | CF₂ | Cl | SO₂CF₃ | CN |
| NO₂ | H | CF₂ | O | CF₂ | F | SO₂CF₃ | CN |
| NO₂ | H | CF₂ | O | CF₂ | COCH₃ | SO₂CF₃ | CN |
| NO₂ | H | CF₂ | O | CF₂ | H | SCF₂CH₃ | CN |
| NO₂ | H | CF₂ | O | CF₂ | NH₂ | SCF₂CH₃ | CN |
| NO₂ | H | CF₂ | O | CF₂ | N=CHPh | SCF₂CH₃ | CN |
| NO₂ | H | CF₂ | O | CF₂ | CH₃ | SCF₂CH₃ | CN |
| NO₂ | H | CF₂ | O | CF₂ | CF₃ | SCF₂CH₃ | CN |

TABLE 88

| X | Y | Z¹ | Z² | Z³ | R¹ | R² | R³ |
|---|---|---|---|---|---|---|---|
| NO₂ | H | CF₂ | O | CF₂ | Cl | SCF₂CH₃ | CN |
| NO₂ | H | CF₂ | O | CF₂ | F | SCF₂CH₃ | CN |
| NO₂ | H | CF₂ | O | CF₂ | COCH₃ | SCF₂CH₃ | CN |
| NO₂ | H | CF₂ | O | CF₂ | H | SOCF₂CH₃ | CN |
| NO₂ | H | CF₂ | O | CF₂ | NH₂ | SOCF₂CH₃ | CN |
| NO₂ | H | CF₂ | O | CF₂ | N=CHPh | SOCF₂CH₃ | CN |
| NO₂ | H | CF₂ | O | CF₂ | CH₃ | SOCF₂CH₃ | CN |
| NO₂ | H | CF₂ | O | CF₂ | CF₃ | SOCF₂CH₃ | CN |
| NO₂ | H | CF₂ | O | CF₂ | Cl | SOCF₂CH₃ | CN |
| NO₂ | H | CF₂ | O | CF₂ | F | SOCF₂CH₃ | CN |

TABLE 88-continued

| X | Y | Z¹ | Z² | Z³ | R¹ | R² | R³ |
|---|---|---|---|---|---|---|---|
| $NO_2$ | H | $CF_2$ | O | $CF_2$ | $COCH_3$ | $SOCF_2CH_3$ | CN |
| $NO_2$ | H | $CF_2$ | O | $CF_2$ | H | $SO_2CF_2CH_3$ | CN |
| $NO_2$ | H | $CF_2$ | O | $CF_2$ | $NH_2$ | $SO_2CF_2CH_3$ | CN |
| $NO_2$ | H | $CF_2$ | O | $CF_2$ | N = CHPh | $SO_2CF_2CH_3$ | CN |
| $NO_2$ | H | $CF_2$ | O | $CF_2$ | $CH_3$ | $SO_2CF_2CH_3$ | CN |
| $NO_2$ | H | $CF_2$ | O | $CF_2$ | $CF_3$ | $SO_2CF_2CH_3$ | CN |
| $NO_2$ | H | $CF_2$ | O | $CF_2$ | Cl | $SO_2CF_2CH_3$ | CN |
| $NO_2$ | H | $CF_2$ | O | $CF_2$ | F | $SO_2CF_2CH_3$ | CN |
| $NO_2$ | H | $CF_2$ | O | $CF_2$ | $COCH_3$ | $SO_2CF_2CH_3$ | CN |
| $NO_2$ | H | $CF_2$ | O | $CF_2$ | $NH_2$ | $COCF_3$ | CN |
| $NO_2$ | H | $CF_2$ | O | $CF_2$ | N = CHPh | $COCF_3$ | CN |
| $NO_2$ | H | $CF_2$ | O | $CF_2$ | $CH_3$ | $COCF_3$ | CN |
| $NO_2$ | H | $CF_2$ | O | $CF_2$ | $CF_3$ | $COCF_3$ | CN |
| $NO_2$ | H | $CF_2$ | O | $CF_2$ | Cl | $COCF_3$ | CN |
| $NO_2$ | H | $CF_2$ | O | $CF_2$ | F | $COCF_3$ | CN |
| $NO_2$ | H | $CF_2$ | O | $CF_2$ | $COCH_3$ | $COCF_3$ | CN |

TABLE 89

| X | Y | Z¹ | Z² | Z³ | R¹ | R² | R³ |
|---|---|---|---|---|---|---|---|
| $NO_2$ | H | $CF_2$ | O | $CF_2$ | H | $COCF_3$ | CN |
| $NO_2$ | H | $CF_2$ | O | $CF_2$ | $NH_2$ | $COCF_3$ | CN |
| $NO_2$ | H | $CF_2$ | O | $CF_2$ | N = CHPh | $COCF_3$ | CN |
| $NO_2$ | H | $CF_2$ | O | $CF_2$ | $CH_3$ | $COCF_3$ | CN |
| $NO_2$ | H | $CF_2$ | O | $CF_2$ | $CF_3$ | $COCF_3$ | CN |
| $NO_2$ | H | $CF_2$ | O | $CF_2$ | Cl | $COCF_3$ | CN |
| $NO_2$ | H | $CF_2$ | O | $CF_2$ | F | $COCF_3$ | CN |
| $NO_2$ | H | $CF_2$ | O | $CF_2$ | $COCH_3$ | $COCF_3$ | CN |
| $NO_2$ | H | $CF_2$ | O | $CF_2$ | $NH_2$ | $C_2F_5$ | CN |
| $NO_2$ | H | $CF_2$ | O | $CF_2$ | N = CHPh | $C_2F_5$ | CN |
| $NO_2$ | H | $CF_2$ | O | $CF_2$ | $CH_3$ | $C_2F_5$ | CN |
| $NO_2$ | H | $CF_2$ | O | $CF_2$ | $CF_3$ | $C_2F_5$ | CN |
| $NO_2$ | H | $CF_2$ | O | $CF_2$ | Cl | $C_2F_5$ | CN |
| $NO_2$ | H | $CF_2$ | O | $CF_2$ | F | $C_2F_5$ | CN |
| $NO_2$ | H | $CF_2$ | O | $CF_2$ | $COCH_3$ | $C_2F_5$ | CN |
| $NO_2$ | H | $CF_2$ | O | $CF_2$ | H | $C_2F_5$ | CN |
| $NO_2$ | H | $CF_2$ | O | $CF_2$ | $NH_2$ | $C_2F_5$ | CN |
| $NO_2$ | H | $CF_2$ | O | $CF_2$ | N = CHPh | $C_2F_5$ | CN |
| $NO_2$ | H | $CF_2$ | O | $CF_2$ | $CH_3$ | $C_2F_5$ | CN |
| $NO_2$ | H | $CF_2$ | O | $CF_2$ | $CF_3$ | $C_2F_5$ | CN |
| $NO_2$ | H | $CF_2$ | O | $CF_2$ | Cl | $C_2F_5$ | CN |
| $NO_2$ | H | $CF_2$ | O | $CF_2$ | F | $C_2F_5$ | CN |
| $NO_2$ | H | $CF_2$ | O | $CF_2$ | $COCH_3$ | $C_2F_5$ | CN |
| $NO_2$ | H | $CF_2$ | O | $CF_2$ | $NH_2$ | $SFCl_2$ | CN |
| $NO_2$ | H | $CF_2$ | O | $CF_2$ | N = CHPh | $SFCl_2$ | CN |
| $NO_2$ | H | $CF_2$ | O | $CF_2$ | $CH_3$ | $SFCl_2$ | CN |

TABLE 90

| X | Y | Z¹ | Z² | Z³ | R¹ | R² | R³ |
|---|---|---|---|---|---|---|---|
| $NO_2$ | H | $CF_2$ | O | $CF_2$ | $CF_3$ | $SFCl_2$ | CN |
| $NO_2$ | H | $CF_2$ | O | $CF_2$ | Cl | $SFCl_2$ | CN |
| $NO_2$ | H | $CF_2$ | O | $CF_2$ | F | $SFCl_2$ | CN |
| $NO_2$ | H | $CF_2$ | O | $CF_2$ | $COCH_3$ | $SFCl_2$ | CN |
| $NO_2$ | H | $CF_2$ | O | $CF_2$ | H | $SFCl_2$ | CN |
| $NO_2$ | H | $CF_2$ | O | $CF_2$ | $NH_2$ | $SFCl_2$ | CN |
| $NO_2$ | H | $CF_2$ | O | $CF_2$ | N = CHPh | $SFCl_2$ | CN |
| $NO_2$ | H | $CF_2$ | O | $CF_2$ | $CH_3$ | $SFCl_2$ | CN |
| $NO_2$ | H | $CF_2$ | O | $CF_2$ | $CF_3$ | $SFCl_2$ | CN |
| $NO_2$ | H | $CF_2$ | O | $CF_2$ | Cl | $SFCl_2$ | CN |
| $NO_2$ | H | $CF_2$ | O | $CF_2$ | F | $SFCl_2$ | CN |
| $NO_2$ | H | $CF_2$ | O | $CF_2$ | $COCH_3$ | $SFCl_2$ | CN |
| F | F | $CF_2$ | O | $CF_2$ | H | $SCF_3$ | H |
| F | F | $CF_2$ | O | $CF_2$ | $NH_2$ | $SCF_3$ | H |
| F | F | $CF_2$ | O | $CF_2$ | N = CHPh | $SCF_3$ | H |
| F | F | $CF_2$ | O | $CF_2$ | $CH_3$ | $SCF_3$ | H |
| F | F | $CF_2$ | O | $CF_2$ | $CF_3$ | $SCF_3$ | H |
| F | F | $CF_2$ | O | $CF_2$ | Cl | $SCF_3$ | H |
| F | F | $CF_2$ | O | $CF_2$ | F | $SCF_3$ | H |
| F | F | $CF_2$ | O | $CF_2$ | $COCH_3$ | $SCF_3$ | H |

TABLE 90-continued

| X | Y | Z¹ | Z² | Z³ | R¹ | R² | R³ |
|---|---|---|---|---|---|---|---|
| F | F | $CF_2$ | O | $CF_2$ | H | $SOCF_3$ | H |
| F | F | $CF_2$ | O | $CF_2$ | $NH_2$ | $SOCF_3$ | H |
| F | F | $CF_2$ | O | $CF_2$ | N = CHPh | $SOCF_3$ | H |
| F | F | $CF_2$ | O | $CF_2$ | $CH_3$ | $SOCF_3$ | H |
| F | F | $CF_2$ | O | $CF_2$ | $CF_3$ | $SOCF_3$ | H |
| F | F | $CF_2$ | O | $CF_2$ | Cl | $SOCF_3$ | H |

TABLE 91

| X | Y | Z¹ | Z² | Z³ | R¹ | R² | R³ |
|---|---|---|---|---|---|---|---|
| F | F | $CF_2$ | O | $CF_2$ | F | $SOCF_3$ | H |
| F | F | $CF_2$ | O | $CF_2$ | $COCH_3$ | $SOCF_3$ | H |
| F | F | $CF_2$ | O | $CF_2$ | H | $SO_2CF_3$ | H |
| F | F | $CF_2$ | O | $CF_2$ | $NH_2$ | $SO_2CF_3$ | H |
| F | F | $CF_2$ | O | $CF_2$ | N = CHPh | $SO_2CF_3$ | H |
| F | F | $CF_2$ | O | $CF_2$ | $CH_3$ | $SO_2CF_3$ | H |
| F | F | $CF_2$ | O | $CF_2$ | $CF_3$ | $SO_2CF_3$ | H |
| F | F | $CF_2$ | O | $CF_2$ | Cl | $SO_2CF_3$ | H |
| F | F | $CF_2$ | O | $CF_2$ | F | $SO_2CF_3$ | H |
| F | F | $CF_2$ | O | $CF_2$ | $COCH_3$ | $SO_2CF_3$ | H |
| F | F | $CF_2$ | O | $CF_2$ | H | $SCF_2CH_3$ | H |
| F | F | $CF_2$ | O | $CF_2$ | $NH_2$ | $SCF_2CH_3$ | H |
| F | F | $CF_2$ | O | $CF_2$ | N = CHPh | $SCF_2CH_3$ | H |
| F | F | $CF_2$ | O | $CF_2$ | $CH_3$ | $SCF_2CH_3$ | H |
| F | F | $CF_2$ | O | $CF_2$ | $CF_3$ | $SCF_2CH_3$ | H |
| F | F | $CF_2$ | O | $CF_2$ | Cl | $SCF_2CH_3$ | H |
| F | F | $CF_2$ | O | $CF_2$ | F | $SCF_2CH_3$ | H |
| F | F | $CF_2$ | O | $CF_2$ | $COCH_3$ | $SCF_2CH_3$ | H |
| F | F | $CF_2$ | O | $CF_2$ | H | $SOCF_2CH_3$ | H |
| F | F | $CF_2$ | O | $CF_2$ | $NH_2$ | $SOCF_2CH_3$ | H |
| F | F | $CF_2$ | O | $CF_2$ | N = CHPh | $SOCF_2CH_3$ | H |
| F | F | $CF_2$ | O | $CF_2$ | $CH_3$ | $SOCF_2CH_3$ | H |
| F | F | $CF_2$ | O | $CF_2$ | $CF_3$ | $SOCF_2CH_3$ | H |
| F | F | $CF_2$ | O | $CF_2$ | Cl | $SOCF_2CH_3$ | H |
| F | F | $CF_2$ | O | $CF_2$ | F | $SOCF_2CH_3$ | H |
| F | F | $CF_2$ | O | $CF_2$ | $COCH_3$ | $SOCF_2CH_3$ | H |

TABLE 92

| X | Y | Z¹ | Z² | Z³ | R¹ | R² | R³ |
|---|---|---|---|---|---|---|---|
| F | F | $CF_2$ | O | $CF_2$ | H | $SO_2CF_2CH_3$ | H |
| F | F | $CF_2$ | O | $CF_2$ | $NH_2$ | $SO_2CF_2CH_3$ | H |
| F | F | $CF_2$ | O | $CF_2$ | N = CHPh | $SO_2CF_2CH_3$ | H |
| F | F | $CF_2$ | O | $CF_2$ | $CH_3$ | $SO_2CF_2CH_3$ | H |
| F | F | $CF_2$ | O | $CF_2$ | $CF_3$ | $SO_2CF_2CH_3$ | H |
| F | F | $CF_2$ | O | $CF_2$ | Cl | $SO_2CF_2CH_3$ | H |
| F | F | $CF_2$ | O | $CF_2$ | F | $SO_2CF_2CH_3$ | H |
| F | F | $CF_2$ | O | $CF_2$ | $COCH_3$ | $SO_2CF_2CH_3$ | H |
| F | F | $CF_2$ | O | $CF_2$ | $NH_2$ | $COCF_3$ | H |
| F | F | $CF_2$ | O | $CF_2$ | N = CHPh | $COCF_3$ | H |
| F | F | $CF_2$ | O | $CF_2$ | $CH_3$ | $COCF_3$ | H |
| F | F | $CF_2$ | O | $CF_2$ | $CF_3$ | $COCF_3$ | H |
| F | F | $CF_2$ | O | $CF_2$ | Cl | $COCF_3$ | H |
| F | F | $CF_2$ | O | $CF_2$ | F | $COCF_3$ | H |
| F | F | $CF_2$ | O | $CF_2$ | $COCH_3$ | $COCF_3$ | H |
| F | F | $CF_2$ | O | $CF_2$ | H | $COCF_3$ | H |
| F | F | $CF_2$ | O | $CF_2$ | $NH_2$ | $COCF_3$ | H |
| F | F | $CF_2$ | O | $CF_2$ | N = CHPh | $COCF_3$ | H |
| F | F | $CF_2$ | O | $CF_2$ | $CH_3$ | $COCF_3$ | H |
| F | F | $CF_2$ | O | $CF_2$ | $CF_3$ | $COCF_3$ | H |
| F | F | $CF_2$ | O | $CF_2$ | Cl | $COCF_3$ | H |
| F | F | $CF_2$ | O | $CF_2$ | F | $COCF_3$ | H |
| F | F | $CF_2$ | O | $CF_2$ | $COCH_3$ | $COCF_3$ | H |
| F | F | $CF_2$ | O | $CF_2$ | $NH_2$ | $C_2F_5$ | H |
| F | F | $CF_2$ | O | $CF_2$ | N = CHPh | $C_2F_5$ | H |
| F | F | $CF_2$ | O | $CF_2$ | $CH_3$ | $C_2F_5$ | H |

TABLE 93

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CF_3$ | $C_2F_5$ | H |
| F | F | $CF_2$ | O | $CF_2$ | Cl | $C_2F_5$ | H |
| F | F | $CF_2$ | O | $CF_2$ | F | $C_2F_5$ | H |
| F | F | $CF_2$ | O | $CF_2$ | $COCH_3$ | $C_2F_5$ | H |
| F | F | $CF_2$ | O | $CF_2$ | H | $C_2F_5$ | H |
| F | F | $CF_2$ | O | $CF_2$ | $NH_2$ | $C_2F_5$ | H |
| F | F | $CF_2$ | O | $CF_2$ | N=CHPh | $C_2F_5$ | H |
| F | F | $CF_2$ | O | $CF_2$ | $CH_3$ | $C_2F_5$ | H |
| F | F | $CF_2$ | O | $CF_2$ | $CF_3$ | $C_2F_5$ | H |
| F | F | $CF_2$ | O | $CF_2$ | Cl | $C_2F_5$ | H |
| F | F | $CF_2$ | O | $CF_2$ | F | $C_2F_5$ | H |
| F | F | $CF_2$ | O | $CF_2$ | $COCH_3$ | $C_2F_5$ | H |
| F | F | $CF_2$ | O | $CF_2$ | $NH_2$ | $SFCl_2$ | H |
| F | F | $CF_2$ | O | $CF_2$ | N=CHPh | $SFCl_2$ | H |
| F | F | $CF_2$ | O | $CF_2$ | $CH_3$ | $SFCl_2$ | H |
| F | F | $CF_2$ | O | $CF_2$ | $CF_3$ | $SFCl_2$ | H |
| F | F | $CF_2$ | O | $CF_2$ | Cl | $SFCl_2$ | H |
| F | F | $CF_2$ | O | $CF_2$ | F | $SFCl_2$ | H |
| F | F | $CF_2$ | O | $CF_2$ | $COCH_3$ | $SFCl_2$ | H |
| F | F | $CF_2$ | O | $CF_2$ | H | $SFCl_2$ | H |
| F | F | $CF_2$ | O | $CF_2$ | $NH_2$ | $SFCl_2$ | H |
| F | F | $CF_2$ | O | $CF_2$ | N=CHPh | $SFCl_2$ | H |
| F | F | $CF_2$ | O | $CF_2$ | $CH_3$ | $SFCl_2$ | H |
| F | F | $CF_2$ | O | $CF_2$ | $CF_3$ | $SFCl_2$ | H |
| F | F | $CF_2$ | O | $CF_2$ | Cl | $SFCl_2$ | H |
| F | F | $CF_2$ | O | $CF_2$ | F | $SFCl_2$ | H |

TABLE 94

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $COCH_3$ | $SFCl_2$ | H |
| F | F | $CF_2$ | O | $CF_2$ | H | $SCF_3$ | $CF_3$ |
| F | F | $CF_2$ | O | $CF_2$ | $NH_2$ | $SCF_3$ | $CF_3$ |
| F | F | $CF_2$ | O | $CF_2$ | N=CHPh | $SCF_3$ | $CF_3$ |
| F | F | $CF_2$ | O | $CF_2$ | $CH_3$ | $SCF_3$ | $CF_3$ |
| F | F | $CF_2$ | O | $CF_2$ | $CF_3$ | $SCF_3$ | $CF_3$ |
| F | F | $CF_2$ | O | $CF_2$ | Cl | $SCF_3$ | $CF_3$ |
| F | F | $CF_2$ | O | $CF_2$ | F | $SCF_3$ | $CF_3$ |
| F | F | $CF_2$ | O | $CF_2$ | $COCH_3$ | $SCF_3$ | $CF_3$ |
| F | F | $CF_2$ | O | $CF_2$ | H | $SOCF_3$ | $CF_3$ |
| F | F | $CF_2$ | O | $CF_2$ | $NH_2$ | $SOCF_3$ | $CF_3$ |
| F | F | $CF_2$ | O | $CF_2$ | N=CHPh | $SOCF_3$ | $CF_3$ |
| F | F | $CF_2$ | O | $CF_2$ | $CH_3$ | $SOCF_3$ | $CF_3$ |
| F | F | $CF_2$ | O | $CF_2$ | $CF_3$ | $SOCF_3$ | $CF_3$ |
| F | F | $CF_2$ | O | $CF_2$ | Cl | $SOCF_3$ | $CF_3$ |
| F | F | $CF_2$ | O | $CF_2$ | F | $SOCF_3$ | $CF_3$ |
| F | F | $CF_2$ | O | $CF_2$ | $COCH_3$ | $SOCF_3$ | $CF_3$ |
| F | F | $CF_2$ | O | $CF_2$ | H | $SO_2CF_3$ | $CF_3$ |
| F | F | $CF_2$ | O | $CF_2$ | $NH_2$ | $SO_2CF_3$ | $CF_3$ |
| F | F | $CF_2$ | O | $CF_2$ | N=CHPh | $SO_2CF_3$ | $CF_3$ |
| F | F | $CF_2$ | O | $CF_2$ | $CH_3$ | $SO_2CF_3$ | $CF_3$ |
| F | F | $CF_2$ | O | $CF_2$ | $CF_3$ | $SO_2CF_3$ | $CF_3$ |
| F | F | $CF_2$ | O | $CF_2$ | Cl | $SO_2CF_3$ | $CF_3$ |
| F | F | $CF_2$ | O | $CF_2$ | F | $SO_2CF_3$ | $CF_3$ |
| F | F | $CF_2$ | O | $CF_2$ | $COCH_3$ | $SO_2CF_3$ | $CF_3$ |
| F | F | $CF_2$ | O | $CF_2$ | H | $SCF_2CH_3$ | $CF_3$ |

TABLE 95

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $NH_2$ | $SCF_2CH_3$ | $CF_3$ |
| F | F | $CF_2$ | O | $CF_2$ | N=CHPh | $SCF_2CH_3$ | $CF_3$ |
| F | F | $CF_2$ | O | $CF_2$ | $CH_3$ | $SCF_2CH_3$ | $CF_3$ |
| F | F | $CF_2$ | O | $CF_2$ | $CF_3$ | $SCF_2CH_3$ | $CF_3$ |
| F | F | $CF_2$ | O | $CF_2$ | Cl | $SCF_2CH_3$ | $CF_3$ |
| F | F | $CF_2$ | O | $CF_2$ | F | $SCF_2CH_3$ | $CF_3$ |
| F | F | $CF_2$ | O | $CF_2$ | $COCH_3$ | $SCF_2CH_3$ | $CF_3$ |
| F | F | $CF_2$ | O | $CF_2$ | H | $SOCF_2CH_3$ | $CF_3$ |
| F | F | $CF_2$ | O | $CF_2$ | $NH_2$ | $SOCF_2CH_3$ | $CF_3$ |
| F | F | $CF_2$ | O | $CF_2$ | N=CHPh | $SOCF_2CH_3$ | $CF_3$ |

TABLE 95-continued

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CH_3$ | $SOCF_2CH_3$ | $CF_3$ |
| F | F | $CF_2$ | O | $CF_2$ | $CF_3$ | $SOCF_2CH_3$ | $CF_3$ |
| F | F | $CF_2$ | O | $CF_2$ | Cl | $SOCF_2CH_3$ | $CF_3$ |
| F | F | $CF_2$ | O | $CF_2$ | F | $SOCF_2CH_3$ | $CF_3$ |
| F | F | $CF_2$ | O | $CF_2$ | $COCH_3$ | $SOCF_2CH_3$ | $CF_3$ |
| F | F | $CF_2$ | O | $CF_2$ | H | $SO_2CF_2CH_3$ | $CF_3$ |
| F | F | $CF_2$ | O | $CF_2$ | $NH_2$ | $SO_2CF_2CH_3$ | $CF_3$ |
| F | F | $CF_2$ | O | $CF_2$ | N=CHPh | $SO_2CF_2CH_3$ | $CF_3$ |
| F | F | $CF_2$ | O | $CF_2$ | $CH_3$ | $SO_2CF_2CH_3$ | $CF_3$ |
| F | F | $CF_2$ | O | $CF_2$ | $CF_3$ | $SO_2CF_2CH_3$ | $CF_3$ |
| F | F | $CF_2$ | O | $CF_2$ | Cl | $SO_2CF_2CH_3$ | $CF_3$ |
| F | F | $CF_2$ | O | $CF_2$ | F | $SO_2CF_2CH_3$ | $CF_3$ |
| F | F | $CF_2$ | O | $CF_2$ | $COCH_3$ | $SO_2CF_2CH_3$ | $CF_3$ |
| F | F | $CF_2$ | O | $CF_2$ | $NH_2$ | $COCF_3$ | $CF_3$ |
| F | F | $CF_2$ | O | $CF_2$ | N=CHPh | $COCF_3$ | $CF_3$ |
| F | F | $CF_2$ | O | $CF_2$ | $CH_3$ | $COCF_3$ | $CF_3$ |

TABLE 96

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CF_3$ | $COCF_3$ | $CF_3$ |
| F | F | $CF_2$ | O | $CF_2$ | Cl | $COCF_3$ | $CF_3$ |
| F | F | $CF_2$ | O | $CF_2$ | F | $COCF_3$ | $CF_3$ |
| F | F | $CF_2$ | O | $CF_2$ | $COCH_3$ | $COCF_3$ | $CF_3$ |
| F | F | $CF_2$ | O | $CF_2$ | H | $COCF_3$ | $CF_3$ |
| F | F | $CF_2$ | O | $CF_2$ | $NH_2$ | $COCF_3$ | $CF_3$ |
| F | F | $CF_2$ | O | $CF_2$ | N=CHPh | $COCF_3$ | $CF_3$ |
| F | F | $CF_2$ | O | $CF_2$ | $CH_3$ | $COCF_3$ | $CF_3$ |
| F | F | $CF_2$ | O | $CF_2$ | $CF_3$ | $COCF_3$ | $CF_3$ |
| F | F | $CF_2$ | O | $CF_2$ | Cl | $COCF_3$ | $CF_3$ |
| F | F | $CF_2$ | O | $CF_2$ | F | $COCF_3$ | $CF_3$ |
| F | F | $CF_2$ | O | $CF_2$ | $COCH_3$ | $COCF_3$ | $CF_3$ |
| F | F | $CF_2$ | O | $CF_2$ | $NH_2$ | $C_2F_5$ | $CF_3$ |
| F | F | $CF_2$ | O | $CF_2$ | N=CHPh | $C_2F_5$ | $CF_3$ |
| F | F | $CF_2$ | O | $CF_2$ | $CH_3$ | $C_2F_5$ | $CF_3$ |
| F | F | $CF_2$ | O | $CF_2$ | $CF_3$ | $C_2F_5$ | $CF_3$ |
| F | F | $CF_2$ | O | $CF_2$ | Cl | $C_2F_5$ | $CF_3$ |
| F | F | $CF_2$ | O | $CF_2$ | F | $C_2F_5$ | $CF_3$ |
| F | F | $CF_2$ | O | $CF_2$ | $COCH_3$ | $C_2F_5$ | $CF_3$ |
| F | F | $CF_2$ | O | $CF_2$ | H | $C_2F_5$ | $CF_3$ |
| F | F | $CF_2$ | O | $CF_2$ | $NH_2$ | $C_2F_5$ | $CF_3$ |
| F | F | $CF_2$ | O | $CF_2$ | N=CHPh | $C_2F_5$ | $CF_3$ |
| F | F | $CF_2$ | O | $CF_2$ | $CH_3$ | $C_2F_5$ | $CF_3$ |
| F | F | $CF_2$ | O | $CF_2$ | $CF_3$ | $C_2F_5$ | $CF_3$ |
| F | F | $CF_2$ | O | $CF_2$ | Cl | $C_2F_5$ | $CF_3$ |
| F | F | $CF_2$ | O | $CF_2$ | F | $C_2F_5$ | $CF_3$ |

TABLE 97

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $COCH_3$ | $C_2F_5$ | $CF_3$ |
| F | F | $CF_2$ | O | $CF_2$ | $NH_2$ | $SFCl_2$ | $CF_3$ |
| F | F | $CF_2$ | O | $CF_2$ | N=CHPh | $SFCl_2$ | $CF_3$ |
| F | F | $CF_2$ | O | $CF_2$ | $CH_3$ | $SFCl_2$ | $CF_3$ |
| F | F | $CF_2$ | O | $CF_2$ | $CF_3$ | $SFCl_2$ | $CF_3$ |
| F | F | $CF_2$ | O | $CF_2$ | Cl | $SFCl_2$ | $CF_3$ |
| F | F | $CF_2$ | O | $CF_2$ | F | $SFCl_2$ | $CF_3$ |
| F | F | $CF_2$ | O | $CF_2$ | $COCH_3$ | $SFCl_2$ | $CF_3$ |
| F | F | $CF_2$ | O | $CF_2$ | H | $SFCl_2$ | $CF_3$ |
| F | F | $CF_2$ | O | $CF_2$ | $NH_2$ | $SFCl_2$ | $CF_3$ |
| F | F | $CF_2$ | O | $CF_2$ | N=CHPh | $SFCl_2$ | $CF_3$ |
| F | F | $CF_2$ | O | $CF_2$ | $CH_3$ | $SFCl_2$ | $CF_3$ |
| F | F | $CF_2$ | O | $CF_2$ | $CF_3$ | $SFCl_2$ | $CF_3$ |
| F | F | $CF_2$ | O | $CF_2$ | Cl | $SFCl_2$ | $CF_3$ |
| F | F | $CF_2$ | O | $CF_2$ | F | $SFCl_2$ | $CF_3$ |
| F | F | $CF_2$ | O | $CF_2$ | $COCH_3$ | $SFCl_2$ | $CF_3$ |
| F | F | $CF_2$ | O | $CF_2$ | H | $SCF_3$ | $C_2F_5$ |
| F | F | $CF_2$ | O | $CF_2$ | $NH_2$ | $SCF_3$ | $C_2F_5$ |
| F | F | $CF_2$ | O | $CF_2$ | N=CHPh | $SCF_3$ | $C_2F_5$ |
| F | F | $CF_2$ | O | $CF_2$ | $CH_3$ | $SCF_3$ | $C_2F_5$ |

TABLE 97-continued

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CF_3$ | $SCF_3$ | $C_2F_5$ |
| F | F | $CF_2$ | O | $CF_2$ | Cl | $SCF_3$ | $C_2F_5$ |
| F | F | $CF_2$ | O | $CF_2$ | F | $SCF_3$ | $C_2F_5$ |
| F | F | $CF_2$ | O | $CF_2$ | $COCH_3$ | $SCF_3$ | $C_2F_5$ |
| F | F | $CF_2$ | O | $CF_2$ | H | $SOCF_3$ | $C_2F_5$ |
| F | F | $CF_2$ | O | $CF_2$ | $NH_2$ | $SOCF_3$ | $C_2F_5$ |

TABLE 98

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | N=CHPh | $SOCF_3$ | $C_2F_5$ |
| F | F | $CF_2$ | O | $CF_2$ | $CH_3$ | $SOCF_3$ | $C_2F_5$ |
| F | F | $CF_2$ | O | $CF_2$ | $CF_3$ | $SOCF_3$ | $C_2F_5$ |
| F | F | $CF_2$ | O | $CF_2$ | Cl | $SOCF_3$ | $C_2F_5$ |
| F | F | $CF_2$ | O | $CF_2$ | F | $SOCF_3$ | $C_2F_5$ |
| F | F | $CF_2$ | O | $CF_2$ | $COCH_3$ | $SOCF_3$ | $C_2F_5$ |
| F | F | $CF_2$ | O | $CF_2$ | H | $SO_2CF_3$ | $C_2F_5$ |
| F | F | $CF_2$ | O | $CF_2$ | $NH_2$ | $SO_2CF_3$ | $C_2F_5$ |
| F | F | $CF_2$ | O | $CF_2$ | N=CHPh | $SO_2CF_3$ | $C_2F_5$ |
| F | F | $CF_2$ | O | $CF_2$ | $CH_3$ | $SO_2CF_3$ | $C_2F_5$ |
| F | F | $CF_2$ | O | $CF_2$ | $CF_3$ | $SO_2CF_3$ | $C_2F_5$ |
| F | F | $CF_2$ | O | $CF_2$ | Cl | $SO_2CF_3$ | $C_2F_5$ |
| F | F | $CF_2$ | O | $CF_2$ | F | $SO_2CF_3$ | $C_2F_5$ |
| F | F | $CF_2$ | O | $CF_2$ | $COCH_3$ | $SO_2CF_3$ | $C_2F_5$ |
| F | F | $CF_2$ | O | $CF_2$ | H | $SCF_2CH_3$ | $C_2F_5$ |
| F | F | $CF_2$ | O | $CF_2$ | $NH_2$ | $SCF_2CH_3$ | $C_2F_5$ |
| F | F | $CF_2$ | O | $CF_2$ | N=CHPh | $SCF_2CH_3$ | $C_2F_5$ |
| F | F | $CF_2$ | O | $CF_2$ | $CH_3$ | $SCF_2CH_3$ | $C_2F_5$ |
| F | F | $CF_2$ | O | $CF_2$ | $CF_3$ | $SCF_2CH_3$ | $C_2F_5$ |
| F | F | $CF_2$ | O | $CF_2$ | Cl | $SCF_2CH_3$ | $C_2F_5$ |
| F | F | $CF_2$ | O | $CF_2$ | F | $SCF_2CH_3$ | $C_2F_5$ |
| F | F | $CF_2$ | O | $CF_2$ | $COCH_3$ | $SCF_2CH_3$ | $C_2F_5$ |
| F | F | $CF_2$ | O | $CF_2$ | H | $SOCF_2CH_3$ | $C_2F_5$ |
| F | F | $CF_2$ | O | $CF_2$ | $NH_2$ | $SOCF_2CH_3$ | $C_2F_5$ |
| F | F | $CF_2$ | O | $CF_2$ | N=CHPh | $SOCF_2CH_3$ | $C_2F_5$ |
| F | F | $CF_2$ | O | $CF_2$ | $CH_3$ | $SOCF_2CH_3$ | $C_2F_5$ |

TABLE 99

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CF_3$ | $SOCF_2CH_3$ | $C_2F_5$ |
| F | F | $CF_2$ | O | $CF_2$ | Cl | $SOCF_2CH_3$ | $C_2F_5$ |
| F | F | $CF_2$ | O | $CF_2$ | F | $SOCF_2CH_3$ | $C_2F_5$ |
| F | F | $CF_2$ | O | $CF_2$ | $COCH_3$ | $SOCF_2CH_3$ | $C_2F_5$ |
| F | F | $CF_2$ | O | $CF_2$ | H | $SO_2CF_2CH_3$ | $C_2F_5$ |
| F | F | $CF_2$ | O | $CF_2$ | $NH_2$ | $SO_2CF_2CH_3$ | $C_2F_5$ |
| F | F | $CF_2$ | O | $CF_2$ | N=CHPh | $SO_2CF_2CH_3$ | $C_2F_5$ |
| F | F | $CF_2$ | O | $CF_2$ | $CH_3$ | $SO_2CF_2CH_3$ | $C_2F_5$ |
| F | F | $CF_2$ | O | $CF_2$ | $CF_3$ | $SO_2CF_2CH_3$ | $C_2F_5$ |
| F | F | $CF_2$ | O | $CF_2$ | Cl | $SO_2CF_2CH_3$ | $C_2F_5$ |
| F | F | $CF_2$ | O | $CF_2$ | F | $SO_2CF_2CH_3$ | $C_2F_5$ |
| F | F | $CF_2$ | O | $CF_2$ | $COCH_3$ | $SO_2CF_2CH_3$ | $C_2F_5$ |
| F | F | $CF_2$ | O | $CF_2$ | $NH_2$ | $COCF_3$ | $C_2F_5$ |
| F | F | $CF_2$ | O | $CF_2$ | N=CHPh | $COCF_3$ | $C_2F_5$ |
| F | F | $CF_2$ | O | $CF_2$ | $CH_3$ | $COCF_3$ | $C_2F_5$ |
| F | F | $CF_2$ | O | $CF_2$ | $CF_3$ | $COCF_3$ | $C_2F_5$ |
| F | F | $CF_2$ | O | $CF_2$ | Cl | $COCF_3$ | $C_2F_5$ |
| F | F | $CF_2$ | O | $CF_2$ | F | $COCF_3$ | $C_2F_5$ |
| F | F | $CF_2$ | O | $CF_2$ | $COCH_3$ | $COCF_3$ | $C_2F_5$ |
| F | F | $CF_2$ | O | $CF_2$ | H | $COCF_3$ | $C_2F_5$ |
| F | F | $CF_2$ | O | $CF_2$ | $NH_2$ | $COCF_3$ | $C_2F_5$ |
| F | F | $CF_2$ | O | $CF_2$ | N=CHPh | $COCF_3$ | $C_2F_5$ |
| F | F | $CF_2$ | O | $CF_2$ | $CH_3$ | $COCF_3$ | $C_2F_5$ |
| F | F | $CF_2$ | O | $CF_2$ | $CF_3$ | $COCF_3$ | $C_2F_5$ |
| F | F | $CF_2$ | O | $CF_2$ | Cl | $COCF_3$ | $C_2F_5$ |
| F | F | $CF_2$ | O | $CF_2$ | F | $COCF_3$ | $C_2F_5$ |

TABLE 100

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $COCH_3$ | $COCF_3$ | $C_2F_5$ |
| F | F | $CF_2$ | O | $CF_2$ | $NH_2$ | $C_2F_5$ | $C_2F_5$ |
| F | F | $CF_2$ | O | $CF_2$ | N=CHPh | $C_2F_5$ | $C_2F_5$ |
| F | F | $CF_2$ | O | $CF_2$ | $CH_3$ | $C_2F_5$ | $C_2F_5$ |
| F | F | $CF_2$ | O | $CF_2$ | $CF_3$ | $C_2F_5$ | $C_2F_5$ |
| F | F | $CF_2$ | O | $CF_2$ | Cl | $C_2F_5$ | $C_2F_5$ |
| F | F | $CF_2$ | O | $CF_2$ | F | $C_2F_5$ | $C_2F_5$ |
| F | F | $CF_2$ | O | $CF_2$ | $COCH_3$ | $C_2F_5$ | $C_2F_5$ |
| F | F | $CF_2$ | O | $CF_2$ | H | $C_2F_5$ | $C_2F_5$ |
| F | F | $CF_2$ | O | $CF_2$ | $NH_2$ | $C_2F_5$ | $C_2F_5$ |
| F | F | $CF_2$ | O | $CF_2$ | N=CHPh | $C_2F_5$ | $C_2F_5$ |
| F | F | $CF_2$ | O | $CF_2$ | $CH_3$ | $C_2F_5$ | $C_2F_5$ |
| F | F | $CF_2$ | O | $CF_2$ | $CF_3$ | $C_2F_5$ | $C_2F_5$ |
| F | F | $CF_2$ | O | $CF_2$ | Cl | $C_2F_5$ | $C_2F_5$ |
| F | F | $CF_2$ | O | $CF_2$ | F | $C_2F_5$ | $C_2F_5$ |
| F | F | $CF_2$ | O | $CF_2$ | $COCH_3$ | $C_2F_5$ | $C_2F_5$ |
| F | F | $CF_2$ | O | $CF_2$ | $NH_2$ | $SFCl_2$ | $C_2F_5$ |
| F | F | $CF_2$ | O | $CF_2$ | N=CHPh | $SFCl_2$ | $C_2F_5$ |
| F | F | $CF_2$ | O | $CF_2$ | $CH_3$ | $SFCl_2$ | $C_2F_5$ |
| F | F | $CF_2$ | O | $CF_2$ | $CF_3$ | $SFCl_2$ | $C_2F_5$ |
| F | F | $CF_2$ | O | $CF_2$ | Cl | $SFCl_2$ | $C_2F_5$ |
| F | F | $CF_2$ | O | $CF_2$ | F | $SFCl_2$ | $C_2F_5$ |
| F | F | $CF_2$ | O | $CF_2$ | $COCH_3$ | $SFCl_2$ | $C_2F_5$ |
| F | F | $CF_2$ | O | $CF_2$ | H | $SFCl_2$ | $C_2F_5$ |
| F | F | $CF_2$ | O | $CF_2$ | $NH_2$ | $SFCl_2$ | $C_2F_5$ |
| F | F | $CF_2$ | O | $CF_2$ | N=CHPh | $SFCl_2$ | $C_2F_5$ |

TABLE 101

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CH_3$ | $SFCl_2$ | $C_2F_5$ |
| F | F | $CF_2$ | O | $CF_2$ | $CF_3$ | $SFCl_2$ | $C_2F_5$ |
| F | F | $CF_2$ | O | $CF_2$ | Cl | $SFCl_2$ | $C_2F_5$ |
| F | F | $CF_2$ | O | $CF_2$ | F | $SFCl_2$ | $C_2F_5$ |
| F | F | $CF_2$ | O | $CF_2$ | $COCH_3$ | $SFCl_2$ | $C_2F_5$ |
| F | F | $CF_2$ | O | $CF_2$ | H | $SCF_3$ | $CSNH_2$ |
| F | F | $CF_2$ | O | $CF_2$ | $NH_2$ | $SCF_3$ | $CSNH_2$ |
| F | F | $CF_2$ | O | $CF_2$ | N=CHPh | $SCF_3$ | $CSNH_2$ |
| F | F | $CF_2$ | O | $CF_2$ | $CH_3$ | $SCF_3$ | $CSNH_2$ |
| F | F | $CF_2$ | O | $CF_2$ | $CF_3$ | $SCF_3$ | $CSNH_2$ |
| F | F | $CF_2$ | O | $CF_2$ | Cl | $SCF_3$ | $CSNH_2$ |
| F | F | $CF_2$ | O | $CF_2$ | F | $SCF_3$ | $CSNH_2$ |
| F | F | $CF_2$ | O | $CF_2$ | $COCH_3$ | $SCF_3$ | $CSNH_2$ |
| F | F | $CF_2$ | O | $CF_2$ | H | $SOCF_3$ | $CSNH_2$ |
| F | F | $CF_2$ | O | $CF_2$ | $NH_2$ | $SOCF_3$ | $CSNH_2$ |
| F | F | $CF_2$ | O | $CF_2$ | N=CHPh | $SOCF_3$ | $CSNH_2$ |
| F | F | $CF_2$ | O | $CF_2$ | $CH_3$ | $SOCF_3$ | $CSNH_2$ |
| F | F | $CF_2$ | O | $CF_2$ | $CF_3$ | $SOCF_3$ | $CSNH_2$ |
| F | F | $CF_2$ | O | $CF_2$ | Cl | $SOCF_3$ | $CSNH_2$ |
| F | F | $CF_2$ | O | $CF_2$ | F | $SOCF_3$ | $CSNH_2$ |
| F | F | $CF_2$ | O | $CF_2$ | $COCH_3$ | $SOCF_3$ | $CSNH_2$ |
| F | F | $CF_2$ | O | $CF_2$ | H | $SO_2CF_3$ | $CSNH_2$ |
| F | F | $CF_2$ | O | $CF_2$ | $NH_2$ | $SO_2CF_3$ | $CSNH_2$ |
| F | F | $CF_2$ | O | $CF_2$ | N=CHPh | $SO_2CF_3$ | $CSNH_2$ |
| F | F | $CF_2$ | O | $CF_2$ | $CH_3$ | $SO_2CF_3$ | $CSNH_2$ |
| F | F | $CF_2$ | O | $CF_2$ | $CF_3$ | $SO_2CF_3$ | $CSNH_2$ |

TABLE 102

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | Cl | $SO_2CF_3$ | $CSNH_2$ |
| F | F | $CF_2$ | O | $CF_2$ | F | $SO_2CF_3$ | $CSNH_2$ |
| F | F | $CF_2$ | O | $CF_2$ | $COCH_3$ | $SO_2CF_3$ | $CSNH_2$ |
| F | F | $CF_2$ | O | $CF_2$ | H | $SCF_2CH_3$ | $CSNH_2$ |
| F | F | $CF_2$ | O | $CF_2$ | $NH_2$ | $SCF_2CH_3$ | $CSNH_2$ |
| F | F | $CF_2$ | O | $CF_2$ | N=CHPh | $SCF_2CH_3$ | $CSNH_2$ |
| F | F | $CF_2$ | O | $CF_2$ | $CH_3$ | $SCF_2CH_3$ | $CSNH_2$ |
| F | F | $CF_2$ | O | $CF_2$ | $CF_3$ | $SCF_2CH_3$ | $CSNH_2$ |
| F | F | $CF_2$ | O | $CF_2$ | Cl | $SCF_2CH_3$ | $CSNH_2$ |
| F | F | $CF_2$ | O | $CF_2$ | F | $SCF_2CH_3$ | $CSNH_2$ |

TABLE 102-continued

| X | Y | Z¹ | Z² | Z³ | R¹ | R² | R³ |
|---|---|---|---|---|---|---|---|
| F | F | CF$_2$ | O | CF$_2$ | COCH$_3$ | SCF$_2$CH$_3$ | CSNH$_2$ |
| F | F | CF$_2$ | O | CF$_2$ | H | SOCF$_2$CH$_3$ | CSNH$_2$ |
| F | F | CF$_2$ | O | CF$_2$ | NH$_2$ | SOCF$_2$CH$_3$ | CSNH$_2$ |
| F | F | CF$_2$ | O | CF$_2$ | N = CHPh | SOCF$_2$CH$_3$ | CSNH$_2$ |
| F | F | CF$_2$ | O | CF$_2$ | CH$_3$ | SOCF$_2$CH$_3$ | CSNH$_2$ |
| F | F | CF$_2$ | O | CF$_2$ | CF$_3$ | SOCF$_2$CH$_3$ | CSNH$_2$ |
| F | F | CF$_2$ | O | CF$_2$ | Cl | SOCF$_2$CH$_3$ | CSNH$_2$ |
| F | F | CF$_2$ | O | CF$_2$ | F | SOCF$_2$CH$_3$ | CSNH$_2$ |
| F | F | CF$_2$ | O | CF$_2$ | COCH$_3$ | SOCF$_2$CH$_3$ | CSNH$_2$ |
| F | F | CF$_2$ | O | CF$_2$ | H | SO$_2$CF$_2$CH$_3$ | CSNH$_2$ |
| F | F | CF$_2$ | O | CF$_2$ | NH$_2$ | SO$_2$CF$_2$CH$_3$ | CSNH$_2$ |
| F | F | CF$_2$ | O | CF$_2$ | N = CHPh | SO$_2$CF$_2$CH$_3$ | CSNH$_2$ |
| F | F | CF$_2$ | O | CF$_2$ | CH$_3$ | SO$_2$CF$_2$CH$_3$ | CSNH$_2$ |
| F | F | CF$_2$ | O | CF$_2$ | CF$_3$ | SO$_2$CF$_2$CH$_3$ | CSNH$_2$ |
| F | F | CF$_2$ | O | CF$_2$ | Cl | SO$_2$CF$_2$CH$_3$ | CSNH$_2$ |
| F | F | CF$_2$ | O | CF$_2$ | F | SO$_2$CF$_2$CH$_3$ | CSNH$_2$ |

TABLE 103

| X | Y | Z¹ | Z² | Z³ | R¹ | R² | R³ |
|---|---|---|---|---|---|---|---|
| F | F | CF$_2$ | O | CF$_2$ | COCH$_3$ | SO$_2$CF$_2$CH$_3$ | CSNH$_2$ |
| F | F | CF$_2$ | O | CF$_2$ | NH$_2$ | COCF$_3$ | CSNH$_2$ |
| F | F | CF$_2$ | O | CF$_2$ | N = CHPh | COCF$_3$ | CSNH$_2$ |
| F | F | CF$_2$ | O | CF$_2$ | CH$_3$ | COCF$_3$ | CSNH$_2$ |
| F | F | CF$_2$ | O | CF$_2$ | CF$_3$ | COCF$_3$ | CSNH$_2$ |
| F | F | CF$_2$ | O | CF$_2$ | Cl | COCF$_3$ | CSNH$_2$ |
| F | F | CF$_2$ | O | CF$_2$ | F | COCF$_3$ | CSNH$_2$ |
| F | F | CF$_2$ | O | CF$_2$ | COCH$_3$ | COCF$_3$ | CSNH$_2$ |
| F | F | CF$_2$ | O | CF$_2$ | H | COCF$_3$ | CSNH$_2$ |
| F | F | CF$_2$ | O | CF$_2$ | NH$_2$ | COCF$_3$ | CSNH$_2$ |
| F | F | CF$_2$ | O | CF$_2$ | N = CHPh | COCF$_3$ | CSNH$_2$ |
| F | F | CF$_2$ | O | CF$_2$ | CH$_3$ | COCF$_3$ | CSNH$_2$ |
| F | F | CF$_2$ | O | CF$_2$ | CF$_3$ | COCF$_3$ | CSNH$_2$ |
| F | F | CF$_2$ | O | CF$_2$ | Cl | COCF$_3$ | CSNH$_2$ |
| F | F | CF$_2$ | O | CF$_2$ | F | COCF$_3$ | CSNH$_2$ |
| F | F | CF$_2$ | O | CF$_2$ | COCH$_3$ | COCF$_3$ | CSNH$_2$ |
| F | F | CF$_2$ | O | CF$_2$ | NH$_2$ | C$_2$F$_5$ | CSNH$_2$ |
| F | F | CF$_2$ | O | CF$_2$ | N = CHPh | C$_2$F$_5$ | CSNH$_2$ |
| F | F | CF$_2$ | O | CF$_2$ | CH$_3$ | C$_2$F$_5$ | CSNH$_2$ |
| F | F | CF$_2$ | O | CF$_2$ | CF$_3$ | C$_2$F$_5$ | CSNH$_2$ |
| F | F | CF$_2$ | O | CF$_2$ | Cl | C$_2$F$_5$ | CSNH$_2$ |
| F | F | CF$_2$ | O | CF$_2$ | F | C$_2$F$_5$ | CSNH$_2$ |
| F | F | CF$_2$ | O | CF$_2$ | COCH$_3$ | C$_2$F$_5$ | CSNH$_2$ |
| F | F | CF$_2$ | O | CF$_2$ | H | C$_2$F$_5$ | CSNH$_2$ |
| F | F | CF$_2$ | O | CF$_2$ | NH$_2$ | C$_2$F$_5$ | CSNH$_2$ |
| F | F | CF$_2$ | O | CF$_2$ | N = CHPh | C$_2$F$_5$ | CSNH$_2$ |

TABLE 104

| X | Y | Z¹ | Z² | Z³ | R¹ | R² | R³ |
|---|---|---|---|---|---|---|---|
| F | F | CF$_2$ | O | CF$_2$ | CH$_3$ | C$_2$F$_5$ | CSNH$_2$ |
| F | F | CF$_2$ | O | CF$_2$ | CF$_3$ | C$_2$F$_5$ | CSNH$_2$ |
| F | F | CF$_2$ | O | CF$_2$ | Cl | C$_2$F$_5$ | CSNH$_2$ |
| F | F | CF$_2$ | O | CF$_2$ | F | C$_2$F$_5$ | CSNH$_2$ |
| F | F | CF$_2$ | O | CF$_2$ | COCH$_3$ | C$_2$F$_5$ | CSNH$_2$ |
| F | F | CF$_2$ | O | CF$_2$ | NH$_2$ | SFCl$_2$ | CSNH$_2$ |
| F | F | CF$_2$ | O | CF$_2$ | N = CHPh | SFCl$_2$ | CSNH$_2$ |
| F | F | CF$_2$ | O | CF$_2$ | CH$_3$ | SFCl$_2$ | CSNH$_2$ |
| F | F | CF$_2$ | O | CF$_2$ | CF$_3$ | SFCl$_2$ | CSNH$_2$ |
| F | F | CF$_2$ | O | CF$_2$ | Cl | SFCl$_2$ | CSNH$_2$ |
| F | F | CF$_2$ | O | CF$_2$ | F | SFCl$_2$ | CSNH$_2$ |
| F | F | CF$_2$ | O | CF$_2$ | COCH$_3$ | SFCl$_2$ | CSNH$_2$ |
| F | F | CF$_2$ | O | CF$_2$ | H | SFCl$_2$ | CSNH$_2$ |
| F | F | CF$_2$ | O | CF$_2$ | NH$_2$ | SFCl$_2$ | CSNH$_2$ |
| F | F | CF$_2$ | O | CF$_2$ | N = CHPh | SFCl$_2$ | CSNH$_2$ |
| F | F | CF$_2$ | O | CF$_2$ | CH$_3$ | SFCl$_2$ | CSNH$_2$ |
| F | F | CF$_2$ | O | CF$_2$ | CF$_3$ | SFCl$_2$ | CSNH$_2$ |
| F | F | CF$_2$ | O | CF$_2$ | Cl | SFCl$_2$ | CSNH$_2$ |
| F | F | CF$_2$ | O | CF$_2$ | F | SFCl$_2$ | CSNH$_2$ |
| F | F | CF$_2$ | O | CF$_2$ | COCH$_3$ | SFCl$_2$ | CSNH$_2$ |

TABLE 104-continued

| X | Y | Z¹ | Z² | Z³ | R¹ | R² | R³ |
|---|---|---|---|---|---|---|---|
| F | F | CF$_2$ | O | CF$_2$ | H | SCF$_3$ | CN |
| F | F | CF$_2$ | O | CF$_2$ | NH$_2$ | SCF$_3$ | CN |
| F | F | CF$_2$ | O | CF$_2$ | N = CHPh | SCF$_3$ | CN |
| F | F | CF$_2$ | O | CF$_2$ | CH$_3$ | SCF$_3$ | CN |
| F | F | CF$_2$ | O | CF$_2$ | CF$_3$ | SCF$_3$ | CN |
| F | F | CF$_2$ | O | CF$_2$ | Cl | SCF$_3$ | CN |

TABLE 105

| X | Y | Z¹ | Z² | Z³ | R¹ | R² | R³ |
|---|---|---|---|---|---|---|---|
| F | F | CF$_2$ | O | CF$_2$ | F | SCF$_3$ | CN |
| F | F | CF$_2$ | O | CF$_2$ | COCH$_3$ | SCF$_3$ | CN |
| F | F | CF$_2$ | O | CF$_2$ | H | SOCF$_3$ | CN |
| F | F | CF$_2$ | O | CF$_2$ | NH$_2$ | SOCF$_3$ | CN |
| F | F | CF$_2$ | O | CF$_2$ | N = CHPh | SOCF$_3$ | CN |
| F | F | CF$_2$ | O | CF$_2$ | CH$_3$ | SOCF$_3$ | CN |
| F | F | CF$_2$ | O | CF$_2$ | CF$_3$ | SOCF$_3$ | CN |
| F | F | CF$_2$ | O | CF$_2$ | Cl | SOCF$_3$ | CN |
| F | F | CF$_2$ | O | CF$_2$ | F | SOCF$_3$ | CN |
| F | F | CF$_2$ | O | CF$_2$ | COCH$_3$ | SOCF$_3$ | CN |
| F | F | CF$_2$ | O | CF$_2$ | H | SO$_2$CF$_3$ | CN |
| F | F | CF$_2$ | O | CF$_2$ | NH$_2$ | SO$_2$CF$_3$ | CN |
| F | F | CF$_2$ | O | CF$_2$ | N = CHPh | SO$_2$CF$_3$ | CN |
| F | F | CF$_2$ | O | CF$_2$ | CH$_3$ | SO$_2$CF$_3$ | CN |
| F | F | CF$_2$ | G | CF$_2$ | CF$_3$ | SO$_2$CF$_3$ | CN |
| F | F | CF$_2$ | O | CF$_2$ | Cl | SO$_2$CF$_3$ | CN |
| F | F | CF$_2$ | O | CF$_2$ | F | SO$_2$CF$_3$ | CN |
| F | F | CF$_2$ | O | CF$_2$ | COCH$_3$ | SO$_2$CF$_3$ | CN |
| F | F | CF$_2$ | O | CF$_2$ | H | SCF$_2$CH$_3$ | CN |
| F | F | CF$_2$ | O | CF$_2$ | NH$_2$ | SCF$_2$CH$_3$ | CN |
| F | F | CF$_2$ | O | CF$_2$ | N = CHPh | SCF$_2$CH$_3$ | CN |
| F | F | CF$_2$ | O | CF$_2$ | CH$_3$ | SCF$_2$CH$_3$ | CN |
| F | F | CF$_2$ | O | CF$_2$ | CF$_3$ | SCF$_2$CH$_3$ | CN |
| F | F | CF$_2$ | O | CF$_2$ | Cl | SCF$_2$CH$_3$ | CN |
| F | F | CF$_2$ | O | CF$_2$ | F | SCF$_2$CH$_3$ | CN |
| F | F | CF$_2$ | O | CF$_2$ | COCH$_3$ | SCF$_2$CH$_3$ | CN |

TABLE 106

| X | Y | Z¹ | Z² | Z³ | R¹ | R² | R³ |
|---|---|---|---|---|---|---|---|
| F | F | CF$_2$ | O | CF$_2$ | H | SOCF$_2$CH$_3$ | CN |
| F | F | CF$_2$ | O | CF$_2$ | NH$_2$ | SOCF$_2$CH$_3$ | CN |
| F | F | CF$_2$ | O | CF$_2$ | N = CHPh | SOCF$_2$CH$_3$ | CN |
| F | F | CF$_2$ | O | CF$_2$ | CH$_3$ | SOCF$_2$CH$_3$ | CN |
| F | F | CF$_2$ | O | CF$_2$ | CF$_3$ | SOCF$_2$CH$_3$ | CN |
| F | F | CF$_2$ | O | CF$_2$ | Cl | SOCF$_2$CH$_3$ | CN |
| F | F | CF$_2$ | O | CF$_2$ | F | SOCF$_2$CH$_3$ | CN |
| F | F | CF$_2$ | O | CF$_2$ | COCH$_3$ | SOCF$_2$CH$_3$ | CN |
| F | F | CF$_2$ | O | CF$_2$ | H | SO$_2$CF$_2$CH$_3$ | CN |
| F | F | CF$_2$ | O | CF$_2$ | NH$_2$ | SO$_2$CF$_2$CH$_3$ | CN |
| F | F | CF$_2$ | O | CF$_2$ | N = CHPh | SO$_2$CF$_2$CH$_3$ | CN |
| F | F | CF$_2$ | O | CF$_2$ | CH$_3$ | SO$_2$CF$_2$CH$_3$ | CN |
| F | F | CF$_2$ | O | CF$_2$ | CF$_3$ | SO$_2$CF$_2$CH$_3$ | CN |
| F | F | CF$_2$ | O | CF$_2$ | Cl | SO$_2$CF$_2$CH$_3$ | CN |
| F | F | CF$_2$ | O | CF$_2$ | F | SO$_2$CF$_2$CH$_3$ | CN |
| F | F | CF$_2$ | O | CF$_2$ | COCH$_3$ | SO$_2$CF$_2$CH$_3$ | CN |
| F | F | CF$_2$ | O | CF$_2$ | NH$_2$ | COCF$_3$ | CN |
| F | F | CF$_2$ | O | CF$_2$ | N = CHPh | COCF$_3$ | CN |
| F | F | CF$_2$ | O | CF$_2$ | CH$_3$ | COCF$_3$ | CN |
| F | F | CF$_2$ | O | CF$_2$ | CF$_3$ | COCF$_3$ | CN |
| F | F | CF$_2$ | O | CF$_2$ | Cl | COCF$_3$ | CN |
| F | F | CF$_2$ | O | CF$_2$ | F | COCF$_3$ | CN |
| F | F | CF$_2$ | O | CF$_2$ | COCH$_3$ | COCF$_3$ | CN |
| F | F | CF$_2$ | O | CF$_2$ | H | COCF$_3$ | CN |
| F | F | CF$_2$ | O | CF$_2$ | NH$_2$ | COCF$_3$ | CN |
| F | F | CF$_2$ | O | CF$_2$ | N = CHPh | COCF$_3$ | CN |

TABLE 107

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $CH_3$ | $COCF_3$ | CN |
| F | F | $CF_2$ | O | $CF_2$ | $CF_3$ | $COCF_3$ | CN |
| F | F | $CF_2$ | O | $CF_2$ | Cl | $COCF_3$ | CN |
| F | F | $CF_2$ | O | $CF_2$ | F | $COCF_3$ | CN |
| F | F | $CF_2$ | O | $CF_2$ | $COCH_3$ | $COCF_3$ | CN |
| F | F | $CF_2$ | O | $CF_2$ | $NH_2$ | $C_2F_5$ | CN |
| F | F | $CF_2$ | O | $CF_2$ | N = CHPh | $C_2F_5$ | CN |
| F | F | $CF_2$ | O | $CF_2$ | $CH_3$ | $C_2F_5$ | CN |
| F | F | $CF_2$ | O | $CF_2$ | $CF_3$ | $C_2F_5$ | CN |
| F | F | $CF_2$ | O | $CF_2$ | Cl | $C_2F_5$ | CN |
| F | F | $CF_2$ | O | $CF_2$ | F | $C_2F_5$ | CN |
| F | F | $CF_2$ | O | $CF_2$ | $COCH_3$ | $C_2F_5$ | CN |
| F | F | $CF_2$ | O | $CF_2$ | H | $C_2F_5$ | CN |
| F | F | $CF_2$ | O | $CF_2$ | $NH_2$ | $C_2F_5$ | CN |
| F | F | $CF_2$ | O | $CF_2$ | N = CHPh | $C_2F_5$ | CN |
| F | F | $CF_2$ | O | $CF_2$ | $CH_3$ | $C_2F_5$ | CN |
| F | F | $CF_2$ | O | $CF_2$ | $CF_3$ | $C_2F_5$ | CN |
| F | F | $CF_2$ | O | $CF_2$ | Cl | $C_2F_5$ | CN |
| F | F | $CF_2$ | O | $CF_2$ | F | $C_2F_5$ | CN |
| F | F | $CF_2$ | O | $CF_2$ | $COCH_3$ | $C_2F_5$ | CN |
| F | F | $CF_2$ | O | $CF_2$ | $NH_2$ | $SFCl_2$ | CN |
| F | F | $CF_2$ | O | $CF_2$ | N = CHPh | $SFCl_2$ | CN |
| F | F | $CF_2$ | O | $CF_2$ | $CH_3$ | $SFCl_2$ | CN |
| F | F | $CF_2$ | O | $CF_2$ | $CF_3$ | $SFCl_2$ | CN |
| F | F | $CF_2$ | O | $CF_2$ | Cl | $SFCl_2$ | CN |
| F | F | $CF_2$ | O | $CF_2$ | F | $SFCl_2$ | CN |

TABLE 108

| X | Y | $Z^1$ | $Z^2$ | $Z^3$ | $R^1$ | $R^2$ | $R^3$ |
|---|---|---|---|---|---|---|---|
| F | F | $CF_2$ | O | $CF_2$ | $COCH_3$ | $SFCl_2$ | CN |
| F | F | $CF_2$ | O | $CF_2$ | H | $SFCl_2$ | CN |
| F | F | $CF_2$ | O | $CF_2$ | $NH_2$ | $SFCl_2$ | CN |
| F | F | $CF_2$ | O | $CF_2$ | N = CHPh | $SFCl_2$ | CN |
| F | F | $CF_2$ | O | $CF_2$ | $CH_3$ | $SFCl_2$ | CN |
| F | F | $CF_2$ | O | $CF_2$ | $CF_3$ | $SFCl_2$ | CN |
| F | F | $CF_2$ | O | $CF_2$ | Cl | $SFCl_2$ | CN |
| F | F | $CF_2$ | O | $CF_2$ | F | $SFCl_2$ | CN |
| F | F | $CF_2$ | O | $CF_2$ | $COCH_3$ | $SFCl_2$ | CN |
| Cl | Cl | $CF_2$ | $CF_2$ | O | H | $SCF_3$ | H |
| Cl | Cl | $CF_2$ | $CF_2$ | O | $NH_2$ | $SCF_3$ | H |
| Cl | Cl | $CF_2$ | $CF_2$ | O | N = CHPh | $SCF_3$ | H |
| Cl | Cl | $CF_2$ | $CF_2$ | O | $CH_3$ | $SCF_3$ | H |
| Cl | Cl | $CF_2$ | $CF_2$ | O | $CF_3$ | $SCF_3$ | H |
| Cl | Cl | $CF_2$ | $CF_2$ | O | Cl | $SCF_3$ | H |
| Cl | Cl | $CF_2$ | $CF_2$ | O | F | $SCF_3$ | H |
| Cl | Cl | $CF_2$ | $CF_2$ | O | $COCH_3$ | $SCF_3$ | H |
| Cl | Cl | $CF_2$ | $CF_2$ | O | H | $SOCF_3$ | H |
| Cl | Cl | $CF_2$ | $CF_2$ | O | $NH_2$ | $SOCF_3$ | H |
| Cl | Cl | $CF_2$ | $CF_2$ | O | N = CHPh | $SOCF_3$ | H |
| Cl | Cl | $CF_2$ | $CF_2$ | O | $CH_3$ | $SOCF_3$ | H |
| Cl | Cl | $CF_2$ | $CF_2$ | O | $CF_3$ | $SOCF_3$ | H |
| Cl | Cl | $CF_2$ | $CF_2$ | O | Cl | $SOCF_3$ | H |
| Cl | Cl | $CF_2$ | $CF_2$ | O | F | $SOCF_3$ | H |
| Cl | Cl | $CF_2$ | $CF_2$ | O | $COCH_3$ | $SOCF_3$ | H |
| Cl | Cl | $CF_2$ | $CF_2$ | O | H | $SO_2CF_3$ | H |

TABLE 109

| X | Y | $Z^1$ | $Z^2$ | $Z^3$ | $R^1$ | $R^2$ | $R^3$ |
|---|---|---|---|---|---|---|---|
| Cl | Cl | $CF_2$ | $CF_2$ | O | $NH_2$ | $SO_2CF_3$ | H |
| Cl | Cl | $CF_2$ | $CF_2$ | O | N = CHPh | $SO_2CF_3$ | H |
| Cl | Cl | $CF_2$ | $CF_2$ | O | $CH_3$ | $SO_2CF_3$ | H |
| Cl | Cl | $CF_2$ | $CF_2$ | O | $CF_3$ | $SO_2CF_3$ | H |
| Cl | Cl | $CF_2$ | $CF_2$ | O | Cl | $SO_2CF_3$ | H |
| Cl | Cl | $CF_2$ | $CF_2$ | O | F | $SO_2CF_3$ | H |
| Cl | Cl | $CF_2$ | $CF_2$ | O | $COCH_3$ | $SO_2CF_3$ | H |
| Cl | Cl | $CF_2$ | $CF_2$ | O | H | $SCF_2CH_3$ | H |
| Cl | Cl | $CF_2$ | $CF_2$ | O | $NH_2$ | $SCF_2CH_3$ | H |
| Cl | Cl | $CF_2$ | $CF_2$ | O | N = CHPh | $SCF_2CH_3$ | H |

TABLE 109-continued

| X | Y | $Z^1$ | $Z^2$ | $Z^3$ | $R^1$ | $R^2$ | $R^3$ |
|---|---|---|---|---|---|---|---|
| Cl | Cl | $CF_2$ | $CF_2$ | O | $CH_3$ | $SCF_2CH_3$ | H |
| Cl | Cl | $CF_2$ | $CF_2$ | O | $CF_3$ | $SCF_2CH_3$ | H |
| Cl | Cl | $CF_2$ | $CF_2$ | O | Cl | $SCF_2CH_3$ | H |
| Cl | Cl | $CF_2$ | $CF_2$ | O | F | $SCF_2CH_3$ | H |
| Cl | Cl | $CF_2$ | $CF_2$ | O | $COCH_3$ | $SCF_2CH_3$ | H |
| Cl | Cl | $CF_2$ | $CF_2$ | O | H | $SOCF_2CH_3$ | H |
| Cl | Cl | $CF_2$ | $CF_2$ | O | $NH_2$ | $SOCF_2CH_3$ | H |
| Cl | Cl | $CF_2$ | $CF_2$ | O | N = CHPh | $SOCF_2CH_3$ | H |
| Cl | Cl | $CF_2$ | $CF_2$ | O | $CH_3$ | $SOCF_2CH_3$ | H |
| Cl | Cl | $CF_2$ | $CF_2$ | O | $CF_3$ | $SOCF_2CH_3$ | H |
| Cl | Cl | $CF_2$ | $CF_2$ | O | Cl | $SOCF_2CH_3$ | H |
| Cl | Cl | $CF_2$ | $CF_2$ | O | F | $SOCF_2CH_3$ | H |
| Cl | Cl | $CF_2$ | $CF_2$ | O | $COCH_3$ | $SOCF_2CH_3$ | H |
| Cl | Cl | $CF_2$ | $CF_2$ | O | H | $SO_2CF_2CH_3$ | H |
| Cl | Cl | $CF_2$ | $CF_2$ | O | $NH_2$ | $SO_2CF_2CH_3$ | H |
| Cl | Cl | $CF_2$ | $CF_2$ | O | N = CHPh | $SO_2CF_2CH_3$ | H |

TABLE 110

| X | Y | $Z^1$ | $Z^2$ | $Z^3$ | $R^1$ | $R^2$ | $R^3$ |
|---|---|---|---|---|---|---|---|
| Cl | Cl | $CF_2$ | $CF_2$ | O | $CH_3$ | $SO_2CF_2CH_3$ | H |
| Cl | Cl | $CF_2$ | $CF_2$ | O | $CF_3$ | $SO_2CF_2CH_3$ | H |
| Cl | Cl | $CF_2$ | $CF_2$ | O | Cl | $SO_2CF_2CH_3$ | H |
| Cl | Cl | $CF_2$ | $CF_2$ | O | F | $SO_2CF_2CH_3$ | H |
| Cl | Cl | $CF_2$ | $CF_2$ | O | $COCH_3$ | $SO_2CF_2CH_3$ | H |
| Cl | CL | $CF_2$ | $CF_2$ | O | $NH_2$ | $COCF_3$ | H |
| Cl | Cl | $CF_2$ | $CF_2$ | O | N = CHPh | $COCF_3$ | H |
| Cl | Cl | $CF_2$ | $CF_2$ | O | $CH_3$ | $COCF_3$ | H |
| Cl | Cl | $CF_2$ | $CF_2$ | O | $CF_3$ | $COCF_3$ | H |
| Cl | Cl | $CF_2$ | $CF_2$ | O | Cl | $COCF_3$ | H |
| Cl | Cl | $CF_2$ | $CF_2$ | O | F | $COCF_3$ | H |
| Cl | Cl | $CF_2$ | $CF_2$ | O | $COCH_3$ | $COCF_3$ | H |
| Cl | Cl | $CF_2$ | $CF_2$ | O | H | $COCF_3$ | H |
| Cl | Cl | $CF_2$ | $CF_2$ | O | $NH_2$ | $COCF_3$ | H |
| Cl | Cl | $CF_2$ | $CF_2$ | O | N = CHPh | $COCF_3$ | H |
| Cl | Cl | $CF_2$ | $CF_2$ | O | $CH_3$ | $COCF_3$ | H |
| Cl | Cl | $CF_2$ | $CF_2$ | O | $CF_3$ | $COCF_3$ | H |
| Cl | Cl | $CF_2$ | $CF_2$ | O | Cl | $COCF_3$ | H |
| Cl | Cl | $CF_2$ | $CF_2$ | O | F | $COCF_3$ | H |
| Cl | Cl | $CF_2$ | $CF_2$ | O | $COCH_3$ | $COCF_3$ | H |
| Cl | Cl | $CF_2$ | $CF_2$ | O | $NH_2$ | $C_2F_5$ | H |
| Cl | Cl | $CF_2$ | $CF_2$ | O | N = CHPh | $C_2F_5$ | H |
| Cl | Cl | $CF_2$ | $CF_2$ | O | $CH_3$ | $C_2F_5$ | H |
| Cl | Cl | $CF_2$ | $CF_2$ | O | $CF_3$ | $C_2F_5$ | H |
| Cl | Cl | $CF_2$ | $CF_2$ | O | Cl | $C_2F_5$ | H |
| Cl | Cl | $CF_2$ | $CF_2$ | O | F | $C_2F_5$ | H |

TABLE 111

| X | Y | $Z^1$ | $Z^2$ | $Z^3$ | $R^1$ | $R^2$ | $R^3$ |
|---|---|---|---|---|---|---|---|
| Cl | Cl | $CF_2$ | $CF_2$ | O | $COCH_3$ | $C_2F_5$ | H |
| Cl | Cl | $CF_2$ | $CF_2$ | O | H | $C_2F_5$ | H |
| Cl | Cl | $CF_2$ | $CF_2$ | O | $NH_2$ | $C_2F_5$ | H |
| Cl | Cl | $CF_2$ | $CF_2$ | O | N = CHPh | $C_2F_5$ | H |
| Cl | Cl | $CF_2$ | $CF_2$ | O | $CH_3$ | $C_2F_5$ | H |
| Cl | Cl | $CF_2$ | $CF_2$ | O | $CF_3$ | $C_2F_5$ | H |
| Cl | Cl | $CF_2$ | $CF_2$ | O | Cl | $C_2F_5$ | H |
| Cl | Cl | $CF_2$ | $CF_2$ | O | F | $C_2F_5$ | H |
| Cl | Cl | $CF_2$ | $CF_2$ | O | $COCH_3$ | $C_2F_5$ | H |
| Cl | Cl | $CF_2$ | $CF_2$ | O | $NH_2$ | $SFCl_2$ | H |
| Cl | Cl | $CF_2$ | $CF_2$ | O | N = CHPh | $SFCl_2$ | H |
| Cl | Cl | $CF_2$ | $CF_2$ | O | $CH_3$ | $SFCl_2$ | H |
| Cl | Cl | $CF_2$ | $CF_2$ | O | $CF_3$ | $SFCl_2$ | H |
| Cl | Cl | $CF_2$ | $CF_2$ | O | Cl | $SFCl_2$ | H |
| Cl | Cl | $CF_2$ | $CF_2$ | O | F | $SFCl_2$ | H |
| Cl | Cl | $CF_2$ | $CF_2$ | O | $COCH_3$ | $SFCl_2$ | H |
| Cl | Cl | $CF_2$ | $CF_2$ | O | H | $SFCl_2$ | H |
| Cl | Cl | $CF_2$ | $CF_2$ | O | $NH_2$ | $SFCl_2$ | H |
| Cl | Cl | $CF_2$ | $CF_2$ | O | N = CHPh | $SFCl_2$ | H |
| Cl | Cl | $CF_2$ | $CF_2$ | O | $CH_3$ | $SFCl_2$ | H |

TABLE 111-continued

| X | Y | Z¹ | Z² | Z³ | R¹ | R² | R³ |
|---|---|---|---|---|---|---|---|
| Cl | Cl | $CF_2$ | $CF_2$ | O | $CF_3$ | $SFCl_2$ | H |
| Cl | Cl | $CF_2$ | $CF_2$ | O | Cl | $SFCl_2$ | H |
| Cl | Cl | $CF_2$ | $CF_2$ | O | F | $SFCl_2$ | H |
| Cl | Cl | $CF_2$ | $CF_2$ | O | $COCH_3$ | $SFCl_2$ | H |
| Cl | Cl | $CF_2$ | $CF_2$ | O | H | $SCF_3$ | $CF_3$ |
| Cl | Cl | $CF_2$ | $CF_2$ | O | $NH_2$ | $SCF_3$ | $CF_3$ |

TABLE 112

| X | Y | Z¹ | Z² | Z³ | R¹ | R² | R³ |
|---|---|---|---|---|---|---|---|
| Cl | Cl | $CF_2$ | $CF_2$ | O | N=CHPh | $SCF_3$ | $CF_3$ |
| Cl | Cl | $CF_2$ | $CF_2$ | O | $CH_3$ | $SCF_3$ | $CF_3$ |
| Cl | Cl | $CF_2$ | $CF_2$ | O | $CF_3$ | $SCF_3$ | $CF_3$ |
| Cl | Cl | $CF_2$ | $CF_2$ | O | Cl | $SCF_3$ | $CF_3$ |
| Cl | Cl | $CF_2$ | $CF_2$ | O | F | $SCF_3$ | $CF_3$ |
| Cl | Cl | $CF_2$ | $CF_2$ | O | $COCH_3$ | $SCF_3$ | $CF_3$ |
| Cl | Cl | $CF_2$ | $CF_2$ | O | H | $SOCF_3$ | $CF_3$ |
| Cl | Cl | $CF_2$ | $CF_2$ | O | $NH_2$ | $SOCF_3$ | $CF_3$ |
| Cl | Cl | $CF_2$ | $CF_2$ | O | N=CHPh | $SOCF_3$ | $CF_3$ |
| Cl | Cl | $CF_2$ | $CF_2$ | O | $CH_3$ | $SOCF_3$ | $CF_3$ |
| Cl | Cl | $CF_2$ | $CF_2$ | O | $CF_3$ | $SOCF_3$ | $CF_3$ |
| Cl | Cl | $CF_2$ | $CF_2$ | O | Cl | $SOCF_3$ | $CF_3$ |
| Cl | Cl | $CF_2$ | $CF_2$ | O | F | $SOCF_3$ | $CF_3$ |
| Cl | Cl | $CF_2$ | $CF_2$ | O | $COCH_3$ | $SOCF_3$ | $CF_3$ |
| Cl | Cl | $CF_2$ | $CF_2$ | O | H | $SO_2CF_3$ | $CF_3$ |
| Cl | Cl | $CF_2$ | $CF_2$ | O | $NH_2$ | $SO_2CF_3$ | $CF_3$ |
| Cl | Cl | $CF_2$ | $CF_2$ | O | N=CHPh | $SO_2CF_3$ | $CF_3$ |
| Cl | Cl | $CF_2$ | $CF_2$ | O | $CH_3$ | $SO_2CF_3$ | $CF_3$ |
| Cl | Cl | $CF_2$ | $CF_2$ | O | $CF_3$ | $SO_2CF_3$ | $CF_3$ |
| Cl | Cl | $CF_2$ | $CF_2$ | O | Cl | $SO_2CF_3$ | $CF_3$ |
| Cl | Cl | $CF_2$ | $CF_2$ | O | F | $SO_2CF_3$ | $CF_3$ |
| Cl | Cl | $CF_2$ | $CF_2$ | O | $COCH_3$ | $SO_2CF_3$ | $CF_3$ |
| Cl | Cl | $CF_2$ | $CF_2$ | O | H | $SCF_2CH_3$ | $CF_3$ |
| Cl | Cl | $CF_2$ | $CF_2$ | O | $NH_2$ | $SCF_2CH_3$ | $CF_3$ |
| Cl | Cl | $CF_2$ | $CF_2$ | O | N=CHPh | $SCF_2CH_3$ | $CF_3$ |
| Cl | Cl | $CF_2$ | $CF_2$ | O | $CH_3$ | $SCF_2CH_3$ | $CF_3$ |

TABLE 113

| X | Y | Z¹ | Z² | Z³ | R¹ | R² | R³ |
|---|---|---|---|---|---|---|---|
| Cl | Cl | $CF_2$ | $CF_2$ | O | $CF_3$ | $SCF_2CH_3$ | $CF_3$ |
| Cl | Cl | $CF_2$ | $CF_2$ | O | Cl | $SCF_2CH_3$ | $CF_3$ |
| Cl | Cl | $CF_2$ | $CF_2$ | O | F | $SCF_2CH_3$ | $CF_3$ |
| Cl | Cl | $CF_2$ | $CF_2$ | O | $COCH_3$ | $SCF_2CH_3$ | $CF_3$ |
| Cl | Cl | $CF_2$ | $CF_2$ | O | H | $SOCF_2CH_3$ | $CF_3$ |
| Cl | Cl | $CF_2$ | $CF_2$ | O | $NH_2$ | $SOCF_2CH_3$ | $CF_3$ |
| Cl | Cl | $CF_2$ | $CF_2$ | O | N=CHPh | $SOCF_2CH_3$ | $CF_3$ |
| Cl | Cl | $CF_2$ | $CF_2$ | O | $CH_3$ | $SOCF_2CH_3$ | $CF_3$ |
| Cl | Cl | $CF_2$ | $CF_2$ | O | $CF_3$ | $SOCF_2CH_3$ | $CF_3$ |
| Cl | Cl | $CF_2$ | $CF_2$ | O | Cl | $SOCF_2CH_3$ | $CF_3$ |
| Cl | Cl | $CF_2$ | $CF_2$ | O | F | $SOCF_2CH_3$ | $CF_3$ |
| Cl | Cl | $CF_2$ | $CF_2$ | O | $COCH_3$ | $SOCF_2CH_3$ | $CF_3$ |
| Cl | Cl | $CF_2$ | $CF_2$ | O | H | $SO_2CF_2CH_3$ | $CF_3$ |
| Cl | Cl | $CF_2$ | $CF_2$ | O | $NH_2$ | $SO_2CF_2CH_3$ | $CF_3$ |
| Cl | Cl | $CF_2$ | $CF_2$ | O | N=CHPh | $SO_2CF_2CH_3$ | $CF_3$ |
| Cl | Cl | $CF_2$ | $CF_2$ | O | $CH_3$ | $SO_2CF_2CH_3$ | $CF_3$ |
| Cl | Cl | $CF_2$ | $CF_2$ | O | $CF_3$ | $SO_2CF_2CH_3$ | $CF_3$ |
| Cl | Cl | $CF_2$ | $CF_2$ | O | Cl | $SO_2CF_2CH_3$ | $CF_3$ |
| Cl | Cl | $CF_2$ | $CF_2$ | O | F | $SO_2CF_2CH_3$ | $CF_3$ |
| Cl | Cl | $CF_2$ | $CF_2$ | O | $COCH_3$ | $SO_2CF_2CH_3$ | $CF_3$ |
| Cl | Cl | $CF_2$ | $CF_2$ | O | $NH_2$ | $COCF_3$ | $CF_3$ |
| Cl | Cl | $CF_2$ | $CF_2$ | O | N=CHPh | $COCF_3$ | $CF_3$ |
| Cl | Cl | $CF_2$ | $CF_2$ | O | $CH_3$ | $COCF_3$ | $CF_3$ |
| Cl | Cl | $CF_2$ | $CF_2$ | O | $CF_3$ | $COCF_3$ | $CF_3$ |
| Cl | Cl | $CF_2$ | $CF_2$ | O | Cl | $COCF_3$ | $CF_3$ |
| Cl | Cl | $CF_2$ | $CF_2$ | O | F | $COCF_3$ | $CF_3$ |

TABLE 114

| X | Y | Z¹ | Z² | Z³ | R¹ | R² | R³ |
|---|---|---|---|---|---|---|---|
| Cl | Cl | $CF_2$ | $CF_2$ | O | $COCH_3$ | $COCF_3$ | $CF_3$ |
| Cl | Cl | $CF_2$ | $CF_2$ | O | H | $COCF_3$ | $CF_3$ |
| Cl | Cl | $CF_2$ | $CF_2$ | O | $NH_2$ | $COCF_3$ | $CF_3$ |
| Cl | Cl | $CF_2$ | $CF_2$ | O | N=CHPh | $COCF_3$ | $CF_3$ |
| Cl | Cl | $CF_2$ | $CF_2$ | O | $CH_3$ | $COCF_3$ | $CF_3$ |
| Cl | Cl | $CF_2$ | $CF_2$ | O | $CF_3$ | $COCF_3$ | $CF_3$ |
| Cl | Cl | $CF_2$ | $CF_2$ | O | Cl | $COCF_3$ | $CF_3$ |
| Cl | Cl | $CF_2$ | $CF_2$ | O | F | $COCF_3$ | $CF_3$ |
| Cl | Cl | $CF_2$ | $CF_2$ | O | $COCH_3$ | $COCF_3$ | $CF_3$ |
| Cl | Cl | $CF_2$ | $CF_2$ | O | $NH_2$ | $C_2F_5$ | $CF_3$ |
| Cl | Cl | $CF_2$ | $CF_2$ | O | N=CHPh | $C_2F_5$ | $CF_3$ |
| Cl | Cl | $CF_2$ | $CF_2$ | O | $CH_3$ | $C_2F_5$ | $CF_3$ |
| Cl | Cl | $CF_2$ | $CF_2$ | O | $CF_3$ | $C_2F_5$ | $CF_3$ |
| Cl | Cl | $CF_2$ | $CF_2$ | O | Cl | $C_2F_5$ | $CF_3$ |
| Cl | Cl | $CF_2$ | $CF_2$ | O | F | $C_2F_5$ | $CF_3$ |
| Cl | Cl | $CF_2$ | $CF_2$ | O | $COCH_3$ | $C_2F_5$ | $CF_3$ |
| Cl | Cl | $CF_2$ | $CF_2$ | O | H | $C_2F_5$ | $CF_3$ |
| Cl | Cl | $CF_2$ | $CF_2$ | O | $NH_2$ | $C_2F_5$ | $CF_3$ |
| Cl | Cl | $CF_2$ | $CF_2$ | O | N=CHPh | $C_2F_5$ | $CF_3$ |
| Cl | Cl | $CF_2$ | $CF_2$ | O | $CH_3$ | $C_2F_5$ | $CF_3$ |
| Cl | Cl | $CF_2$ | $CF_2$ | O | $CF_3$ | $C_2F_5$ | $CF_3$ |
| Cl | Cl | $CF_2$ | $CF_2$ | O | Cl | $C_2F_5$ | $CF_3$ |
| Cl | Cl | $CF_2$ | $CF_2$ | O | F | $C_2F_5$ | $CF_3$ |
| Cl | Cl | $CF_2$ | $CF_2$ | O | $COCH_3$ | $C_2F_5$ | $CF_3$ |
| Cl | Cl | $CF_2$ | $CF_2$ | O | $NH_2$ | $SFCl_2$ | $CF_3$ |
| Cl | Cl | $CF_2$ | $CF_2$ | O | N=CHPh | $SFCl_2$ | $CF_3$ |

TABLE 115

| X | Y | Z¹ | Z² | Z³ | R¹ | R² | R³ |
|---|---|---|---|---|---|---|---|
| Cl | Cl | $CF_2$ | $CF_2$ | O | $CH_3$ | $SFCl_2$ | $CF_3$ |
| Cl | Cl | $CF_2$ | $CF_2$ | O | $CF_3$ | $SFCl_2$ | $CF_3$ |
| Cl | Cl | $CF_2$ | $CF_2$ | O | Cl | $SFCl_2$ | $CF_3$ |
| Cl | Cl | $CF_2$ | $CF_2$ | O | F | $SFCl_2$ | $CF_3$ |
| Cl | Cl | $CF_2$ | $CF_2$ | O | $COCH_3$ | $SFCl_2$ | $CF_3$ |
| Cl | Cl | $CF_2$ | $CF_2$ | O | H | $SFCl_2$ | $CF_3$ |
| Cl | Cl | $CF_2$ | $CF_2$ | O | $NH_2$ | $SFCl_2$ | $CF_3$ |
| Cl | Cl | $CF_2$ | $CF_2$ | O | N=CHPh | $SFCl_2$ | $CF_3$ |
| Cl | Cl | $CF_2$ | $CF_2$ | O | $CH_3$ | $SFCl_2$ | $CF_3$ |
| Cl | Cl | $CF_2$ | $CF_2$ | O | $CF_3$ | $SFCl_2$ | $CF_3$ |
| Cl | Cl | $CF_2$ | $CF_2$ | O | Cl | $SFCl_2$ | $CF_3$ |
| Cl | Cl | $CF_2$ | $CF_2$ | O | F | $SFCl_2$ | $CF_3$ |
| Cl | Cl | $CF_2$ | $CF_2$ | O | $COCH_3$ | $SFCl_2$ | $CF_3$ |
| Cl | Cl | $CF_2$ | $CF_2$ | O | H | $SCF_3$ | $C_2F_5$ |
| Cl | Cl | $CF_2$ | $CF_2$ | O | $NH_2$ | $SCF_3$ | $C_2F_5$ |
| Cl | Cl | $CF_2$ | $CF_2$ | O | N=CHPh | $SCF_3$ | $C_2F_5$ |
| Cl | Cl | $CF_2$ | $CF_2$ | O | $CH_3$ | $SCF_3$ | $C_2F_5$ |
| Cl | Cl | $CF_2$ | $CF_2$ | O | $CF_3$ | $SCF_3$ | $C_2F_5$ |
| Cl | Cl | $CF_2$ | $CF_2$ | O | Cl | $SCF_3$ | $C_2F_5$ |
| Cl | Cl | $CF_2$ | $CF_2$ | O | F | $SCF_3$ | $C_2F_5$ |
| Cl | Cl | $CF_2$ | $CF_2$ | O | $COCH_3$ | $SCF_3$ | $C_2F_5$ |
| Cl | Cl | $CF_2$ | $CF_2$ | O | H | $SOCF_3$ | $C_2F_5$ |
| Cl | Cl | $CF_2$ | $CF_2$ | O | $NH_2$ | $SOCF_3$ | $C_2F_5$ |
| Cl | Cl | $CF_2$ | $CF_2$ | O | N=CHPh | $SOCF_3$ | $C_2F_5$ |
| Cl | Cl | $CF_2$ | $CF_2$ | O | $CH_3$ | $SOCF_3$ | $C_2F_5$ |
| Cl | Cl | $CF_2$ | $CF_2$ | O | $CF_3$ | $SOCF_3$ | $C_2F_5$ |

TABLE 116

| X | Y | Z¹ | Z² | Z³ | R¹ | R² | R³ |
|---|---|---|---|---|---|---|---|
| Cl | Cl | $CF_2$ | $CF_2$ | O | Cl | $SOCF_3$ | $C_2F_5$ |
| Cl | Cl | $CF_2$ | $CF_2$ | O | F | $SOCF_3$ | $C_2F_5$ |
| Cl | Cl | $CF_2$ | $CF_2$ | O | $COCH_3$ | $SOCF_3$ | $C_2F_5$ |
| Cl | Cl | $CF_2$ | $CF_2$ | O | H | $SO_2CF_3$ | $C_2F_5$ |
| Cl | Cl | $CF_2$ | $CF_2$ | O | $NH_2$ | $SO_2CF_3$ | $C_2F_5$ |
| Cl | Cl | $CF_2$ | $CF_2$ | O | N=CHPh | $SO_2CF_3$ | $C_2F_5$ |
| Cl | Cl | $CF_2$ | $CF_2$ | O | $CH_3$ | $SO_2CF_3$ | $C_2F_5$ |
| Cl | Cl | $CF_2$ | $CF_2$ | O | $CF_3$ | $SO_2CF_3$ | $C_2F_5$ |
| Cl | Cl | $CF_2$ | $CF_2$ | O | Cl | $SO_2CF_3$ | $C_2F_5$ |
| Cl | Cl | $CF_2$ | $CF_2$ | O | F | $SO_2CF_3$ | $C_2F_5$ |

TABLE 116-continued

| X | Y | Z¹ | Z² | Z³ | R¹ | R² | R³ |
|---|---|---|---|---|---|---|---|
| Cl | Cl | CF₂ | CF₂ | O | COCH₃ | SO₂CF₃ | C₂F₅ |
| Cl | Cl | CF₂ | CF₂ | O | H | SCF₂CH₃ | C₂F₅ |
| Cl | Cl | CF₂ | CF₂ | O | NH₂ | SCF₂CH₃ | C₂F₅ |
| Cl | Cl | CF₂ | CF₂ | O | N = CHPh | SCF₂CH₃ | C₂F₅ |
| Cl | Cl | CF₂ | CF₂ | O | CH₃ | SCF₂CH₃ | C₂F₅ |
| Cl | Cl | CF₂ | CF₂ | O | CF₃ | SCF₂CH₃ | C₂F₅ |
| Cl | Cl | CF₂ | CF₂ | O | Cl | SCF₂CH₃ | C₂F₅ |
| Cl | Cl | CF₂ | CF₂ | O | F | SCF₂CH₃ | C₂F₅ |
| Cl | Cl | CF₂ | CF₂ | O | COCH₃ | SCF₂CH₃ | C₂F₅ |
| Cl | Cl | CF₂ | CF₂ | O | H | SOCF₂CH₃ | C₂F₅ |
| Cl | Cl | CF₂ | CF₂ | O | NH₂ | SOCF₂CH₃ | C₂F₅ |
| Cl | Cl | CF₂ | CF₂ | O | N = CHPh | SOCF₂CH₃ | C₂F₅ |
| Cl | Cl | CF₂ | CF₂ | O | CH₃ | SOCF₂CH₃ | C₂F₅ |
| Cl | Cl | CF₂ | CF₂ | O | CF₃ | SOCF₂CH₃ | C₂F₅ |
| Cl | Cl | CF₂ | CF₂ | O | Cl | SOCF₂CH₃ | C₂F₅ |
| Cl | Cl | CF₂ | CF₂ | O | F | SOCF₂CH₃ | C₂F₅ |

TABLE 117

| X | Y | Z¹ | Z² | Z³ | R¹ | R² | R³ |
|---|---|---|---|---|---|---|---|
| Cl | Cl | CF₂ | CF₂ | O | COCH₃ | SOCF₂CH₃ | C₂F₅ |
| Cl | Cl | CF₂ | CF₂ | O | H | SO₂CF₂CH₃ | C₂F₅ |
| Cl | Cl | CF₂ | CF₂ | O | NH₂ | SO₂CF₂CH₃ | C₂F₅ |
| Cl | Cl | CF₂ | CF₂ | O | N = CHPh | SO₂CF₂CH₃ | C₂F₅ |
| Cl | Cl | CF₂ | CF₂ | O | CH₃ | SO₂CF₂CH₃ | C₂F₅ |
| Cl | Cl | CF₂ | CF₂ | O | CF₃ | SO₂CF₂CH₃ | C₂F₅ |
| Cl | Cl | CF₂ | CF₂ | O | Cl | SO₂CF₂CH₃ | C₂F₅ |
| Cl | Cl | CF₂ | CF₂ | O | F | SO₂CF₂CH₃ | C₂F₅ |
| Cl | Cl | CF₂ | CF₂ | O | COCH₃ | SO₂CF₂CH₃ | C₂F₅ |
| Cl | Cl | CF₂ | CF₂ | O | NH₂ | COCF₃ | C₂F₅ |
| Cl | Cl | CF₂ | CF₂ | O | N = CHPh | COCF₃ | C₂F₅ |
| Cl | Cl | CF₂ | CF₂ | O | CH₃ | COCF₃ | C₂F₅ |
| Cl | Cl | CF₂ | CF₂ | O | CF₃ | COCF₃ | C₂F₅ |
| Cl | Cl | CF₂ | CF₂ | O | Cl | COCF₃ | C₂F₅ |
| Cl | Cl | CF₂ | CF₂ | O | F | COCF₃ | C₂F₅ |
| Cl | Cl | CF₂ | CF₂ | O | COCH₃ | COCF₃ | C₂F₅ |
| Cl | Cl | CF₂ | CF₂ | O | H | COCF₃ | C₂F₅ |
| Cl | Cl | CF₂ | CF₂ | O | NH₂ | COCF₃ | C₂F₅ |
| Cl | Cl | CF₂ | CF₂ | O | N = CHPh | COCF₃ | C₂F₅ |
| Cl | Cl | CF₂ | CF₂ | O | CH₃ | COCF₃ | C₂F₅ |
| Cl | Cl | CF₂ | CF₂ | O | CF₃ | COCF₃ | C₂F₅ |
| Cl | Cl | CF₂ | CF₂ | O | Cl | COCF₃ | C₂F₅ |
| Cl | Cl | CF₂ | CF₂ | O | F | COCF₃ | C₂F₅ |
| Cl | Cl | CF₂ | CF₂ | O | COCH₃ | COCF₃ | C₂F₅ |
| Cl | Cl | CF₂ | CF₂ | O | NH₂ | C₂F₅ | C₂F₅ |
| Cl | Cl | CF₂ | CF₂ | O | N = CHPh | C₂F₅ | C₂F₅ |

TABLE 118

| X | Y | Z¹ | Z² | Z³ | R¹ | R² | R³ |
|---|---|---|---|---|---|---|---|
| Cl | Cl | CF₂ | CF₂ | O | CH₃ | C₂F₅ | C₂F₅ |
| Cl | Cl | CF₂ | CF₂ | O | CF₃ | C₂F₅ | C₂F₅ |
| Cl | Cl | CF₂ | CF₂ | O | Cl | C₂F₅ | C₂F₅ |
| Cl | Cl | CF₂ | CF₂ | O | F | C₂F₅ | C₂F₅ |
| Cl | Cl | CF₂ | CF₂ | O | COCH₃ | C₂F₅ | C₂F₅ |
| Cl | Cl | CF₂ | CF₂ | O | H | C₂F₅ | C₂F₅ |
| Cl | Cl | CF₂ | CF₂ | O | NH₂ | C₂F₅ | C₂F₅ |
| Cl | Cl | CF₂ | CF₂ | O | N = CHPh | C₂F₅ | C₂F₅ |
| Cl | Cl | CF₂ | CF₂ | O | CH₃ | C₂F₅ | C₂F₅ |
| Cl | Cl | CF₂ | CF₂ | O | CF₃ | C₂F₅ | C₂F₅ |
| Cl | Cl | CF₂ | CF₂ | O | Cl | C₂F₅ | C₂F₅ |
| Cl | Cl | CF₂ | CF₂ | O | F | C₂F₅ | C₂F₅ |
| Cl | Cl | CF₂ | CF₂ | O | COCH₃ | C₂F₅ | C₂F₅ |
| Cl | Cl | CF₂ | CF₂ | O | NH₂ | SFCl₂ | C₂F₅ |
| Cl | Cl | CF₂ | CF₂ | O | N = CHPh | SFCl₂ | C₂F₅ |
| Cl | Cl | CF₂ | CF₂ | O | CH₃ | SFCl₂ | C₂F₅ |
| Cl | Cl | CF₂ | CF₂ | O | CF₃ | SFCl₂ | C₂F₅ |
| Cl | Cl | CF₂ | CF₂ | O | Cl | SFCl₂ | C₂F₅ |
| Cl | Cl | CF₂ | CF₂ | O | F | SFCl₂ | C₂F₅ |
| Cl | Cl | CF₂ | CF₂ | O | COCH₃ | SFCl₂ | C₂F₅ |

TABLE 118-continued

| X | Y | Z¹ | Z² | Z³ | R¹ | R² | R³ |
|---|---|---|---|---|---|---|---|
| Cl | Cl | CF₂ | CF₂ | O | H | SFCl₂ | C₂F₅ |
| Cl | Cl | CF₂ | CF₂ | O | NH₂ | SFCl₂ | C₂F₅ |
| Cl | Cl | CF₂ | CF₂ | O | N = CHPh | SFCl₂ | C₂F₅ |
| Cl | Cl | CF₂ | CF₂ | O | CH₃ | SFCl₂ | C₂F₅ |
| Cl | Cl | CF₂ | CF₂ | O | CF₃ | SFCl₂ | C₂F₅ |
| Cl | Cl | CF₂ | CF₂ | O | Cl | SFCl₂ | C₂F₅ |

TABLE 119

| X | Y | Z¹ | Z² | Z³ | R¹ | R² | R³ |
|---|---|---|---|---|---|---|---|
| Cl | Cl | CF₂ | CF₂ | O | F | SFCl₂ | C₂F₅ |
| Cl | Cl | CF₂ | CF₂ | O | COCH₃ | SFCl₂ | C₂F₅ |
| Cl | Cl | CF₂ | CF₂ | O | H | SCF₃ | CSNH₂ |
| Cl | Cl | CF₂ | CF₂ | O | NH₂ | SCF₃ | CSNH₂ |
| Cl | Cl | CF₂ | CF₂ | O | N = CHPh | SCF₃ | CSNH₂ |
| Cl | Cl | CF₂ | CF₂ | O | CH₃ | SCF₃ | CSNH₂ |
| Cl | Cl | CF₂ | CF₂ | O | CF₃ | SCF₃ | CSNH₂ |
| Cl | Cl | CF₂ | CF₂ | O | Cl | SCF₃ | CSNH₂ |
| Cl | Cl | CF₂ | CF₂ | O | F | SCF₃ | CSNH₂ |
| Cl | Cl | CF₂ | CF₂ | O | COCH₃ | SCF₃ | CSNH₂ |
| Cl | Cl | CF₂ | CF₂ | O | H | SOCF₃ | CSNH₂ |
| Cl | Cl | CF₂ | CF₂ | O | NH₂ | SOCF₃ | CSNH₂ |
| Cl | Cl | CF₂ | CF₂ | O | N = CHPh | SOCF₃ | CSNH₂ |
| Cl | Cl | CF₂ | CF₂ | O | CH₃ | SOCF₃ | CSNH₂ |
| Cl | Cl | CF₂ | CF₂ | O | CF₃ | SOCF₃ | CSNH₂ |
| Cl | Cl | CF₂ | CF₂ | O | Cl | SOCF₃ | CSNH₂ |
| Cl | Cl | CF₂ | CF₂ | O | F | SOCF₃ | CSNH₂ |
| Cl | Cl | CF₂ | CF₂ | O | COCH₃ | SOCF₃ | CSNH₂ |
| Cl | Cl | CF₂ | CF₂ | O | H | SO₂CF₃ | CSNH₂ |
| Cl | Cl | CF₂ | CF₂ | O | NH₂ | SO₂CF₃ | CSNH₂ |
| Cl | Cl | CF₂ | CF₂ | O | N = CHPh | SO₂CF₃ | CSNH₂ |
| Cl | Cl | CF₂ | CF₂ | O | CH₃ | SO₂CF₃ | CSNH₂ |
| Cl | Cl | CF₂ | CF₂ | O | CF₃ | SO₂CF₃ | CSNH₂ |
| Cl | Cl | CF₂ | CF₂ | O | Cl | SO₂CF₃ | CSNH₂ |
| Cl | Cl | CF₂ | CF₂ | O | F | SO₂CF₃ | CSNH₂ |
| Cl | Cl | CF₂ | CF₂ | O | COCH₃ | SO₂CF₃ | CSNH₂ |

TABLE 120

| X | Y | Z¹ | Z² | Z³ | R¹ | R² | R³ |
|---|---|---|---|---|---|---|---|
| Cl | Cl | CF₂ | CF₂ | O | H | SCF₂CH₃ | CSNH₂ |
| Cl | Cl | CF₂ | CF₂ | O | NH₂ | SCF₂CH₃ | CSNH₂ |
| Cl | Cl | CF₂ | CF₂ | O | N = CHPh | SCF₂CH₃ | CSNH₂ |
| Cl | Cl | CF₂ | CF₂ | O | CH₃ | SCF₂CH₃ | CSNH₂ |
| Cl | Cl | CF₂ | CF₂ | O | CF₃ | SCF₂CH₃ | CSNH₂ |
| Cl | Cl | CF₂ | CF₂ | O | Cl | SCF₂CH₃ | CSNH₂ |
| Cl | Cl | CF₂ | CF₂ | O | F | SCF₂CH₃ | CSNH₂ |
| Cl | Cl | CF₂ | CF₂ | O | COCH₃ | SCF₂CH₃ | CSNH₂ |
| Cl | Cl | CF₂ | CF₂ | O | H | SOCF₂CH₃ | CSNH₂ |
| Cl | Cl | CF₂ | CF₂ | O | NH₂ | SOCF₂CH₃ | CSNH₂ |
| Cl | Cl | CF₂ | CF₂ | O | N =CHPh | SOCF₂CH₃ | CSNH₂ |
| Cl | Cl | CF₂ | CF₂ | O | CH₃ | SOCF₂CH₃ | CSNH₂ |
| Cl | Cl | CF₂ | CF₂ | O | CF₃ | SOCF₂CH₃ | CSNH₂ |
| Cl | Cl | CF₂ | CF₂ | O | Cl | SOCF₂CH₃ | CSNH₂ |
| Cl | Cl | CF₂ | CF₂ | O | F | SOCF₂CH₃ | CSNH₂ |
| Cl | Cl | CF₂ | CF₂ | O | COCH₃ | SOCF₂CH₃ | CSNH₂ |
| Cl | Cl | CF₂ | CF₂ | O | H | SO₂CF₂CH₃ | CSNH₂ |
| Cl | Cl | CF₂ | CF₂ | O | NH₂ | SO₂CF₂CH₃ | CSNH₂ |
| Cl | Cl | CF₂ | CF₂ | O | N = CHPh | SO₂CF₂CH₃ | CSNH₂ |
| Cl | Cl | CF₂ | CF₂ | O | CH₃ | SO₂CF₂CH₃ | CSNH₂ |
| Cl | Cl | CF₂ | CF₂ | O | CF₃ | SO₂CF₂CH₃ | CSNH₂ |
| Cl | Cl | CF₂ | CF₂ | O | Cl | SO₂CF₂CH₃ | CSNH₂ |
| Cl | Cl | CF₂ | CF₂ | O | F | SO₂CF₂CH₃ | CSNH₂ |
| Cl | Cl | CF₂ | CF₂ | O | COCH₃ | SO₂CF₂CH₃ | CSNH₂ |
| Cl | Cl | CF₂ | CF₂ | O | NH₂ | COCF₃ | CSNH₂ |
| Cl | Cl | CF₂ | CF₂ | O | N = CHPh | COCF₃ | CSNH₂ |

TABLE 121

| X | Y | Z¹ | Z² | Z³ | R¹ | R² | R³ |
|---|---|----|----|----|----|----|----|
| Cl | Cl | $CF_2$ | $CF_2$ | O | $CH_3$ | $COCF_3$ | $CSNH_2$ |
| Cl | Cl | $CF_2$ | $CF_2$ | O | $CF_3$ | $COCF_3$ | $CSNH_2$ |
| Cl | Cl | $CF_2$ | $CF_2$ | O | Cl | $COCF_3$ | $CSNH_2$ |
| Cl | Cl | $CF_2$ | $CF_2$ | O | F | $COCF_3$ | $CSNH_2$ |
| Cl | Cl | $CF_2$ | $CF_2$ | O | $COCH_3$ | $COCF_3$ | $CSNH_2$ |
| Cl | Cl | $CF_2$ | $CF_2$ | O | H | $COCF_3$ | $CSNH_2$ |
| Cl | Cl | $CF_2$ | $CF_2$ | O | $NH_2$ | $COCF_3$ | $CSNH_2$ |
| Cl | Cl | $CF_2$ | $CF_2$ | O | N = CHPh | $COCF_3$ | $CSNH_2$ |
| Cl | Cl | $CF_2$ | $CF_2$ | O | $CH_3$ | $COCF_3$ | $CSNH_2$ |
| Cl | Cl | $CF_2$ | $CF_2$ | O | $CF_3$ | $COCF_3$ | $CSNH_2$ |
| Cl | Cl | $CF_2$ | $CF_2$ | O | Cl | $COCF_3$ | $CSNH_2$ |
| Cl | Cl | $CF_2$ | $CF_2$ | O | F | $COCH_3$ | $CSNH_2$ |
| Cl | Cl | $CF_2$ | $CF_2$ | O | $COCH_3$ | $COCF_3$ | $CSNH_2$ |
| Cl | Cl | $CF_2$ | $CF_2$ | O | $NH_2$ | $C_2F_5$ | $CSNH_2$ |
| Cl | Cl | $CF_2$ | $CF_2$ | O | N = CHPh | $C_2F_5$ | $CSNH_2$ |
| Cl | Cl | $CF_2$ | $CF_2$ | O | $CH_3$ | $C_2F_5$ | $CSNH_2$ |
| Cl | Cl | $CF_2$ | $CF_2$ | O | $CF_3$ | $C_2F_5$ | $CSNH_2$ |
| Cl | Cl | $CF_2$ | $CF_2$ | O | Cl | $C_2F_5$ | $CSNH_2$ |
| Cl | Cl | $CF_2$ | $CF_2$ | O | F | $C_2F_5$ | $CSNH_2$ |
| Cl | Cl | $CF_2$ | $CF_2$ | O | $COCH_3$ | $C_2F_5$ | $CSNH_2$ |
| Cl | Cl | $CF_2$ | $CF_2$ | O | H | $C_2F_5$ | $CSNH_2$ |
| Cl | Cl | $CF_2$ | $CF_2$ | O | $NH_2$ | $C_2F_5$ | $CSNH_2$ |
| Cl | Cl | $CF_2$ | $CF_2$ | O | N = CHPh | $C_2F_5$ | $CSNH_2$ |
| Cl | Cl | $CF_2$ | $CF_2$ | O | $CH_3$ | $C_2F_5$ | $CSNH_2$ |
| Cl | Cl | $CF_2$ | $CF_2$ | O | $CF_3$ | $C_2F_5$ | $CSNH_2$ |
| Cl | Cl | $CF_2$ | $CF_2$ | O | Cl | $C_2F_5$ | $CSNH_2$ |

TABLE 122

| X | Y | Z¹ | Z² | Z³ | R¹ | R² | R³ |
|---|---|----|----|----|----|----|----|
| Cl | Cl | $CF_2$ | $CF_2$ | O | F | $C_2F_5$ | $CSNH_2$ |
| Cl | Cl | $CF_2$ | $CF_2$ | O | $COCH_3$ | $C_2F_5$ | $CSNH_2$ |
| Cl | Cl | $CF_2$ | $CF_2$ | O | $NH_2$ | $SFCl_2$ | $CSNH_2$ |
| Cl | Cl | $CF_2$ | $CF_2$ | O | N = CHPh | $SFCl_2$ | $CSNH_2$ |
| Cl | Cl | $CF_2$ | $CF_2$ | O | $CH_3$ | $SFCl_2$ | $CSNH_2$ |
| Cl | Cl | $CF_2$ | $CF_2$ | O | $CF_3$ | $SFCl_2$ | $CSNH_2$ |
| Cl | Cl | $CF_2$ | $CF_2$ | O | Cl | $SFCl_2$ | $CSNH_2$ |
| Cl | Cl | $CF_2$ | $CF_2$ | O | F | $SFCl_2$ | $CSNH_2$ |
| Cl | Cl | $CF_2$ | $CF_2$ | O | $COCH_3$ | $SFCl_2$ | $CSNH_2$ |
| Cl | Cl | $CF_2$ | $CF_2$ | O | H | $SFCl_2$ | $CSNH_2$ |
| Cl | Cl | $CF_2$ | $CF_2$ | O | $NH_2$ | $SFCl_2$ | $CSNH_2$ |
| Cl | Cl | $CF_2$ | $CF_2$ | O | N = CHPh | $SFCl_2$ | $CSNH_2$ |
| Cl | Cl | $CF_2$ | $CF_2$ | O | $CH_3$ | $SFCl_2$ | $CSNH_2$ |
| Cl | Cl | $CF_2$ | $CF_2$ | O | $CF_3$ | $SFCl_2$ | $CSNH_2$ |
| Cl | Cl | $CF_2$ | $CF_2$ | O | Cl | $SFCl_2$ | $CSNH_2$ |
| Cl | Cl | $CF_2$ | $CF_2$ | O | F | $SFCl_2$ | $CSNH_2$ |
| Cl | Cl | $CF_2$ | $CF_2$ | O | $COCH_3$ | $SFCl_2$ | $CSNH_2$ |
| Cl | Cl | $CF_2$ | $CF_2$ | O | H | $SCF_3$ | CN |
| Cl | Cl | $CF_2$ | $CF_2$ | O | $NH_2$ | $SCF_3$ | CN |
| Cl | Cl | $CF_2$ | $CF_2$ | O | N = CHPh | $SCF_3$ | CN |
| Cl | Cl | $CF_2$ | $CF_2$ | O | $CH_3$ | $SCF_3$ | CN |
| Cl | Cl | $CF_2$ | $CF_2$ | O | $CF_3$ | $SCF_3$ | CN |
| Cl | Cl | $CF_2$ | $CF_2$ | O | Cl | $SCF_3$ | CN |
| Cl | Cl | $CF_2$ | $CF_2$ | O | F | $SCF_3$ | CN |
| Cl | Cl | $CF_2$ | $CF_2$ | O | $COCH_3$ | $SCF_3$ | CN |
| Cl | Cl | $CF_2$ | $CF_2$ | O | H | $SOCF_3$ | CN |

TABLE 123

| X | Y | Z¹ | Z² | Z³ | R¹ | R² | R³ |
|---|---|----|----|----|----|----|----|
| Cl | Cl | $CF_2$ | $CF_2$ | O | $NH_2$ | $SOCF_3$ | CN |
| Cl | Cl | $CF_2$ | $CF_2$ | O | N = CHPh | $SOCF_3$ | CN |
| Cl | Cl | $CF_2$ | $CF_2$ | O | $CH_3$ | $SOCF_3$ | CN |
| Cl | Cl | $CF_2$ | $CF_2$ | O | $CF_3$ | $SOCF_3$ | CN |
| Cl | Cl | $CF_2$ | $CF_2$ | O | Cl | $SOCF_3$ | CN |
| Cl | Cl | $CF_2$ | $CF_2$ | O | F | $SOCF_3$ | CN |
| Cl | Cl | $CF_2$ | $CF_2$ | O | $COCH_3$ | $SOCF_3$ | CN |
| Cl | Cl | $CF_2$ | $CF_2$ | O | H | $SO_2CF_3$ | CN |
| Cl | Cl | $CF_2$ | $CF_2$ | O | $NH_2$ | $SO_2CF_3$ | CN |
| Cl | Cl | $CF_2$ | $CF_2$ | O | N = CHPh | $SO_2CF_3$ | CN |

TABLE 123-continued

| X | Y | Z¹ | Z² | Z³ | R¹ | R² | R³ |
|---|---|----|----|----|----|----|----|
| Cl | Cl | $CF_2$ | $CF_2$ | O | $CH_3$ | $SO_2CF_3$ | CN |
| Cl | Cl | $CF_2$ | $CF_2$ | O | $CF_3$ | $SO_2CF_3$ | CN |
| Cl | Cl | $CF_2$ | $CF_2$ | O | Cl | $SO_2CF_3$ | CN |
| Cl | Cl | $CF_2$ | $CF_2$ | O | F | $SO_2CF_3$ | CN |
| Cl | Cl | $CF_2$ | $CF_2$ | O | $COCH_3$ | $SO_2CF_3$ | CN |
| Cl | Cl | $CF_2$ | $CF_2$ | O | H | $SCF_2CH_3$ | CN |
| Cl | Cl | $CF_2$ | $CF_2$ | O | $NH_2$ | $SCF_2CH_3$ | CN |
| Cl | Cl | $CF_2$ | $CF_2$ | O | N = CHPh | $SCF_2CH_3$ | CN |
| Cl | Cl | $CF_2$ | $CF_2$ | O | $CH_3$ | $SCF_2CH_3$ | CN |
| Cl | Cl | $CF_2$ | $CF_2$ | O | $CF_3$ | $SCF_2CH_3$ | CN |
| Cl | Cl | $CF_2$ | $CF_2$ | O | Cl | $SCF_2CH_3$ | CN |
| Cl | Cl | $CF_2$ | $CF_2$ | O | F | $SCF_2CH_3$ | CN |
| Cl | Cl | $CF_2$ | $CF_2$ | O | $COCH_3$ | $SCF_2CH_3$ | CN |
| Cl | Cl | $CF_2$ | $CF_2$ | O | H | $SOCF_2CH_3$ | CN |
| Cl | Cl | $CF_2$ | $CF_2$ | O | $NH_2$ | $SOCF_2CH_3$ | CN |
| Cl | Cl | $CF_2$ | $CF_2$ | O | N = CHPh | $SOCF_2CH_3$ | CN |

TABLE 124

| X | Y | Z¹ | Z² | Z³ | R¹ | R² | R³ |
|---|---|----|----|----|----|----|----|
| Cl | Cl | $CF_2$ | $CF_2$ | O | $CH_3$ | $SOCF_2CH_3$ | CN |
| Cl | Cl | $CF_2$ | $CF_2$ | O | $CF_3$ | $SOCF_2CH_3$ | CN |
| Cl | Cl | $CF_2$ | $CF_2$ | O | Cl | $SOCF_2CH_3$ | CN |
| Cl | Cl | $CF_2$ | $CF_2$ | O | F | $SOCF_2CH_3$ | CN |
| Cl | Cl | $CF_2$ | $CF_2$ | O | $COCH_3$ | $SOCF_2CH_3$ | CN |
| Cl | Cl | $CF_2$ | $CF_2$ | O | H | $SO_2CF_2CH_3$ | CN |
| Cl | Cl | $CF_2$ | $CF_2$ | O | $NH_2$ | $SO_2CF_2CH_3$ | CN |
| Cl | Cl | $CF_2$ | $CF_2$ | O | N = CHPh | $SO_2CF_2CH_3$ | CN |
| Cl | Cl | $CF_2$ | $CF_2$ | O | $CH_3$ | $SO_2CF_2CH_3$ | CN |
| Cl | Cl | $CF_2$ | $CF_2$ | O | $CF_3$ | $SO_2CF_2CH_3$ | CN |
| Cl | Cl | $CF_2$ | $CF_2$ | O | Cl | $SO_2CF_2CH_3$ | CN |
| Cl | Cl | $CF_2$ | $CF_2$ | O | F | $SO_2CF_2CH_3$ | CN |
| Cl | Cl | $CF_2$ | $CF_2$ | O | $COCH_3$ | $SO_2CF_2CH_3$ | CN |
| Cl | Cl | $CF_2$ | $CF_2$ | O | $NH_2$ | $COCF_3$ | CN |
| Cl | Cl | $CF_2$ | $CF_2$ | O | N = CHPh | $COCF_3$ | CN |
| Cl | Cl | $CF_2$ | $CF_2$ | O | $CH_3$ | $COCF_3$ | CN |
| Cl | Cl | $CF_2$ | $CF_2$ | O | $CF_3$ | $COCF_3$ | CN |
| Cl | Cl | $CF_2$ | $CF_2$ | O | Cl | $COCF_3$ | CN |
| Cl | Cl | $CF_2$ | $CF_2$ | O | F | $COCF_3$ | CN |
| Cl | Cl | $CF_2$ | $CF_2$ | O | $COCH_3$ | $COCF_3$ | CN |
| Cl | Cl | $CF_2$ | $CF_2$ | O | H | $COCF_3$ | CN |
| Cl | Cl | $CF_2$ | $CF_2$ | O | $NH_2$ | $COCF_3$ | CN |
| Cl | Cl | $CF_2$ | $CF_2$ | O | N = CHPh | $COCF_3$ | CN |
| Cl | Cl | $CF_2$ | $CF_2$ | O | $CH_3$ | $COCF_3$ | CN |
| Cl | Cl | $CF_2$ | $CF_2$ | O | $CF_3$ | $COCF_3$ | CN |
| Cl | Cl | $CF_2$ | $CF_2$ | O | Cl | $COCF_3$ | CN |

TABLE 125

| X | Y | Z¹ | Z² | Z³ | R¹ | R² | R³ |
|---|---|----|----|----|----|----|----|
| Cl | Cl | $CF_2$ | $CF_2$ | O | F | $COCF_3$ | CN |
| Cl | Cl | $CF_2$ | $CF_2$ | O | $COCH_3$ | $COCF_3$ | CN |
| Cl | Cl | $CF_2$ | $CF_2$ | O | $NH_2$ | $C_2F_5$ | CN |
| Cl | Cl | $CF_2$ | $CF_2$ | O | N = CHPh | $C_2F_5$ | CN |
| Cl | Cl | $CF_2$ | $CF_2$ | O | $CH_3$ | $C_2F_5$ | CN |
| Cl | Cl | $CF_2$ | $CF_2$ | G | $CF_3$ | $C_2F_5$ | CN |
| Cl | Cl | $CF_2$ | $CF_2$ | O | Cl | $C_2F_5$ | CN |
| Cl | Cl | $CF_2$ | $CF_2$ | O | F | $C_2F_5$ | CN |
| Cl | Cl | $CF_2$ | $CF_2$ | O | $COCH_3$ | $C_2F_5$ | CN |
| Cl | Cl | $CF_2$ | $CF_2$ | O | H | $C_2F_5$ | CN |
| Cl | Cl | $CF_2$ | $CF_2$ | O | $NH_2$ | $C_2F_5$ | CN |
| Cl | Cl | $CF_2$ | $CF_2$ | O | N = CHPh | $C_2F_5$ | CN |
| Cl | Cl | $CF_2$ | $CF_2$ | O | $CH_3$ | $C_2F_5$ | CN |
| Cl | Cl | $CF_2$ | $CF_2$ | O | $CF_3$ | $C_2F_5$ | CN |
| Cl | Cl | $CF_2$ | $CF_2$ | O | Cl | $C_2F_5$ | CN |
| Cl | Cl | $CF_2$ | $CF_2$ | O | F | $C_2F_5$ | CN |
| Cl | Cl | $CF_2$ | $CF_2$ | O | $COCH_3$ | $C_2F_5$ | CN |
| Cl | Cl | $CF_2$ | $CF_2$ | O | $NH_2$ | $SFCl_2$ | CN |
| Cl | Cl | $CF_2$ | $CF_2$ | O | N = CHPh | $SFCl_2$ | CN |
| Cl | Cl | $CF_2$ | $CF_2$ | O | $CH_3$ | $SFCl_2$ | CN |

TABLE 125-continued

| X | Y | Z$^1$ | Z$^2$ | Z$^3$ | R$^1$ | R$^2$ | R$^3$ |
|---|---|---|---|---|---|---|---|
| Cl | Cl | CF$_2$ | CF$_2$ | O | CF$_3$ | SFCl$_2$ | CN |
| Cl | Cl | CF$_2$ | CF$_2$ | O | Cl | SFCl$_2$ | CN |
| Cl | Cl | CF$_2$ | CF$_2$ | O | F | SFCl$_2$ | CN |
| Cl | Cl | CF$_2$ | CF$_2$ | O | COCH$_3$ | SFCl$_2$ | CN |
| Cl | Cl | CF$_2$ | CF$_2$ | O | H | SFCl$_2$ | CN |
| Cl | Cl | CF$_2$ | CF$_2$ | O | NH$_2$ | SFCl$_2$ | CN |

TABLE 126

| X | Y | Z$^1$ | Z$^2$ | Z$^3$ | R$^1$ | R$^2$ | R$^3$ |
|---|---|---|---|---|---|---|---|
| Cl | Cl | CF$_2$ | CF$_2$ | O | N=CHPh | SFCl$_2$ | CN |
| Cl | Cl | CF$_2$ | CF$_2$ | O | CH$_3$ | SFCl$_2$ | CN |
| Cl | Cl | CF$_2$ | CF$_2$ | O | CF$_3$ | SFCl$_2$ | CN |
| Cl | Cl | CF$_2$ | CF$_2$ | O | Cl | SFCl$_2$ | CN |
| Cl | Cl | CF$_2$ | CF$_2$ | O | F | SFCl$_2$ | CN |
| Cl | Cl | CF$_2$ | CF$_2$ | O | COCH$_3$ | SFCl$_2$ | CN |
| F | Cl | CF$_2$ | CF$_2$ | O | H | SCF$_3$ | H |
| F | Cl | CF$_2$ | CF$_2$ | O | NH$_2$ | SCF$_3$ | H |
| F | Cl | CF$_2$ | CF$_2$ | O | N=CHPh | SCF$_3$ | H |
| F | Cl | CF$_2$ | CF$_2$ | O | CH$_3$ | SCF$_3$ | H |
| F | Cl | CF$_2$ | CF$_2$ | O | CF$_3$ | SCF$_3$ | H |
| F | Cl | CF$_2$ | CF$_2$ | O | Cl | SCF$_3$ | H |
| F | Cl | CF$_2$ | CF$_2$ | O | F | SCF$_3$ | H |
| F | Cl | CF$_2$ | CF$_2$ | O | COCH$_3$ | SCF$_3$ | H |
| F | Cl | CF$_2$ | CF$_2$ | O | H | SOCF$_3$ | H |
| F | Cl | CF$_2$ | CF$_2$ | O | NH$_2$ | SOCF$_3$ | H |
| F | Cl | CF$_2$ | CF$_2$ | O | N=CHPh | SOCF$_3$ | H |
| F | Cl | CF$_2$ | CF$_2$ | O | CH$_3$ | SOCF$_3$ | H |
| F | Cl | CF$_2$ | CF$_2$ | O | CF$_3$ | SOCF$_3$ | H |
| F | Cl | CF$_2$ | CF$_2$ | O | Cl | SOCF$_3$ | H |
| F | Cl | CF$_2$ | CF$_2$ | O | F | SOCF$_3$ | H |
| F | Cl | CF$_2$ | CF$_2$ | O | COCH$_3$ | SOCF$_3$ | H |
| F | Cl | CF$_2$ | CF$_2$ | O | H | SO$_2$CF$_3$ | H |
| F | Cl | CF$_2$ | CF$_2$ | O | NH$_2$ | SO$_2$CF$_3$ | H |
| F | Cl | CF$_2$ | CF$_2$ | O | N=CHPh | SO$_2$CF$_3$ | H |
| F | Cl | CF$_2$ | CF$_2$ | O | CH$_3$ | SO$_2$CF$_3$ | H |

TABLE 127

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | CF$_3$ | SO$_2$CF$_3$ | H |
| F | Cl | CF$_2$ | CF$_2$ | O | Cl | SO$_2$CF$_3$ | H |
| F | Cl | CF$_2$ | CF$_2$ | O | F | SO$_2$CF$_3$ | H |
| F | Cl | CF$_2$ | CF$_2$ | O | COCH$_3$ | SO$_2$CF$_3$ | H |
| F | Cl | CF$_2$ | CF$_2$ | O | H | SCF$_2$CH$_3$ | H |
| F | Cl | CF$_2$ | CF$_2$ | O | NH$_2$ | SCF$_2$CH$_3$ | H |
| F | Cl | CF$_2$ | CF$_2$ | O | N=CHPh | SCF$_2$CH$_3$ | H |
| F | Cl | CF$_2$ | CF$_2$ | O | CH$_3$ | SCF$_2$CH$_3$ | H |
| F | Cl | CF$_2$ | CF$_2$ | O | CF$_3$ | SCF$_2$CH$_3$ | H |
| F | Cl | CF$_2$ | CF$_2$ | O | Cl | SCF$_2$CH$_3$ | H |
| F | Cl | CF$_2$ | CF$_2$ | O | F | SCF$_2$CH$_3$ | H |
| F | Cl | CF$_2$ | CF$_2$ | O | COCH$_3$ | SCF$_2$CH$_3$ | H |
| F | Cl | CF$_2$ | CF$_2$ | O | H | SOCF$_2$CH$_3$ | H |
| F | Cl | CF$_2$ | CF$_2$ | O | NH$_2$ | SOCF$_2$CH$_3$ | H |
| F | Cl | CF$_2$ | CF$_2$ | O | N=CHPh | SOCF$_2$CH$_3$ | H |
| F | Cl | CF$_2$ | CF$_2$ | O | CH$_3$ | SOCF$_2$CH$_3$ | H |
| F | Cl | CF$_2$ | CF$_2$ | O | CF$_3$ | SOCF$_2$CH$_3$ | H |
| F | Cl | CF$_2$ | CF$_2$ | O | Cl | SOCF$_2$CH$_3$ | H |
| F | Cl | CF$_2$ | CF$_2$ | O | F | SOCF$_2$CH$_3$ | H |
| F | Cl | CF$_2$ | CF$_2$ | O | COCH$_3$ | SOCF$_2$CH$_3$ | H |
| F | Cl | CF$_2$ | CF$_2$ | O | H | SO$_2$CF$_2$CH$_3$ | H |
| F | Cl | CF$_2$ | CF$_2$ | O | NH$_2$ | SO$_2$CF$_2$CH$_3$ | H |
| F | Cl | CF$_2$ | CF$_2$ | O | N=CHPh | SO$_2$CF$_2$CH$_3$ | H |
| F | Cl | CF$_2$ | CF$_2$ | O | CH$_3$ | SO$_2$CF$_2$CH$_3$ | H |
| F | Cl | CF$_2$ | CF$_2$ | O | CF$_3$ | SO$_2$CF$_2$CH$_3$ | H |
| F | Cl | CF$_2$ | CF$_2$ | O | Cl | SO$_2$CF$_2$CH$_3$ | H |

TABLE 128

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | F | SO$_2$CF$_2$CH$_3$ | H |
| F | Cl | CF$_2$ | CF$_2$ | O | COCH$_3$ | SO$_2$CF$_2$CH$_3$ | H |
| F | Cl | CF$_2$ | CF$_2$ | O | NH$_2$ | COCF$_3$ | H |
| F | Cl | CF$_2$ | CF$_2$ | O | N=CHPh | COCF$_3$ | H |
| F | Cl | CF$_2$ | CF$_2$ | O | CH$_3$ | COCF$_3$ | H |
| F | Cl | CF$_2$ | CF$_2$ | O | CF$_3$ | COCF$_3$ | H |
| F | Cl | CF$_2$ | CF$_2$ | O | Cl | COCF$_3$ | H |
| F | Cl | CF$_2$ | CF$_2$ | O | F | COCF$_3$ | H |
| F | Cl | CF$_2$ | CF$_2$ | O | COCH$_3$ | COCF$_3$ | H |
| F | Cl | CF$_2$ | CF$_2$ | O | H | COCF$_3$ | H |
| F | Cl | CF$_2$ | CF$_2$ | O | NH$_2$ | COCF$_3$ | H |
| F | Cl | CF$_2$ | CF$_2$ | O | N=CHPh | COCF$_3$ | H |
| F | Cl | CF$_2$ | CF$_2$ | O | CH$_3$ | COCF$_3$ | H |
| F | Cl | CF$_2$ | CF$_2$ | O | CF$_3$ | COCF$_3$ | H |
| F | Cl | CF$_2$ | CF$_2$ | O | Cl | COCF$_3$ | H |
| F | Cl | CF$_2$ | CF$_2$ | O | F | COCF$_3$ | H |
| F | Cl | CF$_2$ | CF$_2$ | O | COCH$_3$ | COCF$_3$ | H |
| F | Cl | CF$_2$ | CF$_2$ | O | NH$_2$ | C$_2$F$_5$ | H |
| F | Cl | CF$_2$ | CF$_2$ | O | N=CHPh | C$_2$F$_5$ | H |
| F | Cl | CF$_2$ | CF$_2$ | O | CH$_3$ | C$_2$F$_5$ | H |
| F | Cl | CF$_2$ | CF$_2$ | O | CF$_3$ | C$_2$F$_5$ | H |
| F | Cl | CF$_2$ | CF$_2$ | O | Cl | C$_2$F$_5$ | H |
| F | Cl | CF$_2$ | CF$_2$ | O | F | C$_2$F$_5$ | H |
| F | Cl | CF$_2$ | CF$_2$ | O | COCH$_3$ | C$_2$F$_5$ | H |
| F | Cl | CF$_2$ | CF$_2$ | O | H | C$_2$F$_5$ | H |
| F | Cl | CF$_2$ | CF$_2$ | O | NH$_2$ | C$_2$F$_5$ | H |

TABLE 129

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | N=CHPh | C$_2$F$_5$ | H |
| F | Cl | CF$_2$ | CF$_2$ | O | CH$_3$ | C$_2$F$_5$ | H |
| F | Cl | CF$_2$ | CF$_2$ | O | CF$_3$ | C$_2$F$_5$ | H |
| F | Cl | CF$_2$ | CF$_2$ | O | Cl | C$_2$F$_5$ | H |
| F | Cl | CF$_2$ | CF$_2$ | O | F | C$_2$F$_5$ | H |
| F | Cl | CF$_2$ | CF$_2$ | O | COCH$_3$ | C$_2$F$_5$ | H |
| F | Cl | CF$_2$ | CF$_2$ | O | NH$_2$ | SFCl$_2$ | H |
| F | Cl | CF$_2$ | CF$_2$ | O | N=CHPh | SFCl$_2$ | H |
| F | Cl | CF$_2$ | CF$_2$ | O | CH$_3$ | SFCl$_2$ | H |
| F | Cl | CF$_2$ | CF$_2$ | O | CF$_3$ | SFCl$_2$ | H |
| F | Cl | CF$_2$ | CF$_2$ | O | Cl | SFCl$_2$ | H |
| F | Cl | CF$_2$ | CF$_2$ | O | F | SFCl$_2$ | H |
| F | Cl | CF$_2$ | CF$_2$ | O | COCH$_3$ | SFCl$_2$ | H |
| F | Cl | CF$_2$ | CF$_2$ | O | H | SFCl$_2$ | H |
| F | Cl | CF$_2$ | CF$_2$ | O | NH$_2$ | SFCl$_2$ | H |
| F | Cl | CF$_2$ | CF$_2$ | O | N=CHPh | SFCl$_2$ | H |
| F | Cl | CF$_2$ | CF$_2$ | O | CH$_3$ | SFCl$_2$ | H |
| F | Cl | CF$_2$ | CF$_2$ | O | CF$_3$ | SFCl$_2$ | H |
| F | Cl | CF$_2$ | CF$_2$ | O | Cl | SFCl$_2$ | H |
| F | Cl | CF$_2$ | CF$_2$ | O | F | SFCl$_2$ | H |
| F | Cl | CF$_2$ | CF$_2$ | O | COCH$_3$ | SFCl$_2$ | H |
| F | Cl | CF$_2$ | CF$_2$ | O | H | SCF$_3$ | CF$_3$ |
| F | Cl | CF$_2$ | CF$_2$ | O | NH$_2$ | SCF$_3$ | CF$_3$ |
| F | Cl | CF$_2$ | CF$_2$ | O | N=CHPh | SCF$_3$ | CF$_3$ |
| F | Cl | CF$_2$ | CF$_2$ | O | CH$_3$ | SCF$_3$ | CF$_3$ |
| F | Cl | CF$_2$ | CF$_2$ | O | CF$_3$ | SCF$_3$ | CF$_3$ |

TABLE 130

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | Cl | SCF$_3$ | CF$_3$ |
| F | Cl | CF$_2$ | CF$_2$ | O | F | SCF$_3$ | CF$_3$ |
| F | Cl | CF$_2$ | CF$_2$ | O | COCH$_3$ | SCF$_3$ | CF$_3$ |
| F | Cl | CF$_2$ | CF$_2$ | O | H | SOCF$_3$ | CF$_3$ |
| F | Cl | CF$_2$ | CF$_2$ | O | NH$_2$ | SOCF$_3$ | CF$_3$ |
| F | Cl | CF$_2$ | CF$_2$ | O | N=CHPh | SOCF$_3$ | CF$_3$ |
| F | Cl | CF$_2$ | CF$_2$ | O | CH$_3$ | SOCF$_3$ | CF$_3$ |
| F | Cl | CF$_2$ | CF$_2$ | O | CF$_3$ | SOCF$_3$ | CF$_3$ |
| F | Cl | CF$_2$ | CF$_2$ | O | Cl | SOCF$_3$ | CF$_3$ |
| F | Cl | CF$_2$ | CF$_2$ | O | F | SOCF$_3$ | CF$_3$ |

TABLE 130-continued

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | COCH$_3$ | SOCF$_3$ | CF$_3$ |
| F | Cl | CF$_2$ | CF$_2$ | O | H | SO$_2$CF$_3$ | CF$_3$ |
| F | Cl | CF$_2$ | CF$_2$ | O | NH$_2$ | SO$_2$CF$_3$ | CF$_3$ |
| F | Cl | CF$_2$ | CF$_2$ | O | N = CHPh | SO$_2$CF$_3$ | CF$_3$ |
| F | Cl | CF$_2$ | CF$_2$ | O | CH$_3$ | SO$_2$CF$_3$ | CF$_3$ |
| F | Cl | CF$_2$ | CF$_2$ | O | CF$_3$ | SO$_2$CF$_3$ | CF$_3$ |
| F | Cl | CF$_2$ | CF$_2$ | O | Cl | SO$_2$CF$_3$ | CF$_3$ |
| F | Cl | CF$_2$ | CF$_2$ | O | F | SO$_2$CF$_3$ | CF$_3$ |
| F | Cl | CF$_2$ | CF$_2$ | O | COCH$_3$ | SO$_2$CF$_3$ | CF$_3$ |
| F | Cl | CF$_2$ | CF$_2$ | O | H | SCF$_2$CH$_3$ | CF$_3$ |
| F | Cl | CF$_2$ | CF$_2$ | O | NH$_2$ | SCF$_2$CH$_3$ | CF$_3$ |
| F | Cl | CF$_2$ | CF$_2$ | O | N = CHPh | SCF$_2$CH$_3$ | CF$_3$ |
| F | Cl | CF$_2$ | CF$_2$ | O | CH$_3$ | SCF$_2$CH$_3$ | CF$_3$ |
| F | Cl | CF$_2$ | CF$_2$ | O | CF$_3$ | SCF$_2$CH$_3$ | CF$_3$ |
| F | Cl | CF$_2$ | CF$_2$ | O | Cl | SCF$_2$CH$_3$ | CF$_3$ |
| F | Cl | CF$_2$ | CF$_2$ | O | F | SCF$_2$CH$_3$ | CF$_3$ |

TABLE 131

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | COCH$_3$ | SCF$_2$CH$_3$ | CF$_3$ |
| F | Cl | CF$_2$ | CF$_2$ | O | H | SOCF$_2$CH$_3$ | CF$_3$ |
| F | Cl | CF$_2$ | CF$_2$ | O | NH$_2$ | SOCF$_2$CH$_3$ | CF$_3$ |
| F | Cl | CF$_2$ | CF$_2$ | O | N = CHPh | SOCF$_2$CH$_3$ | CF$_3$ |
| F | Cl | CF$_2$ | CF$_2$ | O | CH$_3$ | SOCF$_2$CH$_3$ | CF$_3$ |
| F | Cl | CF$_2$ | CF$_2$ | O | CF$_3$ | SOCF$_2$CH$_3$ | CF$_3$ |
| F | Cl | CF$_2$ | CF$_2$ | O | Cl | SOCF$_2$CH$_3$ | CF$_3$ |
| F | Cl | CF$_2$ | CF$_2$ | O | F | SOCF$_2$CH$_3$ | CF$_3$ |
| F | Cl | CF$_2$ | CF$_2$ | O | COCH$_3$ | SOCF$_2$CH$_3$ | CF$_3$ |
| F | Cl | CF$_2$ | CF$_2$ | O | H | SO$_2$CF$_2$CH$_3$ | CF$_3$ |
| F | Cl | CF$_2$ | CF$_2$ | O | NH$_2$ | SO$_2$CF$_2$CH$_3$ | CF$_3$ |
| F | Cl | CF$_2$ | CF$_2$ | O | N = CHPh | SO$_2$CF$_2$CH$_3$ | CF$_3$ |
| F | Cl | CF$_2$ | CF$_2$ | O | CH$_3$ | SO$_2$CF$_2$CH$_3$ | CF$_3$ |
| F | Cl | CF$_2$ | CF$_2$ | O | CF$_3$ | SO$_2$CF$_2$CH$_3$ | CF$_3$ |
| F | Cl | CF$_2$ | CF$_2$ | O | Cl | SO$_2$CF$_2$CH$_3$ | CF$_3$ |
| F | Cl | CF$_2$ | CF$_2$ | O | F | SO$_2$CF$_2$CH$_3$ | CF$_3$ |
| F | Cl | CF$_2$ | CF$_2$ | O | COCH$_3$ | SO$_2$CF$_2$CH$_3$ | CF$_3$ |
| F | Cl | CF$_2$ | CF$_2$ | O | NH$_2$ | COCF$_3$ | CF$_3$ |
| F | Cl | CF$_2$ | CF$_2$ | O | N = CHPh | COCF$_3$ | CF$_3$ |
| F | Cl | CF$_2$ | CF$_2$ | O | CH$_3$ | COCF$_3$ | CF$_3$ |
| F | Cl | CF$_2$ | CF$_2$ | O | CF$_3$ | COCF$_3$ | CF$_3$ |
| F | Cl | CF$_2$ | CF$_2$ | O | Cl | COCF$_3$ | CF$_3$ |
| F | Cl | CF$_2$ | CF$_2$ | O | F | COCF$_3$ | CF$_3$ |
| F | Cl | CF$_2$ | CF$_2$ | O | COCH$_3$ | COCF$_3$ | CF$_3$ |
| F | Cl | CF$_2$ | CF$_2$ | O | H | COCF$_3$ | CF$_3$ |
| F | Cl | CF$_2$ | CF$_2$ | O | NH$_2$ | COCF$_3$ | CF$_3$ |

TABLE 132

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | N = CHPh | COCF$_3$ | CF$_3$ |
| F | Cl | CF$_2$ | CF$_2$ | O | CH$_3$ | COCF$_3$ | CF$_3$ |
| F | Cl | CF$_2$ | CF$_2$ | O | CF$_3$ | COCF$_3$ | CF$_3$ |
| F | Cl | CF$_2$ | CF$_2$ | O | Cl | COCF$_3$ | CF$_3$ |
| F | Cl | CF$_2$ | CF$_2$ | O | F | COCF$_3$ | CF$_3$ |
| F | Cl | CF$_2$ | CF$_2$ | O | COCH$_3$ | COCF$_3$ | CF$_3$ |
| F | Cl | CF$_2$ | CF$_2$ | O | NH$_2$ | C$_2$F$_5$ | CF$_3$ |
| F | Cl | CF$_2$ | CF$_2$ | O | N = CHPh | C$_2$F$_5$ | CF$_3$ |
| F | Cl | CF$_2$ | CF$_2$ | O | CH$_3$ | C$_2$F$_5$ | CF$_3$ |
| F | Cl | CF$_2$ | CF$_2$ | O | CF$_3$ | C$_2$F$_5$ | CF$_3$ |
| F | Cl | CF$_2$ | CF$_2$ | O | Cl | C$_2$F$_5$ | CF$_3$ |
| F | Cl | CF$_2$ | CF$_2$ | O | F | C$_2$F$_5$ | CF$_3$ |
| F | Cl | CF$_2$ | CF$_2$ | O | COCH$_3$ | C$_2$F$_5$ | CF$_3$ |
| F | Cl | CF$_2$ | CF$_2$ | O | H | C$_2$F$_5$ | CF$_3$ |
| F | Cl | CF$_2$ | CF$_2$ | O | NH$_2$ | C$_2$F$_5$ | CF$_3$ |
| F | Cl | CF$_2$ | CF$_2$ | O | N = CHPh | C$_2$F$_5$ | CF$_3$ |
| F | Cl | CF$_2$ | CF$_2$ | O | CH$_3$ | C$_2$F$_5$ | CF$_3$ |
| F | Cl | CF$_2$ | CF$_2$ | O | CF$_3$ | C$_2$F$_5$ | CF$_3$ |
| F | Cl | CF$_2$ | CF$_2$ | O | Cl | C$_2$F$_5$ | CF$_3$ |
| F | Cl | CF$_2$ | CF$_2$ | O | F | C$_2$F$_5$ | CF$_3$ |

TABLE 132-continued

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | COCH$_3$ | C$_2$F$_5$ | CF$_3$ |
| F | Cl | CF$_2$ | CF$_2$ | O | NH$_2$ | SFCl$_2$ | CF$_3$ |
| F | Cl | CF$_2$ | CF$_2$ | O | N = CHPh | SFCl$_2$ | CF$_3$ |
| F | Cl | CF$_2$ | CF$_2$ | O | CH$_3$ | SFCl$_2$ | CF$_3$ |
| F | Cl | CF$_2$ | CF$_2$ | O | CF$_3$ | SFCl$_2$ | CF$_3$ |
| F | Cl | CF$_2$ | CF$_2$ | O | Cl | SFCl$_2$ | CF$_3$ |

TABLE 133

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | F | SFCl$_2$ | CF$_3$ |
| F | Cl | CF$_2$ | CF$_2$ | O | COCH$_3$ | SFCl$_2$ | CF$_3$ |
| F | Cl | CF$_2$ | CF$_2$ | O | H | SFCl$_2$ | CF$_3$ |
| F | Cl | CF$_2$ | CF$_2$ | O | NH$_2$ | SFCl$_2$ | CF$_3$ |
| F | Cl | CF$_2$ | CF$_2$ | O | N = CHPh | SFCl$_2$ | CF$_3$ |
| F | Cl | CF$_2$ | CF$_2$ | O | CH$_3$ | SFCl$_2$ | CF$_3$ |
| F | Cl | CF$_2$ | CF$_2$ | O | CF$_3$ | SFCl$_2$ | CF$_3$ |
| F | Cl | CF$_2$ | CF$_2$ | O | Cl | SFCl$_2$ | CF$_3$ |
| F | Cl | CF$_2$ | CF$_2$ | O | F | SFCl$_2$ | CF$_3$ |
| F | Cl | CF$_2$ | CF$_2$ | O | COCH$_3$ | SFCl$_2$ | CF$_3$ |
| F | Cl | CF$_2$ | CF$_2$ | O | H | SCF$_3$ | C$_2$F$_5$ |
| F | Cl | CF$_2$ | CF$_2$ | O | NH$_2$ | SCF$_3$ | C$_2$F$_5$ |
| F | Cl | CF$_2$ | CF$_2$ | O | N = CHPh | SCF$_3$ | C$_2$F$_5$ |
| F | Cl | CF$_2$ | CF$_2$ | O | CH$_3$ | SCF$_3$ | C$_2$F$_5$ |
| F | Cl | CF$_2$ | CF$_2$ | O | CF$_3$ | SCF$_3$ | C$_2$F$_5$ |
| F | Cl | CF$_2$ | CF$_2$ | O | Cl | SCF$_3$ | C$_2$F$_5$ |
| F | Cl | CF$_2$ | CF$_2$ | O | F | SCF$_3$ | C$_2$F$_5$ |
| F | Cl | CF$_2$ | CF$_2$ | O | COCH$_3$ | SCF$_3$ | C$_2$F$_5$ |
| F | Cl | CF$_2$ | CF$_2$ | O | H | SOCF$_3$ | C$_2$F$_5$ |
| F | Cl | CF$_2$ | CF$_2$ | O | NH$_2$ | SOCF$_3$ | C$_2$F$_5$ |
| F | Cl | CF$_2$ | CF$_2$ | O | N = CHPh | SOCF$_3$ | C$_2$F$_5$ |
| F | Cl | CF$_2$ | CF$_2$ | O | CH$_3$ | SOCF$_3$ | C$_2$F$_5$ |
| F | Cl | CF$_2$ | CF$_2$ | O | CF$_3$ | SOCF$_3$ | C$_2$F$_5$ |
| F | Cl | CF$_2$ | CF$_2$ | O | Cl | SOCF$_3$ | C$_2$F$_5$ |
| F | Cl | CF$_2$ | CF$_2$ | O | F | SOCF$_3$ | C$_2$F$_5$ |
| F | Cl | CF$_2$ | CF$_2$ | O | COCH$_3$ | SOCF$_3$ | C$_2$F$_5$ |

TABLE 134

| X | Y | Z$^1$ | Z$^2$ | Z$^3$ | R$^1$ | R$^2$ | R$^3$ |
|---|---|---|---|---|---|---|---|
| F | Cl | CF$_2$ | CF$_2$ | O | H | SO$_2$CF$_3$ | C$_2$F$_5$ |
| F | Cl | CF$_2$ | CF$_2$ | O | NH$_2$ | SO$_2$CF$_3$ | C$_2$F$_5$ |
| F | Cl | CF$_2$ | CF$_2$ | O | N = CHPh | SO$_2$CF$_3$ | C$_2$F$_5$ |
| F | Cl | CF$_2$ | CF$_2$ | O | CH$_3$ | SO$_2$CF$_3$ | C$_2$F$_5$ |
| F | Cl | CF$_2$ | CF$_2$ | O | CF$_3$ | SO$_2$CF$_3$ | C$_2$F$_5$ |
| F | Cl | CF$_2$ | CF$_2$ | O | Cl | SO$_2$CF$_3$ | C$_2$F$_5$ |
| F | Cl | CF$_2$ | CF$_2$ | O | F | SO$_2$CF$_3$ | C$_2$F$_5$ |
| F | Cl | CF$_2$ | CF$_2$ | O | COCH$_3$ | SO$_2$CF$_3$ | C$_2$F$_5$ |
| F | Cl | CF$_2$ | CF$_2$ | O | H | SCF$_2$CH$_3$ | C$_2$F$_5$ |
| F | Cl | CF$_2$ | CF$_2$ | O | NH$_2$ | SCF$_2$CH$_3$ | C$_2$F$_5$ |
| F | Cl | CF$_2$ | CF$_2$ | O | N = CHPh | SCF$_2$CH$_3$ | C$_2$F$_5$ |
| F | Cl | CF$_2$ | CF$_2$ | O | CH$_3$ | SCF$_2$CH$_3$ | C$_2$F$_5$ |
| F | Cl | CF$_2$ | CF$_2$ | O | CF$_3$ | SCF$_2$CH$_3$ | C$_2$F$_5$ |
| F | Cl | CF$_2$ | CF$_2$ | O | Cl | SCF$_2$CH$_3$ | C$_2$F$_5$ |
| F | Cl | CF$_2$ | CF$_2$ | O | F | SCF$_2$CH$_3$ | C$_2$F$_5$ |
| F | Cl | CF$_2$ | CF$_2$ | O | COCH$_3$ | SCF$_2$CH$_3$ | C$_2$F$_5$ |
| F | Cl | CF$_2$ | CF$_2$ | O | H | SOCF$_2$CH$_3$ | C$_2$F$_5$ |
| F | Cl | CF$_2$ | CF$_2$ | O | NH$_2$ | SOCF$_2$CH$_3$ | C$_2$F$_5$ |
| F | Cl | CF$_2$ | CF$_2$ | O | N = CHPh | SOCF$_2$CH$_3$ | C$_2$F$_5$ |
| F | Cl | CF$_2$ | CF$_2$ | O | CH$_3$ | SOCF$_2$CH$_3$ | C$_2$F$_5$ |
| F | Cl | CF$_2$ | CF$_2$ | O | CF$_3$ | SOCF$_2$CH$_3$ | C$_2$F$_5$ |
| F | Cl | CF$_2$ | CF$_2$ | O | Cl | SOCF$_2$CH$_3$ | C$_2$F$_5$ |
| F | Cl | CF$_2$ | CF$_2$ | O | F | SOCF$_2$CH$_3$ | C$_2$F$_5$ |
| F | Cl | CF$_2$ | CF$_2$ | O | COCH$_3$ | SOCF$_2$CH$_3$ | C$_2$F$_5$ |
| F | Cl | CF$_2$ | CF$_2$ | O | H | SO$_2$CF$_2$CH$_3$ | C$_2$F$_5$ |
| F | Cl | CF$_2$ | CF$_2$ | O | NH$_2$ | SO$_2$CF$_2$CH$_3$ | C$_2$F$_5$ |

TABLE 135

| X | Y | Z¹ | Z² | Z³ | R¹ | R² | R³ |
|---|---|---|---|---|---|---|---|
| F | Cl | $CF_2$ | $CF_2$ | O | N=CHPh | $SO_2CF_2CH_3$ | $C_2F_5$ |
| F | Cl | $CF_2$ | $CF_2$ | O | $CH_3$ | $SO_2CF_2CH_3$ | $C_2F_5$ |
| F | Cl | $CF_2$ | $CF_2$ | O | $CF_3$ | $SO_2CF_2CH_3$ | $C_2F_5$ |
| F | Cl | $CF_2$ | $CF_2$ | O | Cl | $SO_2CF_2CH_3$ | $C_2F_5$ |
| F | Cl | $CF_2$ | $CF_2$ | O | F | $SO_2CF_2CH_3$ | $C_2F_5$ |
| F | Cl | $CF_2$ | $CF_2$ | O | $COCH_3$ | $SO_2CF_2CH_3$ | $C_2F_5$ |
| F | Cl | $CF_2$ | $CF_2$ | O | $NH_2$ | $COCF_3$ | $C_2F_5$ |
| F | Cl | $CF_2$ | $CF_2$ | O | N=CHPh | $COCF_3$ | $C_2F_5$ |
| F | Cl | $CF_2$ | $CF_2$ | O | $CH_3$ | $COCF_3$ | $C_2F_5$ |
| F | Cl | $CF_2$ | $CF_2$ | O | $CF_3$ | $COCF_3$ | $C_2F_5$ |
| F | Cl | $CF_2$ | $CF_2$ | O | Cl | $COCF_3$ | $C_2F_5$ |
| F | Cl | $CF_2$ | $CF_2$ | O | F | $COCF_3$ | $C_2F_5$ |
| F | Cl | $CF_2$ | $CF_2$ | O | $COCH_3$ | $COCF_3$ | $C_2F_5$ |
| F | Cl | $CF_2$ | $CF_2$ | O | H | $COCF_3$ | $C_2F_5$ |
| F | Cl | $CF_2$ | $CF_2$ | O | $NH_2$ | $COCF_3$ | $C_2F_5$ |
| F | Cl | $CF_2$ | $CF_2$ | O | N=CHPh | $COCF_3$ | $C_2F_5$ |
| F | Cl | $CF_2$ | $CF_2$ | O | $CH_3$ | $COCF_3$ | $C_2F_5$ |
| F | Cl | $CF_2$ | $CF_2$ | O | $CF_3$ | $COCF_3$ | $C_2F_5$ |
| F | Cl | $CF_2$ | $CF_2$ | O | Cl | $COCF_3$ | $C_2F_5$ |
| F | Cl | $CF_2$ | $CF_2$ | O | F | $COCF_3$ | $C_2F_5$ |
| F | Cl | $CF_2$ | $CF_2$ | O | $COCH_3$ | $COCF_3$ | $C_2F_5$ |
| F | Cl | $CF_2$ | $CF_2$ | O | $NH_2$ | $C_2F_5$ | $C_2F_5$ |
| F | Cl | $CF_2$ | $CF_2$ | O | N=CHPh | $C_2F_5$ | $C_2F_5$ |
| F | Cl | $CF_2$ | $CF_2$ | O | $CH_3$ | $C_2F_5$ | $C_2F_5$ |
| F | Cl | $CF_2$ | $CF_2$ | O | $CF_3$ | $C_2F_5$ | $C_2F_5$ |
| F | Cl | $CF_2$ | $CF_2$ | O | Cl | $C_2F_5$ | $C_2F_5$ |

TABLE 136

| X | Y | Z¹ | Z² | Z³ | R¹ | R² | R³ |
|---|---|---|---|---|---|---|---|
| F | Cl | $CF_2$ | $CF_2$ | O | F | $C_2F_5$ | $C_2F_5$ |
| F | Cl | $CF_2$ | $CF_2$ | O | $COCH_3$ | $C_2F_5$ | $C_2F_5$ |
| F | Cl | $CF_2$ | $CF_2$ | O | H | $C_2F_5$ | $C_2F_5$ |
| F | Cl | $CF_2$ | $CF_2$ | O | $NH_2$ | $C_2F_5$ | $C_2F_5$ |
| F | Cl | $CF_2$ | $CF_2$ | O | N=CHPh | $C_2F_5$ | $C_2F_5$ |
| F | Cl | $CF_2$ | $CF_2$ | O | $CH_3$ | $C_2F_5$ | $C_2F_5$ |
| F | Cl | $CF_2$ | $CF_2$ | O | $CF_3$ | $C_2F_5$ | $C_2F_5$ |
| F | Cl | $CF_2$ | $CF_2$ | O | Cl | $C_2F_5$ | $C_2F_5$ |
| F | Cl | $CF_2$ | $CF_2$ | O | F | $C_2F_5$ | $C_2F_5$ |
| F | Cl | $CF_2$ | $CF_2$ | O | $COCH_3$ | $C_2F_5$ | $C_2F_5$ |
| F | Cl | $CF_2$ | $CF_2$ | O | $NH_2$ | $SFCl_2$ | $C_2F_5$ |
| F | Cl | $CF_2$ | $CF_2$ | O | N=CHPh | $SFCl_2$ | $C_2F_5$ |
| F | Cl | $CF_2$ | $CF_2$ | O | $CH_3$ | $SFCl_2$ | $C_2F_5$ |
| F | Cl | $CF_2$ | $CF_2$ | O | $CF_3$ | $SFCl_2$ | $C_2F_5$ |
| F | Cl | $CF_2$ | $CF_2$ | O | Cl | $SFCl_2$ | $C_2F_5$ |
| F | Cl | $CF_2$ | $CF_2$ | O | F | $SFCl_2$ | $C_2F_5$ |
| F | Cl | $CF_2$ | $CF_2$ | O | $COCH_3$ | $SFCl_2$ | $C_2F_5$ |
| F | Cl | $CF_2$ | $CF_2$ | O | H | $SFCl_2$ | $C_2F_5$ |
| F | Cl | $CF_2$ | $CF_2$ | O | $NH_2$ | $SFCl_2$ | $C_2F_5$ |
| F | Cl | $CF_2$ | $CF_2$ | O | N=CHPh | $SFCl_2$ | $C_2F_5$ |
| F | Cl | $CF_2$ | $CF_2$ | O | $CH_3$ | $SFCl_2$ | $C_2F_5$ |
| F | Cl | $CF_2$ | $CF_2$ | O | $CF_3$ | $SFCl_2$ | $C_2F_5$ |
| F | Cl | $CF_2$ | $CF_2$ | O | Cl | $SFCl_2$ | $C_2F_5$ |
| F | Cl | $CF_2$ | $CF_2$ | O | F | $SFCl_2$ | $C_2F_5$ |
| F | Cl | $CF_2$ | $CF_2$ | O | $COCH_3$ | $SFCl_2$ | $C_2F_5$ |
| F | Cl | $CF_2$ | $CF_2$ | O | H | $SCF_3$ | $CSNH_2$ |

TABLE 137

| X | Y | Z¹ | Z² | Z³ | R¹ | R² | R³ |
|---|---|---|---|---|---|---|---|
| F | Cl | $CF_2$ | $CF_2$ | O | $NH_2$ | $SCF_3$ | $CSNH_2$ |
| F | Cl | $CF_2$ | $CF_2$ | O | N=CHPh | $SCF_3$ | $CSNH_2$ |
| F | Cl | $CF_2$ | $CF_2$ | O | $CH_3$ | $SCF_3$ | $CSNH_2$ |
| F | Cl | $CF_2$ | $CF_2$ | O | $CF_3$ | $SCF_3$ | $CSNH_2$ |
| F | Cl | $CF_2$ | $CF_2$ | O | Cl | $SCF_3$ | $CSNH_2$ |
| F | Cl | $CF_2$ | $CF_2$ | O | F | $SCF_3$ | $CSNH_2$ |
| F | Cl | $CF_2$ | $CF_2$ | O | $COCH_3$ | $SCF_3$ | $CSNH_2$ |
| F | Cl | $CF_2$ | $CF_2$ | O | H | $SOCF_3$ | $CSNH_2$ |
| F | Cl | $CF_2$ | $CF_2$ | O | $NH_2$ | $SOCF_3$ | $CSNH_2$ |
| F | Cl | $CF_2$ | $CF_2$ | O | N=CHPh | $SOCF_3$ | $CSNH_2$ |

TABLE 137-continued

| X | Y | Z¹ | Z² | Z³ | R¹ | R² | R³ |
|---|---|---|---|---|---|---|---|
| F | Cl | $CF_2$ | $CF_2$ | O | $CH_3$ | $SOCF_3$ | $CSNH_2$ |
| F | Cl | $CF_2$ | $CF_2$ | O | $CF_3$ | $SOCF_3$ | $CSNH_2$ |
| F | Cl | $CF_2$ | $CF_2$ | O | Cl | $SOCF_3$ | $CSNH_2$ |
| F | Cl | $CF_2$ | $CF_2$ | O | F | $SOCF_3$ | $CSNH_2$ |
| F | Cl | $CF_2$ | $CF_2$ | O | $COCH_3$ | $SOCF_3$ | $CSNH_2$ |
| F | Cl | $CF_2$ | $CF_2$ | O | H | $SO_2CF_3$ | $CSNH_2$ |
| F | Cl | $CF_2$ | $CF_2$ | O | $NH_2$ | $SO_2CF_3$ | $CSNH_2$ |
| F | Cl | $CF_2$ | $CF_2$ | O | N=CHPh | $SO_2CF_3$ | $CSNH_2$ |
| F | Cl | $CF_2$ | $CF_2$ | O | $CH_3$ | $SO_2CF_3$ | $CSNH_2$ |
| F | Cl | $CF_2$ | $CF_2$ | O | $CF_3$ | $SO_2CF_3$ | $CSNH_2$ |
| F | Cl | $CF_2$ | $CF_2$ | O | Cl | $SO_2CF_3$ | $CSNH_2$ |
| F | Cl | $CF_2$ | $CF_2$ | O | F | $SO_2CF_3$ | $CSNH_2$ |
| F | Cl | $CF_2$ | $CF_2$ | O | $COCH_3$ | $SO_2CF_3$ | $CSNH_2$ |
| F | Cl | $CF_2$ | $CF_2$ | O | H | $SCF_2CH_3$ | $CSNH_2$ |
| F | Cl | $CF_2$ | $CF_2$ | O | $NH_2$ | $SCF_2CH_3$ | $CSNH_2$ |
| F | Cl | $CF_2$ | $CF_2$ | O | N=CHPh | $SCF_2CH_3$ | $CSNH_2$ |

TABLE 138

| X | Y | Z¹ | Z² | Z³ | R¹ | R² | R³ |
|---|---|---|---|---|---|---|---|
| F | Cl | $CF_2$ | $CF_2$ | O | $CH_3$ | $SCF_2CH_3$ | $CSNH_2$ |
| F | Cl | $CF_2$ | $CF_2$ | O | $CF_3$ | $SCF_2CH_3$ | $CSNH_2$ |
| F | Cl | $CF_2$ | $CF_2$ | O | Cl | $SCF_2CH_3$ | $CSNH_2$ |
| F | Cl | $CF_2$ | $CF_2$ | O | F | $SCF_2CH_3$ | $CSNH_2$ |
| F | Cl | $CF_2$ | $CF_2$ | O | $COCH_3$ | $SCF_2CH_3$ | $CSNH_2$ |
| F | Cl | $CF_2$ | $CF_2$ | O | H | $SOCF_2CH_3$ | $CSNH_2$ |
| F | Cl | $CF_2$ | $CF_2$ | O | $NH_2$ | $SOCF_2CH_3$ | $CSNH_2$ |
| F | Cl | $CF_2$ | $CF_2$ | O | N=CHPh | $SOCF_2CH_3$ | $CSNH_2$ |
| F | Cl | $CF_2$ | $CF_2$ | O | $CH_3$ | $SOCF_2CH_3$ | $CSNH_2$ |
| F | Cl | $CF_2$ | $CF_2$ | O | $CF_3$ | $SOCF_2CH_3$ | $CSNH_2$ |
| F | Cl | $CF_2$ | $CF_2$ | O | Cl | $SOCF_2CH_3$ | $CSNH_2$ |
| F | Cl | $CF_2$ | $CF_2$ | O | F | $SOCF_2CH_3$ | $CSNH_2$ |
| F | Cl | $CF_2$ | $CF_2$ | O | $COCH_3$ | $SOCF_2CH_3$ | $CSNH_2$ |
| F | Cl | $CF_2$ | $CF_2$ | O | H | $SO_2CF_2CH_3$ | $CSNH_2$ |
| F | Cl | $CF_2$ | $CF_2$ | O | $NH_2$ | $SO_2CF_2CH_3$ | $CSNH_2$ |
| F | Cl | $CF_2$ | $CF_2$ | O | N=CHPh | $SO_2CF_2CH_3$ | $CSNH_2$ |
| F | Cl | $CF_2$ | $CF_2$ | O | $CH_3$ | $SO_2CF_2CH_3$ | $CSNH_2$ |
| F | Cl | $CF_2$ | $CF_2$ | O | $CF_3$ | $SO_2CF_2CH_3$ | $CSNH_2$ |
| F | Cl | $CF_2$ | $CF_2$ | O | Cl | $SO_2CF_2CH_3$ | $CSNH_2$ |
| F | Cl | $CF_2$ | $CF_2$ | O | F | $SO_2CF_2CH_3$ | $CSNH_2$ |
| F | Cl | $CF_2$ | $CF_2$ | O | $COCH_3$ | $SO_2CF_2CH_3$ | $CSNH_2$ |
| F | Cl | $CF_2$ | $CF_2$ | O | $NH_2$ | $COCF_3$ | $CSNH_2$ |
| F | Cl | $CF_2$ | $CF_2$ | O | N=CHPh | $COCF_3$ | $CSNH_2$ |
| F | Cl | $CF_2$ | $CF_2$ | O | $CH_3$ | $COCF_3$ | $CSNH_2$ |
| F | Cl | $CF_2$ | $CF_2$ | O | $CF_3$ | $COCF_3$ | $CSNH_2$ |
| F | Cl | $CF_2$ | $CF_2$ | O | Cl | $COCF_3$ | $CSNH_2$ |

TABLE 139

| X | Y | Z¹ | Z² | Z³ | R¹ | R² | R³ |
|---|---|---|---|---|---|---|---|
| F | Cl | $CF_2$ | $CF_2$ | O | F | $COCF_3$ | $CSNH_2$ |
| F | Cl | $CF_2$ | $CF_2$ | O | $COCH_3$ | $COCF_3$ | $CSNH_2$ |
| F | Cl | $CF_2$ | $CF_2$ | O | H | $COCF_3$ | $CSNH_2$ |
| F | Cl | $CF_2$ | $CF_2$ | O | $NH_2$ | $COCF_3$ | $CSNH_2$ |
| F | Cl | $CF_2$ | $CF_2$ | O | N=CHPh | $COCF_3$ | $CSNH_2$ |
| F | Cl | $CF_2$ | $CF_2$ | O | $CH_3$ | $COCF_3$ | $CSNH_2$ |
| F | Cl | $CF_2$ | $CF_2$ | O | $CF_3$ | $COCF_3$ | $CSNH_2$ |
| F | Cl | $CF_2$ | $CF_2$ | O | Cl | $COCF_3$ | $CSNH_2$ |
| F | Cl | $CF_2$ | $CF_2$ | O | F | $COCF_3$ | $CSNH_2$ |
| F | Cl | $CF_2$ | $CF_2$ | O | $COCH_3$ | $COCF_3$ | $CSNH_2$ |
| F | Cl | $CF_2$ | $CF_2$ | O | $NH_2$ | $C_2F_5$ | $CSNH_2$ |
| F | Cl | $CF_2$ | $CF_2$ | O | N=CHPh | $C_2F_5$ | $CSNH_2$ |
| F | Cl | $CF_2$ | $CF_2$ | O | $CH_3$ | $C_2F_5$ | $CSNH_2$ |
| F | Cl | $CF_2$ | $CF_2$ | O | $CF_3$ | $C_2F_5$ | $CSNH_2$ |
| F | Cl | $CF_2$ | $CF_2$ | O | Cl | $C_2F_5$ | $CSNH_2$ |
| F | Cl | $CF_2$ | $CF_2$ | O | F | $C_2F_5$ | $CSNH_2$ |
| F | Cl | $CF_2$ | $CF_2$ | O | $COCH_3$ | $C_2F_5$ | $CSNH_2$ |
| F | Cl | $CF_2$ | $CF_2$ | O | H | $C_2F_5$ | $CSNH_2$ |
| F | Cl | $CF_2$ | $CF_2$ | O | $NH_2$ | $C_2F_5$ | $CSNH_2$ |
| F | Cl | $CF_2$ | $CF_2$ | O | N=CHPh | $C_2F_5$ | $CSNH_2$ |

TABLE 139-continued

| X | Y | $Z^1$ | $Z^2$ | $Z^3$ | $R^1$ | $R^2$ | $R^3$ |
|---|---|---|---|---|---|---|---|
| F | Cl | $CF_2$ | $CF_2$ | O | $CH_3$ | $C_2F_5$ | $CSNH_2$ |
| F | Cl | $CF_2$ | $CF_2$ | O | $CF_3$ | $C_2F_5$ | $CSNH_2$ |
| F | Cl | $CF_2$ | $CF_2$ | O | Cl | $C_2F_5$ | $CSNH_2$ |
| F | Cl | $CF_2$ | $CF_2$ | O | F | $C_2F_5$ | $CSNH_2$ |
| F | Cl | $CF_2$ | $CF_2$ | O | $COCH_3$ | $C_2F_5$ | $CSNH_2$ |
| F | Cl | $CF_2$ | $CF_2$ | O | $NH_2$ | $SFCl_2$ | $CSNH_2$ |

TABLE 140

| X | Y | $Z^1$ | $Z^2$ | $Z^3$ | $R^1$ | $R^2$ | $R^3$ |
|---|---|---|---|---|---|---|---|
| F | Cl | $CF_2$ | $CF_2$ | O | N = CHPh | $SFCl_2$ | $CSNH_2$ |
| F | Cl | $CF_2$ | $CF_2$ | O | $CH_3$ | $SFCl_2$ | $CSNH_2$ |
| F | Cl | $CF_2$ | $CF_2$ | O | $CF_3$ | $SFCl_2$ | $CSNH_2$ |
| F | Cl | $CF_2$ | $CF_2$ | O | Cl | $SFCl_2$ | $CSNH_2$ |
| F | Cl | $CF_2$ | $CF_2$ | O | F | $SFCl_2$ | $CSNH_2$ |
| F | Cl | $CF_2$ | $CF_2$ | O | $COCH_3$ | $SFCl_2$ | $CSNH_2$ |
| F | Cl | $CF_2$ | $CF_2$ | O | H | $SFCl_2$ | $CSNH_2$ |
| F | Cl | $CF_2$ | $CF_2$ | O | $NH_2$ | $SFCl_2$ | $CSNH_2$ |
| F | Cl | $CF_2$ | $CF_2$ | O | N = CHPh | $SFCl_2$ | $CSNH_2$ |
| F | Cl | $CF_2$ | $CF_2$ | O | $CH_3$ | $SFCl_2$ | $CSNH_2$ |
| F | Cl | $CF_2$ | $CF_2$ | O | $CF_3$ | $SFCl_2$ | $CSNH_2$ |
| F | Cl | $CF_2$ | $CF_2$ | O | Cl | $SFCl_2$ | $CSNH_2$ |
| F | Cl | $CF_2$ | $CF_2$ | O | F | $SFCl_2$ | $CSNH_2$ |
| F | Cl | $CF_2$ | $CF_2$ | O | $COCH_3$ | $SFCl_2$ | $CSNH_2$ |
| F | Cl | $CF_2$ | $CF_2$ | O | H | $SCF_3$ | CN |
| F | Cl | $CF_2$ | $CF_2$ | O | $NH_2$ | $SCF_3$ | CN |
| F | Cl | $CF_2$ | $CF_2$ | O | N = CHPh | $SCF_3$ | CN |
| F | Cl | $CF_2$ | $CF_2$ | O | $CH_3$ | $SCF_3$ | CN |
| F | Cl | $CF_2$ | $CF_2$ | O | $CF_3$ | $SCF_3$ | CN |
| F | Cl | $CF_2$ | $CF_2$ | O | Cl | $SCF_3$ | CN |
| F | Cl | $CF_2$ | $CF_2$ | O | F | $SCF_3$ | CN |
| F | Cl | $CF_2$ | $CF_2$ | O | $COCH_3$ | $SCF_3$ | CN |
| F | Cl | $CF_2$ | $CF_2$ | O | H | $SOCF_3$ | CN |
| F | Cl | $CF_2$ | $CF_2$ | O | $NH_2$ | $SOCF_3$ | CN |
| F | Cl | $CF_2$ | $CF_2$ | O | N = CHPh | $SOCF_3$ | CN |
| F | Cl | $CF_2$ | $CF_2$ | O | $CH_3$ | $SOCF_3$ | CN |

TABLE 141

| X | Y | $Z^1$ | $Z^2$ | $Z^3$ | $R^1$ | $R^2$ | $R^3$ |
|---|---|---|---|---|---|---|---|
| F | Cl | $CF_2$ | $CF_2$ | O | $CF_3$ | $SOCF_3$ | CN |
| F | Cl | $CF_2$ | $CF_2$ | O | Cl | $SOCF_3$ | CN |
| F | Cl | $CF_2$ | $CF_2$ | O | F | $SOCF_3$ | CN |
| F | Cl | $CF_2$ | $CF_2$ | O | $COCH_3$ | $SOCF_3$ | CN |
| F | Cl | $CF_2$ | $CF_2$ | O | H | $SO_2CF_3$ | CN |
| F | Cl | $CF_2$ | $CF_2$ | O | $NH_2$ | $SO_2CF_3$ | CN |
| F | Cl | $CF_2$ | $CF_2$ | O | N = CHPh | $SO_2CF_3$ | CN |
| F | Cl | $CF_2$ | $CF_2$ | O | $CH_3$ | $SO_2CF_3$ | CN |
| F | Cl | $CF_2$ | $CF_2$ | O | $CF_3$ | $SO_2CF_3$ | CN |
| F | Cl | $CF_2$ | $CF_2$ | O | Cl | $SO_2CF_3$ | CN |
| F | Cl | $CF_2$ | $CF_2$ | O | F | $SO_2CF_3$ | CN |
| F | Cl | $CF_2$ | $CF_2$ | O | $COCH_3$ | $SO_2CF_3$ | CN |
| F | Cl | $CF_2$ | $CF_2$ | O | H | $SCF_2CH_3$ | CN |
| F | Cl | $CF_2$ | $CF_2$ | O | $NH_2$ | $SCF_2CH_3$ | CN |
| F | Cl | $CF_2$ | $CF_2$ | O | N = CHPh | $SCF_2CH_3$ | CN |
| F | Cl | $CF_2$ | $CF_2$ | G | $CH_3$ | $SCF_2CH_3$ | CN |
| F | Cl | $CF_2$ | $CF_2$ | O | $CF_3$ | $SCF_2CH_3$ | CN |
| F | Cl | $CF_2$ | $CF_2$ | O | Cl | $SCF_2CH_3$ | CN |
| F | Cl | $CF_2$ | $CF_2$ | O | F | $SCF_2CH_3$ | CN |
| F | Cl | $CF_2$ | $CF_2$ | O | $COCH_3$ | $SCF_2CH_3$ | CN |
| F | Cl | $CF_2$ | $CF_2$ | O | H | $SOCF_2CH_3$ | CN |
| F | Cl | $CF_2$ | $CF_2$ | O | $NH_2$ | $SOCF_2CH_3$ | CN |
| F | Cl | $CF_2$ | $CF_2$ | O | N = CHPh | $SOCF_2CH_3$ | CN |
| F | Cl | $CF_2$ | $CF_2$ | O | $CH_3$ | $SOCF_2CH_3$ | CN |
| F | Cl | $CF_2$ | $CF_2$ | G | $CF_3$ | $SOCF_{2CH3}$ | CN |
| F | Cl | $CF_2$ | $CF_2$ | O | Cl | $SOCF_2CH_3$ | CN |

TABLE 142

| X | Y | $Z^1$ | $Z^2$ | $Z^3$ | $R^1$ | $R^2$ | $R^3$ |
|---|---|---|---|---|---|---|---|
| F | Cl | $CF_2$ | $CF_2$ | O | F | $SOCF_2CH_3$ | CN |
| F | Cl | $CF_2$ | $CF_2$ | O | $COCH_3$ | $SOCF_2CH_3$ | CN |
| F | Cl | $CF_2$ | $CF_2$ | O | H | $SO_2CF_2CH_3$ | CN |
| F | Cl | $CF_2$ | $CF_2$ | O | $NH_2$ | $SO_2CF_2CH_3$ | CN |
| F | Cl | $CF_2$ | $CF_2$ | O | N = CHPh | $SO_2CF_2CH_3$ | CN |
| F | Cl | $CF_2$ | $CF_2$ | O | $CH_3$ | $SO_2CF_2CH_3$ | CN |
| F | Cl | $CF_2$ | $CF_2$ | O | $CF_3$ | $SO_2CF_2CH_3$ | CN |
| F | Cl | $CF_2$ | $CF_2$ | O | Cl | $SO_2CF_2CH_3$ | CN |
| F | Cl | $CF_2$ | $CF_2$ | O | F | $SO_2CF_2CH_3$ | CN |
| F | Cl | $CF_2$ | $CF_2$ | O | $COCH_3$ | $SO_2CF_2CH_3$ | CN |
| F | Cl | $CF_2$ | $CF_2$ | O | $NH_2$ | $COCF_3$ | CN |
| F | Cl | $CF_2$ | $CF_2$ | O | N = CHPh | $COCF_3$ | CN |
| F | Cl | $CF_2$ | $CF_2$ | O | $CH_3$ | $COCF_3$ | CN |
| F | Cl | $CF_2$ | $CF_2$ | O | $CF_3$ | $COCF_3$ | CN |
| F | Cl | $CF_2$ | $CF_2$ | O | Cl | $COCF_3$ | CN |
| F | Cl | $CF_2$ | $CF_2$ | O | F | $COCF_3$ | CN |
| F | Cl | $CF_2$ | $CF_2$ | O | $COCH_3$ | $COCF_3$ | CN |
| F | Cl | $CF_2$ | $CF_2$ | O | H | $COCF_3$ | CN |
| F | Cl | $CF_2$ | $CF_2$ | O | $NH_2$ | $COCF_3$ | CN |
| F | Cl | $CF_2$ | $CF_2$ | O | N = CHPh | $COCF_3$ | CN |
| F | Cl | $CF_2$ | $CF_2$ | O | $CH_3$ | $COCF_3$ | CN |
| F | Cl | $CF_2$ | $CF_2$ | O | $CF_3$ | $COCF_3$ | CN |
| F | Cl | $CF_2$ | $CF_2$ | O | Cl | $COCF_3$ | CN |
| F | Cl | $CF_2$ | $CF_2$ | O | F | $COCF_3$ | CN |
| F | Cl | $CF_2$ | $CF_2$ | O | $COCH_3$ | $COCF_3$ | CN |
| F | Cl | $CF_2$ | $CF_2$ | O | $NH_2$ | $C_2F_5$ | CN |

TABLE 143

| X | Y | $Z^1$ | $Z^2$ | $Z^3$ | $R^1$ | $R^2$ | $R^3$ |
|---|---|---|---|---|---|---|---|
| F | Cl | $CF_2$ | $CF_2$ | O | N = CHPh | $C_2F_5$ | CN |
| F | Cl | $CF_2$ | $CF_2$ | O | $CH_3$ | $C_2F_5$ | CN |
| F | Cl | $CF_2$ | $CF_2$ | O | $CF_3$ | $C_2F_5$ | CN |
| F | Cl | $CF_2$ | $CF_2$ | O | Cl | $C_2F_5$ | CN |
| F | Cl | $CF_2$ | $CF_2$ | O | F | $C_2F_5$ | CN |
| F | Cl | $CF_2$ | $CF_2$ | O | $COCH_3$ | $C_2F_5$ | CN |
| F | Cl | $CF_2$ | $CF_2$ | O | H | $C_2F_5$ | CN |
| F | Cl | $CF_2$ | $CF_2$ | O | $NH_2$ | $C_2F_5$ | CN |
| F | Cl | $CF_2$ | $CF_2$ | O | N = CHPh | $C_2F_5$ | CN |
| F | Cl | $CF_2$ | $CF_2$ | O | $CH_3$ | $C_2F_5$ | CN |
| F | Cl | $CF_2$ | $CF_2$ | O | $CF_3$ | $C_2F_5$ | CN |
| F | Cl | $CF_2$ | $CF_2$ | O | Cl | $C_2F_5$ | CN |
| F | Cl | $CF_2$ | $CF_2$ | O | F | $C_2F_5$ | CN |
| F | Cl | $CF_2$ | $CF_2$ | O | $COCH_3$ | $C_2F_5$ | CN |
| F | Cl | $CF_2$ | $CF_2$ | O | $NH_2$ | $SFCl_2$ | CN |
| F | Cl | $CF_2$ | $CF_2$ | O | N = CHPh | $SFCl_2$ | CN |
| F | Cl | $CF_2$ | $CF_2$ | O | $CH_3$ | $SFCl_2$ | CN |
| F | Cl | $CF_2$ | $CF_2$ | O | $CF_3$ | $SFCl_2$ | CN |
| F | Cl | $CF_2$ | $CF_2$ | O | Cl | $SFCl_2$ | CN |
| F | Cl | $CF_2$ | $CF_2$ | O | F | $SFCl_2$ | CN |
| F | Cl | $CF_2$ | $CF_2$ | O | $COCH_3$ | $SFCl_2$ | CN |
| F | Cl | $CF_2$ | $CF_2$ | O | H | $SFCl_2$ | CN |
| F | Cl | $CF_2$ | $CF_2$ | O | $NH_2$ | $SFCl_2$ | CN |
| F | Cl | $CF_2$ | $CF_2$ | O | N = CHPh | $SFCl_2$ | CN |
| F | Cl | $CF_2$ | $CF_2$ | O | $CH_3$ | $SFCl_2$ | CN |
| F | Cl | $CF_2$ | $CF_2$ | O | $CF_3$ | $SFCl_2$ | CN |

TABLE 144

| X | Y | $Z^1$ | $Z^2$ | $Z^3$ | $R^1$ | $R^2$ | $R^3$ |
|---|---|---|---|---|---|---|---|
| F | Cl | $CF_2$ | $CF_2$ | O | Cl | $SFCl_2$ | CN |
| F | Cl | $CF_2$ | $CF_2$ | O | F | $SFCl_2$ | CN |
| F | Cl | $CF_2$ | $CF_2$ | O | $COCH_3$ | $SFCl_2$ | CN |
| F | F | $CF_2$ | $CF_2$ | O | H | $SCF_3$ | H |
| F | F | $CF_2$ | $CF_2$ | O | $NH_2$ | $SCF_3$ | H |
| F | F | $CF_2$ | $CF_2$ | O | N = CHPh | $SCF_3$ | H |
| F | F | $CF_2$ | $CF_2$ | O | $CH_3$ | $SCF_3$ | H |
| F | F | $CF_2$ | $CF_2$ | O | $CF_3$ | $SCF_3$ | H |
| F | F | $CF_2$ | $CF_2$ | O | Cl | $SCF_3$ | H |
| F | F | $CF_2$ | $CF_2$ | O | F | $SCF_3$ | H |

TABLE 144-continued

| X | Y | Z¹ | Z² | Z³ | R¹ | R² | R³ |
|---|---|---|---|---|---|---|---|
| F | F | CF$_2$ | CF$_2$ | O | COCH$_3$ | SCF$_3$ | H |
| F | F | CF$_2$ | CF$_2$ | O | H | SOCF$_3$ | H |
| F | F | CF$_2$ | CF$_2$ | O | NH$_2$ | SOCF$_3$ | H |
| F | F | CF$_2$ | CF$_2$ | O | N = CHPh | SOCF$_3$ | H |
| F | F | CF$_2$ | CF$_2$ | O | CH$_3$ | SOCF$_3$ | H |
| F | F | CF$_2$ | CF$_2$ | O | CF$_3$ | SOCF$_3$ | H |
| F | F | CF$_2$ | CF$_2$ | O | Cl | SOCF$_3$ | H |
| F | F | CF$_2$ | CF$_2$ | O | F | SOCF$_3$ | H |
| F | F | CF$_2$ | CF$_2$ | O | COCH$_3$ | SOCF$_3$ | H |
| F | F | CF$_2$ | CF$_2$ | O | H | SO$_2$CF$_3$ | H |
| F | F | CF$_2$ | CF$_2$ | O | NH$_2$ | SO$_2$CF$_3$ | H |
| F | F | CF$_2$ | CF$_2$ | O | N = CHPh | SO$_2$CF$_3$ | H |
| F | F | CF$_2$ | CF$_2$ | O | CH$_3$ | SO$_2$CF$_3$ | H |
| F | F | CF$_2$ | CF$_2$ | O | CF$_3$ | SO$_2$CF$_3$ | H |
| F | F | CF$_2$ | CF$_2$ | O | Cl | SO$_2$CF$_3$ | H |
| F | F | CF$_2$ | CF$_2$ | O | F | SO$_2$CF$_3$ | H |

TABLE 145

| X | Y | Z¹ | Z² | Z³ | R¹ | R² | R³ |
|---|---|---|---|---|---|---|---|
| F | F | CF$_2$ | CF$_2$ | O | COCH$_3$ | SO$_2$CF$_3$ | H |
| F | F | CF$_2$ | CF$_2$ | O | H | SCF$_2$CH$_3$ | H |
| F | F | CF$_2$ | CF$_2$ | O | NH$_2$ | SCF$_2$CH$_3$ | H |
| F | F | CF$_2$ | CF$_2$ | O | N = CHPh | SCF$_2$CH$_3$ | H |
| F | F | CF$_2$ | CF$_2$ | O | CH$_3$ | SCF$_2$CH$_3$ | H |
| F | F | CF$_2$ | CF$_2$ | O | CF$_3$ | SCF$_2$CH$_3$ | H |
| F | F | CF$_2$ | CF$_2$ | O | Cl | SCF$_2$CH$_3$ | H |
| F | F | CF$_2$ | CF$_2$ | O | F | SCF$_2$CH$_3$ | H |
| F | F | CF$_2$ | CF$_2$ | O | COCH$_3$ | SCF$_2$CH$_3$ | H |
| F | F | CF$_2$ | CF$_2$ | O | H | SOCF$_2$CH$_3$ | H |
| F | F | CF$_2$ | CF$_2$ | O | NH$_2$ | SOCF$_2$CH$_3$ | H |
| F | F | CF$_2$ | CF$_2$ | O | N = CHPh | SOCF$_2$CH$_3$ | H |
| F | F | CF$_2$ | CF$_2$ | O | CH$_3$ | SOCF$_2$CH$_3$ | H |
| F | F | CF$_2$ | CF$_2$ | O | CF$_3$ | SOCF$_2$CH$_3$ | H |
| F | F | CF$_2$ | CF$_2$ | O | Cl | SOCF$_2$CH$_3$ | H |
| F | F | CF$_2$ | CF$_2$ | O | F | SOCF$_2$CH$_3$ | H |
| F | F | CF$_2$ | CF$_2$ | O | COCH$_3$ | SOCF$_2$CH$_3$ | H |
| F | F | CF$_2$ | CF$_2$ | O | H | SO$_2$CF$_2$CH$_3$ | H |
| F | F | CF$_2$ | CF$_2$ | O | NH$_2$ | SO$_2$CF$_2$CH$_3$ | H |
| F | F | CF$_2$ | CF$_2$ | O | N = CHPh | SO$_2$CF$_2$CH$_3$ | H |
| F | F | CF$_2$ | CF$_2$ | O | CH$_3$ | SO$_2$CF$_2$CH$_3$ | H |
| F | F | CF$_2$ | CF$_2$ | O | CF$_3$ | SO$_2$CF$_2$CH$_3$ | H |
| F | F | CF$_2$ | CF$_2$ | O | Cl | SO$_2$CF$_2$CH$_3$ | H |
| F | F | CF$_2$ | CF$_2$ | O | F | SO$_2$CF$_2$CH$_3$ | H |
| F | F | CF$_2$ | CF$_2$ | O | COCH$_3$ | SO$_2$CF$_2$CH$_3$ | H |
| F | F | CF$_2$ | CF$_2$ | O | NH$_2$ | COCF$_3$ | H |

TABLE 146

| X | Y | Z¹ | Z² | Z³ | R¹ | R² | R³ |
|---|---|---|---|---|---|---|---|
| F | F | CF$_2$ | CF$_2$ | O | N = CHPh | COCF$_3$ | H |
| F | F | CF$_2$ | CF$_2$ | O | CH$_3$ | COCF$_3$ | H |
| F | F | CF$_2$ | CF$_2$ | O | CF$_3$ | COCF$_3$ | H |
| F | F | CF$_2$ | CF$_2$ | O | Cl | COCF$_3$ | H |
| F | F | CF$_2$ | CF$_2$ | O | F | COCF$_3$ | H |
| F | F | CF$_2$ | CF$_2$ | O | COCH$_3$ | COCF$_3$ | H |
| F | F | CF$_2$ | CF$_2$ | O | H | COCF$_3$ | H |
| F | F | CF$_2$ | CF$_2$ | O | NH$_2$ | COCF$_3$ | H |
| F | F | CF$_2$ | CF$_2$ | O | N = CHPh | COCF$_3$ | H |
| F | F | CF$_2$ | CF$_2$ | O | CH$_3$ | COCF$_3$ | H |
| F | F | CF$_2$ | CF$_2$ | O | CF$_3$ | COCF$_3$ | H |
| F | F | CF$_2$ | CF$_2$ | O | Cl | COCF$_3$ | H |
| F | F | CF$_2$ | CF$_2$ | O | F | COCF$_3$ | H |
| F | F | CF$_2$ | CF$_2$ | O | COCH$_3$ | COCF$_3$ | H |
| F | F | CF$_2$ | CF$_2$ | O | NH$_2$ | C$_2$F$_5$ | H |
| F | F | CF$_2$ | CF$_2$ | O | N = CHPh | C$_2$F$_5$ | H |
| F | F | CF$_2$ | CF$_2$ | O | CH$_3$ | C$_2$F$_5$ | H |
| F | F | CF$_2$ | CF$_2$ | O | CF$_3$ | C$_2$F$_5$ | H |
| F | F | CF$_2$ | CF$_2$ | O | Cl | C$_2$F$_5$ | H |
| F | F | CF$_2$ | CF$_2$ | O | F | C$_2$F$_5$ | H |

TABLE 146-continued

| X | Y | Z¹ | Z² | Z³ | R¹ | R² | R³ |
|---|---|---|---|---|---|---|---|
| F | F | CF$_2$ | CF$_2$ | O | COCH$_3$ | C$_2$F$_5$ | H |
| F | F | CF$_2$ | CF$_2$ | O | H | C$_2$F$_5$ | H |
| F | F | CF$_2$ | CF$_2$ | O | NH$_2$ | C$_2$F$_5$ | H |
| F | F | CF$_2$ | CF$_2$ | O | N = CHPh | C$_2$F$_5$ | H |
| F | F | CF$_2$ | CF$_2$ | O | CH$_3$ | C$_2$F$_5$ | H |
| F | F | CF$_2$ | CF$_2$ | O | CF$_3$ | C$_2$F$_5$ | H |

TABLE 147

| X | Y | Z¹ | Z² | Z³ | R¹ | R² | R³ |
|---|---|---|---|---|---|---|---|
| F | F | CF$_2$ | CF$_2$ | O | Cl | C$_2$F$_5$ | H |
| F | F | CF$_2$ | CF$_2$ | O | F | C$_2$F$_5$ | H |
| F | F | CF$_2$ | CF$_2$ | O | COCH$_3$ | C$_2$F$_5$ | H |
| F | F | CF$_2$ | CF$_2$ | O | NH$_2$ | SFCl$_2$ | H |
| F | F | CF$_2$ | CF$_2$ | O | N = CHPh | SFCl$_2$ | H |
| F | F | CF$_2$ | CF$_2$ | O | CH$_3$ | SFCl$_2$ | H |
| F | F | CF$_2$ | CF$_2$ | O | CF$_3$ | SFCl$_2$ | H |
| F | F | CF$_2$ | CF$_2$ | O | Cl | SFCl$_2$ | H |
| F | F | CF$_2$ | CF$_2$ | O | F | SFCl$_2$ | H |
| F | F | CF$_2$ | CF$_2$ | O | COCH$_3$ | SFCl$_2$ | H |
| F | F | CF$_2$ | CF$_2$ | O | H | SFCl$_2$ | H |
| F | F | CF$_2$ | CF$_2$ | O | NH$_2$ | SFCl$_2$ | H |
| F | F | CF$_2$ | CF$_2$ | O | N = CHPh | SFCl$_2$ | H |
| F | F | CF$_2$ | CF$_2$ | O | CH$_3$ | SFCl$_2$ | H |
| F | F | CF$_2$ | CF$_2$ | O | CF$_3$ | SFCl$_2$ | H |
| F | F | CF$_2$ | CF$_2$ | O | Cl | SFCl$_2$ | H |
| F | F | CF$_2$ | CF$_2$ | O | F | SFCl$_2$ | H |
| F | F | CF$_2$ | CF$_2$ | O | COCH$_3$ | SFCl$_2$ | H |
| F | F | CF$_2$ | CF$_2$ | O | H | SCF$_3$ | CF$_3$ |
| F | F | CF$_2$ | CF$_2$ | O | NH$_2$ | SCF$_3$ | CF$_3$ |
| F | F | CF$_2$ | CF$_2$ | O | N = CHPh | SCF$_3$ | CF$_3$ |
| F | F | CF$_2$ | CF$_2$ | O | CH$_3$ | SCF$_3$ | CF$_3$ |
| F | F | CF$_2$ | CF$_2$ | O | CF$_3$ | SCF$_3$ | CF$_3$ |
| F | F | CF$_2$ | CF$_2$ | O | Cl | SCF$_3$ | CF$_3$ |
| F | F | CF$_2$ | CF$_2$ | O | F | SCF$_3$ | CF$_3$ |
| F | F | CF$_2$ | CF$_2$ | O | COCH$_3$ | SCF$_3$ | CF$_3$ |

TABLE 148

| X | Y | Z¹ | Z² | Z³ | R¹ | R² | R³ |
|---|---|---|---|---|---|---|---|
| F | F | CF$_2$ | CF$_2$ | O | H | SOCF$_3$ | CF$_3$ |
| F | F | CF$_2$ | CF$_2$ | O | NH$_2$ | SOCF$_3$ | CF$_3$ |
| F | F | CF$_2$ | CF$_2$ | O | N = CHPh | SOCF$_3$ | CF$_3$ |
| F | F | CF$_2$ | CF$_2$ | O | CH$_3$ | SOCF$_3$ | CF$_3$ |
| F | F | CF$_2$ | CF$_2$ | O | CF$_3$ | SOCF$_3$ | CF$_3$ |
| F | F | CF$_2$ | CF$_2$ | O | Cl | SOCF$_3$ | CF$_3$ |
| F | F | CF$_2$ | CF$_2$ | O | F | SOCF$_3$ | CF$_3$ |
| F | F | CF$_2$ | CF$_2$ | O | COCH$_3$ | SOCF$_3$ | CF$_3$ |
| F | F | CF$_2$ | CF$_2$ | O | H | SO$_2$CF$_3$ | CF$_3$ |
| F | F | CF$_2$ | CF$_2$ | O | NH$_2$ | SO$_2$CF$_3$ | CF$_3$ |
| F | F | CF$_2$ | CF$_2$ | O | N = CHPh | SO$_2$CF$_3$ | CF$_3$ |
| F | F | CF$_2$ | CF$_2$ | O | CH$_3$ | SO$_2$CF$_3$ | CF$_3$ |
| F | F | CF$_2$ | CF$_2$ | O | CF$_3$ | SO$_2$CF$_3$ | CF$_3$ |
| F | F | CF$_2$ | CF$_2$ | O | Cl | SO$_2$CF$_3$ | CF$_3$ |
| F | F | CF$_2$ | CF$_2$ | O | F | SO$_2$CF$_3$ | CF$_3$ |
| F | F | CF$_2$ | CF$_2$ | O | COCH$_3$ | SO$_2$CF$_3$ | CF$_3$ |
| F | F | CF$_2$ | CF$_2$ | O | H | SCF$_2$CH$_3$ | CF$_3$ |
| F | F | CF$_2$ | CF$_2$ | O | NH$_2$ | SCF$_2$CH$_3$ | CF$_3$ |
| F | F | CF$_2$ | CF$_2$ | O | N = CHPh | SCF$_2$CH$_3$ | CF$_3$ |
| F | F | CF$_2$ | CF$_2$ | O | CH$_3$ | SCF$_2$CH$_3$ | CF$_3$ |
| F | F | CF$_2$ | CF$_2$ | O | CF$_3$ | SCF$_2$CH$_3$ | CF$_3$ |
| F | F | CF$_2$ | CF$_2$ | O | Cl | SCF$_2$CH$_3$ | CF$_3$ |
| F | F | CF$_2$ | CF$_2$ | O | F | SCF$_2$CH$_3$ | CF$_3$ |
| F | F | CF$_2$ | CF$_2$ | O | COCH$_3$ | SCF$_2$CH$_3$ | CF$_3$ |
| F | F | CF$_2$ | CF$_2$ | O | H | SOCF$_2$CH$_3$ | CF$_3$ |
| F | F | CF$_2$ | CF$_2$ | O | NH$_2$ | SOCF$_2$CH$_3$ | CF$_3$ |

TABLE 149

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | N = CHPh | $SOCF_2CH_3$ | $CF_3$ |
| F | F | $CF_2$ | $CF_2$ | O | $CH_3$ | $SOCF_2CH_3$ | $CF_3$ |
| F | F | $CF_2$ | $CF_2$ | O | $CF_3$ | $SOCF_2CH_3$ | $CF_3$ |
| F | F | $CF_2$ | $CF_2$ | O | Cl | $SOCF_2CH_3$ | $CF_3$ |
| F | F | $CF_2$ | $CF_2$ | O | F | $SOCF_2CH_3$ | $CF_3$ |
| F | F | $CF_2$ | $CF_2$ | O | $COCH_3$ | $SOCF_2CH_3$ | $CF_3$ |
| F | F | $CF_2$ | $CF_2$ | O | H | $SO_2CF_2CH_3$ | $CF_3$ |
| F | F | $CF_2$ | $CF_2$ | O | $NH_2$ | $SO_2CF_2CH_3$ | $CF_3$ |
| F | F | $CF_2$ | $CF_2$ | O | N = CHPh | $SO_2CF_2CH_3$ | $CF_3$ |
| F | F | $CF_2$ | $CF_2$ | O | $CH_3$ | $SO_2CF_2CH_3$ | $CF_3$ |
| F | F | $CF_2$ | $CF_2$ | O | $CF_3$ | $SO_2CF_2CH_3$ | $CF_3$ |
| F | F | $CF_2$ | $CF_2$ | O | Cl | $SO_2CF_2CH_3$ | $CF_3$ |
| F | F | $CF_2$ | $CF_2$ | O | F | $SO_2CF_2CH_3$ | $CF_3$ |
| F | F | $CF_2$ | $CF_2$ | O | $COCH_3$ | $SO_2CF_2CH_3$ | $CF_3$ |
| F | F | $CF_2$ | $CF_2$ | O | $NH_2$ | $COCF_3$ | $CF_3$ |
| F | F | $CF_2$ | $CF_2$ | O | N = CHPh | $COCF_3$ | $CF_3$ |
| F | F | $CF_2$ | $CF_2$ | O | $CH_3$ | $COCF_3$ | $CF_3$ |
| F | F | $CF_2$ | $CF_2$ | O | $CF_3$ | $COCF_3$ | $CF_3$ |
| F | F | $CF_2$ | $CF_2$ | O | Cl | $COCF_3$ | $CF_3$ |
| F | F | $CF_2$ | $CF_2$ | O | F | $COCF_3$ | $CF_3$ |
| F | F | $CF_2$ | $CF_2$ | O | $COCH_3$ | $COCF_3$ | $CF_3$ |
| F | F | $CF_2$ | $CF_2$ | O | H | $COCF_3$ | $CF_3$ |
| F | F | $CF_2$ | $CF_2$ | O | $NH_2$ | $COCF_3$ | $CF_3$ |
| F | F | $CF_2$ | $CF_2$ | O | N = CHPh | $COCF_3$ | $CF_3$ |
| F | F | $CF_2$ | $CF_2$ | O | $CH_3$ | $COCF_3$ | $CF_3$ |
| F | F | $CF_2$ | $CF_2$ | O | $CF_3$ | $COCF_3$ | $CF_3$ |

TABLE 150

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | Cl | $COCF_3$ | $CF_3$ |
| F | F | $CF_2$ | $CF_2$ | O | F | $COCF_3$ | $CF_3$ |
| F | F | $CF_2$ | $CF_2$ | O | $COCH_3$ | $COCF_3$ | $CF_3$ |
| F | F | $CF_2$ | $CF_2$ | O | $NH_2$ | $C_2F_5$ | $CF_3$ |
| F | F | $CF_2$ | $CF_2$ | O | N = CHPh | $C_2F_5$ | $CF_3$ |
| F | F | $CF_2$ | $CF_2$ | O | $CH_3$ | $C_2F_5$ | $CF_3$ |
| F | F | $CF_2$ | $CF_2$ | O | $CF_3$ | $C_2F_5$ | $CF_3$ |
| F | F | $CF_2$ | $CF_2$ | O | Cl | $C_2F_5$ | $CF_3$ |
| F | F | $CF_2$ | $CF_2$ | O | F | $C_2F_5$ | $CF_3$ |
| F | F | $CF_2$ | $CF_2$ | O | $COCH_3$ | $C_2F_5$ | $CF_3$ |
| F | F | $CF_2$ | $CF_2$ | O | H | $C_2F_5$ | $CF_3$ |
| F | F | $CF_2$ | $CF_2$ | O | $NH_2$ | $C_2F_5$ | $CF_3$ |
| F | F | $CF_2$ | $CF_2$ | O | N = CHPh | $C_2F_5$ | $CF_3$ |
| F | F | $CF_2$ | $CF_2$ | O | $CH_3$ | $C_2F_5$ | $CF_3$ |
| F | F | $CF_2$ | $CF_2$ | O | $CF_3$ | $C_2F_5$ | $CF_3$ |
| F | F | $CF_2$ | $CF_2$ | O | Cl | $C_2F_5$ | $CF_3$ |
| F | F | $CF_2$ | $CF_2$ | O | F | $C_2F_5$ | $CF_3$ |
| F | F | $CF_2$ | $CF_2$ | O | $COCH_3$ | $C_2F_5$ | $CF_3$ |
| F | F | $CF_2$ | $CF_2$ | O | $NH_2$ | $SFCl_2$ | $CF_3$ |
| F | F | $CF_2$ | $CF_2$ | O | N = CHPh | $SFCl_2$ | $CF_3$ |
| F | F | $CF_2$ | $CF_2$ | O | $CH_3$ | $SFCl_2$ | $CF_3$ |
| F | F | $CF_2$ | $CF_2$ | O | $CF_3$ | $SFCl_2$ | $CF_3$ |
| F | F | $CF_2$ | $CF_2$ | O | Cl | $SFCl_2$ | $CF_3$ |
| F | F | $CF_2$ | $CF_2$ | O | F | $SFCl_2$ | $CF_3$ |
| F | F | $CF_2$ | $CF_2$ | O | $COCH_3$ | $SFCl_2$ | $CF_3$ |
| F | F | $CF_2$ | $CF_2$ | O | H | $SFCl_2$ | $CF_3$ |

TABLE 151

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | $NH_2$ | $SFCl_2$ | $CF_3$ |
| F | F | $CF_2$ | $CF_2$ | O | N=CHPh | $SFCl_2$ | $CF_3$ |
| F | F | $CF_2$ | $CF_2$ | O | $CH_3$ | $SFCl_2$ | $CF_3$ |
| F | F | $CF_2$ | $CF_2$ | O | $CF_3$ | $SFCl_2$ | $CF_3$ |
| F | F | $CF_2$ | $CF_2$ | O | Cl | $SFCl_2$ | $CF_3$ |
| F | F | $CF_2$ | $CF_2$ | O | F | $SFCl_2$ | $CF_3$ |
| F | F | $CF_2$ | $CF_2$ | O | $COCH_3$ | $SFCl_2$ | $CF_3$ |
| F | F | $CF_2$ | $CF_2$ | O | H | $SCF_3$ | $C_2F_5$ |
| F | F | $CF_2$ | $CF_2$ | O | $NH_2$ | $SCF_3$ | $C_2F_5$ |
| F | F | $CF_2$ | $CF_2$ | O | N=CHPh | $SCF_3$ | $C_2F_5$ |
| F | F | $CF_2$ | $CF_2$ | O | $CH_3$ | $SCF_3$ | $C_2F_5$ |
| F | F | $CF_2$ | $CF_2$ | O | $CF_3$ | $SCF_3$ | $C_2F_5$ |
| F | F | $CF_2$ | $CF_2$ | O | Cl | $SCF_3$ | $C_2F_5$ |
| F | F | $CF_2$ | $CF_2$ | O | F | $SCF_3$ | $C_2F_5$ |
| F | F | $CF_2$ | $CF_2$ | O | $COCH_3$ | $SCF_3$ | $C_2F_5$ |
| F | F | $CF_2$ | $CF_2$ | O | H | $SOCF_3$ | $C_2F_5$ |
| F | F | $CF_2$ | $CF_2$ | O | $NH_2$ | $SOCF_3$ | $C_2F_5$ |
| F | F | $CF_2$ | $CF_2$ | O | N=CHPh | $SOCF_3$ | $C_2F_5$ |
| F | F | $CF_2$ | $CF_2$ | O | $CH_3$ | $SOCF_3$ | $C_2F_5$ |
| F | F | $CF_2$ | $CF_2$ | O | $CF_3$ | $SOCF_3$ | $C_2F_5$ |
| F | F | $CF_2$ | $CF_2$ | O | Cl | $SOCF_3$ | $C_2F_5$ |
| F | F | $CF_2$ | $CF_2$ | O | F | $SOCF_3$ | $C_2F_5$ |
| F | F | $CF_2$ | $CF_2$ | O | $COCH_3$ | $SOCF_3$ | $C_2F_5$ |
| F | F | $CF_2$ | $CF_2$ | O | H | $SO_2CF_3$ | $C_2F_5$ |
| F | F | $CF_2$ | $CF_2$ | O | $NH_2$ | $SO_2CF_3$ | $C_2F_5$ |
| F | F | $CF_2$ | $CF_2$ | O | N=CHPh | $SO_2CF_3$ | $C_2F_5$ |

TABLE 152

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | $CH_3$ | $SO_2CF_3$ | $C_2F_5$ |
| F | F | $CF_2$ | $CF_2$ | O | $CF_3$ | $SO_2CF_3$ | $C_2F_5$ |
| F | F | $CF_2$ | $CF_2$ | O | Cl | $SO_2CF_3$ | $C_2F_5$ |
| F | F | $CF_2$ | $CF_2$ | O | F | $SO_2CF_3$ | $C_2F_5$ |
| F | F | $CF_2$ | $CF_2$ | O | $COCH_3$ | $SO_2CF_3$ | $C_2F_5$ |
| F | F | $CF_2$ | $CF_2$ | O | H | $SCF_2CH_3$ | $C_2F_5$ |
| F | F | $CF_2$ | $CF_2$ | O | $NH_2$ | $SCF_2CH_3$ | $C_2F_5$ |
| F | F | $CF_2$ | $CF_2$ | O | N=CHPh | $SCF_2CH_3$ | $C_2F_5$ |
| F | F | $CF_2$ | $CF_2$ | O | $CH_3$ | $SCF_2CH_3$ | $C_2F_5$ |
| F | F | $CF_2$ | $CF_2$ | O | $CF_3$ | $SCF_2CH_3$ | $C_2F_5$ |
| F | F | $CF_2$ | $CF_2$ | O | Cl | $SCF_2CH_3$ | $C_2F_5$ |
| F | F | $CF_2$ | $CF_2$ | O | F | $SCF_2CH_3$ | $C_2F_5$ |
| F | F | $CF_2$ | $CF_2$ | O | $COCH_3$ | $SCF_2CH_3$ | $C_2F_5$ |
| F | F | $CF_2$ | $CF_2$ | O | H | $SOCF_2CH_3$ | $C_2F_5$ |
| F | F | $CF_2$ | $CF_2$ | O | $NH_2$ | $SOCF_2CH_3$ | $C_2F_5$ |
| F | F | $CF_2$ | $CF_2$ | O | N=CHPh | $SOCF_2CH_3$ | $C_2F_5$ |
| F | F | $CF_2$ | $CF_2$ | O | $CH_3$ | $SOCF_2CH_3$ | $C_2F_5$ |
| F | F | $CF_2$ | $CF_2$ | O | $CF_3$ | $SOCF_2CH_3$ | $C_2F_5$ |
| F | F | $CF_2$ | $CF_2$ | O | Cl | $SOCF_2CH_3$ | $C_2F_5$ |
| F | F | $CF_2$ | $CF_2$ | O | F | $SOCF_2CH_3$ | $C_2F_5$ |
| F | F | $CF_2$ | $CF_2$ | O | $COCH_3$ | $SOCF_2CH_3$ | $C_2F_5$ |
| F | F | $CF_2$ | $CF_2$ | O | H | $SO_2CF_2CH_3$ | $C_2F_5$ |
| F | F | $CF_2$ | $CF_2$ | O | $NH_2$ | $SO_2CF_2CH_3$ | $C_2F_5$ |
| F | F | $CF_2$ | $CF_2$ | O | N=CHPh | $SO_2CF_2CH_3$ | $C_2F_5$ |
| F | F | $CF_2$ | $CF_2$ | O | $CH_3$ | $SO_2CF_2CH_3$ | $C_2F_5$ |
| F | F | $CF_2$ | $CF_2$ | O | $CF_3$ | $SO_2CF_2CH_3$ | $C_2F_5$ |

TABLE 153

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | Cl | $SO_2CF_2CH_3$ | $C_2F_5$ |
| F | F | $CF_2$ | $CF_2$ | O | F | $SO_2CF_2CH_3$ | $C_2F_5$ |
| F | F | $CF_2$ | $CF_2$ | O | $COCH_3$ | $SO_2CF_2CH_3$ | $C_2F_5$ |
| F | F | $CF_2$ | $CF_2$ | O | $NH_2$ | $COCF_3$ | $C_2F_5$ |
| F | F | $CF_2$ | $CF_2$ | O | N=CHPh | $COCF_3$ | $C_2F_5$ |
| F | F | $CF_2$ | $CF_2$ | O | $CH_3$ | $COCF_3$ | $C_2F_5$ |
| F | F | $CF_2$ | $CF_2$ | O | $CF_3$ | $COCF_3$ | $C_2F_5$ |
| F | F | $CF_2$ | $CF_2$ | O | Cl | $COCF_3$ | $C_2F_5$ |
| F | F | $CF_2$ | $CF_2$ | O | F | $COCF_3$ | $C_2F_5$ |
| F | F | $CF_2$ | $CF_2$ | O | $COCH_3$ | $COCF_3$ | $C_2F_5$ |
| F | F | $CF_2$ | $CF_2$ | O | H | $COCF_3$ | $C_2F_5$ |
| F | F | $CF_2$ | $CF_2$ | O | $NH_2$ | $COCF_3$ | $C_2F_5$ |
| F | F | $CF_2$ | $CF_2$ | O | N=CHPh | $COCF_3$ | $C_2F_5$ |
| F | F | $CF_2$ | $CF_2$ | O | $CH_3$ | $COCF_3$ | $C_2F_5$ |
| F | F | $CF_2$ | $CF_2$ | O | $CF_3$ | $COCF_3$ | $C_2F_5$ |
| F | F | $CF_2$ | $CF_2$ | O | Cl | $COCF_3$ | $C_2F_5$ |
| F | F | $CF_2$ | $CF_2$ | O | F | $COCF_3$ | $C_2F_5$ |
| F | F | $CF_2$ | $CF_2$ | O | $COCH_3$ | $COCF_3$ | $C_2F_5$ |
| F | F | $CF_2$ | $CF_2$ | O | $NH_2$ | $C_2F_5$ | $C_2F_5$ |
| F | F | $CF_2$ | $CF_2$ | O | N=CHPh | $C_2F_5$ | $C_2F_5$ |

TABLE 153-continued

| X | Y | Z¹ | Z² | Z³ | R¹ | R² | R³ |
|---|---|---|---|---|---|---|---|
| F | F | $CF_2$ | $CF_2$ | O | $CH_3$ | $C_2F_5$ | $C_2F_5$ |
| F | F | $CF_2$ | $CF_2$ | O | $CF_3$ | $C_2F_5$ | $C_2F_5$ |
| F | F | $CF_2$ | $CF_2$ | O | Cl | $C_2F_5$ | $C_2F_5$ |
| F | F | $CF_2$ | $CF_2$ | O | F | $C_2F_5$ | $C_2F_5$ |
| F | F | $CF_2$ | $CF_2$ | O | $COCH_3$ | $C_2F_5$ | $C_2F_5$ |
| F | F | $CF_2$ | $CF_2$ | O | H | $C_2F_5$ | $C_2F_5$ |

TABLE 154

| X | Y | Z¹ | Z² | Z³ | R¹ | R² | R³ |
|---|---|---|---|---|---|---|---|
| F | F | $CF_2$ | $CF_2$ | O | $NH_2$ | $C_2F_5$ | $C_2F_5$ |
| F | F | $CF_2$ | $CF_2$ | O | N=CHPh | $C_2F_5$ | $C_2F_5$ |
| F | F | $CF_2$ | $CF_2$ | O | $CH_3$ | $C_2F_5$ | $C_2F_5$ |
| F | F | $CF_2$ | $CF_2$ | O | $CF_3$ | $C_2F_5$ | $C_2F_5$ |
| F | F | $CF_2$ | $CF_2$ | O | Cl | $C_2F_5$ | $C_2F_5$ |
| F | F | $CF_2$ | $CF_2$ | O | F | $C_2F_5$ | $C_2F_5$ |
| F | F | $CF_2$ | $CF_2$ | O | $COCH_3$ | $C_2F_5$ | $C_2F_5$ |
| F | F | $CF_2$ | $CF_2$ | O | $NH_2$ | $SFCl_2$ | $C_2F_5$ |
| F | F | $CF_2$ | $CF_2$ | O | N=CHPh | $SFCl_2$ | $C_2F_5$ |
| F | F | $CF_2$ | $CF_2$ | O | $CH_3$ | $SFCl_2$ | $C_2F_5$ |
| F | F | $CF_2$ | $CF_2$ | O | $CF_3$ | $SFCl_2$ | $C_2F_5$ |
| F | F | $CF_2$ | $CF_2$ | O | Cl | $SFCl_2$ | $C_2F_5$ |
| F | F | $CF_2$ | $CF_2$ | O | F | $SFCl_2$ | $C_2F_5$ |
| F | F | $CF_2$ | $CF_2$ | O | $COCH_3$ | $SFCl_2$ | $C_2F_5$ |
| F | F | $CF_2$ | $CF_2$ | O | H | $SFCl_2$ | $C_2F_5$ |
| F | F | $CF_2$ | $CF_2$ | O | $NH_2$ | $SFCl_2$ | $C_2F_5$ |
| F | F | $CF_2$ | $CF_2$ | O | N=CHPh | $SFCl_2$ | $C_2F_5$ |
| F | F | $CF_2$ | $CF_2$ | O | $CH_3$ | $SFCl_2$ | $C_2F_5$ |
| F | F | $CF_2$ | $CF_2$ | O | $CF_3$ | $SFCl_2$ | $C_2F_5$ |
| F | F | $CF_2$ | $CF_2$ | O | Cl | $SFCl_2$ | $C_2F_5$ |
| F | F | $CF_2$ | $CF_2$ | O | F | $SFCl_2$ | $C_2F_5$ |
| F | F | $CF_2$ | $CF_2$ | O | $COCH_3$ | $SFCl_2$ | $C_2F_5$ |
| F | F | $CF_2$ | $CF_2$ | O | H | $SCF_3$ | $CSNH_2$ |
| F | F | $CF_2$ | $CF_2$ | O | $NH_2$ | $SCF_3$ | $CSNH_2$ |
| F | F | $CF_2$ | $CF_2$ | O | N=CHPh | $SCF_3$ | $CSNH_2$ |
| F | F | $CF_2$ | $CF_2$ | O | $CH_3$ | $SCF_3$ | $CSNH_2$ |

TABLE 155

| X | Y | Z¹ | Z² | Z³ | R¹ | R² | R³ |
|---|---|---|---|---|---|---|---|
| F | F | $CF_2$ | $CF_2$ | O | $CF_3$ | $SCF_3$ | $CSNH_2$ |
| F | F | $CF_2$ | $CF_2$ | O | Cl | $SCF_3$ | $CSNH_2$ |
| F | F | $CF_2$ | $CF_2$ | O | F | $SCF_3$ | $CSNH_2$ |
| F | F | $CF_2$ | $CF_2$ | O | $COCH_3$ | $SCF_3$ | $CSNH_2$ |
| F | F | $CF_2$ | $CF_2$ | O | H | $SOCF_3$ | $CSNH_2$ |
| F | F | $CF_2$ | $CF_2$ | O | $NH_2$ | $SOCF_3$ | $CSNH_2$ |
| F | F | $CF_2$ | $CF_2$ | O | N=CHPh | $SOCF_3$ | $CSNH_2$ |
| F | F | $CF_2$ | $CF_2$ | O | $CH_3$ | $SOCF_3$ | $CSNH_2$ |
| F | F | $CF_2$ | $CF_2$ | O | $CF_3$ | $SOCF_3$ | $CSNH_2$ |
| F | F | $CF_2$ | $CF_2$ | O | Cl | $SOCF_3$ | $CSNH_2$ |
| F | F | $CF_2$ | $CF_2$ | O | F | $SOCF_3$ | $CSNH_2$ |
| F | F | $CF_2$ | $CF_2$ | O | $COCH_3$ | $SOCF_3$ | $CSNH_2$ |
| F | F | $CF_2$ | $CF_2$ | O | H | $SO_2CF_3$ | $CSNH_2$ |
| F | F | $CF_2$ | $CF_2$ | O | $NH_2$ | $SO_2CF_3$ | $CSNH_2$ |
| F | F | $CF_2$ | $CF_2$ | O | N=CHPh | $SO_2CF_3$ | $CSNH_2$ |
| F | F | $CF_2$ | $CF_2$ | O | $CH_3$ | $SO_2CF_3$ | $CSNH_2$ |
| F | F | $CF_2$ | $CF_2$ | O | $CF_3$ | $SO_2CF_3$ | $CSNH_2$ |
| F | F | $CF_2$ | $CF_2$ | O | Cl | $SO_2CF_3$ | $CSNH_2$ |
| F | F | $CF_2$ | $CF_2$ | O | F | $SO_2CF_3$ | $CSNH_2$ |
| F | F | $CF_2$ | $CF_2$ | O | $COCH_3$ | $SO_2CF_3$ | $CSNH_2$ |
| F | F | $CF_2$ | $CF_2$ | O | H | $SCF_2CH_3$ | $CSNH_2$ |
| F | F | $CF_2$ | $CF_2$ | O | $NH_2$ | $SCF_2CH_3$ | $CSNH_2$ |
| F | F | $CF_2$ | $CF_2$ | O | N=CHPh | $SCF_2CH_3$ | $CSNH_2$ |
| F | F | $CF_2$ | $CF_2$ | O | $CH_3$ | $SCF_2CH_3$ | $CSNH_2$ |
| F | F | $CF_2$ | $CF_2$ | O | $CF_3$ | $SCF_2CH_3$ | $CSNH_2$ |
| F | F | $CF_2$ | $CF_2$ | O | Cl | $SCF_2CH_3$ | $CSNH_2$ |

TABLE 156

| X | Y | Z¹ | Z² | Z³ | R¹ | R² | R³ |
|---|---|---|---|---|---|---|---|
| F | F | $CF_2$ | $CF_2$ | O | F | $SCF_2CH_3$ | $CSNH_2$ |
| F | F | $CF_2$ | $CF_2$ | O | $COCH_3$ | $SCF_2CH_3$ | $CSNH_2$ |
| F | F | $CF_2$ | $CF_2$ | O | H | $SOCF_2CH_3$ | $CSNH_2$ |
| F | F | $CF_2$ | $CF_2$ | O | $NH_2$ | $SOCF_2CH_3$ | $CSNH_2$ |
| F | F | $CF_2$ | $CF_2$ | O | N=CHPh | $SOCF_2CH_3$ | $CSNH_2$ |
| F | F | $CF_2$ | $CF_2$ | O | $CH_3$ | $SOCF_2CH_3$ | $CSNH_2$ |
| F | F | $CF_2$ | $CF_2$ | O | $CF_3$ | $SOCF_2CH_3$ | $CSNH_2$ |
| F | F | $CF_2$ | $CF_2$ | O | Cl | $SOCF_2CH_3$ | $CSNH_2$ |
| F | F | $CF_2$ | $CF_2$ | O | F | $SOCF_2CH_3$ | $CSNH_2$ |
| F | F | $CF_2$ | $CF_2$ | O | $COCH_3$ | $SOCF_2CH_3$ | $CSNH_2$ |
| F | F | $CF_2$ | $CF_2$ | O | H | $SO_2CF_2CH_3$ | $CSNH_2$ |
| F | F | $CF_2$ | $CF_2$ | O | $NH_2$ | $SO_2CF_2CH_3$ | $CSNH_2$ |
| F | F | $CF_2$ | $CF_2$ | O | N=CHPh | $SO_2CF_2CH_3$ | $CSNH_2$ |
| F | F | $CF_2$ | $CF_2$ | O | $CH_3$ | $SO_2CF_2CH_3$ | $CSNH_2$ |
| F | F | $CF_2$ | $CF_2$ | O | $CF_3$ | $SO_2CF_2CH_3$ | $CSNH_2$ |
| F | F | $CF_2$ | $CF_2$ | O | Cl | $SO_2CF_2CH_3$ | $CSNH_2$ |
| F | F | $CF_2$ | $CF_2$ | O | F | $SO_2CF_2CH_3$ | $CSNH_2$ |
| F | F | $CF_2$ | $CF_2$ | O | $COCH_3$ | $SO_2CF_2CH_3$ | $CSNH_2$ |
| F | F | $CF_2$ | $CF_2$ | O | $NH_2$ | $COCF_3$ | $CSNH_2$ |
| F | F | $CF_2$ | $CF_2$ | O | N=CHPh | $COCF_3$ | $CSNH_2$ |
| F | F | $CF_2$ | $CF_2$ | O | $CH_3$ | $COCF_3$ | $CSNH_2$ |
| F | F | $CF_2$ | $CF_2$ | O | $CF_3$ | $COCF_3$ | $CSNH_2$ |
| F | F | $CF_2$ | $CF_2$ | O | Cl | $COCF_3$ | $CSNH_2$ |
| F | F | $CF_2$ | $CF_2$ | O | F | $COCF_3$ | $CSNH_2$ |
| F | F | $CF_2$ | $CF_2$ | O | $COCH_3$ | $COCF_3$ | $CSNH_2$ |
| F | F | $CF_2$ | $CF_2$ | O | H | $COCF_3$ | $CSNH_2$ |

TABLE 157

| X | Y | Z¹ | Z² | Z³ | R¹ | R² | R³ |
|---|---|---|---|---|---|---|---|
| F | F | $CF_2$ | $CF_2$ | O | $NH_2$ | $COCF_3$ | $CSNH_2$ |
| F | F | $CF_2$ | $CF_2$ | O | N=CHPh | $COCF_3$ | $CSNH_2$ |
| F | F | $CF_2$ | $CF_2$ | O | $CH_3$ | $COCF_3$ | $CSNH_2$ |
| F | F | $CF_2$ | $CF_2$ | O | $CF_3$ | $COCF_3$ | $CSNH_2$ |
| F | F | $CF_2$ | $CF_2$ | O | Cl | $COCF_3$ | $CSNH_2$ |
| F | F | $CF_2$ | $CF_2$ | O | F | $COCF_3$ | $CSNH_2$ |
| F | F | $CF_2$ | $CF_2$ | O | $COCH_3$ | $COCF_3$ | $CSNH_2$ |
| F | F | $CF_2$ | $CF_2$ | O | $NH_2$ | $C_2F_5$ | $CSNH_2$ |
| F | F | $CF_2$ | $CF_2$ | O | N=CHPh | $C_2F_5$ | $CSNH_2$ |
| F | F | $CF_2$ | $CF_2$ | O | $CH_3$ | $C_2F_5$ | $CSNH_2$ |
| F | F | $CF_2$ | $CF_2$ | O | $CF_3$ | $C_2F_5$ | $CSNH_2$ |
| F | F | $CF_2$ | $CF_2$ | O | Cl | $C_2F_5$ | $CSNH_2$ |
| F | F | $CF_2$ | $CF_2$ | O | F | $C_2F_5$ | $CSNH_2$ |
| F | F | $CF_2$ | $CF_2$ | O | $COCH_3$ | $C_2F_5$ | $CSNH_2$ |
| F | F | $CF_2$ | $CF_2$ | O | H | $C_2F_5$ | $CSNH_2$ |
| F | F | $CF_2$ | $CF_2$ | O | $NH_2$ | $C_2F_5$ | $CSNH_2$ |
| F | F | $CF_2$ | $CF_2$ | O | N=CHPh | $C_2F_5$ | $CSNH_2$ |
| F | F | $CF_2$ | $CF_2$ | O | $CH_3$ | $C_2F_5$ | $CSNH_2$ |
| F | F | $CF_2$ | $CF_2$ | O | $CF_3$ | $C_2F_5$ | $CSNH_2$ |
| F | F | $CF_2$ | $CF_2$ | O | Cl | $C_2F_5$ | $CSNH_2$ |
| F | F | $CF_2$ | $CF_2$ | O | F | $C_2F_5$ | $CSNH_2$ |
| F | F | $CF_2$ | $CF_2$ | O | $COCH_3$ | $C_2F_5$ | $CSNH_2$ |
| F | F | $CF_2$ | $CF_2$ | O | $NH_2$ | $SFCl_2$ | $CSNH_2$ |
| F | F | $CF_2$ | $CF_2$ | O | N=CHPh | $SFCl_2$ | $CSNH_2$ |
| F | F | $CF_2$ | $CF_2$ | O | $CH_3$ | $SFCl_2$ | $CSNH_2$ |
| F | F | $CF_2$ | $CF_2$ | O | $CF_3$ | $SFCl_2$ | $CSNH_2$ |

TABLE 158

| X | Y | Z¹ | Z² | Z³ | R¹ | R² | R³ |
|---|---|---|---|---|---|---|---|
| F | F | $CF_2$ | $CF_2$ | O | Cl | $SFCl_2$ | $CSNH_2$ |
| F | F | $CF_2$ | $CF_2$ | O | F | $SFCl_2$ | $CSNH_2$ |
| F | F | $CF_2$ | $CF_2$ | O | $COCH_3$ | $SFCl_2$ | $CSNH_2$ |
| F | F | $CF_2$ | $CF_2$ | O | H | $SFCl_2$ | $CSNH_2$ |
| F | F | $CF_2$ | $CF_2$ | O | $NH_2$ | $SFCl_2$ | $CSNH_2$ |
| F | F | $CF_2$ | $CF_2$ | O | N=CHPh | $SFCl_2$ | $CSNH_2$ |
| F | F | $CF_2$ | $CF_2$ | O | $CH_3$ | $SFCl_2$ | $CSNH_2$ |
| F | F | $CF_2$ | $CF_2$ | O | $CF_3$ | $SFCl_2$ | $CSNH_2$ |
| F | F | $CF_2$ | $CF_2$ | O | Cl | $SFCl_2$ | $CSNH_2$ |
| F | F | $CF_2$ | $CF_2$ | O | F | $SFCl_2$ | $CSNH_2$ |

TABLE 158-continued

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | $COCH_3$ | $SFCl_2$ | $CSNH_2$ |
| F | F | $CF_2$ | $CF_2$ | O | H | $SCF_3$ | CN |
| F | F | $CF_2$ | $CF_2$ | O | $NH_2$ | $SCF_3$ | CN |
| F | F | $CF_2$ | $CF_2$ | O | N=CHPh | $SCF_3$ | CN |
| F | F | $CF_2$ | $CF_2$ | O | $CH_3$ | $SCF_3$ | CN |
| F | F | $CF_2$ | $CF_2$ | O | $CF_3$ | $SCF_3$ | CN |
| F | F | $CF_2$ | $CF_2$ | O | Cl | $SCF_3$ | CN |
| F | F | $CF_2$ | $CF_2$ | O | F | $SCF_3$ | CN |
| F | F | $CF_2$ | $CF_2$ | O | $COCH_3$ | $SCF_3$ | CN |
| F | F | $CF_2$ | $CF_2$ | O | H | $SOCF_3$ | CN |
| F | F | $CF_2$ | $CF_2$ | O | $NH_2$ | $SOCF_3$ | CN |
| F | F | $CF_2$ | $CF_2$ | O | N=CHPh | $SOCF_3$ | CN |
| F | F | $CF_2$ | $CF_2$ | O | $CH_3$ | $SOCF_3$ | CN |
| F | F | $CF_2$ | $CF_2$ | O | $CF_3$ | $SOCF_3$ | CN |
| F | F | $CF_2$ | $CF_2$ | O | Cl | $SOCF_3$ | CN |
| F | F | $CF_2$ | $CF_2$ | O | F | $SOCF_3$ | CN |

TABLE 159

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | $COCH_3$ | $SOCF_3$ | CN |
| F | F | $CF_2$ | $CF_2$ | O | H | $SO_2CF_3$ | CN |
| F | F | $CF_2$ | $CF_2$ | O | $NH_2$ | $SO_2CF_3$ | CN |
| F | F | $CF_2$ | $CF_2$ | O | N=CHPh | $SO_2CF_3$ | CN |
| F | F | $CF_2$ | $CF_2$ | O | $CH_3$ | $SO_2CF_3$ | CN |
| F | F | $CF_2$ | $CF_2$ | O | $CF_3$ | $SO_2CF_3$ | CN |
| F | F | $CF_2$ | $CF_2$ | O | Cl | $SO_2CF_3$ | CN |
| F | F | $CF_2$ | $CF_2$ | O | F | $SO_2CF_3$ | CN |
| F | F | $CF_2$ | $CF_2$ | O | $COCH_3$ | $SO_2CF_3$ | CN |
| F | F | $CF_2$ | $CF_2$ | O | H | $SCF_2CH_3$ | CN |
| F | F | $CF_2$ | $CF_2$ | O | $NH_2$ | $SCF_2CH_3$ | CN |
| F | F | $CF_2$ | $CF_2$ | O | N=CHPh | $SCF_2CH_3$ | CN |
| F | F | $CF_2$ | $CF_2$ | O | $CH_3$ | $SCF_2CH_3$ | CN |
| F | F | $CF_2$ | $CF_2$ | O | $CF_3$ | $SCF_2CH_3$ | CN |
| F | F | $CF_2$ | $CF_2$ | O | Cl | $SCF_2CH_3$ | CN |
| F | F | $CF_2$ | $CF_2$ | O | F | $SCF_2CH_3$ | CN |
| F | F | $CF_2$ | $CF_2$ | O | $COCH_3$ | $SCF_2CH_3$ | CN |
| F | F | $CF_2$ | $CF_2$ | O | H | $SOCF_2CH_3$ | CN |
| F | F | $CF_2$ | $CF_2$ | O | $NH_2$ | $SOCF_2CH_3$ | CN |
| F | F | $CF_2$ | $CF_2$ | O | N=CHPh | $SOCF_2CH_3$ | CN |
| F | F | $CF_2$ | $CF_2$ | O | $CH_3$ | $SOCF_2CH_3$ | CN |
| F | F | $CF_2$ | $CF_2$ | O | $CF_3$ | $SOCF_2CH_3$ | CN |
| F | F | $CF_2$ | $CF_2$ | O | Cl | $SOCF_2CH_3$ | CN |
| F | F | $CF_2$ | $CF_2$ | O | F | $SOCF_2CH_3$ | CN |
| F | F | $CF_2$ | $CF_2$ | O | $COCH_3$ | $SOCF_2CH_3$ | CN |
| F | F | $CF_2$ | $CF_2$ | O | H | $SO_2CF_2CH_3$ | CN |

TABLE 160

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | $NH_2$ | $SO_2CF_2CH_3$ | CN |
| F | F | $CF_2$ | $CF_2$ | O | N=CHPh | $SO_2CF_2CH_3$ | CN |
| F | F | $CF_2$ | $CF_2$ | O | $CH_3$ | $SO_2CF_2CH_3$ | CN |
| F | F | $CF_2$ | $CF_2$ | O | $CF_3$ | $SO_2CF_2CH_3$ | CN |
| F | F | $CF_2$ | $CF_2$ | O | Cl | $SO_2CF_2CH_3$ | CN |
| F | F | $CF_2$ | $CF_2$ | O | F | $SO_2CF_2CH_3$ | CN |
| F | F | $CF_2$ | $CF_2$ | O | $COCH_3$ | $SO_2CF_2CH_3$ | CN |
| F | F | $CF_2$ | $CF_2$ | O | $NH_2$ | $COCF_3$ | CN |
| F | F | $CF_2$ | $CF_2$ | O | N=CHPh | $COCF_3$ | CN |
| F | F | $CF_2$ | $CF_2$ | O | $CH_3$ | $COCF_3$ | CN |
| F | F | $CF_2$ | $CF_2$ | O | $CF_3$ | $COCF_3$ | CN |
| F | F | $CF_2$ | $CF_2$ | O | Cl | $COCF_3$ | CN |
| F | F | $CF_2$ | $CF_2$ | O | F | $COCF_3$ | CN |
| F | F | $CF_2$ | $CF_2$ | O | $COCH_3$ | $COCF_3$ | CN |
| F | F | $CF_2$ | $CF_2$ | O | H | $COCF_3$ | CN |
| F | F | $CF_2$ | $CF_2$ | O | $NH_2$ | $COCF_3$ | CN |
| F | F | $CF_2$ | $CF_2$ | O | N=CHPh | $COCF_3$ | CN |
| F | F | $CF_2$ | $CF_2$ | O | $CH_3$ | $COCF_3$ | CN |
| F | F | $CF_2$ | $CF_2$ | O | $CF_3$ | $COCF_3$ | CN |
| F | F | $CF_2$ | $CF_2$ | O | Cl | $COCF_3$ | CN |

TABLE 160-continued

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | F | $COCF_3$ | CN |
| F | F | $CF_2$ | $CF_2$ | O | $COCH_3$ | $COCF_3$ | CN |
| F | F | $CF_2$ | $CF_2$ | O | $NH_2$ | $C_2F_5$ | CN |
| F | F | $CF_2$ | $CF_2$ | O | N=CHPh | $C_2F_5$ | CN |
| F | F | $CF_2$ | $CF_2$ | O | $CH_3$ | $C_2F_5$ | CN |
| F | F | $CF_2$ | $CF_2$ | O | $CF_3$ | $C_2F_5$ | CN |

TABLE 161

| X | Y | $Z^1$ | $Z^2$ | $Z^3$ | $R^1$ | $R^2$ | $R^3$ |
|---|---|---|---|---|---|---|---|
| F | F | $CF_2$ | $CF_2$ | O | Cl | $C_2F_5$ | CN |
| F | F | $CF_2$ | $CF_2$ | O | F | $C_2F_5$ | CN |
| F | F | $CF_2$ | $CF_2$ | O | $COCH_3$ | $C_2F_5$ | CN |
| F | F | $CF_2$ | $CF_2$ | O | H | $C_2F_5$ | CN |
| F | F | $CF_2$ | $CF_2$ | O | $NH_2$ | $C_2F_5$ | CN |
| F | F | $CF_2$ | $CF_2$ | O | N=CHPh | $C_2F_5$ | CN |
| F | F | $CF_2$ | $CF_2$ | O | $CH_3$ | $C_2F_5$ | CN |
| F | F | $CF_2$ | $CF_2$ | O | $CF_3$ | $C_2F_5$ | CN |
| F | F | $CF_2$ | $CF_2$ | O | Cl | $C_2F_5$ | CN |
| F | F | $CF_2$ | $CF_2$ | O | F | $C_2F_5$ | CN |
| F | F | $CF_2$ | $CF_2$ | O | $COCH_3$ | $C_2F_5$ | CN |
| F | F | $CF_2$ | $CF_2$ | O | $NH_2$ | $SFCl_2$ | CN |
| F | F | $CF_2$ | $CF_2$ | O | N=CHPh | $SFCl_2$ | CN |
| F | F | $CF_2$ | $CF_2$ | O | $CH_3$ | $SFCl_2$ | CN |
| F | F | $CF_2$ | $CF_2$ | O | $CF_3$ | $SFCl_2$ | CN |
| F | F | $CF_2$ | $CF_2$ | O | Cl | $SFCl_2$ | CN |
| F | F | $CF_2$ | $CF_2$ | O | F | $SFCl_2$ | CN |
| F | F | $CF_2$ | $CF_2$ | O | $COCH_3$ | $SFCl_2$ | CN |
| F | F | $CF_2$ | $CF_2$ | O | H | $SFCl_2$ | CN |
| F | F | $CF_2$ | $CF_2$ | O | $NH_2$ | $SFCl_2$ | CN |
| F | F | $CF_2$ | $CF_2$ | O | N=CHPh | $SFCl_2$ | CN |
| F | F | $CF_2$ | $CF_2$ | O | $CH_3$ | $SFCl_2$ | CN |
| F | F | $CF_2$ | $CF_2$ | O | $CF_3$ | $SFCl_2$ | CN |
| F | F | $CF_2$ | $CF_2$ | O | Cl | $SFCl_2$ | CN |
| F | F | $CF_2$ | $CF_2$ | O | F | $SFCl_2$ | CN |
| F | F | $CF_2$ | $CF_2$ | O | $COCH_3$ | $SFCl_2$ | CN |

TABLE 162

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | H | $SCF_3$ | H |
| Cl | Cl | O | $CF_2$ | O | $NH_2$ | $SCF_3$ | H |
| Cl | Cl | O | $CF_2$ | O | N=CHPh | $SCF_3$ | H |
| Cl | Cl | O | $CF_2$ | O | $CH_3$ | $SCF_3$ | H |
| Cl | Cl | O | $CF_2$ | O | $CF_3$ | $SCF_3$ | H |
| Cl | Cl | O | $CF_2$ | O | Cl | $SCF_3$ | H |
| Cl | Cl | O | $CF_2$ | O | F | $SCF_3$ | H |
| Cl | Cl | O | $CF_2$ | O | $COCH_3$ | $SCF_3$ | H |
| Cl | Cl | O | $CF_2$ | O | H | $SOCF_3$ | H |
| Cl | Cl | O | $CF_2$ | O | $NH_2$ | $SOCF_3$ | H |
| Cl | Cl | O | $CF_2$ | O | N=CHPh | $SOCF_3$ | H |
| Cl | Cl | O | $CF_2$ | O | $CH_3$ | $SOCF_3$ | H |
| Cl | Cl | O | $CF_2$ | O | $CF_3$ | $SOCF_3$ | H |
| Cl | Cl | O | $CF_2$ | O | Cl | $SOCF_3$ | H |
| Cl | Cl | O | $CF_2$ | O | F | $SOCF_3$ | H |
| Cl | Cl | O | $CF_2$ | O | $COCH_3$ | $SOCF_3$ | H |
| Cl | Cl | O | $CF_2$ | O | H | $SO_2CF_3$ | H |
| Cl | Cl | O | $CF_2$ | O | $NH_2$ | $SO_2CF_3$ | H |
| Cl | Cl | O | $CF_2$ | O | N=CHPh | $SO_2CF_3$ | H |
| Cl | Cl | O | $CF_2$ | O | $CH_3$ | $SO_2CF_3$ | H |
| Cl | Cl | O | $CF_2$ | O | $CF_3$ | $SO_2CF_3$ | H |
| Cl | Cl | O | $CF_2$ | O | Cl | $SO_2CF_3$ | H |
| Cl | Cl | O | $CF_2$ | O | F | $SO_2CF_3$ | H |
| Cl | Cl | O | $CF_2$ | O | $COCH_3$ | $SO_2CF_3$ | H |
| Cl | Cl | O | $CF_2$ | O | H | $SCF_2CH_3$ | H |
| Cl | Cl | O | $CF_2$ | O | $NH_2$ | $SCF_2CH_3$ | H |

TABLE 163

| X | Y | Z$^1$ | Z$^2$ | Z$^3$ | R$^1$ | R$^2$ | R$^3$ |
|---|---|---|---|---|---|---|---|
| Cl | Cl | O | CF$_2$ | O | N=CHPh | SCF$_2$CH$_3$ | H |
| Cl | Cl | O | CF$_2$ | O | CH$_3$ | SCF$_2$CH$_3$ | H |
| Cl | Cl | O | CF$_2$ | O | CF$_3$ | SCF$_2$CH$_3$ | H |
| Cl | Cl | O | CF$_2$ | O | Cl | SCF$_2$CH$_3$ | H |
| Cl | Cl | O | CF$_2$ | O | F | SCF$_2$CH$_3$ | H |
| Cl | Cl | O | CF$_2$ | O | COCH$_3$ | SCF$_2$CH$_3$ | H |
| Cl | Cl | O | CF$_2$ | O | H | SOCF$_2$CH$_3$ | H |
| Cl | Cl | O | CF$_2$ | O | NH$_2$ | SOCF$_2$CH$_3$ | H |
| Cl | Cl | O | CF$_2$ | O | N=CHPh | SOCF$_2$CH$_3$ | H |
| Cl | Cl | O | CF$_2$ | O | CH$_3$ | SOCF$_2$CH$_3$ | H |
| Cl | Cl | O | CF$_2$ | O | CF$_3$ | SOCF$_2$CH$_3$ | H |
| Cl | Cl | O | CF$_2$ | O | Cl | SOCF$_2$CH$_3$ | H |
| Cl | Cl | O | CF$_2$ | O | F | SOCF$_2$CH$_3$ | H |
| Cl | Cl | O | CF$_2$ | O | COCH$_3$ | SOCF$_2$CH$_3$ | H |
| Cl | Cl | O | CF$_2$ | O | H | SO$_2$CF$_2$CH$_3$ | H |
| Cl | Cl | O | CF$_2$ | O | NH$_2$ | SO$_2$CF$_2$CH$_3$ | H |
| Cl | Cl | O | CF$_2$ | O | N=CHPh | SO$_2$CF$_2$CH$_3$ | H |
| Cl | Cl | O | CF$_2$ | O | CH$_3$ | SO$_2$CF$_2$CH$_3$ | H |
| Cl | Cl | O | CF$_2$ | O | CF$_3$ | SO$_2$CF$_2$CH$_3$ | H |
| Cl | Cl | O | CF$_2$ | O | Cl | SO$_2$CF$_2$CH$_3$ | H |
| Cl | Cl | O | CF$_2$ | O | F | SO$_2$CF$_2$CH$_3$ | H |
| Cl | Cl | O | CF$_2$ | O | COCH$_3$ | SO$_2$CF$_2$CH$_3$ | H |
| Cl | Cl | O | CF$_2$ | O | NH$_2$ | COCF$_3$ | H |
| Cl | Cl | O | CF$_2$ | O | N=CHPh | COCF3 | H |
| Cl | Cl | O | CF$_2$ | O | CH$_3$ | COCF$_3$ | H |
| Cl | Cl | O | CF$_2$ | O | CF$_3$ | COCF$_3$ | H |

TABLE 164

| X | Y | Z$^1$ | Z$^2$ | Z$^3$ | R$^1$ | R$^2$ | R$^3$ |
|---|---|---|---|---|---|---|---|
| Cl | Cl | O | CF$_2$ | O | Cl | COCF$_3$ | H |
| Cl | Cl | O | CF$_2$ | O | F | COCF$_3$ | H |
| Cl | Cl | O | CF$_2$ | O | COCH$_3$ | COCF$_3$ | H |
| Cl | Cl | O | CF$_2$ | O | H | COCF$_3$ | H |
| Cl | Cl | O | CF$_2$ | O | NH$_2$ | COCF$_3$ | H |
| Cl | Cl | O | CF$_2$ | O | N=CHPh | COCF$_3$ | H |
| Cl | Cl | O | CF$_2$ | O | CH$_3$ | COCF$_3$ | H |
| Cl | Cl | O | CF$_2$ | O | CF$_3$ | COCF$_3$ | H |
| Cl | Cl | O | CF$_2$ | O | Cl | COCF$_3$ | H |
| Cl | Cl | O | CF$_2$ | O | F | COCF$_3$ | H |
| Cl | Cl | O | CF$_2$ | O | COCH$_3$ | COCF$_3$ | H |
| Cl | Cl | O | CF$_2$ | O | NH$_2$ | C$_2$F$_5$ | H |
| Cl | Cl | O | CF$_2$ | O | N=CHPh | C$_2$F$_5$ | H |
| Cl | Cl | O | CF$_2$ | O | CH$_3$ | C$_2$F$_5$ | H |
| Cl | Cl | O | CF$_2$ | O | CF$_3$ | C$_2$F$_5$ | H |
| Cl | Cl | O | CF$_2$ | O | Cl | C$_2$F$_5$ | H |
| Cl | Cl | O | CF$_2$ | O | F | C$_2$F$_5$ | H |
| Cl | Cl | O | CF$_2$ | O | COCH$_3$ | C$_2$F$_5$ | H |
| Cl | Cl | O | CF$_2$ | O | H | C$_2$F$_5$ | H |
| Cl | Cl | O | CF$_2$ | O | NH$_2$ | C$_2$F$_5$ | H |
| Cl | Cl | O | CF$_2$ | O | N=CHPh | C$_2$F$_5$ | H |
| Cl | Cl | O | CF$_2$ | O | CH$_3$ | C$_2$F$_5$ | H |
| Cl | Cl | O | CF$_2$ | O | CF$_3$ | C$_2$F$_5$ | H |
| Cl | Cl | O | CF$_2$ | O | Cl | C$_2$F$_5$ | H |
| Cl | Cl | O | CF$_2$ | O | F | C$_2$F$_5$ | H |
| Cl | Cl | O | CF$_2$ | O | COCH$_3$ | C$_2$F$_5$ | H |

TABLE 165

| X | Y | Z$^1$ | Z$^2$ | Z$^3$ | R$^1$ | R$^2$ | R$^3$ |
|---|---|---|---|---|---|---|---|
| Cl | Cl | O | CF$_2$ | O | NH$_2$ | SFCl$_2$ | H |
| Cl | Cl | O | CF$_2$ | O | N=CHPh | SFCl$_2$ | H |
| Cl | Cl | O | CF$_2$ | O | CH$_3$ | SFCl$_2$ | H |
| Cl | Cl | O | CF$_2$ | O | CF$_3$ | SFCl$_2$ | H |
| Cl | Cl | O | CF$_2$ | O | Cl | SFCl$_2$ | H |
| Cl | Cl | O | CF$_2$ | O | F | SFCl$_2$ | H |
| Cl | Cl | O | CF$_2$ | O | COCH$_3$ | SFCl$_2$ | H |
| Cl | Cl | O | CF$_2$ | O | H | SFCl$_2$ | H |
| Cl | Cl | O | CF$_2$ | O | NH$_2$ | SFCl$_2$ | H |
| Cl | Cl | O | CF$_2$ | O | N=CHPh | SFCl$_2$ | H |

TABLE 165-continued

| X | Y | Z$^1$ | Z$^2$ | Z$^3$ | R$^1$ | R$^2$ | R$^3$ |
|---|---|---|---|---|---|---|---|
| Cl | Cl | O | CF$_2$ | O | CH$_3$ | SFCl$_2$ | H |
| Cl | Cl | O | CF$_2$ | O | CF$_3$ | SFCl$_2$ | H |
| Cl | Cl | O | CF$_2$ | O | Cl | SFCl$_2$ | H |
| Cl | Cl | O | CF$_2$ | O | F | SFCl$_2$ | H |
| Cl | Cl | O | CF$_2$ | O | COCH$_3$ | SFCl$_2$ | H |
| Cl | Cl | O | CF$_2$ | O | H | SCF$_3$ | CF$_3$ |
| Cl | Cl | O | CF$_2$ | O | NH$_2$ | SCF$_3$ | CF$_3$ |
| Cl | Cl | O | CF$_2$ | O | N=CHPh | SCF$_3$ | CF$_3$ |
| Cl | Cl | O | CF$_2$ | O | CH$_3$ | SCF$_3$ | CF$_3$ |
| Cl | Cl | O | CF$_2$ | O | CF$_3$ | SCF$_3$ | CF$_3$ |
| Cl | Cl | O | CF$_2$ | O | Cl | SCF$_3$ | CF$_3$ |
| Cl | Cl | O | CF$_2$ | O | F | SCF$_3$ | CF$_3$ |
| Cl | Cl | O | CF$_2$ | O | COCH$_3$ | SCF$_3$ | CF$_3$ |
| Cl | Cl | O | CF$_2$ | O | H | SOCF$_3$ | CF$_3$ |
| Cl | Cl | O | CF$_2$ | O | NH$_2$ | SOCF$_3$ | CF$_3$ |
| Cl | Cl | O | CF$_2$ | O | N=CHPh | SOCF$_3$ | CF$_3$ |

TABLE 166

| X | Y | Z$^1$ | Z$^2$ | Z$^3$ | R$^1$ | R$^2$ | R$^3$ |
|---|---|---|---|---|---|---|---|
| Cl | Cl | O | CF$_2$ | O | CH$_3$ | SOCF$_3$ | CF$_3$ |
| Cl | Cl | O | CF$_2$ | O | CF$_3$ | SOCF$_3$ | CF$_3$ |
| Cl | Cl | O | CF$_2$ | O | Cl | SOCF$_3$ | CF$_3$ |
| Cl | Cl | O | CF$_2$ | O | F | SOCF$_3$ | CF$_3$ |
| Cl | Cl | O | CF$_2$ | O | COCH$_3$ | SOCF$_3$ | CF$_3$ |
| Cl | Cl | O | CF$_2$ | O | H | SO$_2$CF$_3$ | CF$_3$ |
| Cl | Cl | O | CF$_2$ | O | NH$_2$ | SO$_2$CF$_3$ | CF$_3$ |
| Cl | Cl | O | CF$_2$ | O | N=CHPh | SO$_2$CF$_3$ | CF$_3$ |
| Cl | Cl | O | CF$_2$ | O | CH$_3$ | SO$_2$CF$_3$ | CF$_3$ |
| Cl | Cl | O | CF$_2$ | O | CF$_3$ | SO$_2$CF$_3$ | CF$_3$ |
| Cl | Cl | O | CF$_2$ | O | Cl | SO$_2$CF$_3$ | CF$_3$ |
| Cl | Cl | O | CF$_2$ | O | F | SO$_2$CF$_3$ | CF$_3$ |
| Cl | Cl | O | CF$_2$ | O | COCH$_3$ | SO$_2$CF$_3$ | CF$_3$ |
| Cl | Cl | O | CF$_2$ | O | H | SCF$_2$CH$_3$ | CF$_3$ |
| Cl | Cl | O | CF$_2$ | O | NH$_2$ | SCF$_2$CH$_3$ | CF$_3$ |
| Cl | Cl | O | CF$_2$ | O | N=CHPh | SCF$_2$CH$_3$ | CF$_3$ |
| Cl | Cl | O | CF$_2$ | O | CH$_3$ | SCF$_2$CH$_3$ | CF$_3$ |
| Cl | Cl | O | CF$_2$ | O | CF$_3$ | SCF$_2$CH$_3$ | CF$_3$ |
| Cl | Cl | O | CF$_2$ | O | Cl | SCF$_2$CH$_3$ | CF$_3$ |
| Cl | Cl | O | CF$_2$ | O | F | SCF$_2$CH$_3$ | CF$_3$ |
| Cl | Cl | O | CF$_2$ | O | COCH$_3$ | SCF$_2$CH$_3$ | CF$_3$ |
| Cl | Cl | O | CF$_2$ | O | H | SOCF$_2$CH$_3$ | CF$_3$ |
| Cl | Cl | O | CF$_2$ | O | NH$_2$ | SOCF$_2$CH$_3$ | CF$_3$ |
| Cl | Cl | O | CF$_2$ | O | N=CHPh | SOCF$_2$CH$_3$ | CF$_3$ |
| Cl | Cl | O | CF$_2$ | O | CH$_3$ | SOCF$_2$CH$_3$ | CF$_3$ |
| Cl | Cl | O | CF$_2$ | O | CF$_3$ | SOCF$_2$CH$_3$ | CF$_3$ |

TABLE 167

| X | Y | Z$^1$ | Z$^2$ | Z$^3$ | R$^1$ | R$^2$ | R$^3$ |
|---|---|---|---|---|---|---|---|
| Cl | Cl | O | CF$_2$ | O | Cl | SOCF$_2$CH$_3$ | CF$_3$ |
| Cl | Cl | O | CF$_2$ | O | F | SOCF$_2$CH$_3$ | CF$_3$ |
| Cl | Cl | O | CF$_2$ | O | COCH$_3$ | SOCF$_2$CH$_3$ | CF$_3$ |
| Cl | Cl | O | CF$_2$ | O | H | SO$_2$CF$_2$CH$_3$ | CF$_3$ |
| Cl | Cl | O | CF$_2$ | O | NH$_2$ | SO$_2$CF$_2$CH$_3$ | CF$_3$ |
| Cl | Cl | O | CF$_2$ | O | N=CHPh | SO$_2$CF$_2$CH$_3$ | CF$_3$ |
| Cl | Cl | O | CF$_2$ | O | CH$_3$ | SO$_2$CF$_2$CH$_3$ | CF$_3$ |
| Cl | Cl | O | CF$_2$ | O | CF$_3$ | SO$_2$CF$_2$CH$_3$ | CF$_3$ |
| Cl | Cl | O | CF$_2$ | O | Cl | SO$_2$CF$_2$CH$_3$ | CF$_3$ |
| Cl | Cl | O | CF$_2$ | O | F | SO$_2$CF$_2$CH$_3$ | CF$_3$ |
| Cl | Cl | O | CF$_2$ | O | COCH$_3$ | SO$_2$CF$_2$CH$_3$ | CF$_3$ |
| Cl | Cl | O | CF$_2$ | O | NH$_2$ | COCF$_3$ | CF$_3$ |
| Cl | Cl | O | CF$_2$ | O | N=CHPh | COCF$_3$ | CF$_3$ |
| Cl | Cl | O | CF$_2$ | O | CH$_3$ | COCF$_3$ | CF$_3$ |
| Cl | Cl | O | CF$_2$ | O | CF$_3$ | COCF$_3$ | CF$_3$ |
| Cl | Cl | O | CF$_2$ | O | Cl | COCF$_3$ | CF$_3$ |
| Cl | Cl | O | CF$_2$ | O | F | COCF$_3$ | CF$_3$ |
| Cl | Cl | O | CF$_2$ | O | COCH$_3$ | COCF$_3$ | CF$_3$ |
| Cl | Cl | O | CF$_2$ | O | H | COCF$_3$ | CF$_3$ |
| Cl | Cl | O | CF$_2$ | O | NH$_2$ | COCF$_3$ | CF$_3$ |

TABLE 167-continued

| X | Y | Z¹ | Z² | Z³ | R¹ | R² | R³ |
|---|---|----|----|----|-----|-----|-----|
| Cl | Cl | O | $CF_2$ | O | N=CHPh | $COCF_3$ | $CF_3$ |
| Cl | Cl | O | $CF_2$ | O | $CH_3$ | $COCF_3$ | $CF_3$ |
| Cl | Cl | O | $CF_2$ | O | $CF_3$ | $COCF_3$ | $CF_3$ |
| Cl | Cl | O | $CF_2$ | O | Cl | $COCF_3$ | $CF_3$ |
| Cl | Cl | O | $CF_2$ | O | F | $COCF_3$ | $CF_3$ |
| Cl | Cl | O | $CF_2$ | O | $COCH_3$ | $COCF_3$ | $CF_3$ |

TABLE 168

| X | Y | Z¹ | Z² | Z³ | R¹ | R² | R³ |
|---|---|----|----|----|-----|-----|-----|
| Cl | Cl | O | $CF_2$ | O | $NH_2$ | $C_2F_5$ | $CF_3$ |
| Cl | Cl | O | $CF_2$ | O | N=CHPh | $C_2F_5$ | $CF_3$ |
| Cl | Cl | O | $CF_2$ | O | $CH_3$ | $C_2F_5$ | $CF_3$ |
| Cl | Cl | O | $CF_3$ | O | $CF_3$ | $C_2F_5$ | $CF_3$ |
| Cl | Cl | O | CF2 | O | Cl | $C_2F_5$ | $CF_3$ |
| Cl | Cl | O | $CF_2$ | O | F | $C_2F_5$ | $CF_3$ |
| Cl | Cl | O | $CF_2$ | O | $COCH_3$ | $C_2F_5$ | $CF_3$ |
| Cl | Cl | O | $CF_2$ | O | H | $C_2F_5$ | $CF_3$ |
| Cl | Cl | O | $CF_2$ | O | $NH_2$ | $C_2F_5$ | $CF_3$ |
| Cl | Cl | O | $CF_2$ | O | N=CHPh | $C_2F_5$ | $CF_3$ |
| Cl | Cl | O | $CF_2$ | O | $CH_3$ | $C_2F_5$ | $CF_3$ |
| Cl | Cl | O | $CF_3$ | O | $CF_3$ | $C_2F_5$ | $CF_3$ |
| Cl | Cl | O | $CF_2$ | O | Cl | $C_2F_5$ | $CF_3$ |
| Cl | Cl | O | $CF_2$ | O | F | $C_2F_5$ | $CF_3$ |
| Cl | Cl | O | $CF_2$ | O | $COCH_3$ | $C_2F_5$ | $CF_3$ |
| Cl | Cl | O | $CF_2$ | O | $NH_2$ | $SFCl_2$ | $CF_3$ |
| Cl | Cl | O | $CF_2$ | O | N=CHPh | $SFCl_2$ | $CF_3$ |
| Cl | Cl | O | $CF_2$ | O | $CH_3$ | $SFCl_2$ | $CF_3$ |
| Cl | Cl | O | $CF_2$ | O | $CF_3$ | $SFCl_2$ | $CF_3$ |
| Cl | Cl | O | $CF_2$ | O | Cl | $SFCl_2$ | $CF_3$ |
| Cl | Cl | O | $CF_2$ | O | F | $SFCl_2$ | $CF_3$ |
| Cl | Cl | O | $CF_2$ | O | $COCH_3$ | $SfCl_2$ | $CF_3$ |
| Cl | Cl | O | $CF_2$ | O | H | $SFCl_2$ | $CF_3$ |
| Cl | Cl | O | $CF_2$ | O | $NH_2$ | $SFCl_2$ | $CF_3$ |
| Cl | Cl | O | $CF_2$ | O | N=CHPh | $SFCl_2$ | $CF_3$ |
| Cl | Cl | O | $CF_2$ | O | $CH_3$ | $SFCl_2$ | $CF_3$ |

TABLE 169

| X | Y | Z¹ | Z² | Z³ | R¹ | R² | R³ |
|---|---|----|----|----|-----|-----|-----|
| Cl | Cl | O | $CF_2$ | O | $CF_3$ | $SFCl_2$ | $CF_3$ |
| Cl | Cl | O | $CF_2$ | O | Cl | $SFCl_2$ | $CF_3$ |
| Cl | Cl | O | $CF_2$ | O | F | $SFCl_2$ | $CF_3$ |
| Cl | Cl | O | $CF_2$ | O | $COCH_3$ | $SFCl_2$ | $CF_3$ |
| Cl | Cl | O | $CF_2$ | O | H | $SCF_3$ | $C_2F_5$ |
| Cl | Cl | O | $CF_2$ | O | $NH_2$ | $SCF_3$ | $C_2F_5$ |
| Cl | Cl | O | $CF_2$ | O | N=CHPh | $SCF_3$ | $C_2F_5$ |
| Cl | Cl | O | $CF_2$ | O | $CH_3$ | $SCF_3$ | $C_2F_5$ |
| Cl | Cl | O | $CF_2$ | O | $CF_3$ | $SCF_3$ | $C_2F_5$ |
| Cl | Cl | O | $CF_2$ | O | Cl | $SCF_3$ | $C_2F_5$ |
| Cl | Cl | O | $CF_2$ | O | F | $SCF_3$ | $C_2F_5$ |
| Cl | Cl | O | $CF_2$ | O | $COCH_3$ | $SCF_3$ | $C_2F_5$ |
| Cl | Cl | O | $CF_2$ | O | H | $SOCF_3$ | $C_2F_5$ |
| Cl | Cl | O | $CF_2$ | O | $NH_2$ | $SOCF_3$ | $C_2F_5$ |
| Cl | Cl | O | $CF_2$ | O | N=CHPh | $SOCF_3$ | $C_2F_5$ |
| Cl | Cl | O | $CF_2$ | O | $CH_3$ | $SOCF_3$ | $C_2F_5$ |
| Cl | Cl | O | $CF_2$ | O | $CF_3$ | $SOCF_3$ | $C_2F_5$ |
| Cl | Cl | O | $CF_2$ | O | Cl | $SOCF_3$ | $C_2F_5$ |
| Cl | Cl | O | $CF_2$ | O | F | $SOCF_3$ | $C_2F_5$ |
| Cl | Cl | O | $CF_2$ | O | $COCH_3$ | $SOCF_3$ | $C_2F_5$ |
| Cl | Cl | O | $CF_2$ | O | H | $SO_2CF_3$ | $C_2F_5$ |
| Cl | Cl | O | $CF_2$ | O | $NH_2$ | $SO_2CF_3$ | $C_2F_5$ |
| Cl | Cl | O | $CF_2$ | O | N=CHPh | $SO_2CF_3$ | $C_2F_5$ |
| Cl | Cl | O | $CF_2$ | O | $CH_3$ | $SO_2CF_3$ | $C_2F_5$ |
| Cl | Cl | O | $CF_2$ | O | $CF_3$ | $SO_2CF_3$ | $C_2F_5$ |
| Cl | Cl | O | $CF_2$ | O | Cl | $SO_2CF_3$ | $C_2F_5$ |

TABLE 170

| X | Y | Z¹ | Z² | Z³ | R¹ | R² | R³ |
|---|---|----|----|----|-----|-----|-----|
| Cl | Cl | O | $CF_2$ | O | F | $SO_2CF_3$ | $C_2F_5$ |
| Cl | Cl | O | $CF_2$ | O | $COCH_3$ | $SO_2CF_3$ | $C_2F_5$ |
| Cl | Cl | O | $CF_2$ | O | H | $SCF_2CH_3$ | $C_2F_5$ |
| Cl | Cl | O | $CF_2$ | O | $NH_2$ | $SCF_2CH_3$ | $C_2F_5$ |
| Cl | Cl | O | $CF_2$ | O | N=CHPh | $SCF_2CH_3$ | $C_2F_5$ |
| Cl | Cl | O | $CF_2$ | O | $CH_3$ | $SCF_2CH_3$ | $C_2F_5$ |
| Cl | Cl | O | $CF_2$ | O | $CF_3$ | $SCF_2CH_3$ | $C_2F_5$ |
| Cl | Cl | O | $CF_2$ | O | Cl | $SCF_2CH_3$ | $C_2F_5$ |
| Cl | Cl | O | $CF_2$ | O | F | $SCF_2CH_3$ | $C_2F_5$ |
| Cl | Cl | O | $CF_2$ | O | $COCH_3$ | $SCF_2CH_3$ | $C_2F_5$ |
| Cl | Cl | O | $CF_2$ | O | H | $SOCF_2CH_3$ | $C_2F_5$ |
| Cl | Cl | O | $CF_2$ | O | $NH_2$ | $SOCF_2CH_3$ | $C_2F_5$ |
| Cl | Cl | O | $CF_2$ | O | N=CHPh | $SOCF_2CH_3$ | $C_2F_5$ |
| Cl | Cl | O | $CF_2$ | O | $CH_3$ | $SOCF_2CH_3$ | $C_2F_5$ |
| Cl | Cl | O | $CF_2$ | O | $CF_3$ | $SOCF_2CH_3$ | $C_2F_5$ |
| Cl | Cl | O | $CF_2$ | O | Cl | $SOCF_2CH_3$ | $C_2F_5$ |
| Cl | Cl | O | $CF_2$ | O | F | $SOCF_2CH_3$ | $C_2F_5$ |
| Cl | Cl | O | $CF_2$ | O | $COCH_3$ | $SOCF_2CH_3$ | $C_2F_5$ |
| Cl | Cl | O | $CF_2$ | O | H | $SO_2CF_2CH_3$ | $C_2F_5$ |
| Cl | Cl | O | $CF_2$ | O | $NH_2$ | $SO_2CF_2CH_3$ | $C_2F_5$ |
| Cl | Cl | O | $CF_2$ | O | N=CHPh | $SO_2CF_2CH_3$ | $C_2F_5$ |
| Cl | Cl | O | $CF_2$ | O | $CH_3$ | $SO_2CF_2CH_3$ | $C_2F_5$ |
| Cl | Cl | O | $CF_2$ | O | $CF_3$ | $SO_2CF_2CH_3$ | $C_2F_5$ |
| Cl | Cl | O | $CF_2$ | O | Cl | $SO_2CF_2CH_3$ | $C_2F_5$ |
| Cl | Cl | O | $CF_2$ | O | F | $SO_2CF_2CH_3$ | $C_2F_5$ |
| Cl | Cl | O | $CF_2$ | O | $COCH_3$ | $SO_2CF_2CH_3$ | $C_2F_5$ |

TABLE 171

| X | Y | Z¹ | Z² | Z³ | R¹ | R² | R³ |
|---|---|----|----|----|-----|-----|-----|
| Cl | Cl | O | $CF_2$ | O | $NH_2$ | $COCF_3$ | $C_2F_5$ |
| Cl | Cl | O | $CF_2$ | O | N=CHPh | $COCF_3$ | $C_2F_5$ |
| Cl | Cl | O | $CF_2$ | O | $CH_3$ | $COCF_3$ | $C_2F_5$ |
| Cl | Cl | O | $CF_2$ | O | $CF_3$ | $COCF_3$ | $C_2F_5$ |
| Cl | Cl | O | $CF_2$ | O | Cl | $COCF_3$ | $C_2F_5$ |
| Cl | Cl | O | $CF_2$ | O | F | $COCF_3$ | $C_2F_5$ |
| Cl | Cl | O | $CF_2$ | O | $COCH_3$ | $COCF_3$ | $C_2F_5$ |
| Cl | Cl | O | $CF_2$ | O | H | $COCF_3$ | $C_2F_5$ |
| Cl | Cl | O | $CF_2$ | O | $NH_2$ | $COCF_3$ | $C_2F_5$ |
| Cl | Cl | O | $CF_2$ | O | N=CHPh | $COCF_3$ | $C_2F_5$ |
| Cl | Cl | O | $CF_2$ | O | $CH_3$ | $COCF_3$ | $C_2F_5$ |
| Cl | Cl | O | $CF_2$ | O | $CF_3$ | $COCF_3$ | $C_2F_5$ |
| Cl | Cl | O | $CF_2$ | O | Cl | $COCF_3$ | $C_2F_5$ |
| Cl | Cl | O | $CF_2$ | O | F | $COCF_3$ | $C_2F_5$ |
| Cl | Cl | O | $CF_2$ | O | $COCH_3$ | $COCF_3$ | $C_2F_5$ |
| Cl | Cl | O | $CF_2$ | O | $NH_2$ | $C_2F_5$ | $C_2F_5$ |
| Cl | Cl | O | $CF_2$ | O | N=CHPh | $C_2F_5$ | $C_2F_5$ |
| Cl | Cl | O | $CF_2$ | O | $CH_3$ | $C_2F_5$ | $C_2F_5$ |
| Cl | Cl | O | $CF_2$ | O | $CF_3$ | $C_2F_5$ | $C_2F_5$ |
| Cl | Cl | O | $CF_2$ | O | Cl | $C_2F_5$ | $C_2F_5$ |
| Cl | Cl | O | $CF_2$ | O | F | $C_2F_5$ | $C_2F_5$ |
| Cl | Cl | O | $CF_2$ | O | $COCH_3$ | $C_2F_5$ | $C_2F_5$ |
| Cl | Cl | O | $CF_2$ | O | H | $C_2F_5$ | $C_2F_5$ |
| Cl | Cl | O | $CF_2$ | O | $NH_2$ | $C_2F_5$ | $C_2F_5$ |
| Cl | Cl | O | $CF_2$ | O | N=CHPh | $C_2F_5$ | $C_2F_5$ |
| Cl | Cl | O | $CF_2$ | O | $CH_3$ | $C_2F_5$ | $C_2F_5$ |

TABLE 172

| X | Y | Z¹ | Z² | Z³ | R¹ | R² | R³ |
|---|---|----|----|----|-----|-----|-----|
| Cl | Cl | O | $CF_2$ | O | $CF_3$ | $C_2F_5$ | $C_2F_5$ |
| Cl | Cl | O | $CF_2$ | O | Cl | $C_2F_5$ | $C_2F_5$ |
| Cl | Cl | O | $CF_2$ | O | F | $C_2F_5$ | $C_2F_5$ |
| Cl | Cl | O | $CF_2$ | O | $COCH_3$ | $C_2F_5$ | $C_2F_5$ |
| Cl | Cl | O | $CF_2$ | O | $NH_2$ | $SFCl_2$ | $C_2F_5$ |
| Cl | Cl | O | $CF_2$ | O | N=CHPh | $SFCl_2$ | $C_2F_5$ |
| Cl | Cl | O | $CF_2$ | O | $CH_3$ | $SFCl_2$ | $C_2F_5$ |
| Cl | Cl | O | $CF_2$ | O | $CF_3$ | $SFCl_2$ | $C_2F_5$ |
| Cl | Cl | O | $CF_2$ | O | Cl | $SFCl_2$ | $C_2F_5$ |
| Cl | Cl | O | $CF_2$ | O | F | $SFCl_2$ | $C_2F_5$ |

TABLE 172-continued

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | $COCH_3$ | $SFCl_2$ | $C_2F_5$ |
| Cl | Cl | O | $CF_2$ | O | H | $SFCl_2$ | $C_2F_5$ |
| Cl | Cl | O | $CF_2$ | O | $NH_2$ | $SFCl_2$ | $C_2F_5$ |
| Cl | Cl | O | $CF_2$ | O | N=CHPh | $SFCl_2$ | $C_2F_5$ |
| Cl | Cl | O | $CF_2$ | O | $CH_3$ | $SFCl_2$ | $C_2F_5$ |
| Cl | Cl | O | $CF_2$ | O | $CF_3$ | $SFCl_2$ | $C_2F_5$ |
| Cl | Cl | O | $CF_2$ | O | Cl | $SFCl_2$ | $C_2F_5$ |
| Cl | Cl | O | $CF_2$ | O | F | $SFCl_2$ | $C_2F_5$ |
| Cl | Cl | O | $CF_2$ | O | $COCH_3$ | $SFCl_2$ | $C_2F_5$ |
| Cl | Cl | O | $CF_2$ | O | H | $SCF_3$ | $CSNH_2$ |
| Cl | Cl | O | $CF_2$ | O | $NH_2$ | $SCF_3$ | $CSNH_2$ |
| Cl | Cl | O | $CF_2$ | O | N=CHPh | $SCF_3$ | $CSNH_2$ |
| Cl | Cl | O | $CF_2$ | O | $CH_3$ | $SCF_3$ | $CSNH_2$ |
| Cl | Cl | O | $CF_2$ | O | $CF_3$ | $SCF_3$ | $CSNH_2$ |
| Cl | Cl | O | $CF_2$ | O | Cl | $SCF_3$ | $CSNH_2$ |
| Cl | Cl | O | $CF_2$ | O | F | $SCF_3$ | $CSNH_2$ |

TABLE 173

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | $COCH_3$ | $SCF_3$ | $CSNH_2$ |
| Cl | Cl | O | $CF_2$ | O | H | $SOCF_3$ | $CSNH_2$ |
| Cl | Cl | O | $CF_2$ | O | $NH_2$ | $SOCF_3$ | $CSNH_2$ |
| Cl | Cl | O | $CF_2$ | O | N=CHPh | $SOCF_3$ | $CSNH_2$ |
| Cl | Cl | O | $CF_2$ | O | $CH_3$ | $SOCF_3$ | $CSNH_2$ |
| Cl | Cl | O | $CF_2$ | O | $CF_3$ | $SOCF_3$ | $CSNH_2$ |
| Cl | Cl | O | $CF_2$ | O | Cl | $SOCF_3$ | $CSNH_2$ |
| Cl | Cl | O | $CF_2$ | O | F | $SOCF_3$ | $CSNH_2$ |
| Cl | Cl | O | $CF_2$ | O | $COCH_3$ | $SOCF_3$ | $CSNH_2$ |
| Cl | Cl | O | $CF_2$ | O | H | $SO_2CF_3$ | $CSNH_2$ |
| Cl | Cl | O | $CF_2$ | O | $NH_2$ | $SO_2CF_3$ | $CSNH_2$ |
| Cl | Cl | O | $CF_2$ | O | N=CHPh | $SO_2CF_3$ | $CSNH_2$ |
| Cl | Cl | O | $CF_2$ | O | $CH_3$ | $SO_2CF_3$ | $CSNH_2$ |
| Cl | Cl | O | $CF_2$ | O | $CF_3$ | $SO_2CF_3$ | $CSNH_2$ |
| Cl | Cl | O | $CF_2$ | O | Cl | $SO_2CF_3$ | $CSNH_2$ |
| Cl | Cl | O | $CF_2$ | O | F | $SO_2CF_3$ | $CSNH_2$ |
| Cl | Cl | O | $CF_2$ | O | $COCH_3$ | $SO_2CF_3$ | $CSNH_2$ |
| Cl | Cl | O | $CF_2$ | O | H | $SCF_2CH_3$ | $CSNH_2$ |
| Cl | Cl | O | $CF_2$ | O | $NH_2$ | $SCF_2CH_3$ | $CSNH_2$ |
| Cl | Cl | O | $CF_2$ | O | N=CHPh | $SCF_2CH_3$ | $CSNH_2$ |
| Cl | Cl | O | $CF_2$ | O | $CH_3$ | $SCF_2CH_3$ | $CSNH_2$ |
| Cl | Cl | O | $CF_2$ | O | $CF_3$ | $SCF_2CH_3$ | $CSNH_2$ |
| Cl | Cl | O | $CF_2$ | O | Cl | $SCF_2CH_3$ | $CSNH_2$ |
| Cl | Cl | O | $CF_2$ | O | F | $SCF_2CH_3$ | $CSNH_2$ |
| Cl | Cl | O | $CF_2$ | O | $COCH_3$ | $SCF_2CH_3$ | $CSNH_2$ |
| Cl | Cl | O | $CF_2$ | O | H | $SOCF_2CH_3$ | $CSNH_2$ |

TABLE 174

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | $NH_2$ | $SOCF_2CH_3$ | $CSNH_2$ |
| Cl | Cl | O | $CF_2$ | O | N=CHPh | $SOCF_2CH_3$ | $CSNH_2$ |
| Cl | Cl | O | $CF_2$ | O | $CH_3$ | $SOCF_2CH_3$ | $CSNH_2$ |
| Cl | Cl | O | $CF_2$ | O | $CF_3$ | $SOCF_2CH_3$ | $CSNH_2$ |
| Cl | Cl | O | $CF_2$ | O | Cl | $SOCF_2CH_3$ | $CSNH_2$ |
| Cl | Cl | O | $CF_2$ | O | F | $SOCF_2CH_3$ | $CSNH_2$ |
| Cl | Cl | O | $CF_2$ | O | $COCH_3$ | $SOCF_2CH_3$ | $CSNH_2$ |
| Cl | Cl | O | $CF_2$ | O | H | $SO_2CF_2CH_3$ | $CSNH_2$ |
| Cl | Cl | O | $CF_2$ | O | $NH_2$ | $SO_2CF_2CH_3$ | $CSNH_2$ |
| Cl | Cl | O | $CF_2$ | O | N=CHPh | $SO_2CF_2CH_3$ | $CSNH_2$ |
| Cl | Cl | O | $CF_2$ | O | $CH_3$ | $SO_2CF_2CH_3$ | $CSNH_2$ |
| Cl | Cl | O | $CF_2$ | O | $CF_3$ | $SO_2CF_2CH_3$ | $CSNH_2$ |
| Cl | Cl | O | $CF_2$ | O | Cl | $SO_2CF_2CH_3$ | $CSNH_2$ |
| Cl | Cl | O | $CF_2$ | O | F | $SO_2CF_2CH_3$ | $CSNH_2$ |
| Cl | Cl | O | $CF_2$ | O | $COCH_3$ | $SO_2CF_2CH_3$ | $CSNH_2$ |
| Cl | Cl | O | $CF_2$ | O | $NH_2$ | $COCF_3$ | $CSNH_2$ |
| Cl | Cl | O | $CF_2$ | O | N=CHPh | $COCF_3$ | $CSNH_2$ |
| Cl | Cl | O | $CF_2$ | O | $CH_3$ | $COCF_3$ | $CSNH_2$ |
| Cl | Cl | O | $CF_2$ | O | $CF_3$ | $COCF_3$ | $CSNH_2$ |
| Cl | Cl | O | $CF_2$ | O | Cl | $COCF_3$ | $CSNH_2$ |

TABLE 174-continued

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | F | $COCF_3$ | $CSNH_2$ |
| Cl | Cl | O | $CF_2$ | O | $COCH_3$ | $COCF_3$ | $CSNH_2$ |
| Cl | Cl | O | $CF_2$ | O | H | $COCF_3$ | $CSNH_2$ |
| Cl | Cl | O | $CF_2$ | O | $NH_2$ | $COCF_3$ | $CSNH_2$ |
| Cl | Cl | O | $CF_2$ | O | N=CHPh | $COCF_3$ | $CSNH_2$ |
| Cl | Cl | O | $CF_2$ | O | $CH_3$ | $COCF_3$ | $CSNH_2$ |

TABLE 175

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | $CF_3$ | $COCF_3$ | $CSNH_2$ |
| Cl | Cl | O | $CF_2$ | O | Cl | $COCF_3$ | $CSNH_2$ |
| Cl | Cl | O | $CF_2$ | O | F | $COCF_3$ | $CSNH_2$ |
| Cl | Cl | O | $CF_2$ | O | $COCH_3$ | $COCF_3$ | $CSNH_2$ |
| Cl | Cl | O | $CF_2$ | O | $NH_2$ | $C_2F_5$ | $CSNH_2$ |
| Cl | Cl | O | $CF_2$ | O | N=CHPh | $C_2F_5$ | $CSNH_2$ |
| Cl | Cl | O | $CF_2$ | O | $CH_3$ | $C_2F_5$ | $CSNH_2$ |
| Cl | Cl | O | $CF_2$ | O | $CF_3$ | $C_2F_5$ | $CSNH_2$ |
| Cl | Cl | O | $CF_2$ | O | Cl | $C_2F_5$ | $CSNH_2$ |
| Cl | Cl | O | $CF_2$ | O | F | $C_2F_5$ | $CSNH_2$ |
| Cl | Cl | O | $CF_2$ | O | $COCH_3$ | $C_2F_5$ | $CSNH_2$ |
| Cl | Cl | O | $CF_2$ | O | H | $C_2F_5$ | $CSNH_2$ |
| Cl | Cl | O | $CF_2$ | O | $NH_2$ | $C_2F_5$ | $CSNH_2$ |
| Cl | Cl | O | $CF_2$ | O | N=CHPh | $C_2F_5$ | $CSNH_2$ |
| Cl | Cl | O | $CF_2$ | O | $CH_3$ | $C_2F_5$ | $CSNH_2$ |
| Cl | Cl | O | $CF_2$ | O | $CF_3$ | $C_2F_5$ | $CSNH_2$ |
| Cl | Cl | O | $CF_2$ | O | Cl | $C_2F_5$ | $CSNH_2$ |
| Cl | Cl | O | $CF_2$ | O | F | $C_2F_5$ | $CSNH_2$ |
| Cl | Cl | O | $CF_2$ | O | $COCH_3$ | $C_2F_5$ | $CSNH_2$ |
| Cl | Cl | O | $CF_2$ | O | $NH_2$ | $SFCl_2$ | $CSNH_2$ |
| Cl | Cl | O | $CF_2$ | O | N=CHPh | $SFCl_2$ | $CSNH_2$ |
| Cl | Cl | O | $CF_2$ | O | $CH_3$ | $SFCl_2$ | $CSNH_2$ |
| Cl | Cl | O | $CF_2$ | O | $CF_3$ | $SFCl_2$ | $CSNH_2$ |
| Cl | Cl | O | $CF_2$ | O | Cl | $SFCl_2$ | $CSNH_2$ |
| Cl | Cl | O | $CF_2$ | O | F | $SFCl_2$ | $CSNH_2$ |
| Cl | Cl | O | $CF_2$ | O | $COCH_3$ | $SFCl_2$ | $CSNH_2$ |

TABLE 176

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | H | $SFCl_2$ | $CSNH_2$ |
| Cl | Cl | O | $CF_2$ | O | $NH_2$ | $SFCl_2$ | $CSNH_2$ |
| Cl | Cl | O | $CF_2$ | O | N=CHPh | $SFCl_2$ | $CSNH_2$ |
| Cl | Cl | O | $CF_2$ | O | $CH_3$ | $SFCl_2$ | $CSNH_2$ |
| Cl | Cl | O | $CF_2$ | O | $CF_3$ | $SFCl_2$ | $CSNH_2$ |
| Cl | Cl | O | $CF_2$ | O | Cl | $SFCl_2$ | $CSNH_2$ |
| Cl | Cl | O | $CF_2$ | O | F | $SFCl_2$ | $CSNH_2$ |
| Cl | Cl | O | $CF_2$ | O | $COCH_3$ | $SFCl_2$ | $CSNH_2$ |
| Cl | Cl | O | $CF_2$ | O | H | $SCF_3$ | CN |
| Cl | Cl | O | $CF_2$ | O | $NH_2$ | $SCF_3$ | CN |
| Cl | Cl | O | $CF_2$ | O | N=CHPh | $SCF_3$ | CN |
| Cl | Cl | O | $CF_2$ | O | $CH_3$ | $SCF_3$ | CN |
| Cl | Cl | O | $CF_2$ | O | $CF_3$ | $SCF_3$ | CN |
| Cl | Cl | O | $CF_2$ | O | Cl | $SCF_3$ | CN |
| Cl | Cl | O | $CF_2$ | O | F | $SCF_3$ | CN |
| Cl | Cl | O | $CF_2$ | O | $COCH_3$ | $SCF_3$ | CN |
| Cl | Cl | O | $CF_2$ | O | H | $SOCF_3$ | CN |
| Cl | Cl | O | $CF_2$ | O | $NH_2$ | $SOCF_3$ | CN |
| Cl | Cl | O | $CF_2$ | O | N=CHPh | $SOCF_3$ | CN |
| Cl | Cl | O | $CF_2$ | O | $CH_3$ | $SOCF_3$ | CN |
| Cl | Cl | O | $CF_2$ | O | $CF_3$ | $SOCF_3$ | CN |
| Cl | Cl | O | $CF_2$ | O | Cl | $SOCF_3$ | CN |
| Cl | Cl | O | $CF_2$ | O | F | $SOCF_3$ | CN |
| Cl | Cl | O | $CF_2$ | O | $COCH_3$ | $SOCF_3$ | CN |
| Cl | Cl | O | $CF_2$ | O | H | $SO_2CF_3$ | CN |
| Cl | Cl | O | $CF_2$ | O | $NH_2$ | $SO_2CF_3$ | CN |

TABLE 177

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | N=CHPh | $SO_2CF_3$ | CN |
| Cl | Cl | O | $CF_2$ | O | $CH_3$ | $SO_2CF_3$ | CN |
| Cl | Cl | O | $CF_2$ | O | $CF_3$ | $SO_2CF_3$ | CN |
| Cl | Cl | O | $CF_2$ | O | Cl | $SO_2CF_3$ | CN |
| Cl | Cl | O | $CF_2$ | O | F | $SO_2CF_3$ | CN |
| Cl | Cl | O | $CF_2$ | O | $COCH_3$ | $SO_2CF_3$ | CN |
| Cl | Cl | O | $CF_2$ | O | H | $SCF_2CH_3$ | CN |
| Cl | Cl | O | $CF_2$ | O | $NH_2$ | $SCF_2CH_3$ | CN |
| Cl | Cl | O | $CF_2$ | O | N=CHPh | $SCF_2CH_3$ | CN |
| Cl | Cl | O | $CF_2$ | O | $CH_3$ | $SCF_2CH_3$ | CN |
| Cl | Cl | O | $CF_2$ | O | $CF_3$ | $SCF_2CH_3$ | CN |
| Cl | Cl | O | $CF_2$ | O | Cl | $SCF_2CH_3$ | CN |
| Cl | Cl | O | $CF_2$ | O | F | $SCF_2CH_3$ | CN |
| Cl | Cl | O | $CF_2$ | O | $COCH_3$ | $SCF_2CH_3$ | CN |
| Cl | Cl | O | $CF_2$ | O | H | $SOCF_2CH_3$ | CN |
| Cl | Cl | O | $CF_2$ | O | $NH_2$ | $SOCF_2CH_3$ | CN |
| Cl | Cl | O | $CF_2$ | O | N=CHPh | $SOCF_2CH_3$ | CN |
| Cl | Cl | O | $CF_2$ | O | $CH_3$ | $SOCF_2CH_3$ | CN |
| Cl | Cl | O | $CF_2$ | O | $CF_3$ | $SOCF_2CH_3$ | CN |
| Cl | Cl | O | $CF_2$ | O | Cl | $SOCF_2CH_3$ | CN |
| Cl | Cl | O | $CF_2$ | O | F | $SOCF_2CH_3$ | CN |
| Cl | Cl | O | $CF_2$ | O | $COCH_3$ | $SOCF_2CH_3$ | CN |
| Cl | Cl | O | $CF_2$ | O | H | $SO_2CF_2CH_3$ | CN |
| Cl | Cl | O | $CF_2$ | O | $NH_2$ | $SO_2CF_2CH_3$ | CN |
| Cl | Cl | O | $CF_2$ | O | N=CHPh | $SO_2CF_2CH_3$ | CN |
| Cl | Cl | O | $CF_2$ | O | $CH_3$ | $SO_2CF_2CH_3$ | CN |

TABLE 178

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | $CF_3$ | $SO_2CF_2CH_3$ | CN |
| Cl | Cl | O | $CF_2$ | O | Cl | $SO_2CF_2CH_3$ | CN |
| Cl | Cl | O | $CF_2$ | O | F | $SO_2CF_2CH_3$ | CN |
| Cl | Cl | O | $CF_2$ | O | $COCH_3$ | $SO_2CF_2CH_3$ | CN |
| Cl | Cl | O | $CF_2$ | O | $NH_2$ | $COCF_3$ | CN |
| Cl | Cl | O | $CF_2$ | O | N=CHPh | $COCF_3$ | CN |
| Cl | Cl | O | $CF_2$ | O | $CH_3$ | $COCF_3$ | CN |
| Cl | Cl | O | $CF_2$ | O | $CF_3$ | $COCF_3$ | CN |
| Cl | Cl | O | $CF_2$ | O | Cl | $COCF_3$ | CN |
| Cl | Cl | O | $CF_2$ | O | F | $COCF_3$ | CN |
| Cl | Cl | O | $CF_2$ | O | $COCH_3$ | $COCF_3$ | CN |
| Cl | Cl | O | $CF_2$ | O | H | $COCF_3$ | CN |
| Cl | Cl | O | $CF_2$ | O | $NH_2$ | $COCF_3$ | CN |
| Cl | Cl | O | $CF_2$ | O | N=CHPh | $COCF_3$ | CN |
| Cl | Cl | O | $CF_2$ | O | $CH_3$ | $COCF_3$ | CN |
| Cl | Cl | O | $CF_2$ | O | $CF_3$ | $COCF_3$ | CN |
| Cl | Cl | O | $CF_2$ | O | Cl | $COCF_3$ | CN |
| Cl | Cl | O | $CF_2$ | O | F | $COCF_3$ | CN |
| Cl | Cl | O | $CF_2$ | O | $COCH_3$ | $COCF_3$ | CN |
| Cl | Cl | O | $CF_2$ | O | $NH_2$ | $C_2F_5$ | CN |
| Cl | Cl | O | $CF_2$ | O | N=CHPh | $C_2F_5$ | CN |
| Cl | Cl | O | $CF_2$ | O | $CH_3$ | $C_2F_5$ | CN |
| Cl | Cl | O | $CF_2$ | O | $CF_3$ | $C_2F_5$ | CN |
| Cl | Cl | O | $CF_2$ | O | Cl | $C_2F_5$ | CN |
| Cl | Cl | O | $CF_2$ | O | F | $C_2F_5$ | CN |
| Cl | Cl | O | $CF_2$ | O | $COCH_3$ | $C_2F_5$ | CN |

TABLE 179

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | H | $C_2F_5$ | CN |
| Cl | Cl | O | $CF_2$ | O | $NH_2$ | $C_2F_5$ | CN |
| Cl | Cl | O | $CF_2$ | O | N=CHPh | $C_2F_5$ | CN |
| Cl | Cl | O | $CF_2$ | O | $CH_3$ | $C_2F_5$ | CN |
| Cl | Cl | O | $CF_2$ | O | $CF_3$ | $C_2F_5$ | CN |
| Cl | Cl | O | $CF_2$ | O | Cl | $C_2F_5$ | CN |
| Cl | Cl | O | $CF_2$ | O | F | $C_2F_5$ | CN |
| Cl | Cl | O | $CF_2$ | O | $COCH_3$ | $C_2F_5$ | CN |
| Cl | Cl | O | $CF_2$ | O | $NH_2$ | $SFCl_2$ | CN |
| Cl | Cl | O | $CF_2$ | O | N=CHPh | $SFCl_2$ | CN |

TABLE 179-continued

| X | Y | $Z^1$ | $Z^2$ | $Z^3$ | $R^1$ | $R^2$ | $R^3$ |
|---|---|---|---|---|---|---|---|
| Cl | Cl | O | $CF_2$ | O | $CH_3$ | $SFCl_2$ | CN |
| Cl | Cl | O | $CF_2$ | O | $CF_3$ | $SFCl_2$ | CN |
| Cl | Cl | O | $CF_2$ | O | Cl | $SFCl_2$ | CN |
| Cl | Cl | O | $CF_2$ | O | F | $SFCl_2$ | CN |
| Cl | Cl | O | $CF_2$ | O | $COCH_3$ | $SFCl_2$ | CN |
| Cl | Cl | O | $CF_2$ | O | H | $SFCl_2$ | CN |
| Cl | Cl | O | $CF_2$ | O | $NH_2$ | $SFCl_2$ | CN |
| Cl | Cl | O | $CF_2$ | O | N=CHPh | $SFCl_2$ | CN |
| Cl | Cl | O | $CF_2$ | O | $CH_3$ | $SFCl_2$ | CN |
| Cl | Cl | O | $CF_2$ | O | $CF_3$ | $SFCl_2$ | CN |
| Cl | Cl | O | $CF_2$ | O | Cl | $SFCl_2$ | CN |
| Cl | Cl | O | $CF_2$ | O | F | $SFCl_2$ | CN |
| Cl | Cl | O | $CF_2$ | O | $COCH_3$ | $SFCl_2$ | CN |

2) Heterocyclic compounds of the formula (I) wherein R is a group of the formula (III)

TABLE 180

| X | Y | $Z^1$ | $Z^2$ | $Z^3$ | $R^1$ | $R^2$ |
|---|---|---|---|---|---|---|
| Cl | H | $CF_2$ | O | $CF_2$ | H | H |
| Cl | H | $CF_2$ | O | $CF_2$ | $CH_3$ | H |
| Cl | H | $CF_2$ | O | $CF_2$ | $CF_3$ | H |
| Cl | H | $CF_2$ | O | $CF_2$ | $NH_2$ | H |
| Cl | H | $CF_2$ | O | $CF_2$ | H | t-Bu |
| Cl | H | $CF_2$ | O | $CF_2$ | $CH_3$ | t-Bu |
| Cl | H | $CF_2$ | O | $CF_2$ | $CF_3$ | t-Bu |
| Cl | H | $CF_2$ | O | $CF_2$ | $NH_2$ | t-Bu |
| Cl | H | $CF_2$ | O | $CF_2$ | H | $C_2F_5$ |
| Cl | H | $CF_2$ | O | $CF_2$ | $CH_3$ | $C_2F_5$ |
| Cl | H | $CF_2$ | O | $CF_2$ | $CF_3$ | $C_2F_5$ |
| Cl | H | $CF_2$ | O | $CF_2$ | $NH_2$ | $C_2F_5$ |
| Cl | H | $CF_2$ | O | $CF_2$ | H | $SCF_3$ |
| Cl | H | $CF_2$ | O | $CF_2$ | $CH_3$ | $SCF_3$ |
| Cl | H | $CF_2$ | O | $CF_2$ | $CF_3$ | $SCF_3$ |
| Cl | H | $CF_2$ | O | $CF_2$ | $NH_2$ | $SCF_3$ |
| Cl | H | $CF_2$ | O | $CF_2$ | H | $SCF_2Br$ |
| Cl | H | $CF_2$ | O | $CF_2$ | $CH_3$ | $SCF_2Br$ |
| Cl | H | $CF_2$ | O | $CF_2$ | $CF_3$ | $SCF_2Br$ |
| Cl | H | $CF_2$ | O | $CF_2$ | $NH_2$ | $SCF_2Br$ |
| Cl | H | $CF_2$ | O | $CF_2$ | H | $SCF_2Cl$ |
| Cl | H | $CF_2$ | O | $CF_2$ | $CH_3$ | $SCF_2Cl$ |
| Cl | H | $CF_2$ | O | $CF_2$ | $CF_3$ | $SCF_2Cl$ |
| Cl | H | $CF_2$ | O | $CF_2$ | $NH_2$ | $SCF_2Cl$ |
| F | H | $CF_2$ | O | $CF_2$ | H | H |

TABLE 181

| X | Y | $Z^1$ | $Z^2$ | $Z^3$ | $R^1$ | $R^9$ |
|---|---|---|---|---|---|---|
| F | H | $CF_2$ | O | $CF_2$ | $CH_3$ | H |
| F | H | $CF_2$ | O | $CF_2$ | $CF_3$ | H |
| F | H | $CF_2$ | O | $CF_2$ | $NH_2$ | H |
| F | H | $CF_2$ | O | $CF_2$ | H | t-Bu |
| F | H | $CF_2$ | O | $CF_2$ | $CH_3$ | t-Bu |
| F | H | $CF_2$ | O | $CF_2$ | $CF_3$ | t-Bu |
| F | H | $CF_2$ | O | $CF_2$ | $NH_2$ | t-Bu |
| F | H | $CF_2$ | O | $CF_2$ | H | $C_2F_5$ |
| F | H | $CF_2$ | O | $CF_2$ | $CH_3$ | $C_2F_5$ |
| F | H | $CF_2$ | O | $CF_2$ | $CF_3$ | $C_2F_5$ |
| F | H | $CF_2$ | O | $CF_2$ | $NH_2$ | $C_2F_5$ |
| F | H | $CF_2$ | O | $CF_2$ | H | $SCF_3$ |
| F | H | $CF_2$ | O | $CF_2$ | $CH_3$ | $SCF_3$ |
| F | H | $CF_2$ | O | $CF_2$ | $CF_3$ | $SCF_3$ |
| F | H | $CF_2$ | O | $CF_2$ | $NH_2$ | $SCF_3$ |
| Br | H | $CF_2$ | O | $CF_2$ | H | H |
| Br | H | $CF_2$ | O | $CF_2$ | $CH_3$ | H |
| Br | H | $CF_2$ | O | $CF_2$ | $CF_3$ | H |
| Br | H | $CF_2$ | O | $CF_2$ | $NH_2$ | H |
| Br | H | $CF_2$ | O | $CF_2$ | H | t-Bu |
| Br | H | $CF_2$ | O | $CF_2$ | $CH_3$ | t-Bu |
| Br | H | $CF_2$ | O | $CF_2$ | $CF_3$ | t-Bu |

TABLE 181-continued

| X | Y | Z¹ | Z² | Z³ | R¹ | R⁹ |
|---|---|----|----|----|----|----|
| Br | H | $CF_2$ | O | $CF_2$ | $NH_2$ | t-Bu |
| Br | H | $CF_2$ | O | $CF_2$ | H | $C_2F_5$ |
| Br | H | $CF_2$ | O | $CF_2$ | $CH_3$ | $C_2F_5$ |
| Br | H | $CF_2$ | O | $CF_2$ | $CF_3$ | $C_2F_5$ |

TABLE 182

| X | Y | Z¹ | Z² | Z³ | R¹ | R⁹ |
|---|---|----|----|----|----|----|
| Br | H | $CF_2$ | O | $CF_2$ | $NH_2$ | $C_2F_5$ |
| Br | H | $CF_2$ | O | $CF_2$ | H | $SCF_3$ |
| Br | H | $CF_2$ | O | $CF_2$ | $CH_3$ | $SCF_3$ |
| Br | H | $CF_2$ | O | $CF_2$ | $CF_3$ | $SCF_3$ |
| Br | H | $CF_2$ | O | $CF_2$ | $NH_2$ | $SCF_3$ |
| CN | H | $CF_2$ | O | $CF_2$ | H | H |
| CN | H | $CF_2$ | O | $CF_2$ | $CH_3$ | H |
| CN | H | $CF_2$ | O | $CF_2$ | $CF_3$ | H |
| CN | H | $CF_2$ | O | $CF_2$ | $NH_2$ | H |
| CN | H | $CF_2$ | O | $CF_2$ | H | t-Bu |
| CN | H | $CF_2$ | O | $CF_2$ | $CH_3$ | t-Bu |
| CN | H | $CF_2$ | O | $CF_2$ | $CF_3$ | t-Bu |
| CN | H | $CF_2$ | O | $CF_2$ | $NH_2$ | t-Bu |
| CN | H | $CF_2$ | O | $CF_2$ | H | $C_2F_5$ |
| CN | H | $CF_2$ | O | $CF_2$ | $CH_3$ | $C_2F_5$ |
| CN | H | $CF_2$ | O | $CF_2$ | $CF_3$ | $C_2F_5$ |
| CN | H | $CF_2$ | O | $CF_2$ | $NH_2$ | $C_2F_5$ |
| CN | H | $CF_2$ | O | $CF_2$ | H | $SCF_3$ |
| CN | H | $CF_2$ | O | $CF_2$ | $CH_3$ | $SCF_3$ |
| CN | H | $CF_2$ | O | $CF_2$ | $CF_3$ | $SCF_3$ |
| CN | H | $CF_2$ | O | $CF_2$ | $NH_2$ | $SCF_3$ |
| Cl | F | $CF_2$ | O | $CF_2$ | H | H |
| Cl | F | $CF_2$ | O | $CF_2$ | $CH_3$ | H |
| Cl | F | $CF_2$ | O | $CF_2$ | $CF_3$ | H |
| Cl | F | $CF_2$ | O | $CF_2$ | $NH_2$ | H |
| Cl | F | $CF_2$ | O | $CF_2$ | H | t-Bu |

TABLE 183

| X | Y | Z¹ | Z² | Z³ | R¹ | R⁹ |
|---|---|----|----|----|----|----|
| Cl | F | $CF_2$ | O | $CF_2$ | $CH_3$ | t-Bu |
| Cl | F | $CF_2$ | O | $CF_2$ | $CF_3$ | t-Bu |
| Cl | F | $CF_2$ | O | $CF_2$ | $NH_2$ | t-Bu |
| Cl | F | $CF_2$ | O | $CF_2$ | H | $C_2F_5$ |
| Cl | F | $CF_2$ | O | $CF_2$ | $CH_3$ | $C_2F_5$ |
| Cl | F | $CF_2$ | O | $CF_2$ | $CF_3$ | $C_2F_5$ |
| Cl | F | $CF_2$ | O | $CF_2$ | $NH_2$ | $C_2F_5$ |
| Cl | F | $CF_2$ | O | $CF_2$ | H | $SCF_3$ |
| Cl | F | $CF_2$ | O | $CF_2$ | $CH_3$ | $SCF_3$ |
| Cl | F | $CF_2$ | O | $CF_2$ | $CF_3$ | $SCF_3$ |
| Cl | F | $CF_2$ | O | $CF_2$ | $NH_2$ | $SCF_3$ |
| Cl | Cl | $CF_2$ | $CF_2$ | O | H | H |
| Cl | Cl | $CF_2$ | $CF_2$ | O | $CH_3$ | H |
| Cl | Cl | $CF_2$ | $CF_2$ | O | $CF_3$ | H |
| Cl | Cl | $CF_2$ | $CF_2$ | O | $NH_2$ | H |
| Cl | Cl | $CF_2$ | $CF_2$ | O | H | t-Bu |
| Cl | Cl | $CF_2$ | $CF_2$ | O | $CH_3$ | t-Bu |
| Cl | Cl | $CF_2$ | $CF_2$ | O | $CF_3$ | t-Bu |
| Cl | Cl | $CF_2$ | $CF_2$ | O | $NH_2$ | t-Bu |
| Cl | Cl | $CF_2$ | $CF_2$ | O | H | $C_2F_5$ |
| Cl | Cl | $CF_2$ | $CF_2$ | O | $CH_3$ | $C_2F_5$ |
| Cl | Cl | $CF_2$ | $CF_2$ | O | $CF_3$ | $C_2F_5$ |
| Cl | Cl | $CF_2$ | $CF_2$ | O | $NH_2$ | $C_2F_5$ |
| Cl | Cl | $CF_2$ | $CF_2$ | O | H | $SCF_3$ |
| Cl | Cl | $CF_2$ | $CF_2$ | O | $CH_3$ | $SCF_3$ |
| Cl | Cl | $CF_2$ | $CF_2$ | O | $CF_3$ | $SCF_3$ |

TABLE 184

| X | Y | Z¹ | Z² | Z³ | R¹ | R⁹ |
|---|---|----|----|----|----|----|
| Cl | Cl | $CF_2$ | $CF_2$ | O | $NH_2$ | $SCF_3$ |
| F | Cl | $CF_2$ | $CF_2$ | O | H | H |
| F | Cl | $CF_2$ | $CF_2$ | O | $CH_3$ | H |
| F | Cl | $CF_2$ | $CF_2$ | O | $CF_3$ | H |
| F | Cl | $CF_2$ | $CF_2$ | O | $NH_2$ | H |
| F | Cl | $CF_2$ | $CF_2$ | O | H | t-Bu |
| F | Cl | $CF_2$ | $CF_2$ | O | $CH_3$ | t-Bu |
| F | Cl | $CF_2$ | $CF_2$ | O | $CF_3$ | t-Bu |
| F | Cl | $CF_2$ | $CF_2$ | O | $NH_2$ | t-Bu |
| F | Cl | $CF_2$ | $CF_2$ | O | H | $C_2F_5$ |
| F | Cl | $CF_2$ | $CF_2$ | O | $CH_3$ | $C_2F_5$ |
| F | Cl | $CF_2$ | $CF_2$ | O | $CF_3$ | $C_2F_5$ |
| F | Cl | $CF_2$ | $CF_2$ | O | $NH_2$ | $C_2F_5$ |
| F | Cl | $CF_2$ | $CF_2$ | O | H | $SCF_3$ |
| F | Cl | $CF_2$ | $CF_2$ | O | $CH_3$ | $SCF_3$ |
| F | Cl | $CF_2$ | $CF_2$ | O | $CF_3$ | $SCF_3$ |
| F | Cl | $CF_2$ | $CF_2$ | O | $NH_2$ | $SCF_3$ |
| Cl | Cl | O | $CF_2$ | O | H | H |
| Cl | Cl | O | $CF_2$ | O | $CH_3$ | H |
| Cl | Cl | O | $CF_2$ | O | $CF_3$ | H |
| Cl | Cl | O | $CF_2$ | O | $NH_2$ | H |
| Cl | Cl | O | $CF_2$ | O | H | t-Bu |
| Cl | Cl | O | $CF_2$ | O | $CH_3$ | t-Bu |
| Cl | Cl | O | $CF_2$ | O | $CF_3$ | t-Bu |
| Cl | Cl | O | $CF_2$ | O | $NH_2$ | t-Bu |
| Cl | Cl | O | $CF_2$ | O | H | $C_2F_5$ |

TABLE 185

| X | Y | Z¹ | Z² | Z³ | R¹ | R⁹ |
|---|---|----|----|----|----|----|
| Cl | Cl | O | $CF_2$ | O | $CH_3$ | $C_2F_5$ |
| Cl | Cl | O | $CF_2$ | O | $CF_3$ | $C_2F_5$ |
| Cl | Cl | O | $CF_2$ | O | $NH_2$ | $C_2F_5$ |
| Cl | Cl | O | $CF_2$ | O | H | $SCF_3$ |
| Cl | Cl | O | $CF_2$ | O | $CH_3$ | $SCF_3$ |
| Cl | Cl | O | $CF_2$ | O | $CF_3$ | $SCF_3$ |
| Cl | Cl | O | $CF_2$ | O | $NH_2$ | $SCF_3$ |

3) Heterocyclic compounds of the formula (I) wherein R is a group of the formula (IV)

TABLE 186

| X | Y | Z¹ | Z² | Z³ | R¹ | R² | R³ | R¹⁰ |
|---|---|----|----|----|----|----|----|-----|
| Cl | H | $CF_2$ | O | $CF_2$ | H | $SCF_3$ | H | H |
| Cl | H | $CF_2$ | O | $CF_2$ | $NH_2$ | $SCF_3$ | H | H |
| Cl | H | $CF_2$ | O | $CF_2$ | H | $SOCF_3$ | H | H |
| Cl | H | $CF_2$ | O | $CF_2$ | $NH_2$ | $SOCF_3$ | H | H |
| Cl | H | $CF_2$ | O | $CF_2$ | H | $SO_2CF_3$ | H | H |
| Cl | H | $CF_2$ | O | $CF_2$ | $NH_2$ | $SO_2CF_3$ | H | H |
| Cl | H | $CF_2$ | O | $CF_2$ | H | $SCF_3$ | CN | H |
| Cl | H | $CF_2$ | O | $CF_2$ | $NH_2$ | $SCF_3$ | CN | H |
| Cl | H | $CF_2$ | O | $CF_2$ | H | $SOCF_3$ | CN | H |
| Cl | H | $CF_2$ | O | $CF_2$ | $NH_2$ | $SOCF_3$ | CN | H |
| Cl | H | $CF_2$ | O | $CF_2$ | H | $SO_2CF_3$ | CN | H |
| Cl | H | $CF_2$ | O | $CF_2$ | $NH_2$ | $SO_2CF_3$ | CN | H |
| F | H | $CF_2$ | O | $CF_2$ | H | $SCF_3$ | H | H |
| F | H | $CF_2$ | O | $CF_2$ | $NH_2$ | $SCF_3$ | H | H |
| F | H | $CF_2$ | O | $CF_2$ | H | $SOCF_3$ | H | H |
| F | H | $CF_2$ | O | $CF_2$ | $NH_2$ | $SOCF_3$ | H | H |
| F | H | $CF_2$ | O | $CF_2$ | H | $SO_2CF_3$ | H | H |
| F | H | $CF_2$ | O | $CF_2$ | $NH_2$ | $SO_2CF_3$ | H | H |
| F | H | $CF_2$ | O | $CF_2$ | H | $SCF_3$ | CN | H |
| F | H | $CF_2$ | O | $CF_2$ | $NH_2$ | $SCF_3$ | CN | H |
| F | H | $CF_2$ | O | $CF_2$ | H | $SOCF_3$ | CN | H |
| F | H | $CF_2$ | O | $CF_2$ | $NH_2$ | $SOCF_3$ | CN | H |
| F | H | $CF_2$ | O | $CF_2$ | H | $SO_2CF_3$ | CN | H |
| F | H | $CF_2$ | O | $CF_2$ | $NH_2$ | $SO_2CF_3$ | CN | H |
| Br | H | $CF_2$ | O | $CF_2$ | H | $SCF_3$ | H | H |

TABLE 187

| X | Y | Z¹ | Z² | Z³ | R¹ | R² | R³ | R¹⁰ |
|---|---|---|---|---|---|---|---|---|
| Br | H | CF₂ | O | CF₂ | NH₂ | SCF₃ | H | H |
| Br | H | CF₂ | O | CF₂ | H | SOCF₃ | H | H |
| Br | H | CF₂ | O | CF₂ | NH₂ | SOCF₃ | H | H |
| Br | H | CF₂ | O | CF₂ | H | SO₂CF₃ | H | H |
| Br | H | CF₂ | O | CF₂ | NH₂ | SO₂CF₃ | H | H |
| Br | H | CF₂ | O | CF₂ | H | SCF₃ | CN | H |
| Br | H | CF₂ | O | CF₂ | NH₂ | SCF₃ | CN | H |
| Br | H | CF₂ | O | CF₂ | H | SOCF₃ | CN | H |
| Br | H | CF₂ | O | CF₂ | NH₂ | SOCF₃ | CN | H |
| Br | H | CF₂ | O | CF₂ | H | SO₂CF₃ | CN | H |
| Br | H | CF₂ | O | CF₂ | NH₂ | SO₂CF₃ | CN | H |
| CN | H | CF₂ | O | CF₂ | H | SCF₃ | H | H |
| CN | H | CF₂ | O | CF₂ | NH₂ | SCF₃ | H | H |
| CN | H | CF₂ | O | CF₂ | H | SOCF₃ | H | H |
| CN | H | CF₂ | O | CF₂ | NH₂ | SOCF₃ | H | H |
| CN | H | CF₂ | O | CF₂ | H | SO₂CF₃ | H | H |
| CN | H | CF₂ | O | CF₂ | NH₂ | SO₂CF₃ | H | H |
| CN | H | CF₂ | O | CF₂ | H | SCF₃ | CN | H |
| CN | H | CF₂ | O | CF₂ | NH₂ | SCF₃ | CN | H |
| CN | H | CF₂ | O | CF₂ | H | SOCF₃ | CN | H |
| CN | H | CF₂ | O | CF₂ | NH₂ | SOCF₃ | CN | H |
| CN | H | CF₂ | O | CF₂ | H | SO₂CF₃ | CN | H |
| CN | H | CF₂ | O | CF₂ | NH₂ | SO₂CF₃ | CN | H |
| Cl | F | CF₂ | O | CF₂ | H | SCF₃ | H | H |
| Cl | F | CF₂ | O | CF₂ | NH₂ | SCF₃ | H | H |
| Cl | F | CF₂ | O | CF₂ | H | SOCF₃ | H | H |

TABLE 188

| X | Y | Z¹ | Z² | Z³ | R¹ | R² | R³ | R¹⁰ |
|---|---|---|---|---|---|---|---|---|
| Cl | F | CF₂ | O | CF₂ | NH₂ | SOCF₃ | H | H |
| Cl | F | CF₂ | O | CF₂ | H | SO₂CF₃ | H | H |
| Cl | F | CF₂ | O | CF₂ | NH₂ | SO₂CF₃ | H | H |
| Cl | F | CF₂ | O | CF₂ | H | SCF₃ | CN | H |
| Cl | F | CF₂ | O | CF₂ | NH₂ | SCF₃ | CN | H |
| Cl | F | CF₂ | O | CF₂ | H | SOCF₃ | CN | H |
| Cl | F | CF₂ | O | CF₂ | NH₂ | SOCF₃ | CN | H |
| Cl | F | CF₂ | O | CF₂ | H | SO₂CF₃ | CN | H |
| Cl | F | CF₂ | O | CF₂ | NH₂ | SO₂CF₃ | CN | H |
| Cl | Cl | CF₂ | CF₂ | O | H | SCF₃ | H | H |
| Cl | Cl | CF₂ | CF₂ | O | NH₂ | SCF₃ | H | H |
| Cl | Cl | CF₂ | CF₂ | O | H | SOCF₃ | H | H |
| Cl | Cl | CF₂ | CF₂ | O | NH₂ | SOCF₃ | H | H |
| Cl | Cl | CF₂ | CF₂ | O | H | SO₂CF₃ | H | H |
| Cl | Cl | CF₂ | CF₂ | O | NH₂ | SO₂CF₃ | H | H |
| Cl | Cl | CF₂ | CF₂ | O | H | SCF₃ | CN | H |
| Cl | Cl | CF₂ | CF₂ | O | NH₂ | SCF₃ | CN | H |
| Cl | Cl | CF₂ | CF₂ | O | H | SOCF₃ | CN | H |
| Cl | Cl | CF₂ | CF₂ | O | NH₂ | SOCF₃ | CN | H |
| Cl | Cl | CF₂ | CF₂ | O | H | SO₂CF₃ | CN | H |
| Cl | Cl | CF₂ | CF₂ | O | NH₂ | SO₂CF₃ | CN | H |
| F | Cl | CF₂ | CF₂ | O | H | SCF₃ | H | H |
| F | Cl | CF₂ | CF₂ | O | NH₂ | SCF₃ | H | H |
| F | Cl | CF₂ | CF₂ | O | H | SOCF₃ | H | H |
| F | Cl | CF₂ | CF₂ | O | NH₂ | SOCF₃ | H | H |
| F | Cl | CF₂ | CF₂ | O | H | SO₂CF₃ | H | H |

TABLE 189

| X | Y | Z¹ | Z² | Z³ | R¹ | R² | R³ | R¹⁰ |
|---|---|---|---|---|---|---|---|---|
| F | Cl | CF₂ | CF₂ | O | NH₂ | SO₂CF₃ | H | H |
| F | Cl | CF₂ | CF₂ | O | H | SCF₃ | CN | H |
| F | Cl | CF₂ | CF₂ | O | NH₂ | SCF₃ | CN | H |
| F | Cl | CF₂ | CF₂ | O | H | SOCF₃ | CN | H |
| F | Cl | CF₂ | CF₂ | O | NH₂ | SOCF₃ | CN | H |
| F | Cl | CF₂ | CF₂ | O | H | SO₂CF₃ | CN | H |
| F | Cl | CF₂ | CF₂ | O | NH₂ | SO₂CF₃ | CN | H |
| Cl | Cl | O | CF₂ | O | H | SCF₃ | H | H |
| Cl | Cl | O | CF₂ | O | NH₂ | SCF₃ | H | H |
| Cl | Cl | O | CF₂ | O | H | SOCF₃ | H | H |

TABLE 189-continued

| X | Y | Z¹ | Z² | Z³ | R¹ | R² | R³ | R¹⁰ |
|---|---|---|---|---|---|---|---|---|
| Cl | Cl | O | CF₂ | O | NH₂ | SOCF₃ | H | H |
| Cl | Cl | O | CF₂ | O | H | SO₂CF₃ | H | H |
| Cl | Cl | O | CF₂ | O | NH₂ | SO₂CF₃ | H | H |
| Cl | Cl | O | CF₂ | O | H | SCF₃ | CN | H |
| Cl | Cl | O | CF₂ | O | NH₂ | SCF₃ | CN | H |
| Cl | Cl | O | CF₂ | O | H | SOCF₃ | CN | H |
| Cl | Cl | O | CF₂ | O | NH₂ | SOCF₃ | CN | H |
| Cl | Cl | O | CF₂ | O | H | SO₂CF₃ | CN | H |
| Cl | Cl | O | CF₂ | O | NH₂ | SO₂CF₃ | CN | H |
| F | Cl | O | CF₂ | O | H | SCF₃ | H | H |
| F | Cl | O | CF₂ | O | NH₂ | SCF₃ | H | H |
| F | Cl | O | CF₂ | O | H | SOCF₃ | H | H |
| F | Cl | O | CF₂ | O | NH₂ | SOCF₃ | H | H |
| F | Cl | O | CF₂ | O | H | SO₂CF₃ | H | H |
| F | Cl | O | CF₂ | O | NH₂ | SO₂CF₃ | H | H |
| F | Cl | O | CF₂ | O | H | SCF₃ | CN | H |

TABLE 190

| X | Y | Z¹ | Z² | Z³ | R¹ | R² | R³ | R¹⁰ |
|---|---|---|---|---|---|---|---|---|
| F | Cl | O | CF₂ | O | NH₂ | SCF₃ | CN | H |
| F | Cl | O | CF₂ | O | H | SOCF₃ | CN | H |
| F | Cl | O | CF₂ | O | NH₂ | SOCF₃ | CN | H |
| F | Cl | O | CF₂ | O | H | SO₂CF₃ | CN | H |
| F | Cl | O | CF₂ | O | NH₂ | SO₂CF₃ | CN | H |

4) Heterocyclic compounds of the formula (I) wherein R is a group of the formula (V)

TABLE 191

| X | Y | Z¹ | Z² | Z³ | R¹¹ | R¹² | R¹³ | R¹⁴ |
|---|---|---|---|---|---|---|---|---|
| Cl | H | CF₂ | O | CF₂ | O | H | CF₃ | H |
| Cl | H | CF₂ | O | CF₂ | O | F | CF₃ | H |
| Cl | H | CF₂ | O | CF₂ | O | Cl | CF₃ | H |
| Cl | H | CF₂ | O | CF₂ | O | CF₃ | CF₃ | H |
| Cl | H | CF₂ | O | CF₂ | O | H | C₂F₅ | H |
| Cl | H | CF₂ | O | CF₂ | O | F | C₂F₅ | H |
| Cl | H | CF₂ | O | CF₂ | O | Cl | C₂F₅ | H |
| Cl | H | CF₂ | O | CF₂ | O | CF₃ | C₂F₅ | H |
| F | H | CF₂ | O | CF₂ | O | H | CF₃ | H |
| F | H | CF₂ | O | CF₂ | O | F | CF₃ | H |
| F | H | CF₂ | O | CF₂ | O | Cl | CF₃ | H |
| F | H | CF₂ | O | CF₂ | O | CF₃ | CF₃ | H |
| F | H | CF₂ | O | CF₂ | O | H | C₂F₅ | H |
| F | H | CF₂ | O | CF₂ | O | F | C₂F₅ | H |
| F | H | CF₂ | O | CF₂ | O | Cl | C₂F₅ | H |
| F | H | CF₂ | O | CF₂ | O | CF₃ | C₂F₅ | H |
| Br | H | CF₂ | O | CF₂ | O | H | CF₃ | H |
| Br | H | CF₂ | O | CF₂ | O | F | CF₃ | H |
| Br | H | CF₂ | O | CF₂ | O | Cl | CF₃ | H |
| Br | H | CF₂ | O | CF₂ | O | CF₃ | CF₃ | H |
| Br | H | CF₂ | O | CF₂ | O | H | C₂F₅ | H |
| Br | H | CF₂ | O | CF₂ | O | F | C₂F₅ | H |
| Br | H | CF₂ | O | CF₂ | O | Cl | C₂F₅ | H |
| Br | H | CF₂ | O | CF₂ | O | CF₃ | C₂F₅ | H |
| CN | H | CF₂ | O | CF₂ | O | H | CF₃ | H |

TABLE 192

| X | Y | Z¹ | Z² | Z³ | R¹¹ | R¹² | R¹³ | R¹⁴ |
|---|---|---|---|---|---|---|---|---|
| CN | H | CF₂ | O | CF₂ | O | F | CF₃ | H |
| CN | H | CF₂ | O | CF₂ | O | Cl | CF₃ | H |
| CN | H | CF₂ | O | CF₂ | O | CF₃ | CF₃ | H |
| CN | H | CF₂ | O | CF₂ | O | H | C₂F₅ | H |
| CN | H | CF₂ | O | CF₂ | O | F | C₂F₅ | H |
| CN | H | CF₂ | O | CF₂ | O | Cl | C₂F₅ | H |

TABLE 192-continued

| X | Y | $Z^1$ | $Z^2$ | $Z^3$ | $R^{11}$ | $R^{12}$ | $R^{13}$ | $R^{14}$ |
|---|---|---|---|---|---|---|---|---|
| CN | H | $CF_2$ | O | $CF_2$ | O | $CF_3$ | $C_2F_5$ | H |
| $NO_2$ | H | $CF_2$ | O | $CF_2$ | O | H | $CF_3$ | H |
| $NO_2$ | H | $CF_2$ | O | $CF_2$ | O | F | $CF_3$ | H |
| $NO_2$ | H | $CF_2$ | O | $CF_2$ | O | Cl | $CF_3$ | H |
| $NO_2$ | H | $CF_2$ | O | $CF_2$ | O | $CF_3$ | $CF_3$ | H |
| $NO_2$ | H | $CF_2$ | O | $CF_2$ | O | H | $C_2F_5$ | H |
| $NO_2$ | H | $CF_2$ | O | $CF_2$ | O | F | $C_2F_5$ | H |
| $NO_2$ | H | $CF_2$ | O | $CF_2$ | O | Cl | $C_2F_5$ | H |
| $NO_2$ | H | $CF_2$ | O | $CF_2$ | O | $CF_3$ | $C_2F_5$ | H |
| Cl | F | $CF_2$ | O | $CF_2$ | O | H | $CF_3$ | H |
| Cl | F | $CF_2$ | O | $CF_2$ | O | F | $CF_3$ | H |
| Cl | F | $CF_2$ | O | $CF_2$ | O | Cl | $CF_3$ | H |
| Cl | F | $CF_2$ | O | $CF_2$ | O | $CF_3$ | $CF_3$ | H |
| Cl | F | $CF_2$ | O | $CF_2$ | O | H | $C_2F_5$ | H |
| Cl | F | $CF_2$ | O | $CF_2$ | O | F | $C_2F_5$ | H |
| Cl | F | $CF_2$ | O | $CF_2$ | O | Cl | $C_2F_5$ | H |
| Cl | F | $CF_2$ | O | $CF_2$ | O | $CF_3$ | $C_2F_5$ | H |
| Cl | Cl | $CF_2$ | $CF_2$ | O | O | H | $CF_3$ | H |
| Cl | Cl | $CF_2$ | $CF_2$ | O | O | F | $CF_3$ | H |
| Cl | Cl | $CF_2$ | $CF_2$ | O | O | Cl | $CF_3$ | H |

TABLE 193

| X | Y | $Z^1$ | $Z^2$ | $Z^3$ | $R^{11}$ | $R^{12}$ | $R^{13}$ | $R^{14}$ |
|---|---|---|---|---|---|---|---|---|
| Cl | Cl | $CF_2$ | $CF_2$ | O | O | $CF_3$ | $CF_3$ | H |
| Cl | Cl | $CF_2$ | $CF_2$ | O | O | H | $C_2F_5$ | H |
| Cl | Cl | $CF_2$ | $CF_2$ | O | O | F | $C_2F_5$ | H |
| Cl | Cl | $CF_2$ | $CF_2$ | O | O | Cl | $C_2F_5$ | H |
| Cl | Cl | $CF_2$ | $CF_2$ | O | O | $CF_3$ | $C_2F_5$ | H |
| F | Cl | $CF_2$ | $CF_2$ | O | O | H | $CF_3$ | H |
| F | Cl | $CF_2$ | $CF_2$ | O | O | F | $CF_3$ | H |
| F | Cl | $CF_2$ | $CF_2$ | O | O | Cl | $CF_3$ | H |
| F | Cl | $CF_2$ | $CF_2$ | O | O | $CF_3$ | $CF_3$ | H |
| F | Cl | $CF_2$ | $CF_2$ | O | O | H | $C_2F_5$ | H |
| F | Cl | $CF_2$ | $CF_2$ | O | O | F | $C_2F_5$ | H |
| F | Cl | $CF_2$ | $CF_2$ | O | O | Cl | $C_2F_5$ | H |
| F | Cl | $CF_2$ | $CF_2$ | O | O | $CF_3$ | $C_2F_5$ | H |
| Cl | F | O | $CF_2$ | O | O | H | $CF_3$ | H |
| Cl | F | O | $CF_2$ | O | O | F | $CF_3$ | H |
| Cl | F | O | $CF_2$ | O | O | Cl | $CF_3$ | H |
| Cl | F | O | $CF_2$ | O | O | $CF_3$ | $CF_3$ | H |
| Cl | F | O | $CF_2$ | O | O | H | $C_2F_5$ | H |
| Cl | F | O | $CF_2$ | O | O | F | $C_2F_5$ | H |
| Cl | F | O | $CF_2$ | O | O | Cl | $C_2F_5$ | H |
| Cl | F | O | $CF_2$ | O | O | $CF_3$ | $C_2F_5$ | H |
| Cl | Cl | O | $CF_2$ | O | O | H | $CF_3$ | H |
| Cl | Cl | O | $CF_2$ | O | O | F | $CF_3$ | H |
| Cl | Cl | O | $CF_2$ | O | O | Cl | $CF_3$ | H |
| Cl | Cl | O | $CF_2$ | O | O | $CF_3$ | $CF_3$ | H |
| Cl | Cl | O | $CF_2$ | O | O | H | $C_2F_5$ | H |

TABLE 194

| X | Y | $Z^1$ | $Z^2$ | $Z^3$ | $R^{11}$ | $R^{12}$ | $R^{13}$ | $R^{14}$ |
|---|---|---|---|---|---|---|---|---|
| Cl | Cl | O | $CF_2$ | O | O | F | $C_2F_5$ | H |
| Cl | Cl | O | $CF_2$ | O | O | Cl | $C_2F_5$ | H |
| Cl | Cl | O | $CF_2$ | O | O | $CF_3$ | $C_2F_5$ | H |
| F | Cl | O | $CF_2$ | O | O | H | $CF_3$ | H |
| F | Cl | O | $CF_2$ | O | O | F | $CF_3$ | H |
| F | Cl | O | $CF_2$ | O | O | Cl | $CF_3$ | H |
| F | Cl | O | $CF_2$ | O | O | $CF_3$ | $CF_3$ | H |
| F | Cl | O | $CF_2$ | O | O | H | $C_2F_5$ | H |
| F | Cl | O | $CF_2$ | O | O | F | $C_2F_5$ | H |
| F | Cl | O | $CF_2$ | O | O | Cl | $C_2F_5$ | H |
| F | Cl | O | $CF_2$ | O | O | $CF_3$ | $C_2F_5$ | H |

5) Heterocyclic compounds of the formula (I) wherein R is a group of the formula (VI)

TABLE 195

| X | Y | $Z^1$ | $Z^2$ | $Z^3$ | $R^{17}$ | $R^{18}$ | $R^{19}$ |
|---|---|---|---|---|---|---|---|
| Cl | H | $CF_2$ | O | $CF_2$ | H | $CF_3$ | H |
| Cl | H | $CF_2$ | O | $CF_2$ | Me | $CF_3$ | H |
| Cl | H | $CF_2$ | O | $CF_2$ | H | $C_2F_5$ | H |
| Cl | H | $CF_2$ | O | $CF_2$ | Me | $C_2F_5$ | H |
| Cl | H | $CF_2$ | O | $CF_2$ | H | $CF_2CF_3$ | H |
| Cl | H | $CF_2$ | O | $CF_2$ | Me | $CF_2CF_3$ | H |
| Cl | H | $CF_2$ | O | $CF_2$ | H | $SCF_3$ | H |
| Cl | H | $CF_2$ | O | $CF_2$ | Me | $SCF_3$ | H |
| Cl | H | $CF_2$ | O | $CF_2$ | H | $SOCF_3$ | H |
| Cl | H | $CF_2$ | O | $CF_2$ | Me | $SOCF_3$ | H |
| Cl | H | $CF_2$ | O | $CF_2$ | H | $SO_2CF_3$ | H |
| Cl | H | $CF_2$ | O | $CF_2$ | Me | $SO_2CF_3$ | H |
| Cl | H | $CF_2$ | O | $CF_2$ | H | $CF_3$ | $NH_2$ |
| Cl | H | $CF_2$ | O | $CF_2$ | Me | $CF_3$ | $NH_2$ |
| Cl | H | $CF_2$ | O | $CF_2$ | H | $C_2F_5$ | $NH_2$ |
| Cl | H | $CF_2$ | O | $CF_2$ | Me | $C_2F_5$ | $NH_2$ |
| Cl | H | $CF_2$ | O | $CF_2$ | H | $CF_2CF_3$ | $NH_2$ |
| Cl | H | $CF_2$ | O | $CF_2$ | Me | $CF_2CF_3$ | $NH_2$ |
| Cl | H | $CF_2$ | O | $CF_2$ | H | $SCF_3$ | $NH_2$ |
| Cl | H | $CF_2$ | O | $CF_2$ | Me | $SCF_3$ | $NH_2$ |
| Cl | H | $CF_2$ | O | $CF_2$ | H | $SOCF_3$ | $NH_2$ |
| Cl | H | $CF_2$ | O | $CF_2$ | Me | $SOCF_3$ | $NH_2$ |
| Cl | H | $CF_2$ | O | $CF_2$ | H | $SO_2CF_3$ | $NH_2$ |
| Cl | H | $CF_2$ | O | $CF_2$ | Me | $SO_2CF_3$ | $NH_2$ |
| F | H | $CF_2$ | O | $CF_2$ | H | $CF_3$ | H |

TABLE 196

| X | Y | $Z^1$ | $Z^2$ | $Z^3$ | $R^{17}$ | $R^{18}$ | $R^{19}$ |
|---|---|---|---|---|---|---|---|
| F | H | $CF_2$ | O | $CF_2$ | Me | $CF_3$ | H |
| F | H | $CF_2$ | O | $CF_2$ | H | $C_2F_5$ | H |
| F | H | $CF_2$ | O | $CF_2$ | Me | $C_2F_5$ | H |
| F | H | $CF_2$ | O | $CF_2$ | H | $CF_2CF_3$ | H |
| F | H | $CF_2$ | O | $CF_2$ | Me | $CF_2CF_3$ | H |
| F | H | $CF_2$ | O | $CF_2$ | H | $SCF_3$ | H |
| F | H | $CF_2$ | O | $CF_2$ | Me | $SCF_3$ | H |
| F | H | $CF_2$ | O | $CF_2$ | H | $SOCF_3$ | H |
| F | H | $CF_2$ | O | $CF_2$ | Me | $SOCF_3$ | H |
| F | H | $CF_2$ | O | $CF_2$ | H | $SO_2CF_3$ | H |
| F | H | $CF_2$ | O | $CF_2$ | Me | $SO_2CF_3$ | H |
| F | H | $CF_2$ | O | $CF_2$ | H | $CF_3$ | $NH_2$ |
| F | H | $CF_2$ | O | $CF_2$ | Me | $CF_3$ | $NH_2$ |
| F | H | $CF_2$ | O | $CF_2$ | H | $C_2F_5$ | $NH_2$ |
| F | H | $CF_2$ | O | $CF_2$ | Me | $C_2F_5$ | $NH_2$ |
| F | H | $CF_2$ | O | $CF_2$ | H | $CF_2CF_3$ | $NH_2$ |
| F | H | $CF_2$ | O | $CF_2$ | Me | $CF_2CF_3$ | $NH_2$ |
| F | H | $CF_2$ | O | $CF_2$ | H | $SCF_3$ | $NH_2$ |
| F | H | $CF_2$ | O | $CF_2$ | Me | $SCF_3$ | $NH_2$ |
| F | H | $CF_2$ | O | $CF_2$ | H | $SOCF_3$ | $NH_2$ |
| F | H | $CF_2$ | O | $CF_2$ | Me | $SOCF_3$ | $NH_2$ |
| F | H | $CF_2$ | O | $CF_2$ | H | $SO_2CF_3$ | $NH_2$ |
| F | H | $CF_2$ | O | $CF_2$ | Me | $SO_2CF_3$ | $NH_2$ |
| Br | H | $CF_2$ | O | $CF_2$ | H | $CF_3$ | H |
| Br | H | $CF_2$ | O | $CF_2$ | Me | $CF_3$ | H |
| Br | H | $CF_2$ | O | $CF_2$ | H | $C_2F_5$ | H |

TABLE 197

| X | Y | $Z^1$ | $Z^2$ | $Z^3$ | $R^{17}$ | $R^{18}$ | $R^{19}$ |
|---|---|---|---|---|---|---|---|
| Br | H | $CF_2$ | O | $CF_2$ | Me | $C_2F_5$ | H |
| Br | H | $CF_2$ | O | $CF_2$ | H | $CF_2CF_3$ | H |
| Br | H | $CF_2$ | O | $CF_2$ | Me | $CF_2CF_3$ | H |
| Br | H | $CF_2$ | O | $CF_2$ | H | $SCF_3$ | H |
| Br | H | $CF_2$ | O | $CF_2$ | Me | $SCF_3$ | H |
| Br | H | $CF_2$ | O | $CF_2$ | H | $SOCF_3$ | H |
| Br | H | $CF_2$ | O | $CF_2$ | Me | $SOCF_3$ | H |
| Br | H | $CF_2$ | O | $CF_2$ | H | $SO_2CF_3$ | H |
| Br | H | $CF_2$ | O | $CF_2$ | Me | $SO_2CF_3$ | H |
| Br | H | $CF_2$ | O | $CF_2$ | H | $CF_3$ | $NH_2$ |
| Br | H | $CF_2$ | O | $CF_2$ | Me | $CF_3$ | $NH_2$ |

TABLE 197-continued

| X | Y | Z$^1$ | Z$^2$ | Z$^3$ | R$^{17}$ | R$^{18}$ | R$^{19}$ |
|---|---|---|---|---|---|---|---|
| Br | H | CF$_2$ | O | CF$_2$ | H | C$_2$F$_5$ | NH$_2$ |
| Br | H | CF$_2$ | O | CF$_2$ | Me | C$_2$F$_5$ | NH$_2$ |
| Br | H | CF$_2$ | O | CF$_2$ | H | CF$_2$CF$_3$ | NH$_2$ |
| Br | H | CF$_2$ | O | CF$_2$ | Me | CF$_2$CF$_3$ | NH$_2$ |
| Br | H | CF$_2$ | O | CF$_2$ | H | SCF$_3$ | NH$_2$ |
| Br | H | CF$_2$ | O | CF$_2$ | Me | SCF$_3$ | NH$_2$ |
| Br | H | CF$_2$ | O | CF$_2$ | H | SOCF$_3$ | NH$_2$ |
| Br | H | CF$_2$ | O | CF$_2$ | Me | SOCF$_3$ | NH$_2$ |
| Br | H | CF$_2$ | O | CF$_2$ | H | SO$_2$CF$_3$ | NH$_2$ |
| Br | H | CF$_2$ | O | CF$_2$ | Me | SO$_2$CF$_3$ | NH$_2$ |
| CN | H | CF$_2$ | O | CF$_2$ | H | CF$_3$ | H |
| CN | H | CF$_2$ | O | CF$_2$ | Me | CF$_3$ | H |
| CN | H | CF$_2$ | O | CF$_2$ | H | C$_2$F$_5$ | H |
| CN | H | CF$_2$ | O | CF$_2$ | Me | C$_2$F$_5$ | H |
| CN | H | CF$_2$ | O | CF$_2$ | H | CF$_2$CF$_3$ | H |

TABLE 198

| X | Y | Z$^1$ | Z$^2$ | Z$^3$ | R$^{17}$ | R$^{18}$ | R$^{19}$ |
|---|---|---|---|---|---|---|---|
| CN | H | CF$_2$ | O | CF$_2$ | Me | CF$_2$CF$_3$ | H |
| CN | H | CF$_2$ | O | CF$_2$ | H | SCF$_3$ | H |
| CN | H | CF$_2$ | O | CF$_2$ | Me | SCF$_3$ | H |
| CN | H | CF$_2$ | O | CF$_2$ | H | SOCF$_3$ | H |
| CN | H | CF$_2$ | O | CF$_2$ | Me | SOCF$_3$ | H |
| CN | H | CF$_2$ | O | CF$_2$ | H | SO$_2$CF$_3$ | H |
| CN | H | CF$_2$ | O | CF$_2$ | Me | SO$_2$CF$_3$ | H |
| CN | H | CF$_2$ | O | CF$_2$ | H | CF$_3$ | NH$_2$ |
| CN | H | CF$_2$ | O | CF$_2$ | Me | CF$_3$ | NH$_2$ |
| CN | H | CF$_2$ | O | CF$_2$ | H | C$_2$F$_5$ | NH$_2$ |
| CN | H | CF$_2$ | O | CF$_2$ | Me | C$_2$F$_5$ | NH$_2$ |
| CN | H | CF$_2$ | O | CF$_2$ | H | CF$_2$CF$_3$ | NH$_2$ |
| CN | H | CF$_2$ | O | CF$_2$ | Me | CF$_2$CF$_3$ | NH$_2$ |
| CN | H | CF$_2$ | O | CF$_2$ | H | SCF$_3$ | NH$_2$ |
| CN | H | CF$_2$ | O | CF$_2$ | Me | SCF$_3$ | NH$_2$ |
| CN | H | CF$_2$ | O | CF$_2$ | H | SOCF$_3$ | NH$_2$ |
| CN | H | CF$_2$ | O | CF$_2$ | Me | SOCF$_3$ | NH$_2$ |
| CN | H | CF$_2$ | O | CF$_2$ | H | SO$_2$CF$_3$ | NH$_2$ |
| CN | H | CF$_2$ | O | CF$_2$ | Me | SO$_2$CF$_3$ | NH$_2$ |
| Cl | F | CF$_2$ | O | CF$_2$ | H | CF$_3$ | H |
| Cl | F | CF$_2$ | O | CF$_2$ | Me | CF$_3$ | H |
| Cl | F | CF$_2$ | O | CF$_2$ | H | C$_2$F$_5$ | H |
| Cl | F | CF$_2$ | O | CF$_2$ | Me | C$_2$F$_5$ | H |
| Cl | F | CF$_2$ | O | CF$_2$ | H | CF$_2$CF$_3$ | H |
| Cl | F | CF$_2$ | O | CF$_2$ | Me | CF$_2$CF$_3$ | H |
| Cl | F | CF$_2$ | O | CF$_2$ | H | SCF$_3$ | H |

TABLE 199

| X | Y | Z$^1$ | Z$^2$ | Z$^3$ | R$^{17}$ | R$^{18}$ | R$^{19}$ |
|---|---|---|---|---|---|---|---|
| Cl | F | CF$_2$ | O | CF$_2$ | Me | SCF$_3$ | H |
| Cl | F | CF$_2$ | O | CF$_2$ | H | SOCF$_3$ | H |
| Cl | F | CF$_2$ | O | CF$_2$ | Me | SOCF$_3$ | H |
| Cl | F | CF$_2$ | O | CF$_2$ | H | SO$_2$CF$_3$ | H |
| Cl | F | CF$_2$ | O | CF$_2$ | Me | SO$_2$CF$_3$ | H |
| Cl | F | CF$_2$ | O | CF$_2$ | H | CF$_3$ | NH$_2$ |
| Cl | F | CF$_2$ | O | CF$_2$ | Me | CF$_3$ | NH$_2$ |
| Cl | F | CF$_2$ | O | CF$_2$ | H | C$_2$F$_5$ | NH$_2$ |
| Cl | F | CF$_2$ | O | CF$_2$ | Me | C$_2$F$_5$ | NH$_2$ |
| Cl | F | CF$_2$ | O | CF$_2$ | H | CF$_2$CF$_3$ | NH$_2$ |
| Cl | F | CF$_2$ | O | CF$_2$ | Me | CF$_2$CF$_3$ | NH$_2$ |
| Cl | F | CF$_2$ | O | CF$_2$ | H | SCF$_3$ | NH$_2$ |
| Cl | F | CF$_2$ | O | CF$_2$ | Me | SCF$_3$ | NH$_2$ |
| Cl | F | CF$_2$ | O | CF$_2$ | H | SOCF$_3$ | NH$_2$ |
| Cl | F | CF$_2$ | O | CF$_2$ | Me | SOCF$_3$ | NH$_2$ |
| Cl | F | CF$_2$ | O | CF$_2$ | H | SO$_2$CF$_3$ | NH$_2$ |
| Cl | F | CF$_2$ | O | CF$_2$ | Me | SO$_2$CF$_3$ | NH$_2$ |
| Cl | Cl | CF$_2$ | CF$_2$ | O | H | CF$_3$ | H |
| Cl | Cl | CF$_2$ | CF$_2$ | O | Me | CF$_3$ | H |
| Cl | Cl | CF$_2$ | CF$_2$ | O | H | C$_2$F$_5$ | H |
| Cl | Cl | CF$_2$ | CF$_2$ | O | Me | C$_2$F$_5$ | H |

TABLE 199-continued

| X | Y | Z$^1$ | Z$^2$ | Z$^3$ | R$^{17}$ | R$^{18}$ | R$^{19}$ |
|---|---|---|---|---|---|---|---|
| Cl | Cl | CF$_2$ | CF$_2$ | O | H | CF$_2$CF$_3$ | H |
| Cl | Cl | CF$_2$ | CF$_2$ | O | Me | CF$_2$CF$_3$ | H |
| Cl | Cl | CF$_2$ | CF$_2$ | O | H | SCF$_3$ | H |
| Cl | Cl | CF$_2$ | CF$_2$ | O | Me | SCF$_3$ | H |
| Cl | Cl | CF$_2$ | CF$_2$ | O | H | SOCF$_3$ | H |

TABLE 200

| X | Y | Z$^1$ | Z$^2$ | Z$^3$ | R$^{17}$ | R$^{18}$ | R$^{19}$ |
|---|---|---|---|---|---|---|---|
| Cl | Cl | CF$_2$ | CF$_2$ | O | Me | SOCF$_3$ | H |
| Cl | Cl | CF$_2$ | CF$_2$ | O | H | SO$_2$CF$_3$ | H |
| Cl | Cl | CF$_2$ | CF$_2$ | O | Me | SO$_2$CF$_3$ | H |
| Cl | Cl | CF$_2$ | CF$_2$ | O | H | CF$_3$ | NH$_2$ |
| Cl | Cl | CF$_2$ | CF$_2$ | O | Me | CF$_3$ | NH$_2$ |
| Cl | Cl | CF$_2$ | CF$_2$ | O | H | C$_2$F$_5$ | NH$_2$ |
| Cl | Cl | CF$_2$ | CF$_2$ | O | Me | C$_2$F$_5$ | NH$_2$ |
| Cl | Cl | CF$_2$ | CF$_2$ | O | H | CF$_2$CF$_3$ | NH$_2$ |
| Cl | Cl | CF$_2$ | CF$_2$ | O | Me | CF$_2$CF$_3$ | NH$_2$ |
| Cl | Cl | CF$_2$ | CF$_2$ | O | H | SCF$_3$ | NH$_2$ |
| Cl | Cl | CF$_2$ | CF$_2$ | O | Me | SCF$_3$ | NH$_2$ |
| Cl | Cl | CF$_2$ | CF$_2$ | O | H | SOCF$_3$ | NH$_2$ |
| Cl | Cl | CF$_2$ | CF$_2$ | O | Me | SOCF$_3$ | NH$_2$ |
| Cl | Cl | CF$_2$ | CF$_2$ | O | H | SO$_2$CF$_3$ | NH$_2$ |
| Cl | Cl | CF$_2$ | CF$_2$ | O | Me | SO$_2$CF$_3$ | NH$_2$ |
| F | Cl | CF$_2$ | CF$_2$ | O | H | CF$_3$ | H |
| F | Cl | CF$_2$ | CF$_2$ | O | Me | CF$_3$ | H |
| F | Cl | CF$_2$ | CF$_2$ | O | H | C$_2$F$_5$ | H |
| F | Cl | CF$_2$ | CF$_2$ | O | Me | C$_2$F$_5$ | H |
| F | Cl | CF$_2$ | CF$_2$ | O | H | CF$_2$CF$_3$ | H |
| F | Cl | CF$_2$ | CF$_2$ | O | Me | CF$_2$CF$_3$ | H |
| F | Cl | CF$_2$ | CF$_2$ | O | H | SCF$_3$ | H |
| F | Cl | CF$_2$ | CF$_2$ | O | Me | SCF$_3$ | H |
| F | Cl | CF$_2$ | CF$_2$ | O | H | SOCF$_3$ | H |
| F | Cl | CF$_2$ | CF$_2$ | O | Me | SOCF$_3$ | H |
| F | Cl | CF$_2$ | CF$_2$ | O | H | SO$_2$CF$_3$ | H |

TABLE 201

| X | Y | Z$^1$ | Z$^2$ | Z$^3$ | R$^{17}$ | R$^{18}$ | R$^{19}$ |
|---|---|---|---|---|---|---|---|
| F | Cl | CF$_2$ | CF$_2$ | O | Me | SO$_2$CF$_3$ | H |
| F | Cl | CF$_2$ | CF$_2$ | O | H | CF$_3$ | NH$_2$ |
| F | Cl | CF$_2$ | CF$_2$ | O | Me | CF$_3$ | NH$_2$ |
| F | Cl | CF$_2$ | CF$_2$ | O | H | C$_2$F$_5$ | NH$_2$ |
| F | Cl | CF$_2$ | CF$_2$ | O | Me | C$_2$F$_5$ | NH$_2$ |
| F | Cl | CF$_2$ | CF$_2$ | O | H | CF$_2$CF$_3$ | NH$_2$ |
| F | Cl | CF$_2$ | CF$_2$ | O | Me | CF$_2$CF$_3$ | NH$_2$ |
| F | Cl | CF$_2$ | CF$_2$ | O | H | SCF$_3$ | NH$_2$ |
| F | Cl | CF$_2$ | CF$_2$ | O | Me | SCF$_3$ | NH$_2$ |
| F | Cl | CF$_2$ | CF$_2$ | O | H | SOCF$_3$ | NH$_2$ |
| F | Cl | CF$_2$ | CF$_2$ | O | Me | SOCF$_3$ | NH$_2$ |
| F | Cl | CF$_2$ | CF$_2$ | O | H | SO$_2$CF$_3$ | NH$_2$ |
| F | Cl | CF$_2$ | CF$_2$ | O | Me | SO$_2$CF$_3$ | NH$_2$ |
| Cl | H | O | CF$_2$ | O | H | CF$_3$ | H |
| Cl | H | O | CF$_2$ | O | Me | CF$_3$ | H |
| Cl | H | O | CF$_2$ | O | H | C$_2$F$_5$ | H |
| Cl | H | O | CF$_2$ | O | Me | C$_2$F$_5$ | H |
| Cl | H | O | CF$_2$ | O | H | CF$_2$CF$_3$ | H |
| Cl | H | O | CF$_2$ | O | Me | CF$_2$CF$_3$ | H |
| Cl | H | O | CF$_2$ | O | H | SCF$_3$ | H |
| Cl | H | O | CF$_2$ | O | Me | SCF$_3$ | H |
| Cl | H | O | CF$_2$ | O | H | SOCF$_3$ | H |
| Cl | H | O | CF$_2$ | O | Me | SOCF$_3$ | H |
| Cl | H | O | CF$_2$ | O | H | SO$_2$CF$_3$ | H |
| Cl | H | O | CF$_2$ | O | Me | SO$_2$CF$_3$ | H |
| Cl | H | O | CF$_2$ | O | H | CF$_3$ | NH$_2$ |

TABLE 202

| X | Y | $Z^1$ | $Z^2$ | $Z^3$ | $R^{17}$ | $R^{18}$ | $R^{19}$ |
|---|---|---|---|---|---|---|---|
| Cl | H | O | $CF_2$ | O | Me | $CF_3$ | $NH_2$ |
| Cl | H | O | $CF_2$ | O | H | $C_2F_5$ | $NH_2$ |
| Cl | H | O | $CF_2$ | O | Me | $C_2F_5$ | $NH_2$ |
| Cl | H | O | $CF_2$ | O | H | $CF_2CF_3$ | $NH_2$ |
| Cl | H | O | $CF_2$ | O | Me | $CF_2CF_3$ | $NH_2$ |
| Cl | H | O | $CF_2$ | O | H | $SCF_3$ | $NH_2$ |
| Cl | H | O | $CF_2$ | O | Me | $SCF_3$ | $NH_2$ |
| Cl | H | O | $CF_2$ | O | H | $SOCF_3$ | $NH_2$ |
| Cl | H | O | $CF_2$ | O | Me | $SOCF_3$ | $NH_2$ |
| Cl | H | O | $CF_2$ | O | H | $SO_2CF_3$ | $NH_2$ |
| Cl | H | O | $CF_2$ | O | Me | $SO_2CF_3$ | $NH_2$ |
| Cl | Cl | O | $CF_2$ | O | H | $CF_3$ | H |
| Cl | Cl | O | $CF_2$ | O | Me | $CF_3$ | H |
| Cl | Cl | O | $CF_2$ | O | H | $C_2F_5$ | H |
| Cl | Cl | O | $CF_2$ | O | Me | $C_2F_5$ | H |
| Cl | Cl | O | $CF_2$ | O | H | $CF_2CF_3$ | H |
| Cl | Cl | O | $CF_2$ | O | Me | $CF_2CF_3$ | H |
| Cl | Cl | O | $CF_2$ | O | H | $SCF_3$ | H |
| Cl | Cl | O | $CF_2$ | O | Me | $SCF_3$ | H |
| Cl | Cl | O | $CF_2$ | O | H | $SOCF_3$ | H |
| Cl | Cl | O | $CF_2$ | O | Me | $SOCF_3$ | H |
| Cl | Cl | O | $CF_2$ | O | H | $SO_2CF_3$ | H |
| Cl | Cl | O | $CF_2$ | O | Me | $SO_2CF_3$ | H |
| Cl | Cl | O | $CF_2$ | O | H | $CF_3$ | $NH_2$ |
| Cl | Cl | O | $CF_2$ | O | Me | $CF_3$ | $NH_2$ |
| Cl | Cl | O | $CF_2$ | O | H | $C_2F_5$ | $NH_2$ |

TABLE 203

| X | Y | $Z^1$ | $Z^2$ | $Z^3$ | $R^{17}$ | $R^{18}$ | $R^{19}$ |
|---|---|---|---|---|---|---|---|
| Cl | Cl | O | $CF_2$ | O | Me | $C_2F_5$ | $NH_2$ |
| Cl | Cl | O | $CF_2$ | O | H | $CF_2CF_3$ | $NH_2$ |
| Cl | Cl | O | $CF_2$ | O | Me | $CF_2CF_3$ | $NH_2$ |
| Cl | Cl | O | $CF_2$ | O | H | $SCF_3$ | $NH_2$ |
| Cl | Cl | O | $CF_2$ | O | Me | $SCF_3$ | $NH_2$ |
| Cl | Cl | O | $CF_2$ | O | H | $SOCF_3$ | $NH_2$ |
| Cl | Cl | O | $CF_2$ | O | Me | $SOCF_3$ | $NH_2$ |
| Cl | Cl | O | $CF_2$ | O | H | $SO_2CF_3$ | $NH_2$ |
| Cl | Cl | O | $CF_2$ | O | Me | $SO_2CF_3$ | $NH_2$ |
| F | Cl | O | $CF_2$ | O | H | $CF_3$ | H |
| F | Cl | O | $CF_2$ | O | Me | $CF_3$ | H |
| F | Cl | O | $CF_2$ | O | H | $C_2F_5$ | H |
| F | Cl | O | $CF_2$ | O | Me | $C_2F_5$ | H |
| F | Cl | O | $CF_2$ | O | H | $CF_2CF_3$ | H |
| F | Cl | O | $CF_2$ | O | Me | $CF_2CF_3$ | H |
| F | Cl | O | $CF_2$ | O | H | $SCF_3$ | H |
| F | Cl | O | $CF_2$ | O | Me | $SCF_3$ | H |
| F | Cl | O | $CF_2$ | O | H | $SOCF_3$ | H |
| F | Cl | O | $CF_2$ | O | Me | $SOCF_3$ | H |
| F | Cl | O | $CF_2$ | O | H | $SO_2CF_3$ | H |
| F | Cl | O | $CF_2$ | O | Me | $SO_2CF_3$ | H |
| F | Cl | O | $CF_2$ | O | H | $CF_3$ | $NH_2$ |
| F | Cl | O | $CF_2$ | O | Me | $CF_3$ | $NH_2$ |
| F | Cl | O | $CF_2$ | O | H | $C_2F_5$ | $NH_2$ |
| F | Cl | O | $CF_2$ | O | Me | $C_2F_5$ | $NH_2$ |
| F | Cl | O | $CF_2$ | O | H | $CF_2CF_3$ | $NH_2$ |

TABLE 204

| X | Y | $Z^1$ | $Z^2$ | $Z^3$ | $R^{17}$ | $R^{18}$ | $R^{19}$ |
|---|---|---|---|---|---|---|---|
| F | Cl | O | $CF_2$ | O | Me | $CF_2CF_3$ | $NH_2$ |
| F | Cl | O | $CF_2$ | O | H | $SCF_3$ | $NH_2$ |
| F | Cl | O | $CF_2$ | O | Me | $SCF_3$ | $NH_2$ |
| F | Cl | O | $CF_2$ | O | H | $SOCF_3$ | $NH_2$ |
| F | Cl | O | $CF_2$ | O | Me | $SOCF_3$ | $NH_2$ |
| F | Cl | O | $CF_2$ | O | H | $SO_2CF_3$ | $NH_2$ |
| F | Cl | O | $CF_2$ | O | Me | $SO_2CF_3$ | $NH_2$ |
| Cl | F | O | $CF_2$ | O | H | $CF_3$ | H |
| Cl | F | O | $CF_2$ | O | Me | $CF_3$ | H |
| Cl | F | O | $CF_2$ | O | H | $C_2F_5$ | H |
| Cl | F | O | $CF_2$ | O | Me | $C_2F_5$ | H |
| Cl | F | O | $CF_2$ | O | H | $CF_2CF_3$ | H |
| Cl | F | O | $CF_2$ | O | Me | $CF_2CF_3$ | H |
| Cl | F | O | $CF_2$ | O | H | $SCF_3$ | H |
| Cl | F | O | $CF_2$ | O | Me | $SCF_3$ | H |
| Cl | F | O | $CF_2$ | O | H | $SOCF_3$ | H |
| Cl | F | O | $CF_2$ | O | Me | $SOCF_3$ | H |
| Cl | F | O | $CF_2$ | O | H | $SO_2CF_3$ | H |
| Cl | F | O | $CF_2$ | O | Me | $SO_2CF_3$ | H |
| Cl | F | O | $CF_2$ | O | H | $CF_3$ | $NH_2$ |
| Cl | F | O | $CF_2$ | O | Me | $CF_3$ | $NH_2$ |
| Cl | F | O | $CF_2$ | O | H | $C_2F_5$ | $NH_2$ |
| Cl | F | O | $CF_2$ | O | Me | $C_2F_5$ | $NH_2$ |
| Cl | F | O | $CF_2$ | O | H | $CF_2CF_3$ | $NH_2$ |
| Cl | F | O | $CF_2$ | O | Me | $CF_2CF_3$ | $NH_2$ |
| Cl | F | O | $CF_2$ | O | H | $SCF_3$ | $NH_2$ |

TABLE 205

| X | Y | $Z^1$ | $Z^2$ | $Z^3$ | $R^{17}$ | $R^{18}$ | $R^{19}$ |
|---|---|---|---|---|---|---|---|
| Cl | F | O | $CF_2$ | O | Me | $SCF_3$ | $NH_2$ |
| Cl | F | O | $CF_2$ | O | H | $SOCF_3$ | $NH_2$ |
| Cl | F | O | $CF_2$ | O | Me | $SOCF_3$ | $NH_2$ |
| Cl | F | O | $CF_2$ | O | H | $SO_2CF_3$ | $NH_2$ |
| Cl | F | O | $CF_2$ | O | Me | $SO_2CF_3$ | $NH_2$ |

Listed below are the examples of the noxious insects and acarines against which the compounds of the present invention show a controlling effect.

Hemiptera: rice insects such as small brown planthopper, brown rice planthopper and whitebacked rice planthopper, leafhoppers such as green rice leafhoppers (*Nephotettix cincticeps* and *Nephotettix virescens*), aphids, stink bugs, whiteflies, scale insects, lace bugs and jumping plantlice.

Lepidoptera: pyralid moths such as rice stem borer, rice leafroller and *Barathra brassicae,* noctuid moths such as common cutworm, armyworm and cabbage armyworm, whites such as common white, tortricids such as apple leafroller, Carposinidae, lyonetiid moths, tussock moths, Agrotis spy. such as cutworm and black cutworm, Helicoverpa spp., Heliothis sop., diamondback moth, rice skipper, casemaking clothes moth and webbing clothes moth.

Diptera: culicidae such as *culex pipiens pallens* and *Culex tritaeniorhynchus,* Aedes spp. such as *Aedes aegypti* and *Aedes albopictus,* Anopheles spp. such as *Anopheles hyrcanus sinensis,* midges, muscid flies such as housefly and non-biting stable flies, blow flies, flesh flies, anthomyiid flies such as seedcorn maggot, small housefly, lesen housefly, and onion maggot, fruit flies, vinegar flies, moth-flies and sand flies, gnats and stable flies.

Coleoptera: corn root worms such as western corn root worm and southern corn root worm, chafers such as aupreous chafer and soybean beetle, snout beetles such as rice weevil, rice water weevil, ball weevil and adzuki bean weevil, darkling beetles such as yellow mealworm and red flour beetle, leaf beetles such as rice leaf beetle, striped flea beetle and cucurbit leaf beetle, deathwatch and drugetose beetles, Epilachna spp. such as twenty-eight-spotted ladybird, powderpost beetles, false powderpost beetles, longicorn beetles, and *Paederus fuscipes.*

Dictyoptera: German cockroach, smokybrown cockroach, American cockroach, brown cockroach and oriental cockroach, etc.

Thysanoptera: *Thrips palmi,* western flower thrips, flower thrips, etc.

Hymenoptera: ants, hornets, wingless wasps and bethylid wasps, sawflies such as cabbage sawfly, etc.

Orthoptera: mole cricket, grasshoppers, etc.

Aphaniptera: *Pulex irritans, Ctenocephalides felis,* etc.

Anoplura: *Pediculus humanus, phthirus pubis,* etc.

Isoptera: *Reticulitermes speratus, Coptotermes formosanus,* etc.

House dust mites: Dermatophagoides spp. such as *Dermatophagoides farinae* and *Dermatophagoides pteronyssinus* acarid mites such as mold mite and brown legged grain mite, glycyphagid mites such as *Glycyphagus prinatus, Glycyphagus domesticuo* and groceries mite, Cheyetidae such as *Cheyletus malaecensis* and *Cheyletus fortis,* tarsonemid mites, Tarsonemidae, *Haplochthonius simplex,* spider mites such as two-spotted spider mite, kanzawa spider mite, citrus red mite, European red mite, Ixodidae such as *Haemaphysalis longiconis,* etc.

The compounds of the present invention are also effective against pests which have developed resistance to the existing pesticides and acaricides.

When used as an pesticide and acaricide, the compounds of the present invention may be applied in the form as they are or the salts thereof (agro-pharmacologically acceptable salts with inorganic acids (hydrochloric acid, sulfuric acid, etc.) or organic acids (p-toluenesulfonic acid, etc.) without adding any other components, but usually are mixed with a solid carrier, liquid carrier, gaseous carrier, feed or such, or impregnated in a base material such as a porous ceramic plate or nonwoven fabric, and if necessary a surfactant and other preparation adjuvants may be added to prepare the desired formulation such as oil solution, emulsifiable concentrate, wettable powder, flowables, granules, dusts, aerosol, smoking preparations (such as fogging), fumigants, poisonous baits, acarid-proof sheets, etc.

These formulations contain the compound of the present invention in an amount of usually 0.01 to 95% by weight as active ingredient.

The solid carriers that may be used in these formulations include fine powders or granular products of clays (kaolin clay, diatomaceous earth, synthetic hydrous silicon oxide, bentonite, Fubasamiclay, acid clay, etc.), talcs, ceramic material, other inorganic minerals (sericite, quartz, sulfur, active carbon, calcium carbonate, hydrated silica, etc.), and chemical fertilizers (ammonium sulfate, ammonium phosphate, ammonium nitrate, urea, ammonium chloride, etc.). The liquid carriers that may be used in these formulations include water, alcohols (methanol, ethanol, etc.), ketones (acetone, methyl ethyl ketone, etc.), aromatic hydrocarbons (benzene, toluene, xylene, ethylbenzene, methylnaphthalene, etc.), aliphatic hydrocarbons (hexane, cyclohexane, kerosene, light oil, etc.), esters (ethyl acetate, butyl acetate, etc.), nitrites (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloroethane, carbon tetrachloride, etc.), dimethyl sulfoxide, and vegetable oils such as soybean oil, cottonseed oil, etc. The gaseous carriers, or propellants, include freon gas, butane gas, LPG (liquefied petroleum gas), dimethyl ether, carbon dioxide, and the like.

As the base material of poisonous bait, that may be used, for instance, feed components such as grain flour, vegetable oil, sugar and crystal cellulose, antioxidants such as dibutylhydroxytoluene and nordihydroguaiaretic acid, preservatives such as dehydroacetic acid, erroneous eating preventives such as powdered Guinea pepper, and attracting flavor such as cheese flavor and onion flavor.

The surfactants that may be used in the preparations include alkylsulfate esters, alkylsulfonate salts, alkylarylsulfonate salts, alkylaryl ethers and their polyoxyethylenized products, polyethylene glycol ethers, polyhydric alcohol esters, and sugar alcohol derivatives.

Examples of preparation adjuvants such as fixing agent and dispersant, that may be used, are casein, gelatin, polysaccharides (starch powder, gum arabic, cellulose derivatives, alginic acid, etc.), lignin derivatives, bentonite, saccharides, and water-soluble synthetic polymers (polyvinyl alcohol, polyvinyl pyrrolidone, polyacrylic acids, etc.). As the stabilizer, one can use, for example, PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids and their esters.

The obtained formulations may be used in the form as they are or in dilution with water.

In the case the compounds of the present invention are used as an agricultural pesticide, they are applied in an amount of usually 1 to 1000 g for the area of 1 hectare. In the case such preparation as emulsion, wettable powder or flowable is used after diluting it with water, its application concentration is usually 1 to 10,000 ppm. The granule, dust and the like are applied without dilution. When the compounds are used as a pesticide for the prevention of epidemics, the emulsion, wettable powder, flowable and so on formulations are applied after diluted to 0.1 to 500 ppm with water, but the oil solution, aerosol, fumigant, poisonous bait, acarid-proof sheet and the like are applied in the form as they are.

The amount and concentration of the compound applied are variable depending on the type of the formulation, the time, place and method of application, the type of the pest to be treated, the degree of damage and other factors, and can be properly adjusted despite the above definitions.

The compounds of the present invention can be used in admixture or in combination with other insecticides, nematocides, acaricides, fungicides, herbicides, plant growth regulators, synergists, fertilizers, soil conditioners, animal feeds, etc.

Examples of the said insecticides, nematocides and acaricides include the following: organic phosphorous compounds such as fenitrothion [O,O-dimethyl O-(3-methyl-4-nitrophenyl)phosphorothioate], fenthion [O,O-dimethyl O-(3-methyl-4-(methylthio)phenyl)phosphorothioate], diazinon [O,O-diethyl-O-2-isopropyl-6-methylpyrimidine-4-yl-phosphorothioate], chlorpyrifos [O,O-diethyl-O-3,5,6-trichloro-2-pyridylphosphorothioate], acephate [O,S-dimethylacetylphosphoramidothioate], methidathion [S-2,3-dihydro- 5-methoxy-2-oxo-1,3,4-thiadiazol-3-ylmethyl O,O-dimethylphosphorodithioate], disulfoton [O,O-diethyl S-2-ethylthioethylphosphorodithioate], DDVP [2,2-dichlorovinyl-dimethylphosphate], sulprofos [O-ethyl O-4-(methylthio)-phenyl S-propylphosphorodithioate], cyanophos [O-4-cyanophenyl O,O-dimethylphosphorothioate], dioxabenzofos [2-methoxy-4H-1,3,2-benzodioxaphosphorine-2-sulfide], dimethoate [O,O-dimethyl-S-(N-methylcarbamoylmethyl) dithiophosphate], phenthoate [ethyl 2-dimethoxy-phosphinothioylthio (phenyl)acetate], malathion [diethyl-(dimethoxyphosphinothioylthio)succinate], trichlorfon [dimethyl 2,2,2-trichloro-1-hydroxyethylphosphonate], azinphos-methyl [S-3,4-dihydro-4-oxo-1,2,3-benzotriazine-3-ylmethyl O,O-dimethylphosphorodithioate], monocrotophos [dimethyl(E)-1-methyl-2-(methylcarbamoyl) vinylphosphate], and ethion [O,O,O',O'-tetraethyl S,S'-methylenebis-(phosphorodithioate)]; carbamate compounds such as BPMC [2-sec-butylphenyl methylcarbamate], benfuracarb [ethyl N-[2,3-dihydro-2,2-dimethylbenzofuran-7-yloxycarbonyl-(methyl)aminothio]-N-isopropyl-β-alaninate], propoxur [2-isopropoxyphenyl N-methylcarbamate], carbosulfan [2,3-dihydro-2,2-dimethyl-7-benzo[b]furanyl N-dibutylaminothio-N-methylcarbamate], carbaryl [1-naphthyl-N-methylcarbamate], methomyl [S-methyl-N-[(methylcarbamoyl) oxy]-thioacetoimidate], ethiofencarb [2-(ethylthiomethyl) phenyl methylcarbamate], aldicarb [2-methyl-2-(methylthio)-propionaldehyde O-methylcarbamoyloxime], oxamyl [N,N-dimethyl-2-methylcarbamoyloxyimino-2-(methylthio)-acetamide], and fenothiocarb [S-(4-phenoxybutyl)-N,N-dimethylthiocarbamate]; pyrethroid compounds such as ethofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methylbutylate], esfenvalerate [(S)-α-cyano-3-phenoxybenzyl (S)-2-(4-chlorophenyl)-3-methylbutylate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS)-cis,trans-3-(2,2-dichlorovinyl)-2,2-dimethylcyclopropanecarboxylate], permethrin [3-phenoxybenzyl (1RS)-cis,trans-3-(2,2-dichlorovinyl)-2,2-dimethylcyclopropanecarboxylate], cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl) cyclopropanecarboxylate], fluvalinate [α-cyano-3-phenoxybenzyl N-(2-chloro-α, α, α-trifluoro-p-tolyl)-D-valinate], bifenthrin [2-methylbiphenyl-3-ylmethyl) (Z)-(1RS)-cis-3-(2-chloro-3,3,3-trifluoro-1-propenyl)-2,2-dimethylcyclopropanecarboxylate, 2-methyl-2-(4-bromodifluoromethoxyphenyl)propyl (3-phenoxybenzyl) ether, tralomethrin [(S)-α-cyano-3-phenoxybenzyl (1R)-cis-3-(1,2,2,2-tetrabromoethyl)-2,2-dimethylcyclopropanecarboxylate], silafluofen [4-ethoxyphenyl{3-(4-fluoro-3-phenoxyphenyl) propyl}dimethylsilane], d-phenothrin [3-phenoxybenzyl (1R-cis,trans)-chrysanthemate], cyphenothrin [(RS)-α-cyano-3-phenoxybenzyl (1R-cis,trans)-chrysanthemate], d-resmethrin [5-benzyl-3-furylmethyl (1R-cis,trans)-chrysanthemate], acrinathrin [(S)-α-cyano-3-phenoxybenzyl (1R-cis(Z))-(2,2-dimethyl-3-(3-oxo-3-(1,1,1,3,3,3-hexafluoropropyloxy)propenyl)-cyclopropanecarboxylate], cyfluthrin [(RS)-α-cyano-4-fluoro-3-phenoxybenzyl-3-(2,2-dichlorovinyl)-2,2-dimethylcyclopropanecarboxylate], tefluthrin [2,3,5,6-tetrafluoro-4-methylbenzyl (1RS-cis(Z))-3-(2-chloro-3,3,3-trifluoroprop-1-enyl)-2,2-dimethylcyclopropanecarboxylate], transfluthrin [2,3,5,6-tetrafluorobenzyl (1R-trans)-3-(2,2-dichlorovinyl)-2,2-dimethylcyclopropanecarboxylate], tetramethrin [3,4,5,6-tetrahydrophthalimidomethyl (1RS)-cis,trans-chrysanthemate], allethrin [(RS)-3-allyl-2-methyl-4-oxycyclopent-2-enyl (1RS)-cis,trans-chrysanthemate], prallethrin [(S)-2-methyl-4-oxo-3-(2-propenyl)cyclopent-2-enyl (1R)-cis,trans-chrysanthemate], empenthrin [(RS)-1-ethynyl-2-methyl-2-pentenyl (1R)-cis,trans-chrysanthemate], imiprothrin [2,5-dioxo-3-(prop-2-inyl) imidazolin-1-ylmethyl (1R)-cis,trans-2,2-dimethyl-3-(2-methyl-1-propenyl)cyclopropanecarboxylate], d-flamethrin [5-(2-propenyl)furfuryl (1R)-cis,trans-chrysanthemate], and 5-(2-propynyl)furfuryl 2,2,3,3-tetramethylcyclopropanecarboxylate; thiadiazine derivatives such as buprofezin [2-tert-butylimino-3-isopropyl-5-phenyl-1,3,5-thiadiazine-4-one], nitroimidazolidine derivatives, neristoxin derivatives such as cartap [S,S'-(2-dimethylamino-trimethylene) bis(thiocarbamate)], thiocyclam [N,N-dimethyl-1,2,3-trithian-5-ylamine] and bensultap [S,S'-2-dimethylaminotrimethylene di(benzenethiosulfonate)]; N-cyanoamidine derivatives such as N-cyano-N'-methyl-N'-(6-chloro-3-pyridylmethyl)acetoamidine, chlorinated hydrocarbons such as endosulfan [6,7,8,9,10,10-hexachloro-1,5,5a,6,9,9a-hexahydro-6,9-methano-2,4,3-benzodioxathiepine oxide], γ-BHC(1,2,3,4,5,6-hexachlorocyclohexane) and 1,1-bis(chlorophenyl)-2,2,2-trichloroethanol; benzoylphenylurea compounds such as chlorfluazuron [1-(3,5-dichloro-4-(3-chloro-5-trifluoro-methylpyridin-2-yloxy)phenyl)-3-(2,6-difluorobenzoyl) urea], teflubenzuron [1-(3,5-dichloro-2,4-difluorophenyl)-3-(2,6-difluorobenzoyl)urea] and flufenoxuron [[1-(4-(2-chloro-4-trifluoromethylphenoxy)-2-fluorophenyl]-3-(2,6-difluoro-benzoyl)urea]; formamizine derivatives such as amitraz [N,N'-[(methylimino)dimethylidine]-di-2,4-xylidine] and chlordimeform [N'-(4-chloro-2-methylphenyl)-N,N-dimethylmethanimidamide]; thiourea derivatives such as diafenthiuron [N-(2,6-diisopropyl-4-phenoxyphenyl)-N'-tert-butylcarbodiimide]; phenylpyrazole compounds; methoxadiazon [5-methoxy-3-(2-methoxyphenyl)-1,3,4-oxadiazol-2-(3H)-one], bromopropylate [isopropyl 4,4,'-dibromobenzylate], tetradifon [4-chlorophenyl 2,4,5-trichlorophenylsulfone], chinomethionate [S,S-6-methylquinoxaline-2,3-diyldithiocarbonate], propargite [2-(4-tert-butylphenoxy) cyclohexyl prop-2-il sulfite], fenbutatin oxide [bis[tris(2-methyl-2-phenylpropyl)tin]oxide], hexythiazox [(4RS, 5RS)-5-(4-chlorophenyl)-N-chlorohexyl- 4-methyl-2-oxo-1,3-thiazolidine-3-carboxyamide], clofentezine [3,6-bis(2-chlorophenyl)-1,2,4,5-tetrazine], pyridaben [2-tert-butyl-5-(4-tert-butylbenzylthio)-4-chloropyridazine-3(2H)-one], fenpyroximate [tert-butyl (E)-4-[(1,3-dimethyl-5-phenoxypyrazole-4-yl)methylenaminooxymethyl] benzoate], debfenpyrado [N-4-tert-butylbenzyl]-4-chloro-3-ethyl-1-methyl-5-pyrazolecarboxamide], polynactin complexes [tetranactin, dinactin, trinactin], pyrimidifen [5-chloro-N-[2-{4-(2-ethoxyethyl)-2,3-dimethylphenoxy}ethyl]-6-ethylpyrimidine-4-amine], milmectin, abamectin ibamectin and azadirachtin [AZAD].

EXAMPLES

The present invention will hereinafter be described in further detail by showing the production examples, formulation examples and test examples, but it should be understood that these examples are merely intended to be illustrative and not to be construed as limiting the scope of the invention.

First, the production examples of the compounds of the present invention are shown.

Production Example 1
[Production of the Compound (1) of the Present Invention]

To a suspension wherein 156 mg of sodium hydride (about 60% dispersion in oil) is in N,N-dimethylformamide (3 ml), an N,N-dimethylformamide (5 ml) solution containing of 4-pentafluoroethylpyrimidin-6-one (760 mg, 3.55 mmol) was added dropwise under ice cooling and stirred at room temperature for 15 minutes. Subsequently, 5-chloro-6-nitro-1,1,3,3-tetrafluoro-1,3-dihydroisobenzofuran (1.92 g, 7.07 mmol) was added and the mixture was heated at 80° C. for 10 hours. After allowing time to cool, the reaction solution was poured into water and extracted with ethyl acetate, and the organic layer was dried over anhydrous magnesium sulfate. The solvent was distilled off under reduced pressure and the residue was subjected to silica gel column chromatography to give 200 mg of 4-pentafluoro-ethyl-1-(4-nitro-1,1,3,3-tetrafluoro-1,3-dihydroisobenzo-furan-5-yl)-pyrimidin-6-one.

$^1$H-NMR (300 MHz; CDCl$_3$/TMS): δ (ppm)=8.54 (s, 1H), 8.00 (s, 1H), 7.87 (s, 1H), 7.00 (s, 1H).

Production Example 2

[Production of the Compound (2) of the Present Invention]

To a suspension wherein 5-amino-1-(6-chloro-1,1,3,3-tetrafluoro-1,3-dihydroisobenzofuran-5-yl)-3-cyanopyrazole (665 mg, 2.00 mmol), sodium trifluoromethanesulfinate (624 mg, 4.00 mmol) and dimethylamine tosylate (1.086 g, 5.00 mmol) are in toluene (5 ml), thionyl chloride (476 mg, 2.00 mmol) was added dropwise under ice cooling over a period of about 10 minutes and stirred at 50 to 60° C. for 10 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 400 mg of 5-amino-1-(6-chloro-1,1,3,3-tetrafluoro-1,3-dihydroisobenzofuran-5-yl)-3-cyano-4-trifluoromethylsulfenylpyrazole.

$^1$H-NMR (300 MHz; CDCl$_3$/TMS): δ (ppm)=7.97 (s, 1H), 7.89 (s, 1H), 4.61 (bs, 2H).

Production Example 3

[Production of the Compound (3) of the Present Invention]

To a suspension wherein 5-amino-3-cyano-1-(4,6-dichloro-1,1,3,3-tetrafluoro-1,3-dihydroisobenzofuran-5-yl) pyrazole (950 mg, 2.59 mmol), sodium trifluoromethanesulfinate (808 mg, 5.18 mmol) and dimethylamine tosylate (1.410 g, 6.48 mmol) are in toluene (7 ml), thionyl chloride (615 mg, 5.17 mmol) was added dropwise under ice cooling over a period of about 10 minutes and stirred at 50 to 60° C. for 14 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 550 mg of 5-amino-3-cyano-1-(4,6-dichloro-1,1,,3,3-tetrafluoro-1,3-dihydroisobenzofuran-5-yl)-4-trifluoromethylsulfenylpyrazole.

$^1$H-NMR (300 MHz; CDCl$_3$/TMS): δ (ppm)=7.88 (s, 1H), 4.64 (bs, 2H).

Production Example 4

[Production of the Compound (4) of the Present Invention]

To a suspension wherein 5-amino-1-(5-chloro-2,2,3,3-tetrafluoro-2,3-dihydrobenzofuran-6-yl)-3-cyanopyrazole (665 mg, 2.00 mmol), sodium trifluoromethanesulfinate (624 mg, 4.00 mmol) and dimethylamine tosylate (1.086 g, 5.00 mmol) are in toluene (5 ml), thionyl chloride (476 mg, 2.00 mmol) was added dropwise under ice cooling over a period of about 10 minutes and stirred at 50 to 60° C. for 10 minutes. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 200 mg of 5-amino-1-(5-chloro-2,2,3,3-tetrafluoro-2,3-dihydrobenzofuran-6-yl)-3-cyano-4-trifluoromethylsulfenylpyrazole.

$^1$H-NMR (300 MHz; CDCl$_3$/TMS): δ (ppm)=7.86 (t; J=1.35 Hz, 1H), 7.29 (s, 1H), 4.52 (bs, 2H).

Production Example 5

[Production of the Compound (5) of the Present Invention]

To a suspension wherein 5-amino-1-(2-chloro-4,5-difluoromethylenedioxyphenyl)-3-cyanopyrazole (897 mg, 3.00 mmol), sodium trifluoromethanesulfinate (936 mg, 6.00 mmol) and dimethylamine tosylate (1.629 g, 7.5 mmol) are in toluene (5 ml), thionyl chloride (714 mg, 3.00 mmol) was added dropwise under ice cooling over a period of about 10 minutes and stirred at 50 to 60° C. for 10 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 300 mg of 5-amino-1-(2-chloro-4,5-difluoromethylenedioxyphenyl)-3-cyano-4-trifluoromethylsulfenylpyrazole. M.p. 125.6° C.

$^1$H-NMR (300 MHz; CDCl$_3$/TMS): δ (ppm)=7.35 (s, 1H), 7.26 (s, 1H), 4.47 (br. s, 2H).

Production Example 6

[Production of the Compound (6) of the Present Invention]

To a suspension wherein 5-amino-3-cyano-1-(5,7-dichloro-2,2,3,3-tetrafluoro-2,3-dihydrobenzofuran-6-yl) pyrazole (734 mg, 2.00 mmol), sodium trifluoromethanesulfinate (624 mg, 4.00 mmol) and dimethylamine tosylate (1.086 g, 5.00 mmol) are in toluene (5 ml), thionyl chloride (476 mg, 2.00 ml) was added dropwise under ice cooling over a period of about 10 minutes and then stirred at 50 to 60° C. for 10 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 230 mg of 5-amino-3-cyano-1-(5,7-dichloro-2,2,3,3-tetrafluoro-2,3-dihydrobenzofuran-6-yl)-4-trifluoromethylsulfenylpyrazole.

$^1$H-NMR (300 MHz; CDCl$_3$/TMS): δ (ppm)=7.86 (t; J=1.36 Hz, 1H), 4.46 (bs, 2H).

Production Example 7

[Production of the Compound (7) of the Present Invention]

To a suspension wherein 5-amino-3-cyano-1-(6-fluoro-1,1,3,3-tetrafluoro-1,3-dihydroisobenzofuran-5-yl)pyrazole (900 mg, 2.85 mmol), sodium trifluoromethanesulfinate (890 mg, 5.70 mmol) and dimethylamine tosylate (1.550 g, 7.13 mmol) are in toluene (5 ml), thionyl chloride (678 mg, 5.70 mmol) was added dropwise under ice cooling over a period of about 10 minutes and stirred at 50 to 60° C. for 10 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 340 mg of 5-amino-3-cyano-1-(6-fluoro-1,1,3,3-tetrafluoro-1,3-dihydroisobenzofuran-5-yl)-4-trifluoromethylsulfenylpyrazole.

¹H-NMR (300 MHz; CDCl₃/TMS): δ (ppm)=7.97 (d; J=6.02 Hz, 1H), 7.68 (d; J=7.97 Hz, 1H), 4.70 (bs, 2H).

Production Example 8
[Production of the Compound (8) of the Present Invention]
To a suspension wherein 5-amino-1-(6-chloro-1,1,3,3-tetrafluoro-1,3-dihydroisobenzofuran-5-yl)-3-cyanopyrazole (600 mg, 1.80 mmol), sodium trifluoromethanesulfinate (366 mg, 2.35 mmol) and dimethylamine tosylate (587 mg, 2.70 mmol) are in toluene (5 ml), thionyl chloride (278 mg, 2.34 mmol) was added dropwise over a period of about 10 minutes and then stirred at 50 to 60° C. for 10 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 150 mg of 5-amino-1-(6-chloro-1,1,3,3-tetrafluoro-1,3-dihydroisobenzofuran-5-yl)-3-cyano-4-trifluoromethylsulfinylpyrazole.
¹H-NMR (300 MHz; CDCl₃/TMS): δ (ppm)=8.00 (s, 1H), 7.90 (s, 1H), 5.27 (bs, 2H).

Production Example 9
[Production of the Compound (9) of the Present Invention]
To a suspension wherein 5-amino-1-(6-bromo-1,1,3,3-tetrafluoro-1,3-dihydroisobenzofuran-5-yl)-3-cyanopyrazole (754 mg, 2.00 ml), sodium trifluoromethanesulfinate (406 mg, 2.60 mmol) and dimethylamine tosylate (652 mg, 3.00 mmol) are in toluene (5 ml), thionyl chloride (309, mg, 2.60 mmol) was added dropwise under ice cooling over a period of about 10 minutes and then stirred under heating at 50 to 60° C. for 10 hours. After allowing time to cool, the reaction solution was poured into water, extracted with ethyl acetate, and the organic layer was dried over anhydrous magnesium sulfate. The solvent was distilled off under reduced pressure and the residue was subjected to silica gel column chromatography to give 200 mg of 5-amino-1-(6-bromo-1,1,3,3-tetrafluoro-1,3-dihydroisobenzofuran-5-yl)-3-cyano-4-trifluoromethylsulfinylpyrazole.
¹H-NMR (300 MHz; CDCl₃/TMS): δ (ppm)=8.17 (s, 1H), 7.87 (s, 1H), 5.24 (bs, 2H).

Production Example 10
[Production of the Compound (10) of the Present Invention]
To a suspension wherein 5-amino-1-(6-chloro-1,1,3,3-tetrafluoro-1,3-dihydroisobenzofuran-5-yl)pyrazole (391 mg, 1.27 mmol), sodium trifluromethanesulfinate (397 mg, 2.54 mmol) and dimethylamine tosylate (690 mg, 3.17 mmol) are in toluene (4 ml), thionyl chloride (302 mg, 2.54 mmol) was added dropwise under ice cooling over a period of about 10 minutes and then stirred under heating at 50 to 60° C. for 14 hours. After allowing to cool, the reaction solution was poured into water, extracted with ethyl acetate, and the organic layer was dried over anhydrous magnesium sulfate. The solvent was distilled off under reduced pressure and the residue was subjected to silica gel column chromatography to give 200 mg of 5-amino-1-(6-chloro-1,1,3,3-tetrafluoro-1,3-dihydroisobenzofuran-5-yl)-4-trifluoromethylsulfenylpyrazole.
¹H-NMR (300 MHz; CDCl₃/TMS): δ (ppm)=7.92 (s, 1H), 7.87 (s, 1H), 7.69 (s, 1H), 4.30 (bs, 2H).

Examples of the compounds of the present invention are shown below with their ¹H-NMR data.
[Compound (11) of the Present Invention]
1-(6-chloro-1,1,3,3-tetrafluoro-1,3-dihydroisobenzofuran-5-yl)- 4-pentafluoroethylpyrimidine-6-one
1H-NMR (300 MHz; CDCl₃/TMS): δ (ppm)=8.12 (s, 1H), 7.99 (s, 1H), 7.80 (s, 1H), 7.06 (s, 1H).
[Compound (12) of the Present Invention]
5-amino-1-(6-chloro-1,1,3,3-tetrafluoro-1,3-dihydroisobenzofuran-5-yl)-3-trifluoromethyl-1,2,4-triazole.
¹H-NMR (300 MHz; CDCl₃/TMS): δ (ppm)=7.97 (s, 1H), 7.90 (s, 1H), 5.12 (bs, 2H).
[Compound (13) of the Present Invention]
5-amino-1-(6-chloro-1,1,3,3-tetrafluoro-1,3-dihydroisobenzofuran-5-yl)-3-cyano-4-ethylsulfenylpyrazole
¹H-NMR (300 MHz; CDCl₃/TMS): δ (ppm)=7.94 (s, 1H), 7.85 (s, 1H), 4.27 (bs, 2H), 2.72 (q; J=7.38 Hz, 2H), 1.29 (t; J=7.34 Hz, 3H).
[Compound (14) of the Present Invention]
5-amino-1-(6-chloro-1,1,3,3-tetrafluoro-1,3-dihydroisobenzofuran-5-yl)-3-cyano-4-ethylsulfinylpyrazole
¹H-NMR (300 MHz; CDCl₃/TMS): δ (ppm)=7.97 (s, 1H), 7.86 (s, 1H), 5.14 (bs, 2H), 3.06–3.24 (m, 2H), 1.40 (t; J=7.40 Hz, 3H).
[Compound (15) of the Present Invention]
5-amino-1-(6-chloro-1,1,3,3-tetrafluoro-1,3-dihydroisobenzofuran-5-yl)-3-cyano-4-ethylsulfonylpyrazole
¹H-NMR (300 MHz; CDCl₃/TMS): δ (ppm)=7.99 (s, 1H), 7.87 (s, 25 1H), 5.20 (bs, 2H), 3.32 (q; J=7,.43 Hz, 2H), 1.43 (t; J =7.39 Hz, 3H).
[Compound (16) of the Present Invention]
5-amino-1-(6-chloro-1,1,3,3-tetrafluoro-1,3-dihydroisobenzofuran- 5-yl)-4-chlorodifluoromethylsulfenyl-3-cyanopyrazole
¹H-NMR (300 MHz; CDCl₃/TMS): δ (ppm)=7.98 (s, 1H), 7.90 (s, 1H), 4.66 (bs, 2H).
[Compound (17) of the Present Invention]
5-amino-4-bromo-1-(6-chloro-1,1,3,3-tetrafluoro-1,3-dihydroisobenzofuran-5-yl)-3-cyanopyrazole
¹H-NMR (250 MHz; CDCl₃/TMS): δ (ppm)=7.95 (s, 1H), 7.83 (s, 1H), 4.11 (bs, 2H).
[Compound (18) of the Present Invention]
5-amino-1-(6-chloro-1,1,3,3-tetrafluoro-1,3-dihydroisobenzofuran-5-yl)-4-isopropylsulfenyl-3-cyanopyrazole
¹H-NMR (300 MHz; CDCl₃/TMS): δ (ppm)=7.95 (S, 1H), 7.86 (s, 1H), 4.30 (bs, 2H), 3.16 (sep; J=6.72 Hz, 1H), 1.30 (d; J =6.82 Hz, 6H).
[Compound (19) of the Present Invention]
5-amino-1-(6-chloro-1,1,3,3-tetrafluoro-1,3-dihydroisobenzofuran-5-yl)-3-cyano-4-methylsulfenylpyrazole
¹H-NMR (300 MHz; CDCl₃/TMS): δ (ppm)=7.95 (s, 1H), 7,.85 (s, 1H), 4.33 (bs, 2H), 2.33 (s, 3H).
[Compound (20) of the Present Invention]
5-amino-1-(6-chloro-1,1,3,3-tetrafluoro-1,3-dihydroisobenzofuran-5-yl)-3-cyano-4-trifluoroacetylpyrazole
¹H-NMR (250 MHz; CDCl₃/TMS): δ (ppm)=8.02 (s, 1H), 7.88 (s, 1H), 6.23 (bs, 2H).
[Compound (21) of the Present Invention]
5-amino-1-(2-chloro-4,5-difluoromethylenedioxyphenyl)-3-cyano-4-trifluoromethylsulfinylpyrazole
¹H-NMR (250 MHz; CDCl₃/TMS): δ (ppm)=7.37 (s, 1H), 7.26 (s, 1H), 5.18 (bs, 2H).

Production of the intermediates in the production processes of the compounds of the present invention is exemplified below.

Referential Production Example 1

To a solution wherein 6-amino-5-chloro-1,1,3,3-tetrafluoro-1,3-dihydroisobenzofuran (2.41 g, 10.0 mmol) is in acetic acid (30 ml), a nitrosylsulfuric acid solution prepared from sodium nitrite (760 mg, 11.0 mmol) and concentrated sulfuric acid (5.5 ml) was added dropwise at 10 to 15° C. over a period of about 10 minutes. The reaction solution was added dropwise to a mixture consisting of sodium acetate (7 g) and a 1:1 mixture (1.45 g) of methyl 2,3-dicyanopropionate and ethyl 2,3-dicyanopropionate, and 50 ml of water under vigorous stirring at room temperature and further stirred for 30 minutes. After reaction solution was extracted with chloroform, the organic layer was washed with a saturated sodium hydrogencarbonate solution, then dried over anhydrous magnesium sulfate and concentrated under reduced pressure until the amount of the solution became about 20 ml. 5 ml of ammonia water was added to the resulting solution and stirred at room temperature for 2 hours. After water was poured into the solution, the solution was extracted with chloroform, the organic layer was washed with a 1N hydrochloric acid solution and then dried over anhydrous magnesium sulfate. The solvent was distilled off under reduced pressure and the residue was subjected to silica gel column chromatography to give 1.0 g of 5-amino-1-(6-chloro-1,1,3,3-tetrafluoro-1,3-dihydroisobenzofuran-5-yl)-3-cyanopyrazole.

$^1$H-NMR (300 MHz; CDCl$_3$/TMS): δ (ppm)=7.94 (s, 1H), 7.84 (s, 1H), 6.03 (s, 1H), 4.03 (bs, 2H).

Referential Production Example 2

To a solution wherein electrolytic iron powder (5.59 g, 100.0 mmol) is in acetic acid (100 ml) and water (10 ml), an acetic acid (20 ml) solution of 5-chloro-6-nitro-1,1,3,3-tetrafluoro-1,3-dihydroisobenzofuran (5.43 g, 20.0 mmol) was added dropwise at 50 to 60° C. over a period of about 10 minutes and further stirred for 30 minutes. The reaction solution was then filtered and water was poured into the filtrate. After the solution was extracted with ethyl acetate, the organic layer was washed with a saturated sodium hydrogencarbonate solution and dried over anhydrous magnesium sulfate. The solvent was distilled off under reduced pressure and the residue was subjected to silica gel column chromatography to give 4.46 g of 6-amino-5-chloro-1,1,3,3-tetrafluoro-1,3-dihydroisobenzofuran.

$^1$H-NMR (300 MHz; CDCl$_3$/TMS): δ (ppm)=7.53 (s, 1H), 6.91 (s, 1H), 4.65 (bs, 2H).

Referential Production Example 3

To a solution wherein 6-amino-5-chloro-1,1,3,3-tetrafluoro-1,3-dihydroisobenzofuran (2.41 g, 10.0 mmol) is in acetic acid (30 ml), a nitrosylsulfuric acid solution prepared from sodium nitrite (760 mg, 11.0 mmol) and concentrated sulfuric acid (5.5 ml) was added dropwise at 10 to 15° C. over a period of about 10 minutes. The reaction solution was then added dropwise into a solution consisting of stannous chloride anhydride (9.5 g) and concentrated hydrochloric acid (8 ml) under vigorous stirring at 0° C. and further stirred for 30 minutes. After a sodium hydroxide solution was added to the reaction mixture to make the solution alkaline, the solution was extracted with diethyl ether, and the organic layer was then dried over anhydrous magnesium sulfate. The solvent was distilled off under reduced pressure and the residue was subjected to silica gel column chromatography to give 1.8 g of 5-chloro-1,1,3,3-tetrafluoro-1,3-dihydroisobenzofuran-6-yl-hydrazine.

$^1$H-NMR (300 MHz; CDCl$_3$/TMS): δ (ppm)=7.49 (s, 1H), 7.46 (s, 1H), 6.22 (bs, 1H), 3.78 (bs, 2H).

Referential Production Example 4

To a solution wherein 5-chloro-1,1,3,3-tetrafluoro-1,3-dihydroisobenzofuran-6-yl-hydrazine (900 mg, 3.5 mmol) and disodium ethylenediaminetetraacetate (1 mg) are in methanol (6 ml), 2-chloroacrylonitrile (919 mg, 10.5 mmol) was added dropwise at 60° C., and under reflux for 8 hours, subsequently concentrated sulfuric acid (0.5 ml, 9.4 mmol) was added to the solution and was further heated under reflux for 6 hours. After the reaction solution was allowed to cool, anhydrous sodium carbonate (1.17 g, 10.5 mmol) was added to the reaction solution, stirred for 4 hours, and had the solvent distilled off under reduced pressure. Subsequently, water was added to the residue, the solution was extracted with ethyl acetate, and the organic layer was dried over anhydrous magnesium sulfate. The solvent was distilled off under reduced pressure and the residue was subjected to silica gel column chromatography to give 400 mg of 5-amino-1-(6-chloro-1,1,3,3-tetrafluoro-1,3-dihydroisobenzofuran-5-yl)-pyrazole.

$^1$H-NMR (250 MHz; CDCl$_3$/TMS): δ (ppm)=7.88 (s, 1H), 7.83 (s, 1H), 7.54 (d; J=1.89 Hz, 1H), 5.71 (d; J=1.89 Hz, 1H), 3.69 (bs, 2H).

The formulation examples using the compounds of the present invention are shown below. In the following description, all "parts" are by weight unless otherwise noted.

Formulation Example 1

(Emulsifiable Concentrate)

After 10 parts of each of the compounds (1) to (21) of the present invention were dissolved in 35 parts of xylene and 35 parts of dimethylformamide, 14 parts of polyoxyethylenestyryl phenyl ether and 6 parts of calcium dodecylbenzenesulfonate were added and mixed well with stirring to obtain a 10% emulsifiable concentrate.

Formulation Example 2

(Wettable Powder)

20 parts of each of the compounds (1) to (21) of the present invention were added to a mixture consisting of 4 parts of sodium laurylsulfate, 2 parts of calcium ligninsulfonate, 20 parts of a fine powder of synthetic hydrous silicon oxide and 54 parts of diatomaceous earth, and were mixed with stirring by a juice mixer to obtain a 20% wettable powder.

Formulation Example 3

(Granules)

5 parts of a fine powder of synthetic hydrous silicon oxide, 5 parts of sodium dodecylbenzenesulfonate, 30 parts of bentonite and 55 parts of clay were added to 5 parts of each of the compounds (1) to (21) of the present invention and mixed well with stirring. Subsequently, a suitable amount of water was added to each mixture. The mixture was then stirred, granulated and air dried to obtain 5% granules.

Formulation Example 4

(Dust)

One part of each of the compounds (1) to (21) of the present invention was dissolved in a suitable amount of acetone. 5 parts of a fine powder of synthetic hydrous silicon oxide, 0.3 part of PAP and 93.7 parts of clay were added and mixed with stirring by a juice mixer. The acetone was evaporated away to obtain a 1% dust.

Formulation Example 5

(Flowable)

20 parts of each of the compounds (1) to (21) of the present invention and 1.5 parts of sorbitan trioleate were mixed with 28.5 parts of an aqueous solution containing 2 parts of polyvinyl alcohol, and the mixture was pulverized (to a particle size of 3 $\mu$ or less) by a sand grinder. Subsequently, 40 parts of an aqueous solution containing 0.05 part of xanthane gum and 0.1 part of aluminum magnesium silicate was added to the pulverized mixture, followed by a further addition of 10 parts of propylene glycol and mixing with stirring to obtain a 20% flowable.

Formulation Example 6

(Oil Solution)

0.1 part of each of the compounds (1) to (21) of the present invention was dissolved in 5 parts of xylene and 5 parts of trichloroethane, and was mixed in 89.9 parts of deodorized kerosene to obtain a 0.1% oil solution.

Formulation Example 7

(Oily Aerosol)

0.1 part of each of the compounds (1) to (21) of the present invention, 0.2 part of tetramethrin, 0.1 part of d-phenothrin, 10 parts of trichloroethane and 59.6 parts of deodorized kerosene were mixed and dissolved. The obtained mixture was filled in an aerosol container. valve was installed to the aerosol container, and 30 parts of a propellant (liquefied petroleum gas) was charged into the container through the valve to obtain an oily aerosol.

Formulation Example 8

(Aqueous Aerosol)

A dissolved mixture of 0.2 part of each of the compounds (1) to (21) of the present invention, 0.2 part of d-allethrin, 0.2 part of d-phenothrin, 5 parts of xylene, 3.4 parts of deodorized kerosene, one part of an emulsifier (trade name: ATMOS 300, produced by Atlas Chemical Co.,), and 50 parts of pure water were filled in an aerosol container. A valve was installed in the aerosol container, and 40 parts of a propellant (liquefied petroleum gas) was charged into the container through the valve to obtain an aqueous aerosol.

Formulation Example 9

(Mosquito Coil)

0.3 part of d-allethrin was added to 0.3 part of each of the compounds (1) to (21) of the present invention, dissolved in 20 ml of acetone and uniformly mixed with 99.4 g of an incense carrier (a 4:3:3 mixture of Tabu powder, pyrethrum marc and woodmeal) with stirring. The mixture was kneaded well by adding 120 ml of water, then molded and dried to obtain a mosquito coil.

Formulation Example 10

(Electric Mosquito-repellent Mat)

To a mixture consisting of 0.4 g of each of the compounds (1) to (21) of the present invention, 0.4 g of d-allethrin and 0.4 g of pipenyl butoxide, acetone was added to make the whole amount of the solution 10 ml. 2.5 cm×1.5 cm×0.3 cm electric mat plate (a plate made by massing and hardening the fibrils comprising a cotton linter/pulp mixture) was then impregnated with 0.5 ml of the obtained solution to obtain an electric mosquito-repellent mat.

Formulation Example 11

(Heat Smoking Agent)

After 100 mg of each of the compounds (1) to (21) of the present invention were dissolved in a suitable amount of acetone, a 4.0 cm×4.0 cm×1.2 cm porous ceramic plate was then impregnated with the obtained solution to make a heat smoking agent.

Formulation Example 12

(Poisonous Bait)

10 mg of each of the compounds (1) to (21) of the present invention was dissolved in 0.5 ml of acetone, and was then uniformly mixed in 5 g of a powdered solid feed for animals (CE-2 produced by Nippon Kurea Co., Ltd.). Subsequently, acetone was removed by air drying to obtain a 0.2% poisonous bait.

Formulation Example 13

(Mite-repellent Sheet)

Each of the compounds (1) to (21) of the present invention was diluted with acetone and dropped onto a nonwoven fabric to impregnate at the density of 1 $g/m^2$. The acetone was then removed by air drying to obtain an mite-repellent sheet.

Formulation Example 14

(Mite-repellent Sheet)

Each of the compounds (1) to (21) of the present invention was diluted with acetone and dropped onto a filter paper to impregnate at the density of 1 $g/m^2$. The acetone was then removed by air drying to obtain an mite-repellent sheet.

The efficacy of the compounds of the present invention as an active ingredient of the insecticidal/acaricidal preparations is shown by the following test examples. The compounds of the present invention used in the tests are indicated by the compound numbers shown above.

Test Example 1

The flowables of the test compounds made according to Formulation Example 5 were diluted with water to an active principle concentration of 500 ppm, and these solutions were sprinkled over the potted paddies at a rate of 20 ml/pot. After air-drying the sprinkled solution, about 20 first-instar larvae of brown rice planthopper were released on the paddies. 6 days later, the numbers of the dead and live insects were counted to determine the mortality.

As a result, compound (2), (5), (6), (7), (8), (10), (13)–(17), (19) and (21) of the present invention set forth a 90% or higher insect fatality.

Test Example 2

The flowables of the test compounds made according to Preparation Example 5 were diluted with water so the concentration of the active ingredient was 500 ppm. 5 ml of each of the thus prepared solutions were put into a plastic cup containing 65 ml of ion exchange water, and the potted paddies were placed therein. 7 days after treatment with the chemical solutions, 20 first-instar larvae of brown rice planthopper were released on the paddies. 6 days later, the numbers of the dead and live insects were counted to determine the mortality.

As a result, compound (1), (2), (5), (8), (9), (10), (11), (13), (14), (15), (17), (19) and (21) of the present invention set forth a 90% or higher insect mortality.

Test Example 3

The flowables of the test compounds made according to Formulation Example 5 were diluted with water so the concentration of the active ingredient was 500 ppm. 2 ml of each of the prepared solutions were infiltrated into 13 g of an artificial feed (Insecta LF produced by Nippon Nosan Kogyo K. K.) in a 11 cm-diameter polyethylene cup. 5 fourth-instar larvae of *Spodoptera litura* were released in the cup. 6 days later, the numbers of the dead and live insects were counted to determine the mortality.

As a result, compound (2), (3), (6), (8), (9), (10) and (11) of the present invention set forth an 80% or higher insect mortality.

Test Example 4

The bottom of a 5.5 cm-diameter polyethylene cup was covered with a circular filter paper of the same size. An emulsifiable concentrate of each of the test compounds made according to Formulation Example 1 was diluted with water so the concentration of the active ingredient was 500 ppm. After 0.7 ml of each of the prepared solutions was dropped onto the filter paper in the polyethylene cup, 30 mg of sucrose was uniformly spread thereon as bait. 10 female larvae of *Musca domestica* were released in the cup and the cup was covered. 24 hours later, the numbers of the dead and live insects were counted to determine the mortality.

As a result, compound (2), (3), (5), (6), (7), (8), (9), (10), (14), (16), (18) and (21) of the present invention set forth a 100% insect mortality.

Test Example 5

The bottom of a 5.5 cm-diameter polyethylene cup was covered with a circular filter paper of the same size. An emulsifiable concentrate of each of the test compounds made according to Formulation Example 1 was diluted with water so the concentration of the active ingredient was 500 ppm. After 0.7 ml of each of the prepared solutions was dropped onto the filter paper in the polyethylene cup, with 30 mg of sucrose was uniformly spread thereon as bait. 2 male imagoes of *Blattella germanica* were released in the cup and the cup was covered. 6 days later, the numbers of the dead and live insects were counted to determine the mortality.

As a result, compound (2)–(10), (11), (16) and (21) of the present invention set forth a 100% insect fatality.

Test Example 6

The emulsifiable concentrates of the test compounds made according to Formulation Example 1 were diluted with water so the concentration of the active ingredient was 500 ppm. 0.7 ml of each of the prepared solutions was then added to 100 ml of ion exchange water (active principle concentration: 3.5 ppm). 20 final-instar larvae of *Culex pipiens* were released therein, and the numbers of the dead and live larvae were counted one day later to determine the mortality.

As a result, compound (2)–(20) of the present invention set forth a 90% or higher insect fatality.

What is claimed is:

1. The heterocyclic compounds represented by the formula (I):

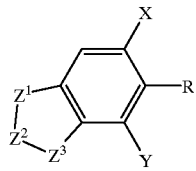

wherein X and Y may be the same or different and represent respectively a hydrogen atom, a halogen atom, a nitro group or a cyano group; $-Z^1-Z^2-Z^3-$ is a formula represented by the group $-CF_2-CF_2-O-$ or $-CF_2-O-CF_2-$; and R is a group represented by the formula (II):

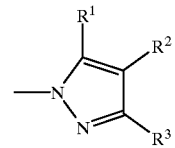

wherein $R_1$ is a hydrogen atom, a $C_1-C_6$ alkyl group, a $C_1-C_6$ haloalkyl group, a halogen atom, a formyl group, a $C_2-C_8$ acyl group, a cyano group, a nitro group, a group represented by $NR^4R^5$ wherein $R^4$ and $R^5$ may be the same or different and represent respectively a hydrogen atom, a $C_1-C_6$ alkyl group, a $C_3-C_6$ cycloalkyl group, a $(C_1-C_6$ alkoxy) $C_1-C_6$ alkyl group, a $(C_1-C_6$ alkylthio) $C_1-C_6$ alkyl group, a $(C_1-C_6$ alkoxy) carbonyl group, a $C_2-C_8$ acyl group or a saturated heterocyclic group, a nitrogen-containing heterocyclic group which is bonded at the nitrogen position and may be substituted, a group represented by $N=CR^6R^7$ wherein $R^6$ is a hydrogen atom, a $C_1-C_6$ alkyl group or a phenyl group which may be substituted, and $R^7$ is a hydrogen atom, a $C_1-C_6$ alkyl group, a $C_1-C_6$ alkoxy group or a $di(C_1-C_6$ alkyl) amino group, or a group represented by $S(O)_nR^8$ wherein $R^8$ is a $C_1-C_6$ alkyl group, a $C_1-C_6$ haloalkyl group or a $C_3-C_6$ cycloalkyl group, and n is a number of 0, 1 or 2; $R^2$ is a halogen atom, a cyano group, a $(C_1-C_6$ alkoxy) carbonyl group, a $C_2-C_8$ acyl group, a halogen-substituted $C_2-C_8$ acyl group, a $C_1-C_6$ alkyl group, a $C_1-C_6$ haloalkyl group, a formyl group, a $C_3-C_6$ cycloalkyl group which may be substituted with at least one halogen, a sulfamoyl group which may be substituted with one or two $C_1-C_6$ alkyl groups, a carbamoyl group which may be substituted with one or two $C_1-C_6$ alkyl groups or a group represented by $S(O)_nR^8$ wherein $R^8$ and n are as defined above; and $R^3$ is a hydrogen atom, a $C_1-C_6$ alkyl group, a thiocarbamoyl group, a $C_1-C_6$ haloalkyl group, $C_3-C_6$ cycloalkyl group, a cyano group, a nitro group or a group represented by $S(O)_nR^8$ wherein $R^8$ and n are as defined above.

2. The heterocyclic compounds according to claim 1, wherein the formula $-Z^1-Z^2-Z^3-$ in the formula (I) is a group represented by $-CF_2-O-CF_2-$.

3. The heterocyclic compounds according to claim 1, wherein the formula $-Z^1-Z^2-Z^3-$ in the formula (I) is a group represented by $-CF_2-CF_2-O-$.

4. The heterocyclic compounds according to claim 1, wherein in the formula (I), the formula $-Z^1-Z^2-Z^3-$ is a group represented by $-CF_2-O-CF_2-$, and R is a group represented by the formula (II):

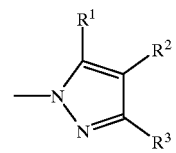

wherein $R^1$ is a hydrogen atom, a $C_1-C_6$ alkyl group, a $C_1-C_6$ haloalkyl group, a halogen atom, a $C_2-C_8$ acyl group, a group represented by $NR^4R^5$ wherein $R^4$ and $R^5$ may be the same or different and represent respectively a hydrogen atom, a $C_1-C_6$ alkyl group, a $C_3-C_6$ cycloalkyl group, a $(C_1-C_6$ alkoxy) $C_1-C_6$ alkyl group, a $(C_1-C_6$ alkylthio) $C_1-C_6$ alkyl group, a $(C_1-C_6$ alkoxy) carbonyl group, a $C_2$–$C_8$ acyl group, or a group represented by N=$CR^6R^7$ wherein $R^6$ is a hydrogen atom, a $C_1$–$C_6$ alkyl group or a phenyl group which may be substituted, and $R^7$ is a hydrogen atom, a $C_1$–$C_6$ alkyl group or a $C_1$–$C_6$ alkoxy group; $R^2$ is a halogen atom, a halogen-substituted $C_2$–$C_8$ acyl group, a $C_1$–$C_6$ haloalkyl a $C_3$–$C_6$ cycloalkyl group which may be substituted with at least one halogen or a group represented by $S(O)_nR^8$ wherein $R^8$ is a $C_1$–$C_6$ alkyl group or a $C_1$–$C_6$ haloalkyl group, and n is as defined above; and $R^3$ is a hydrogen atom, a $C_1$–$C_6$ alkyl group, a thioamide group, a $C_1$–$C_6$ haloalkyl group, a cyano group, or a group represented by $S(O)_nR^8$ wherein $R^8$ is a $C_1$–$C_6$ alkyl group or a $C_1$–$C_6$ haloalkyl group, and n is as defined above.

5. The heterocyclic compounds according to claim 1, wherein in the formula (I), the formula —$Z^1$—$Z^2$—$Z^3$— is a group represented by —$CF_2$—$CF_2$—O— or —$CF_2$—O—$CF_2$—, and R is a group represented by the formula (II):

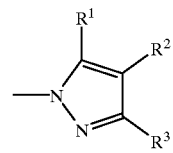

wherein $R_1$ is an amino group; $R^2$ is a halogen atom, a halogen-substituted $C_2$–$C_8$ acyl group or a group represented by $S(O)_nR^8$ wherein $R^8$ is a $C_1$–$C_6$ alkyl group or a $C_1$–$C_6$ haloalkyl group, and n is as defined above; and $R^3$ is a hydrogen atom or a cyano group.

6. An insecticidal and/or acaricidal agent containing a heterocyclic compound of claim 1 as an active ingredient, and an inert carrier.

7. An insect and/or acarid controlling method which comprises applying a heterocyclic compound of claim 1 directly to insects or acarids or to an area where they inhabit.

* * * * *